US010202378B2

(12) United States Patent
Adler et al.

(10) Patent No.: US 10,202,378 B2
(45) Date of Patent: Feb. 12, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Marc Adler, South San Francisco, CA (US); Daniel J. Burdick, South San Francisco, CA (US); Terry Crawford, South San Francisco, CA (US); Martin Duplessis, Cambridge, MA (US); Steven R. Magnuson, South San Francisco, CA (US); Christopher G. Nasveschuk, Cambridge, MA (US); F. Anthony Romero, South San Francisco, CA (US); Yong Tang, Cambridge, MA (US); Vickie Hsiao-Wei Tsui, South San Francisco, CA (US); Shumei Wang, South San Francisco, CA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/658,213

(22) Filed: Jul. 24, 2017

(65) Prior Publication Data

US 2018/0009805 A1 Jan. 11, 2018

Related U.S. Application Data

(63) Continuation of application No. PCT/US2016/015450, filed on Jan. 28, 2016.

(60) Provisional application No. 62/109,522, filed on Jan. 29, 2015.

(51) Int. Cl.

| | |
|---|---|
| *A61K 31/506* | (2006.01) |
| *C07D 471/04* | (2006.01) |
| *A61K 31/437* | (2006.01) |
| *A61K 31/444* | (2006.01) |
| *A61K 31/4545* | (2006.01) |
| *A61K 31/5377* | (2006.01) |
| *A61K 45/06* | (2006.01) |
| *C07D 519/00* | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/506* (2013.01); *A61K 31/5377* (2013.01); *A61K 45/06* (2013.01); *C07D 519/00* (2013.01)

(58) Field of Classification Search
USPC ........................................ 514/256; 544/328
See application file for complete search history.

(56) References Cited

U.S. PATENT DOCUMENTS

| | | | |
|---|---|---|---|
| 9,359,379 B2 | 6/2016 | Seiwert et al. | |
| 9,675,593 B2 | 6/2017 | Ramphal et al. | |
| 9,695,200 B2 | 7/2017 | Jacobsen et al. | |
| 9,763,922 B2 | 9/2017 | Adler et al. | |
| 2014/0094456 A1 | 4/2014 | Buckman et al. | |
| 2014/0107110 A1 | 4/2014 | Buckman et al. | |
| 2014/0162971 A1 | 6/2014 | Wang et al. | |
| 2014/0256710 A1 | 9/2014 | Dachun et al. | |
| 2015/0266899 A1 | 9/2015 | Buckman et al. | |
| 2016/0213653 A1 | 7/2016 | Jacobsen et al. | |
| 2016/0263090 A1 | 9/2016 | Buckman et al. | |

(Continued)

FOREIGN PATENT DOCUMENTS

| | | |
|---|---|---|
| EP | 1953147 A1 | 8/2008 |
| WO | 2007058392 A1 | 5/2007 |

(Continued)

OTHER PUBLICATIONS

Gallenkamp, et al., "Bromodomains and their pharmacological inhibitors", ChemMedChem 9(3), 438-464 (2014).

(Continued)

*Primary Examiner* — Jeffrey H Murray
(74) *Attorney, Agent, or Firm* — Viksnins Harris Padys Malen LLP

(57) ABSTRACT

The present invention relates to compounds of formula (I):

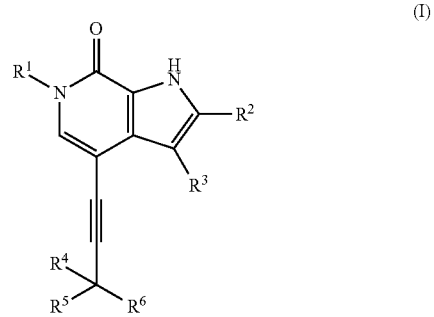

and to salts thereof, wherein $R^1$-$R^6$ have any of the values defined in the specification, and compositions and uses thereof. The compounds are useful as inhibitors of TAF1. Also included are pharmaceutical compositions comprising a compound of formula (I) or a pharmaceutically acceptable salt thereof, and methods of using such compounds and salts in the treatment of various TAF1-mediated disorders.

18 Claims, No Drawings

(56) References Cited

U.S. PATENT DOCUMENTS

| | | | |
|---|---|---|---|
| 2017/0121345 A1 | 5/2017 | Ramphal et al. |
| 2017/0260211 A1 | 9/2017 | Jacobsen et al. |
| 2017/0340604 A1 | 11/2017 | Albrecht et al. |
| 2017/0340605 A1 | 11/2017 | Albrecht et al. |
| 2017/0342067 A1 | 11/2017 | Albrecht et al. |

FOREIGN PATENT DOCUMENTS

| | | |
|---|---|---|
| WO | 2013097052 A1 | 7/2013 |
| WO | 2013097601 A1 | 7/2013 |
| WO | 2014055548 A1 | 4/2014 |
| WO | 2014125408 A2 | 8/2014 |
| WO | 2014139324 A1 | 9/2014 |
| WO | 2014194667 A1 | 12/2014 |
| WO | 2014201161 A1 | 12/2014 |
| WO | 2014206150 A1 | 12/2014 |
| WO | 2014206345 A1 | 12/2014 |
| WO | 2015081203 A1 | 6/2015 |
| WO | 2015081246 A1 | 6/2015 |
| WO | 2015081280 A1 | 6/2015 |
| WO | 2015153683 A1 | 10/2015 |
| WO | 2015164480 A1 | 10/2015 |

OTHER PUBLICATIONS

Garnier, et al., "BET bromodomain inhibitors: a patent review", Expert Opin Ther Patents 24(2), 185-199 (2014).
Jeanmougin, "The bromodomain revisited", Trends Biochem Sci 22(5), 151-153 (1997).
Kloet, et al., "Phosphorylation-Dependent Regulation of Cyclin D1 and Cyclin A Gene Transcription by TFIID Subunits TAF1 and TAF7", Mol Cell Biol 32(16), 3358-3369 (2012).
Muller, et al., "Bromodomains as therapeutic targets", Expert Rev Mol Med 13 (29), 1-21 (2011).
Papai, "New insights into the function of transcription factor TFIID from recent structural studies", Current Opinion in Genetics & Development 21(2), 219-224 (2011).
Patent Cooperation Treaty, International Searching Authority, Search Report and Written Opinion for PCT/US2016/015450, 16 pages, dated Jul. 4, 2016.
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila* homeotic genes structurally related to the yeast transcriptional activator SNF2/SWI2", Cell 68, 561-572 (1992).
Brunton, et al., "Chemotherapy of Neoplastic Diseases", Goodman & Gilman's: The Pharmacological Basis of Therapeutics 11th ed., 853-908 (2008).
CAS Abstract, of US 2014/094456, accession No. 2014:531372, 5 pages (2014).
CAS Abstract, of WO 2014/125408, accession No. 2014:1387149, 3 pages (2014).
Ember, et al., "Acetyl-lysine Binding Site of Bromodomain-Containing Protein 4 (BRD4) Interacts with Diverse Kinase Inhibitors", ACS Chem Biol 9, 1160-1171 (2014).
Filippakopoulos, et al., "Selective inhibition of BET bromodomains", Nature vol. 468 (7327), 1067-1073 (2010).
Filippakopoulos, et al., "Targeting bromodomains: epigenetic readers of lysine acetylation", Nature Reviews 13, 337-356 (2014).
Marelli, et al., "Tumor targeting via integrin ligands", Frontiers in Oncology 3(222), 12 pages (2013).
Medicinenet, "Definition of Cancer", MedicineNet.com, 1 page. (Sep. 18, 2004).
National Cancer Institute, "Prostate Cancer Preventions (PDQ®)", http://www.cancer.gov/>, 2 pages (2010).
Shi, et al., "The Mechanisms behind the Therapeutic Activity of BET Bromodomain Inhibition", Molecular Cell Review 54, 728-736 (2014).
Wang, et al., "Mathematical modeling in cancer drug discovery", Drug Discovery Today 19(2), 145-150 (2014).
U.S. Appl. No. 15/592,012.
U.S. Appl. No. 15/592,013.
U.S. Appl. No. 15/592,017.

THERAPEUTIC COMPOUNDS AND USES THEREOF

CROSS-REFERENCE TO RELATED APPLICATION(S)

This patent application is a continuation of International application serial no. PCT/US2016/015450, filed Jan. 28, 2016, which claims the benefit of priority of U.S. provisional application Ser. No. 62/109,522, filed Jan. 29, 2015, which applications are herein incorporated by reference.

TECHNICAL FIELD OF THE INVENTION

The present invention relates to compounds useful as inhibitors of TAF1.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29):1-20 (September 2011).

TBP-associated factor 1 (TAF1) is a subunit of transcription factor IID and contains both a HAT domain and a double bromodomain (Papai et al., Current Opinion in Genetics & Development 21:219-224 (2011)). While the function of TAF1 has not been fully elucidated, the molecule has been implicated in pathways associated with cancer (see, e.g., Kloet et al., Molecular and Cellular Biology 32(16): 3358-3369 (2012)). Hence, the selective inhibition of TAF1 creates varied opportunities for the development of novel therapeutic agents for the treatment of human dysfunction, including cancer.

Accordingly, there is a need for compounds that inhibit TAF1 for treating diseases such as cancer, as well as for use as tools for studying the pharmacology of TAF1.

SUMMARY OF THE INVENTION

One aspect includes a compound of formula (I):

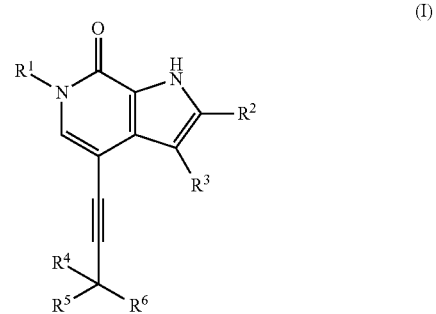

(I)

or a salt thereof wherein:

$R^1$ is $C_{1-6}$alkyl, $C_{2-6}$alkenyl, $C_{2-6}$alkynyl, carbocyclyl, or heterocyclyl, which $C_{1-6}$alkyl, $C_{2-6}$alkenyl, $C_{2-6}$alkynyl, carbocyclyl, and heterocyclyl is optionally substituted with one or more groups independently selected from the group consisting of halo, cyano, $C_{1-3}$alkoxy, and $C_{3-8}$ carbocyclyl that is optionally substituted with one or more groups independently selected from halo;

$R^2$ is $C_{1-6}$alkyl, $C_{2-6}$alkenyl, $C_{2-6}$alkynyl, carbocyclyl, or heterocyclyl, which $C_{1-6}$alkyl, $C_{2-6}$alkenyl, $C_{2-6}$alkynyl, carbocyclyl, and heterocyclyl is optionally substituted with one or more groups independently selected from the group consisting of halo, cyano, $C_{1-3}$alkoxy, and $C_{3-8}$ carbocyclyl that is optionally substituted with one or more groups independently selected from halo;

$R^3$ is H, $C_{1-6}$alkyl, —$N(R^b)_2$, —$C(=O)R^a$, —$C(=O)OR^a$, or a 5-6 membered heteroaryl ring, which $C_{1-6}$alkyl and 5-6 membered heteroaryl ring are optionally substituted with one or more groups independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, and —$N(R^b)$—$S(O)_2$—$R^b$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of $R^f$, oxo, halo, —$NO_2$, —$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—O—$R^b$, —S(O)—$R^b$, —$S(O)_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$;

$R^a$ is selected from the group consisting of hydrogen, $C_{1-10}$alkyl, $C_{2-10}$alkenyl, $C_{2-10}$alkynyl, carbocyclyl, and heterocyclyl, wherein any $C_{1-10}$alkyl, $C_{2-10}$alkenyl, $C_{2-10}$alkynyl, carbocyclyl, and heterocyclyl is optionally substituted with one or more groups independently selected from the group consisting of $R^d$, oxo, halo, —$NO_2$, —N($R^b$)$_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O—$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$;

each $R^b$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of $R^c$, oxo, halo, —$NO_2$, —N($R^c$)$_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo; and each $R^c$ is independently selected from the group consisting of hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^d$ is independently selected from the group consisting of $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of $R^e$, oxo, halo, —$NO_2$, —N($R^e$)$_2$, —CN, —C(O)—N($R^e$)$_2$, —S(O)—N($R^e$)$_2$, —S(O)$_2$—N($R^e$)$_2$, —O—$R^e$, —S—$R^e$, —O—C(O)—$R^e$, —C(O)—$R^e$, —C(O)—O$R^e$, —S(O)—$R^e$, —S(O)$_2$—$R^e$, —N($R^e$)—C(O)—$R^e$, —N($R^e$)—S(O)—$R^e$, —N($R^e$)—C(O)—N($R^e$)$_2$, and —N($R^e$)—S(O)$_2$—$R^e$, each $R^e$ is independently selected from the group consisting of $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^f$ is independently selected from the group consisting of $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo;

$R^4$ is absent, H, hydroxy, or $C_{1-6}$alkyl that is optionally substituted with one or more groups independently selected from the group consisting of halo;

$R^5$ is H or $C_{1-6}$alkyl that is optionally substituted with one or more groups independently selected from the group consisting of halo; and $R^6$ is $C_{1-6}$alkyl, carbocyclyl, or heterocyclyl, which $C_{1-6}$alkyl, carbocyclyl, and heterocyclyl is optionally substituted with one or more $R^g$; or $R^5$ and $R^6$ taken together with the carbon to which they are attached form a carbocyclyl, or heterocyclyl, which carbocyclyl and heterocyclyl is optionally substituted with one or more $R^g$;

each $R^g$ is independently selected from the group consisting of $C_{1-6}$alkyl, $C_{2-6}$alkenyl, $C_{2-6}$alkynyl, carbocyclyl, and heterocyclyl, $R^k$, halo, oxo (=O), —$NO_2$, —N($R^h$)$_2$, —CN, —C(O)—N($R^h$)$_2$, —S(O)—N($R^h$)$_2$, —S(O)$_2$—N($R^h$)$_2$, —O—$R^h$, —S—$R^h$, —O—C(O)—$R^h$, —C(O)—$R^h$, —C(O)—O$R^h$, —S(O)—$R^h$, —S(O)$_2$—$R^h$, —N($R^h$)—C(O)—$R^h$, —N($R^h$)—S(O)—$R^h$, —N($R^h$)—C(O)—N($R^h$)$_2$, and —N($R^h$)—S(O)$_2$—$R^h$;

each $R^h$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^h$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo; and each $R^k$ is independently selected from the group consisting of $C_{1-6}$alkyl, $C_{2-6}$alkenyl, $C_{2-6}$alkynyl, carbocyclyl, and heterocyclyl, which $C_{1-6}$alkyl, $C_{2-6}$alkenyl, $C_{2-6}$alkynyl, carbocyclyl, and heterocyclyl, is substituted with one or more groups independently selected from the group consisting halo, —$NO_2$, —N($R^h$)$_2$, —CN, —C(O)—N($R^h$)$_2$, —S(O)—N($R^h$)$_2$, —S(O)$_2$—N($R^h$)$_2$, —O—$R^h$, —S—$R^h$, —O—C(O)—$R^h$, —C(O)—$R^h$, —C(O)—O$R^h$, —S(O)—$R^h$, —S(O)$_2$—$R^h$, —N($R^h$)—C(O)—$R^h$, —N($R^h$)—S(O)—$R^h$, —N($R^h$)—C(O)—N($R^h$)$_2$, and —N($R^h$)—S(O)$_2$—$R^h$.

Another aspect includes a composition comprising a compound of formula (I) or a pharmaceutically acceptable salt thereof, and a pharmaceutically acceptable adjuvant, carrier, or vehicle.

Another aspect includes a method for treating a TAF1-mediated disorder in an animal comprising administering a compound of formula (I) or a pharmaceutically acceptable salt thereof to the animal.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a TAF1-mediated disorder.

Another aspect includes the use of a compound of formula (I) or a pharmaceutically acceptable salt thereof to prepare a medicament for treating a TAF1-mediated disorder in an animal (e.g. a mammal such as a human).

Another aspect includes a method for inhibiting TAF1 in an animal in need thereof comprising administering a compound of formula (I) or a pharmaceutically acceptable salt thereof to the animal.

Another aspect includes a compound of formula (I) or a pharmaceutically acceptable salt thereof for inhibiting TAF1.

Another aspect includes the use of a compound of formula (I) or a pharmaceutically acceptable salt thereof to prepare a medicament for inhibiting TAF1 in an animal in need thereof.

Another aspect includes a method for treating cancer in an animal comprising administering an effective amount of inhibitor of TAF1 to the animal.

Another aspect includes an inhibitor of TAF1 for use in medical therapy.

Another aspect includes an inhibitor of TAF1 for the prophylactic or therapeutic treatment of cancer.

Another aspect includes the use of an inhibitor of TAF1 to prepare a medicament for treating cancer in an animal.

Another aspect includes compounds for the study of TAF1.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., Tetrahedron 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O or (=O)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane.

The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain monovalent hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), heptyl, octyl, nonyl, decyl, undecyl and dodecyl.

The term "alkenyl," as used herein, denotes a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched monovalent hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl.

The term "alkoxy" refers to a linear or branched monovalent radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein. The term heterocyclyl also includes $C_3$-$C_8$heterocycloalkyl, which is a saturated or partially unsaturated mono-, bi-, or spiro-ring system comprising 3-8 carbons and one or more (1, 2, 3, or 4) heteroatoms.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "polycycle" refers to a ring system with two or more (e.g. 2, 3, 4, or 5) rings that may be fused, bridged, or in a spiro relationship.

As used herein, the term "inhibitor" refers to a compound that binds to and inhibits a TAF1 bromodomain with measurable affinity and activity. In certain embodiments, an inhibitor has an $IC_{50}$ or binding constant of less about 50 µM, less than about 1 µM, less than about 500 nM, less than about 100 nM, or less than about 10 nM.

The terms "measurable affinity" and "measurably inhibit," as used herein, refer to a measurable reduction in activity of a TAF1 bromodomain between: (i) a sample comprising a compound of formula I or composition thereof and such TAF1 bromodomain, and (ii) an equivalent sample comprising such TAF1 bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

As used herein, "a" or "an" means one or more, unless clearly indicated otherwise. As used herein, "another" means at least a second or more.

Exemplary Values

In one embodiment $R^1$ is $C_{1-6}$alkyl that is optionally substituted with one or more groups independently selected from the group consisting of halo, cyano, $C_{1-3}$alkoxy, and $C_{3-8}$ carbocyclyl that is optionally substituted with one or more groups independently selected from halo.

In one embodiment $R^1$ is methyl.

In one embodiment $R^2$ is $C_{1-6}$alkyl that is optionally substituted with one or more groups independently selected from the group consisting of halo, cyano, $C_{1-3}$alkoxy, and $C_{3-8}$ carbocyclyl that is optionally substituted with one or more groups independently selected from halo.

In one embodiment $R^2$ is methyl.

In one embodiment $R^3$ is H.

In one embodiment $R^3$ is $C_{1-6}$alkyl that is optionally substituted with one or more groups independently selected from the group consisting of carbocyclyl, heterocyclyl, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$, wherein any carbocyclyl, and heterocyclyl is optionally substituted with one or more groups independently selected from the group consisting of R$^f$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$.

In one embodiment $R^3$ is —N(R$^b$)$_2$.

In one embodiment $R^3$ is —C(=O)R$^a$.

In one embodiment $R^3$ is —C(=O)OR$^a$.

In one embodiment $R^3$ is a 5-6 membered heteroaryl ring that is optionally substituted with one or more groups independently selected from the group consisting of $C_{1-6}$alkyl, $C_{2-6}$alkenyl, $C_{2-6}$alkynyl, carbocyclyl, heterocyclyl, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of R$^f$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$.

In one embodiment $R^3$ is selected from the group consisting of:

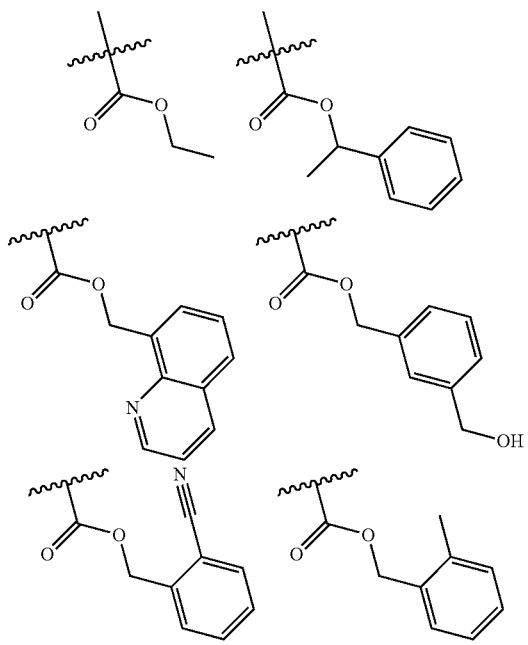

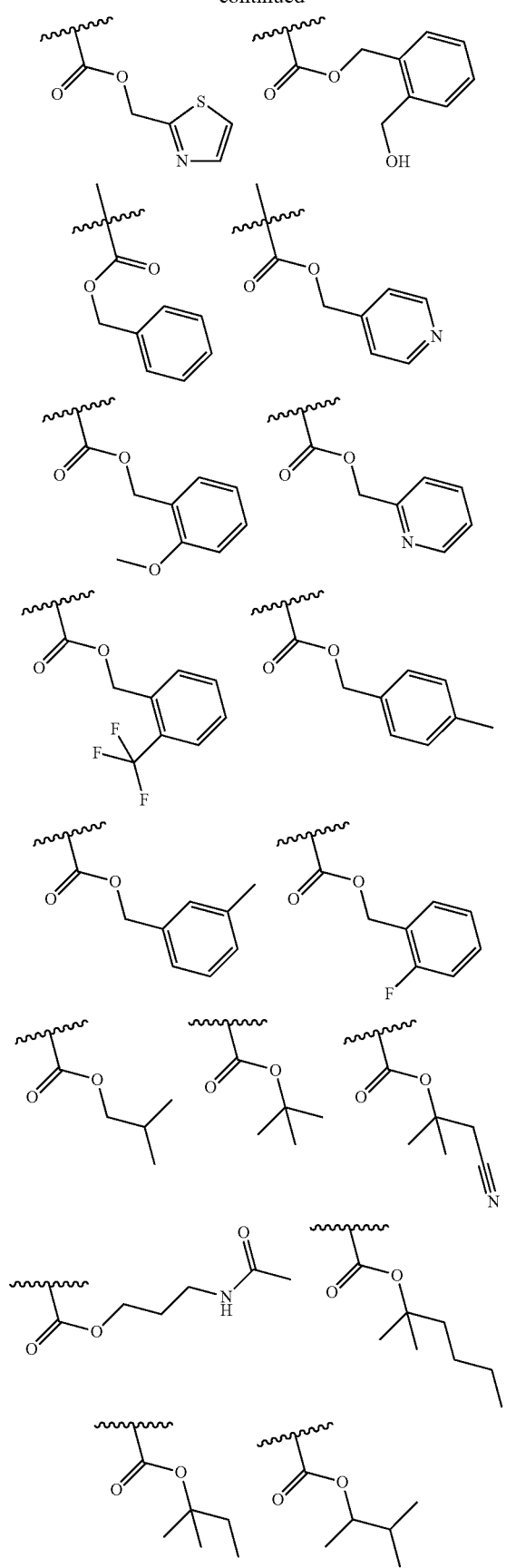
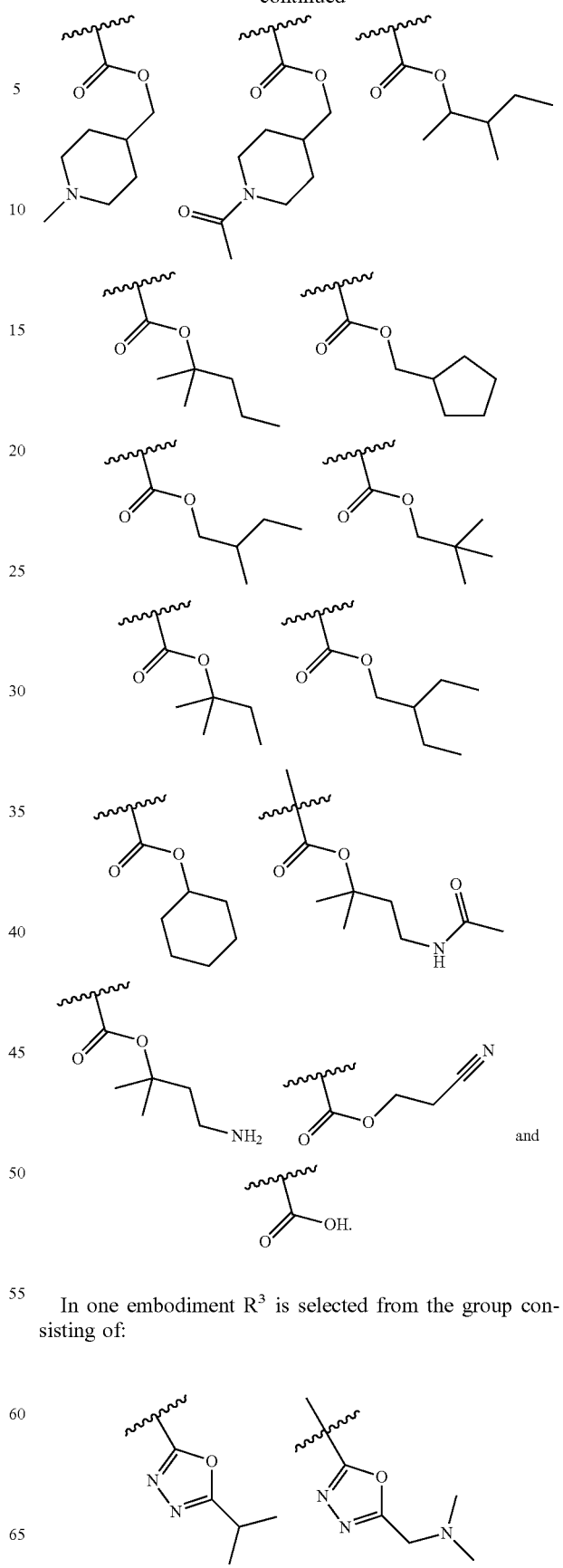
In one embodiment R³ is selected from the group consisting of:

-continued

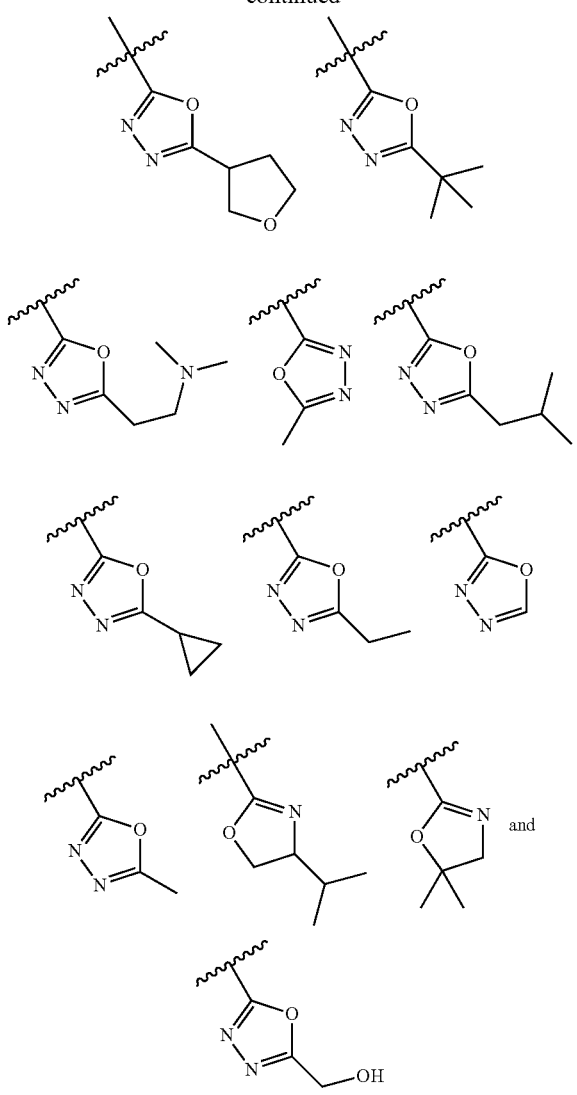

In one embodiment R³ is selected from the group consisting of:

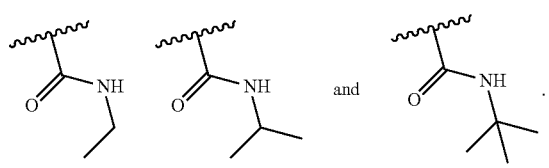

In one embodiment R³ is selected from the group consisting of:

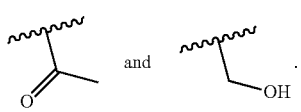

In one embodiment the compound of formula (I) is a compound of formula (Ia):

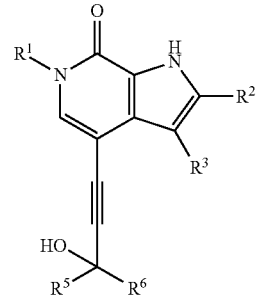

or a salt thereof.

In one embodiment R⁴ is H.

In one embodiment R⁴ is hydroxyl.

In one embodiment R⁴ is $C_{1-6}$alkyl that is optionally substituted with one or more groups independently selected from the group consisting of halo.

In one embodiment R⁵ is H.

In one embodiment R⁵ is $C_{1-6}$alkyl that is optionally substituted with one or more groups independently selected from the group consisting of halo.

In one embodiment R⁶ is $C_{1-6}$alkyl that is optionally substituted with one or more $R^g$.

In one embodiment R⁶ is carbocyclyl that is optionally substituted with one or more $R^g$.

In one embodiment R⁶ is heterocyclyl that is optionally substituted with one or more $R^g$.

In one embodiment R⁶ is $C_1$alkyl substituted with oxo and —N(R$^h$)₂ to form a group —C(O)—N(R$^h$)₂.

In one embodiment R⁵ and R⁶ taken together with the carbon to which they are attached form a carbocyclyl that is optionally substituted with one or more $R^g$.

In one embodiment R⁵ and R⁶ taken together with the carbon to which they are attached form a heterocyclyl that is optionally substituted with one or more $R^g$.

In one embodiment R⁴ is absent; and R⁵ and R⁶ taken together with the carbon to which they are attached form an aryl ring that is optionally substituted with one or more $R^g$, and that is linked to the remainder of formula (I) at an atom of an aromatic ring.

In one embodiment R⁴ is absent; and R⁵ and R⁶ taken together with the carbon to which they are attached form a heterocyclyl that is optionally substituted with one or more $R^g$, and that is linked to the remainder of formula (I) at an atom of an aromatic ring.

In one embodiment the group:

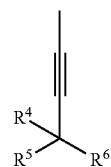

is selected from the group consisting of:
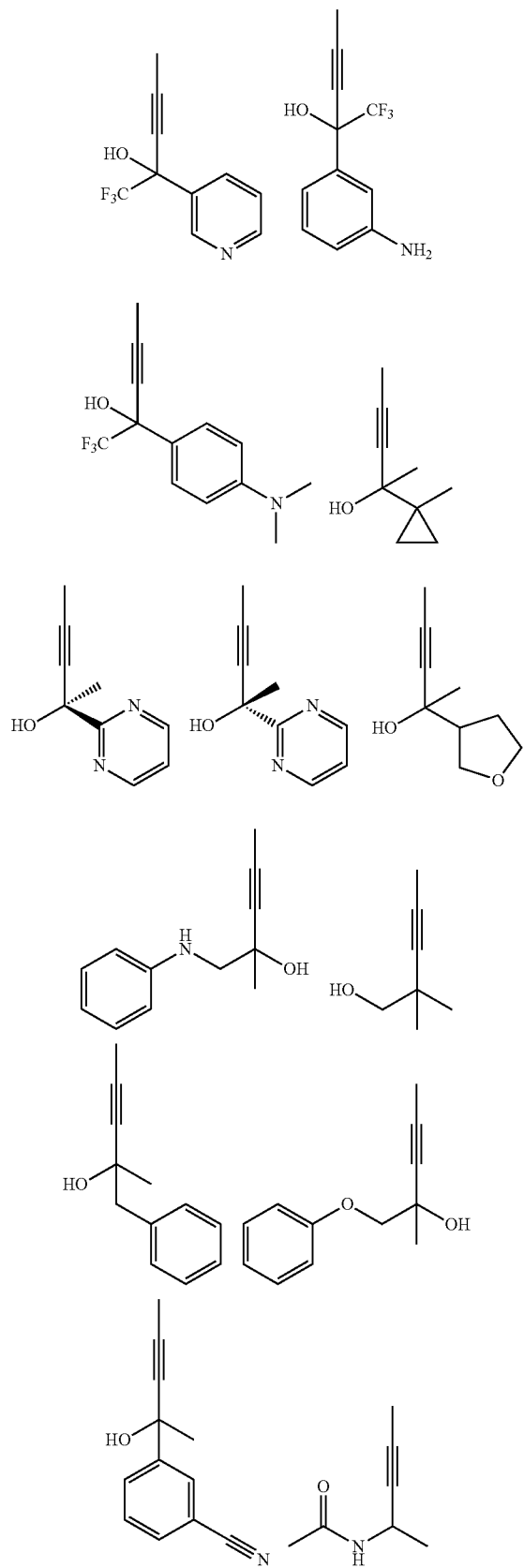
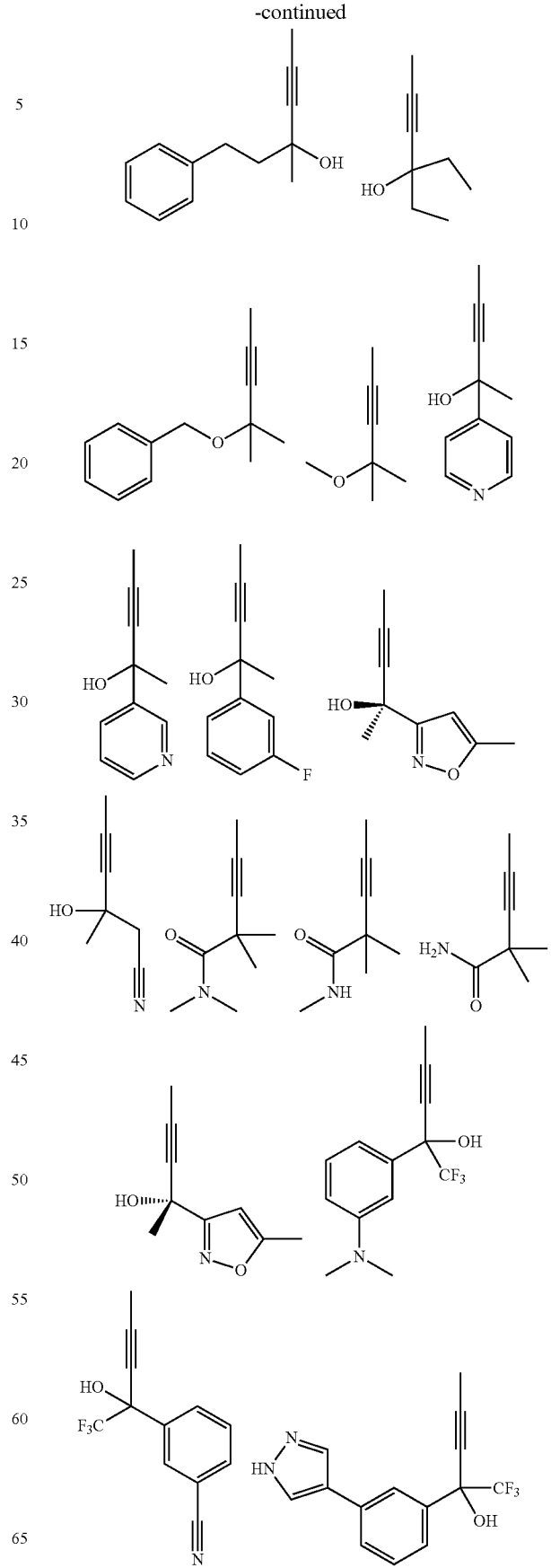

-continued
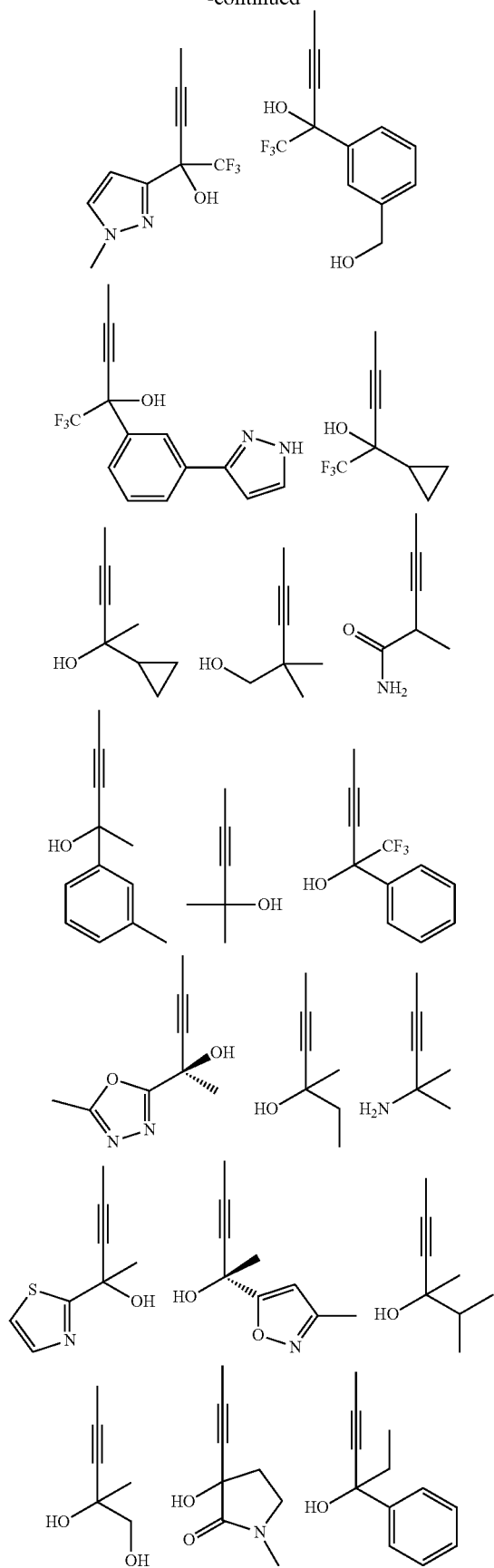
-continued
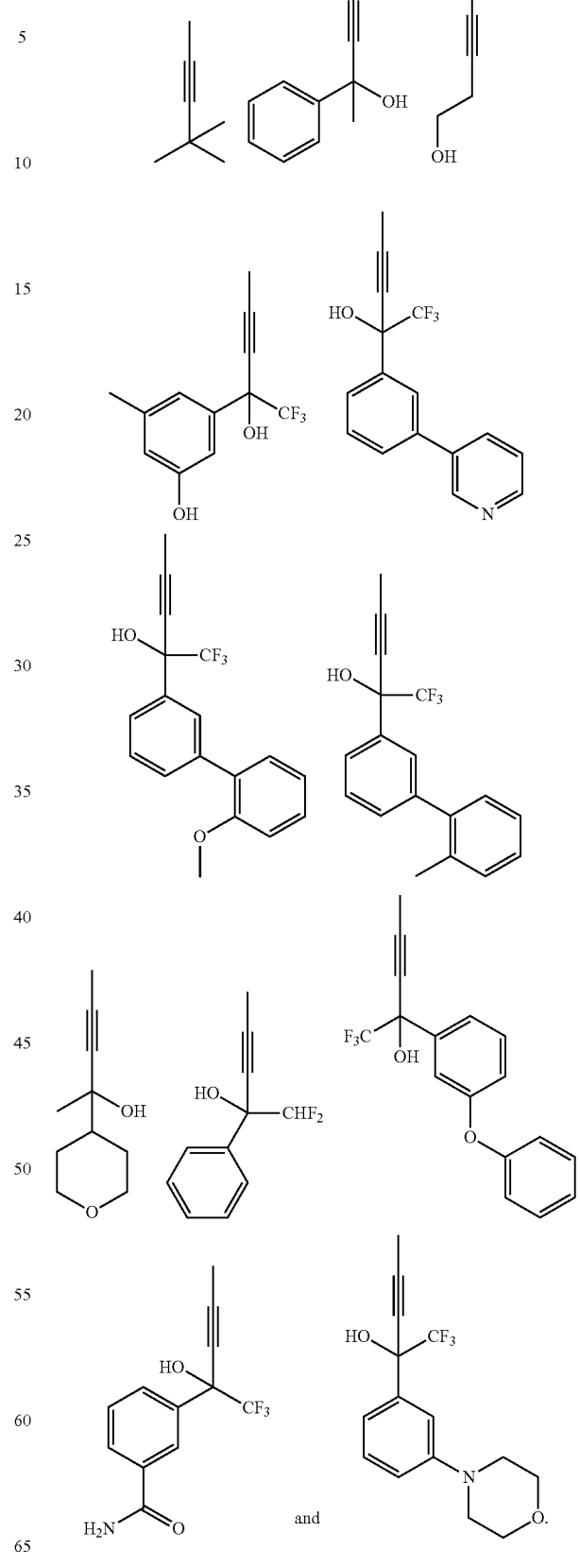
and

In one embodiment the group:

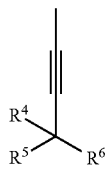

is selected from the group consisting of:

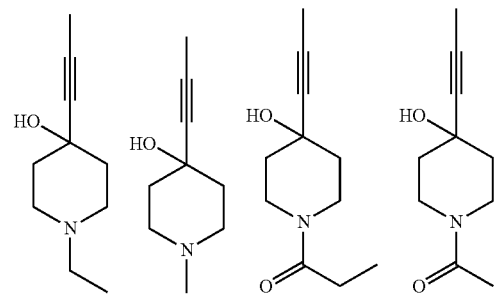

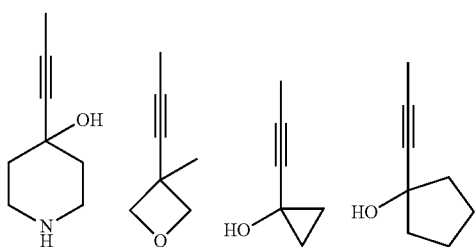

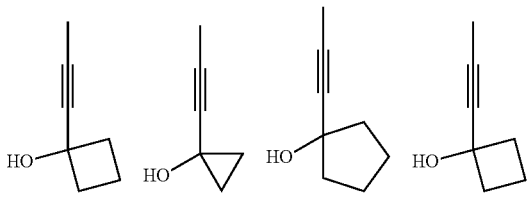

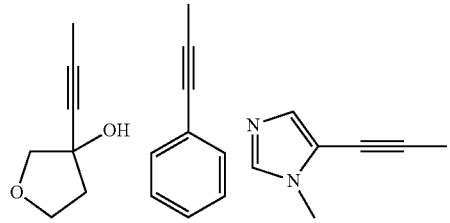

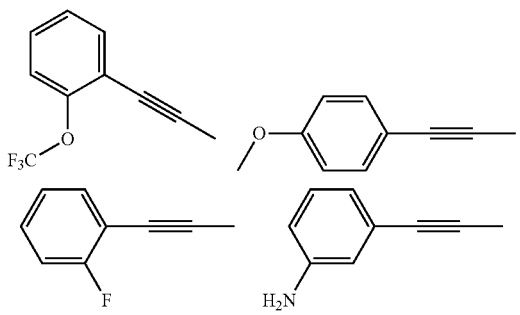

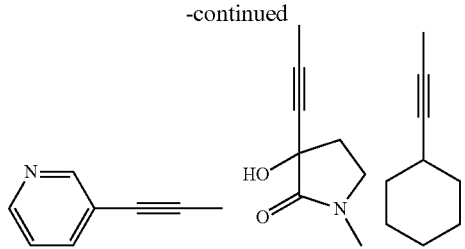

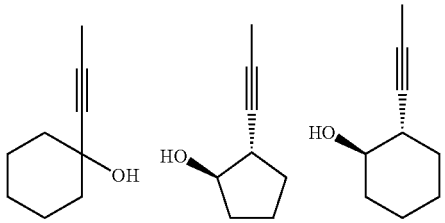

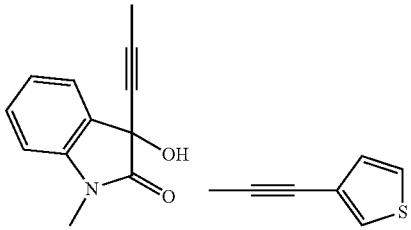

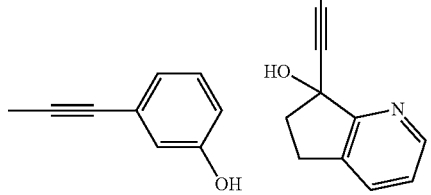

and

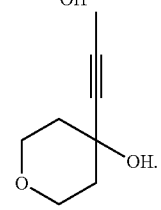

In one embodiment: $R^1$ is $C_{1-6}$alkyl that is optionally substituted with one or more groups independently selected from the group consisting of halo, cyano, $C_{1-3}$alkoxy, and $C_{3-8}$ carbocyclyl that is optionally substituted with one or more groups independently selected from halo;

$R^2$ is $C_{1-6}$alkyl that is optionally substituted with one or more groups independently selected from the group consisting of halo, cyano, $C_{1-3}$alkoxy, and $C_{3-8}$ carbocyclyl that is optionally substituted with one or more groups independently selected from halo; and $R^3$ is $C_{1-6}$alkyl that is optionally substituted with one or more groups independently selected from the group consisting of carbocyclyl, heterocyclyl, oxo, halo, —$NO_2$, —$N(R^b)_2$, —CN, —C(O)—$N(R^b)_2$, —S(O)—$N(R^b)_2$, —S(O)$_2$—$N(R^b)_2$, —O—$R^b$, —S—$R^b$, —O—C(O)—$R^b$, —C(O)—$R^b$, —C(O)—$OR^b$, —S(O)—$R^b$, —S(O)$_2$—$R^b$, —N($R^b$)—C(O)—$R^b$, —N($R^b$)—S(O)—$R^b$, —N($R^b$)—C(O)—$N(R^b)_2$, and —N($R^b$)—S(O)$_2$—$R^b$, wherein any carbocyclyl, and heterocyclyl is optionally substituted with one or more groups independently selected from the group consisting of $R^f$, oxo, halo, —$NO_2$, —$N(R^b)_2$, —CN, —C(O)—$N(R^b)_2$, —S(O)—$N(R^b)_2$, —S(O)$_2$—$N(R^b)_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$.

In one embodiment: R$^1$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo;

R$^2$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo; and R$^3$ is —N(R$^b$)$_2$.

In one embodiment: R$^1$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo;

R$^2$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo; and R$^3$ is —C(=O)OR$^a$.

In one embodiment: R$^1$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo;

R$^2$ is C$_{1-6}$alkyl that is optionally substituted with one or more groups independently selected from the group consisting of halo, cyano, C$_{1-3}$alkoxy, and C$_{3-8}$ carbocyclyl that is optionally substituted with one or more groups independently selected from halo; and R$^3$ is a 5-6 membered heteroaryl ring that is optionally substituted with one or more groups independently selected from the group consisting of C$_{1-6}$alkyl, C$_{2-6}$alkenyl, C$_{2-6}$alkynyl, carbocyclyl, heterocyclyl, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$, wherein any C$_{1-6}$alkyl, C$_{2-6}$alkenyl, C$_{2-6}$alkynyl, carbocyclyl, and heterocyclyl is optionally substituted with one or more groups independently selected from the group consisting of R$^f$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$.

In one embodiment the group:

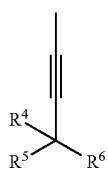

is selected from the group consisting of:

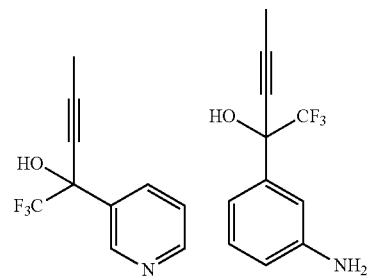

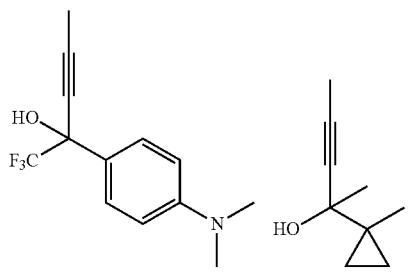

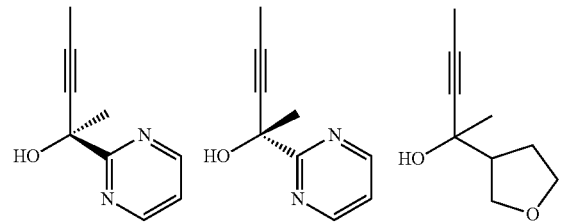

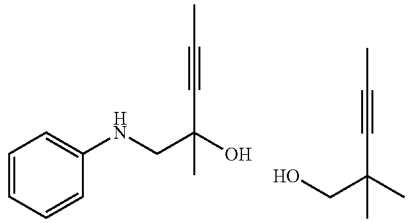

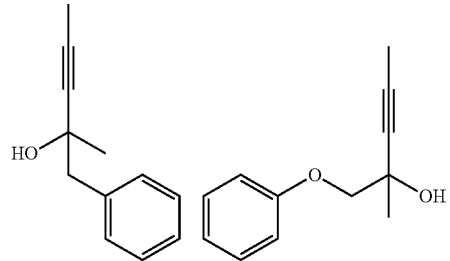

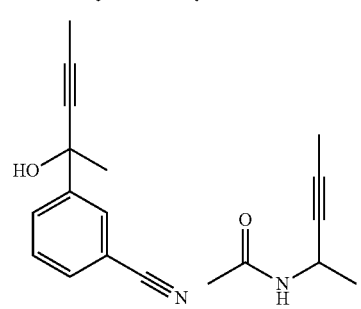

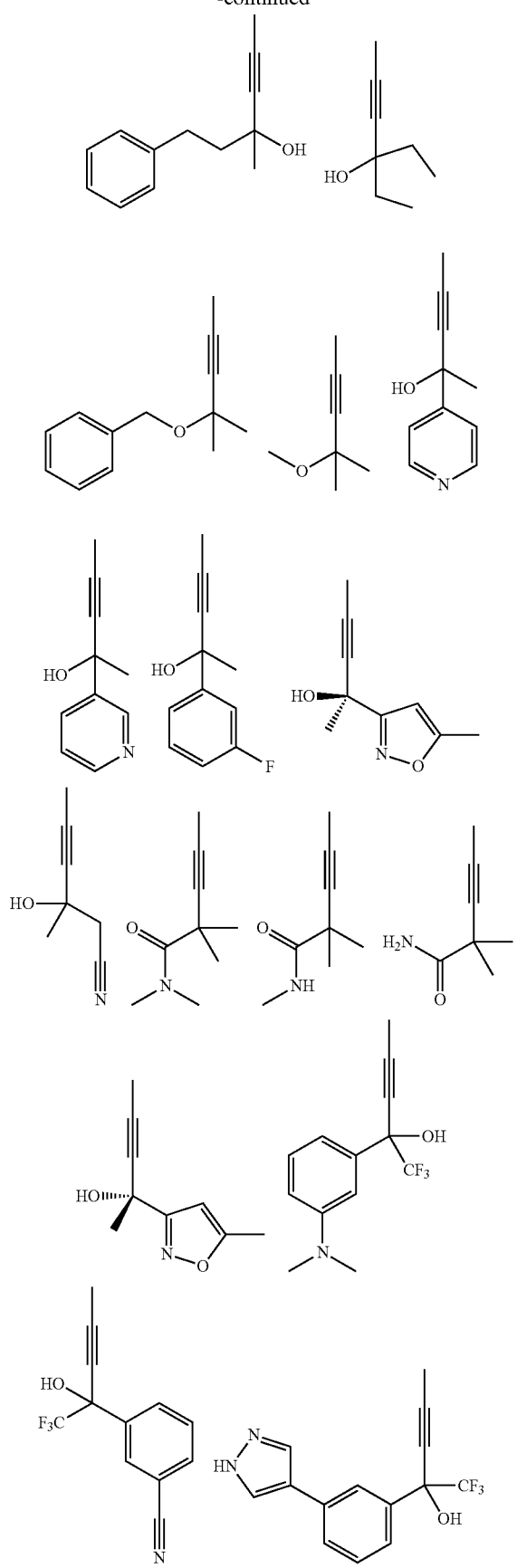
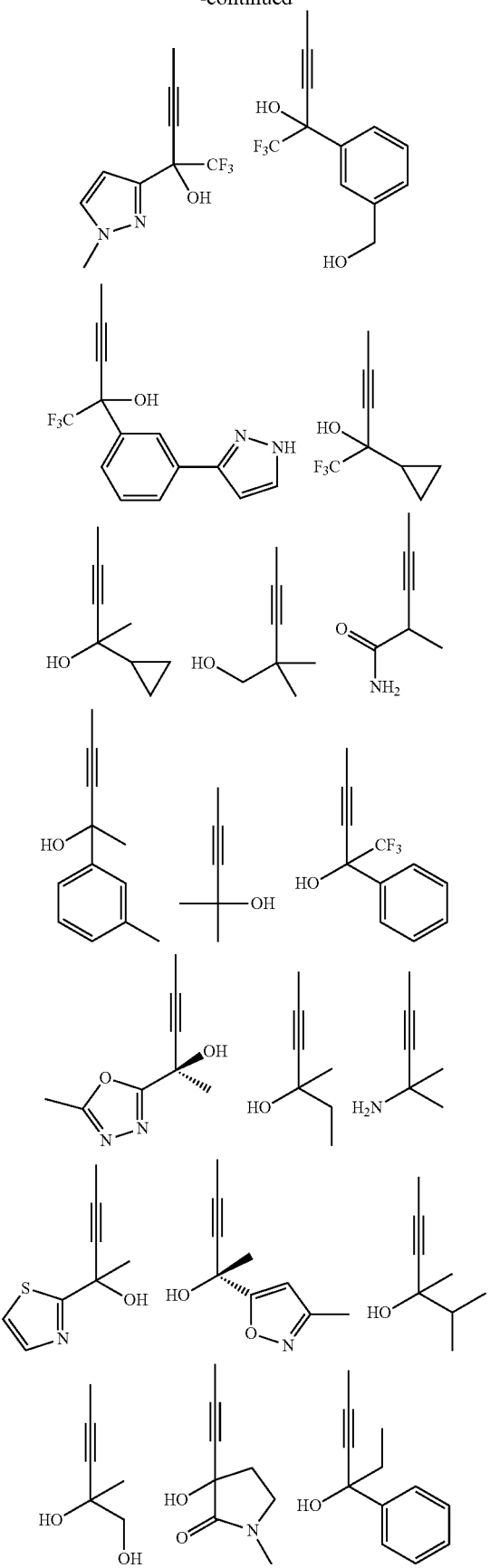

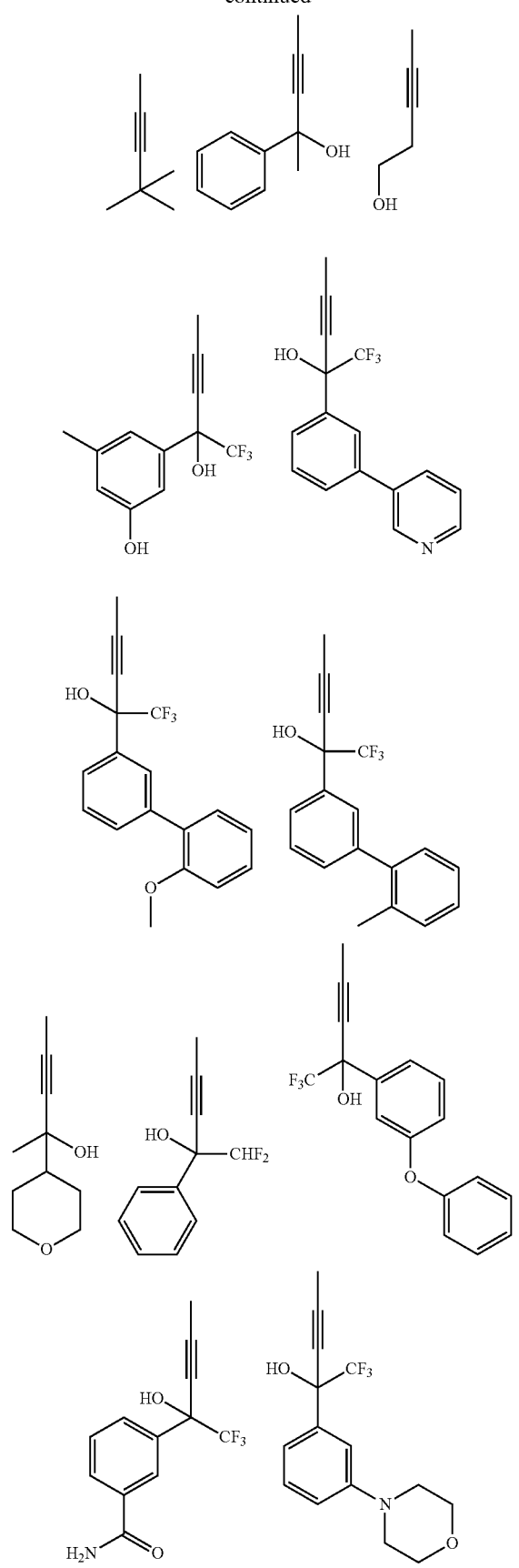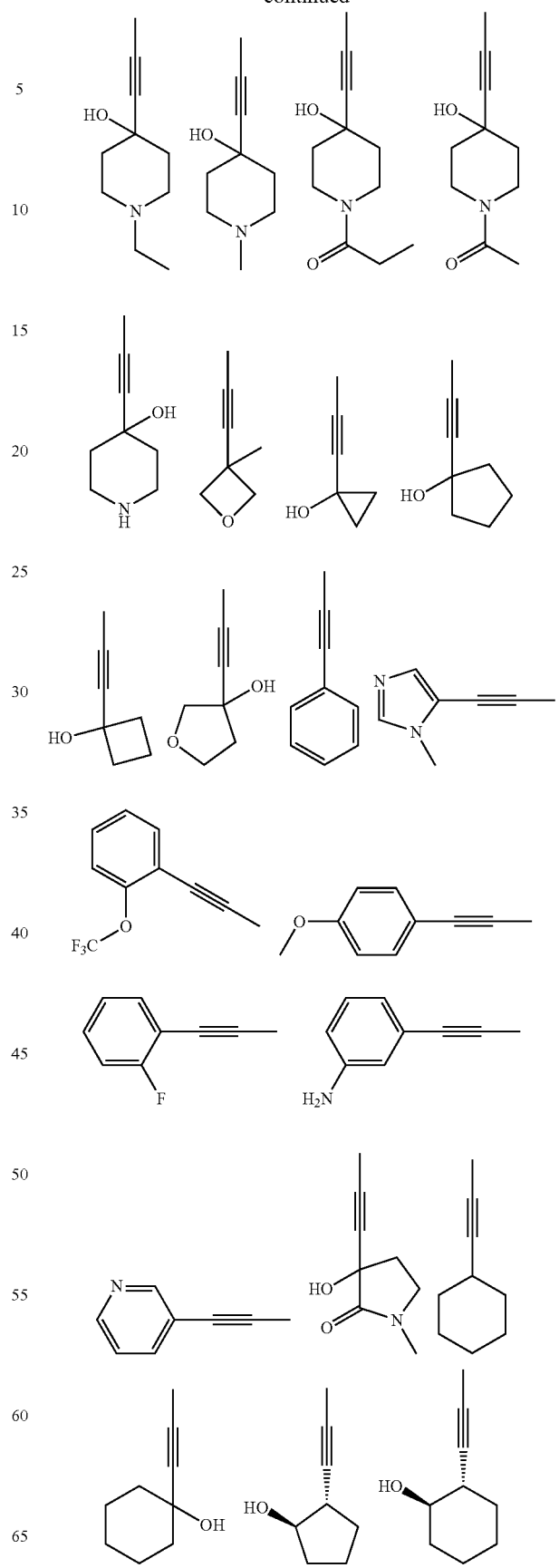

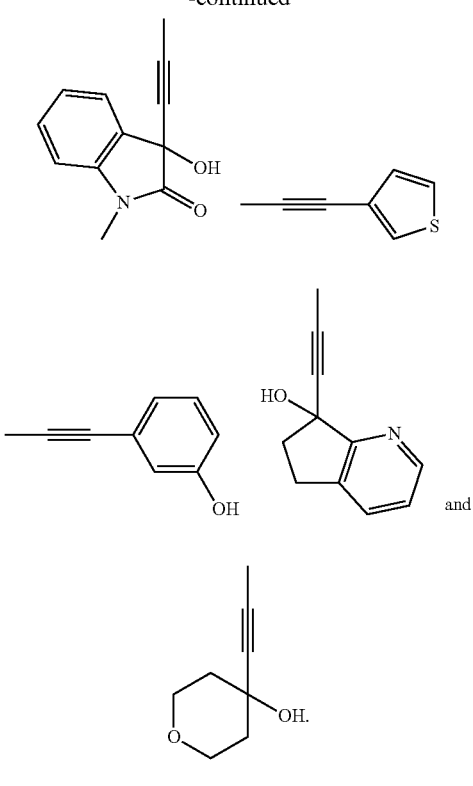
In one embodiment the compound is selected from the group consisting of:
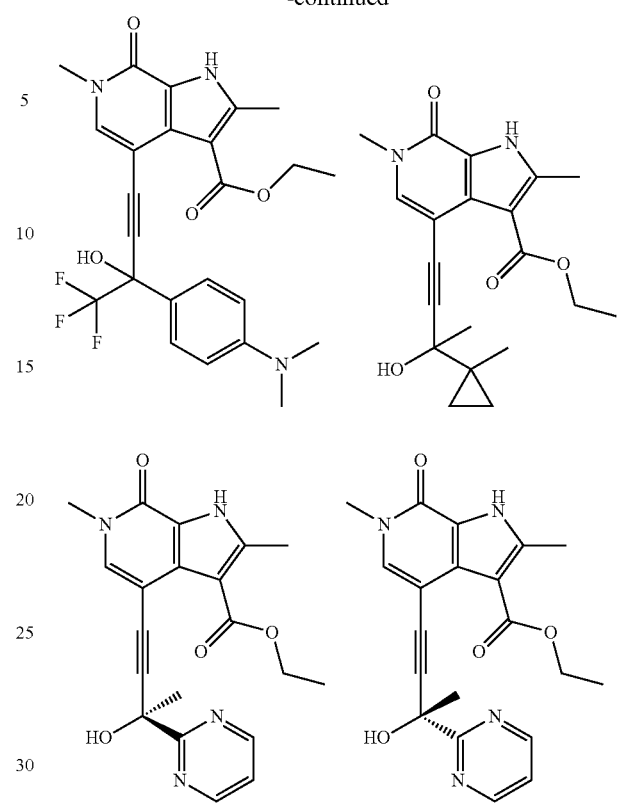
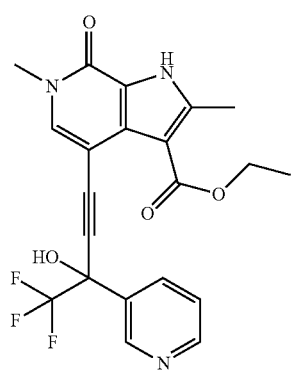
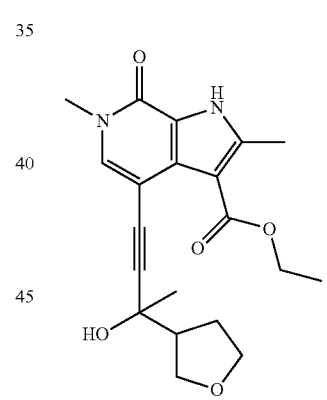
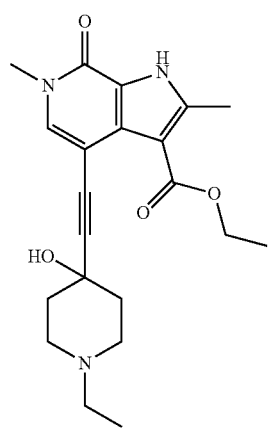
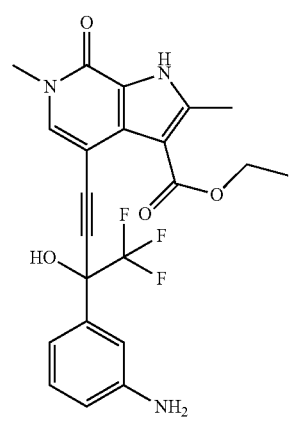
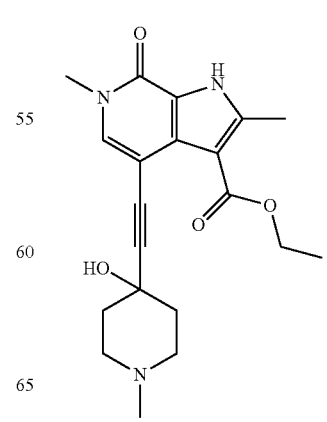
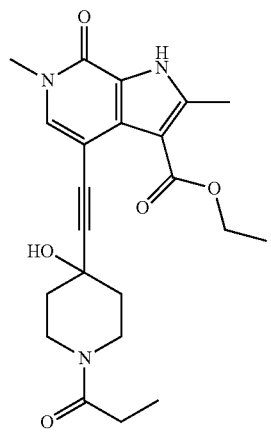

31
-continued
32
-continued
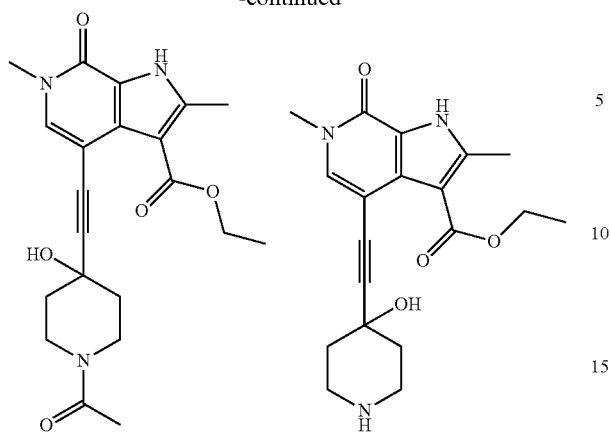
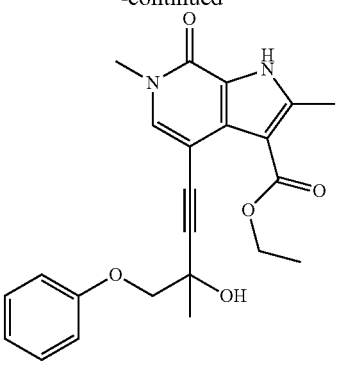
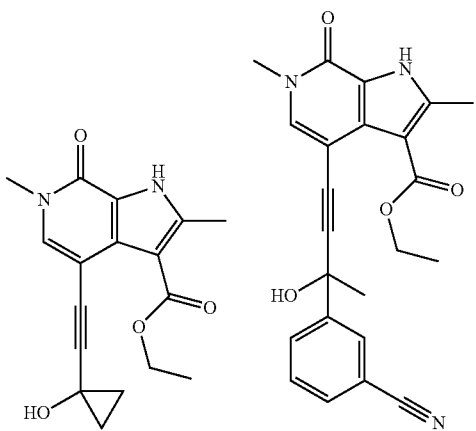
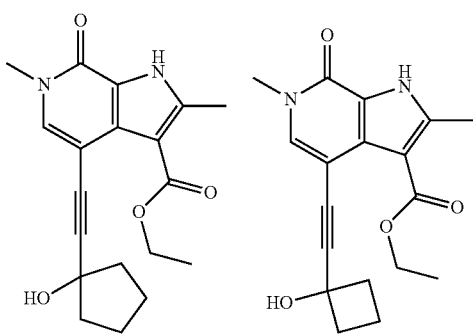
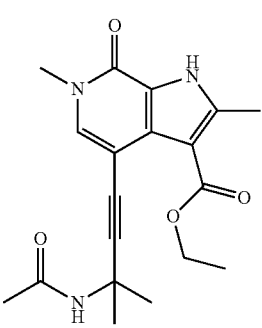

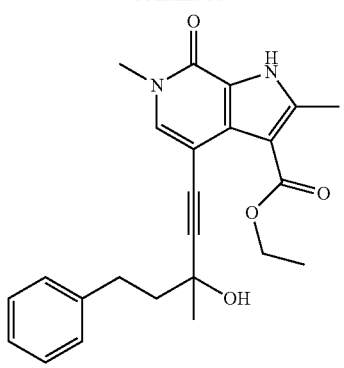
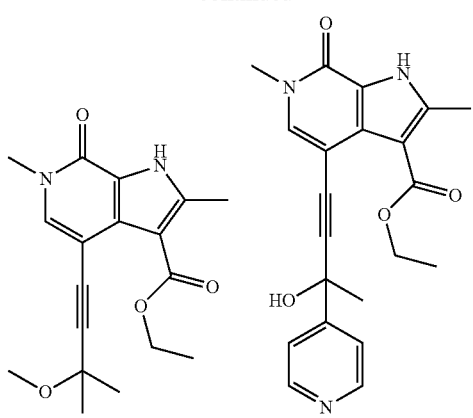
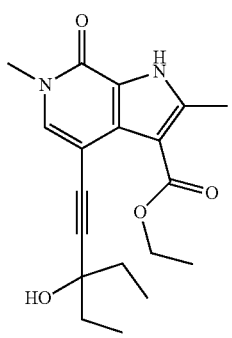
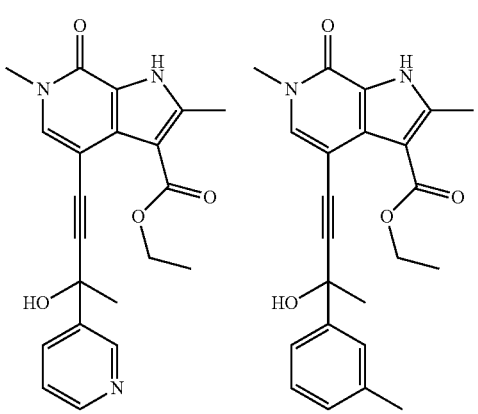
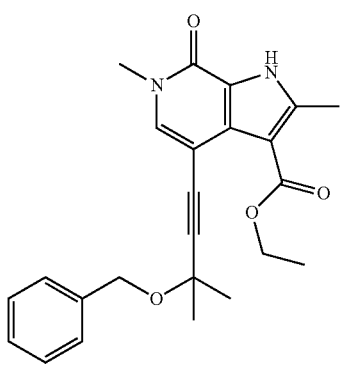
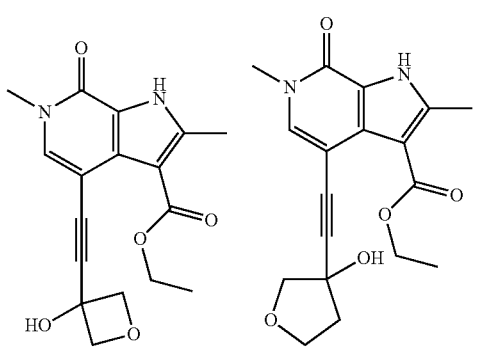
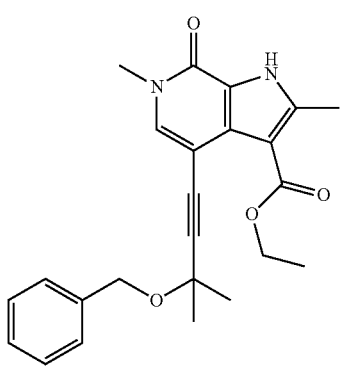
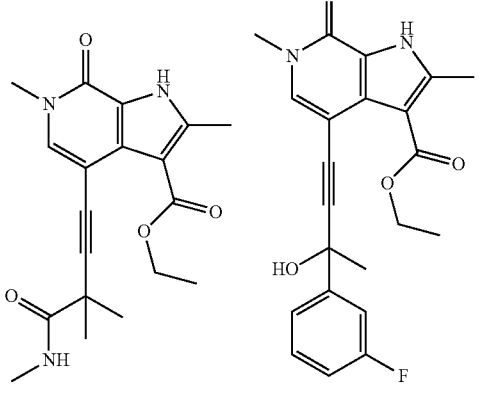

35
-continued
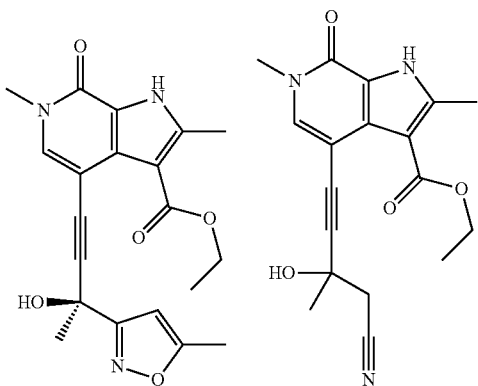
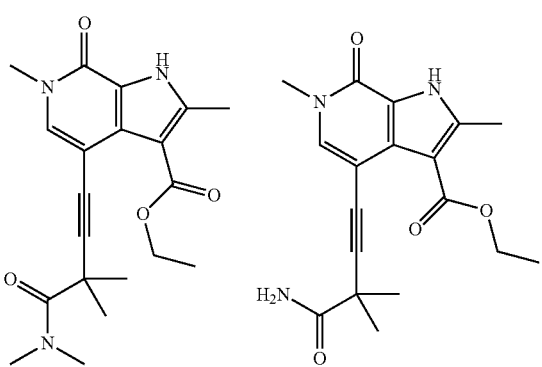
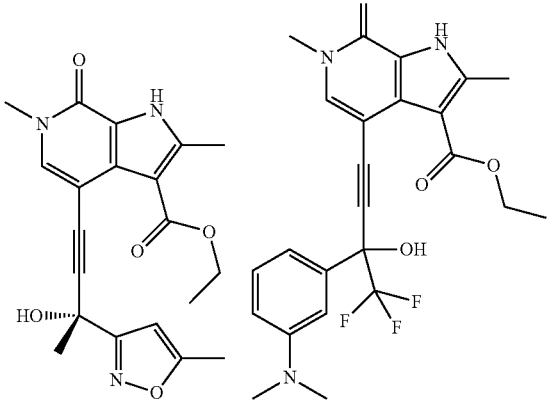
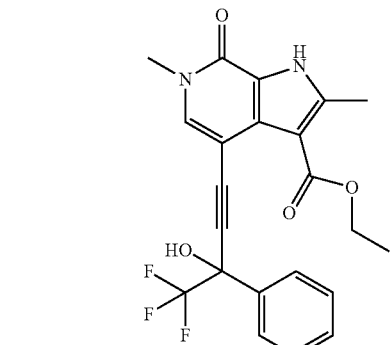
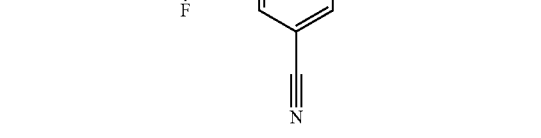
36
-continued
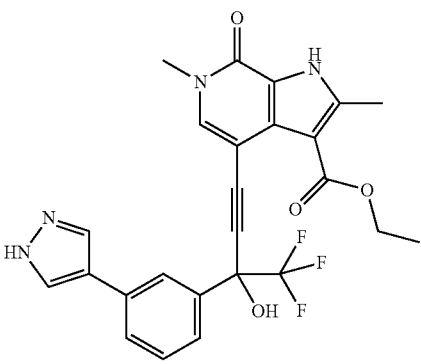
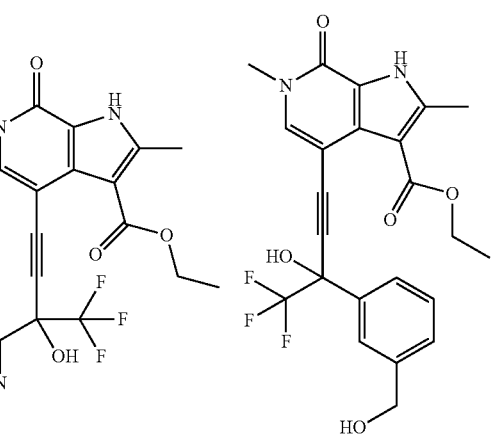
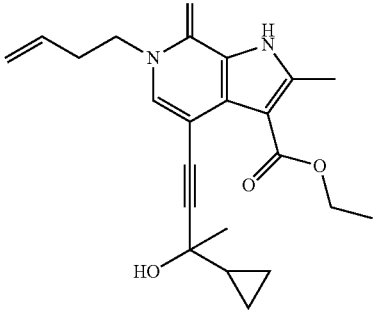

| 37 -continued | 38 -continued |
|---|---|
| 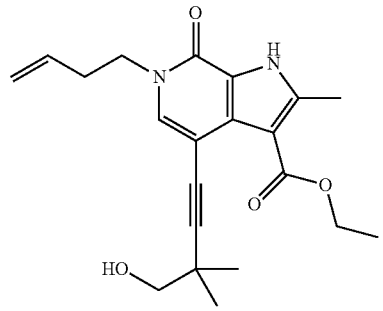 | 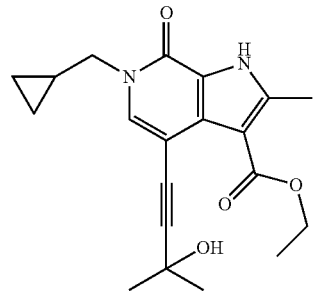 |
| 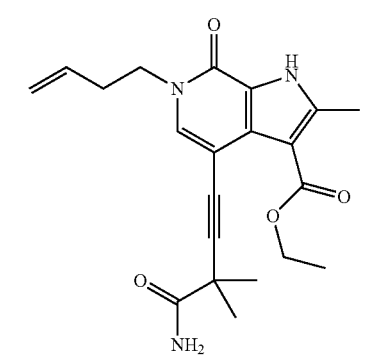 | 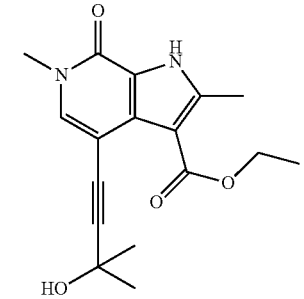 |
| 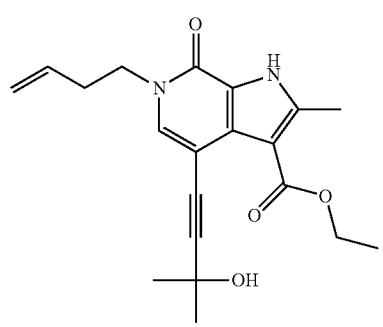 | 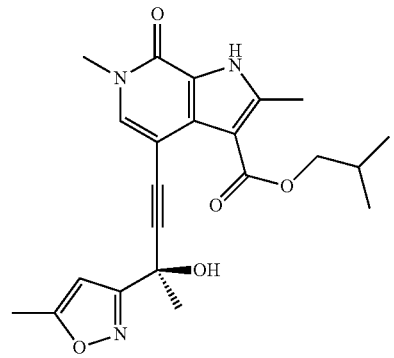 |
| 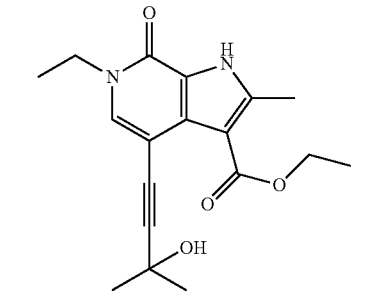 | 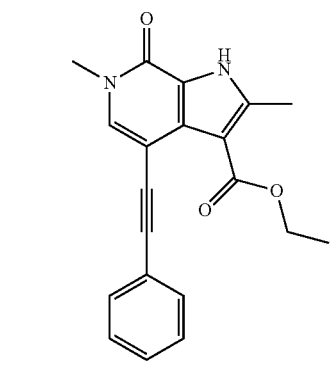 |
| 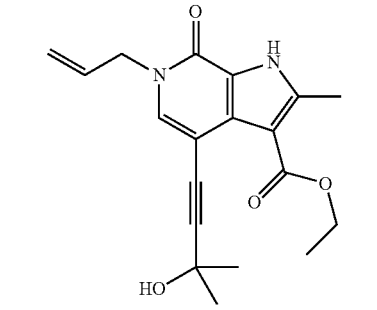 | 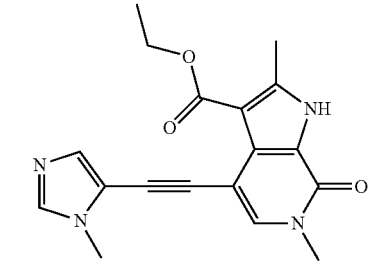 |

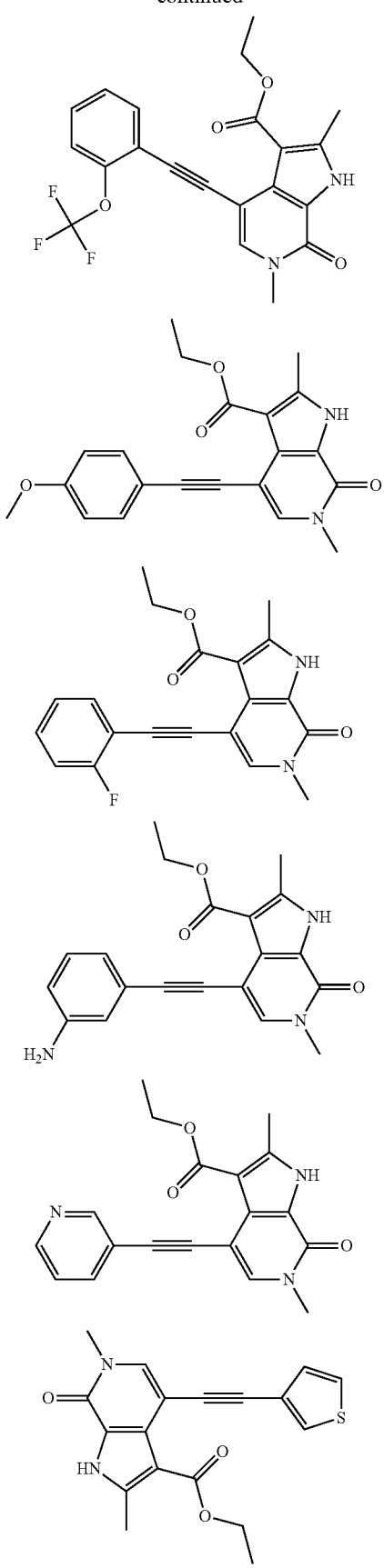
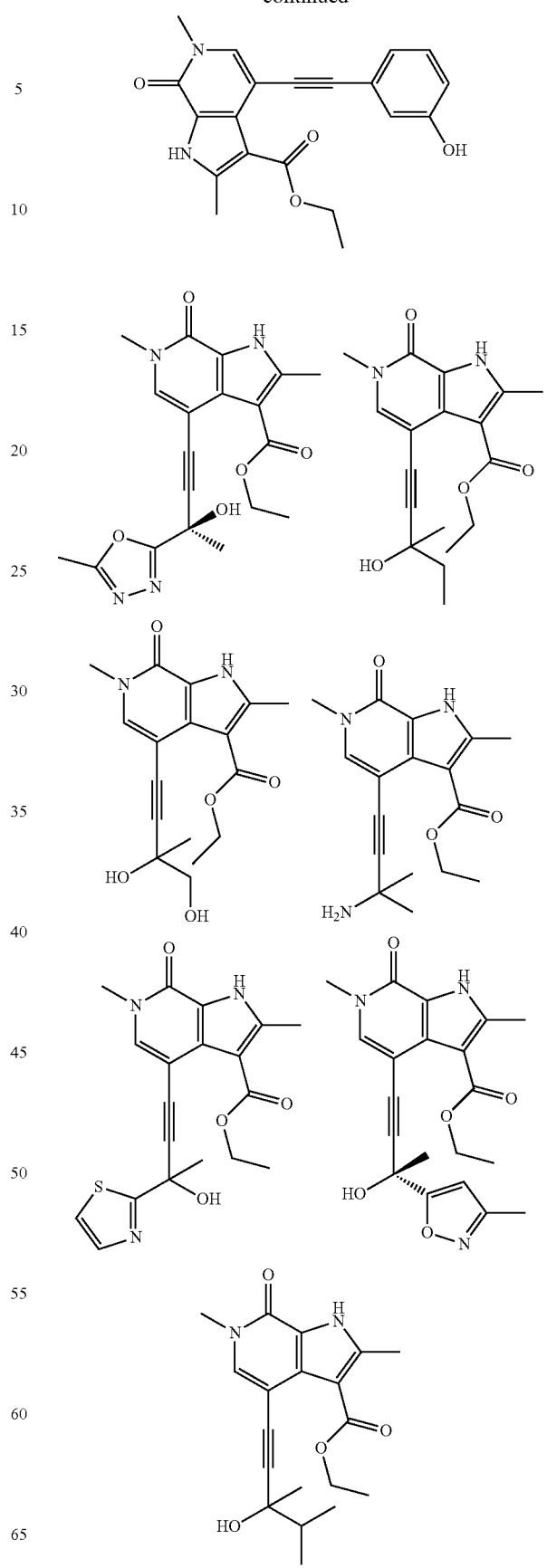

-continued
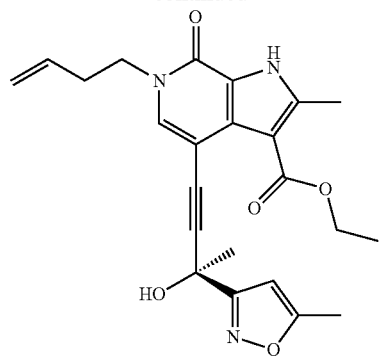
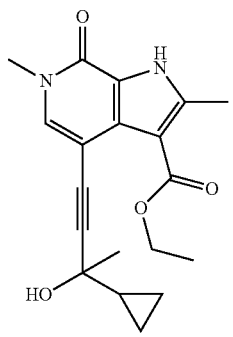
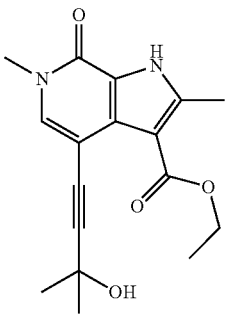
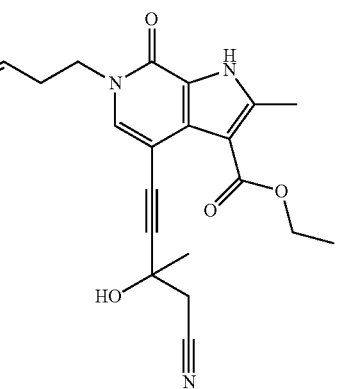
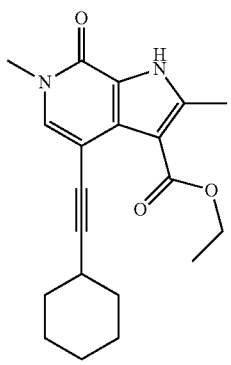
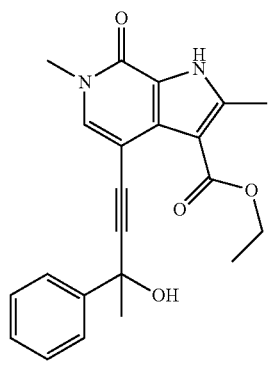
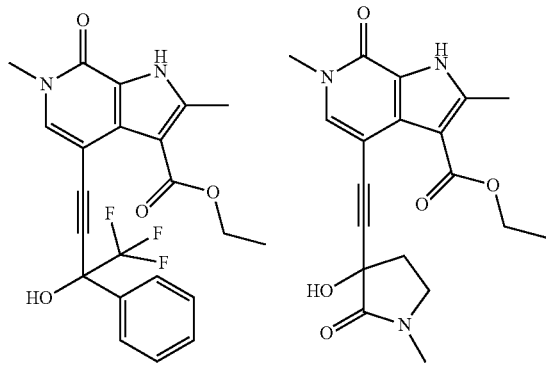
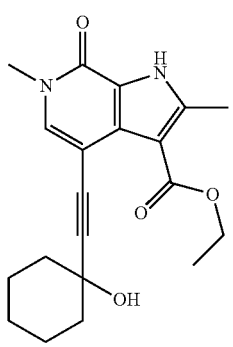
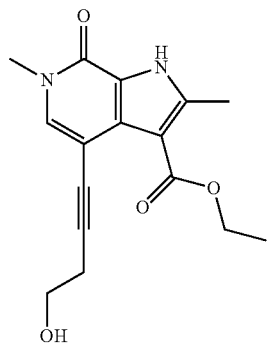
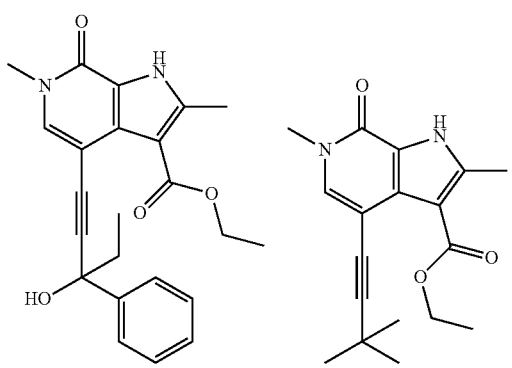
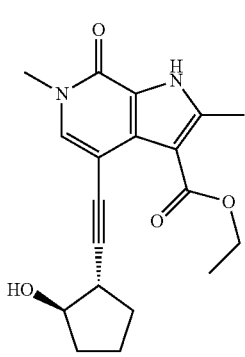
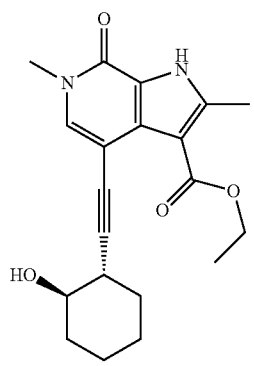

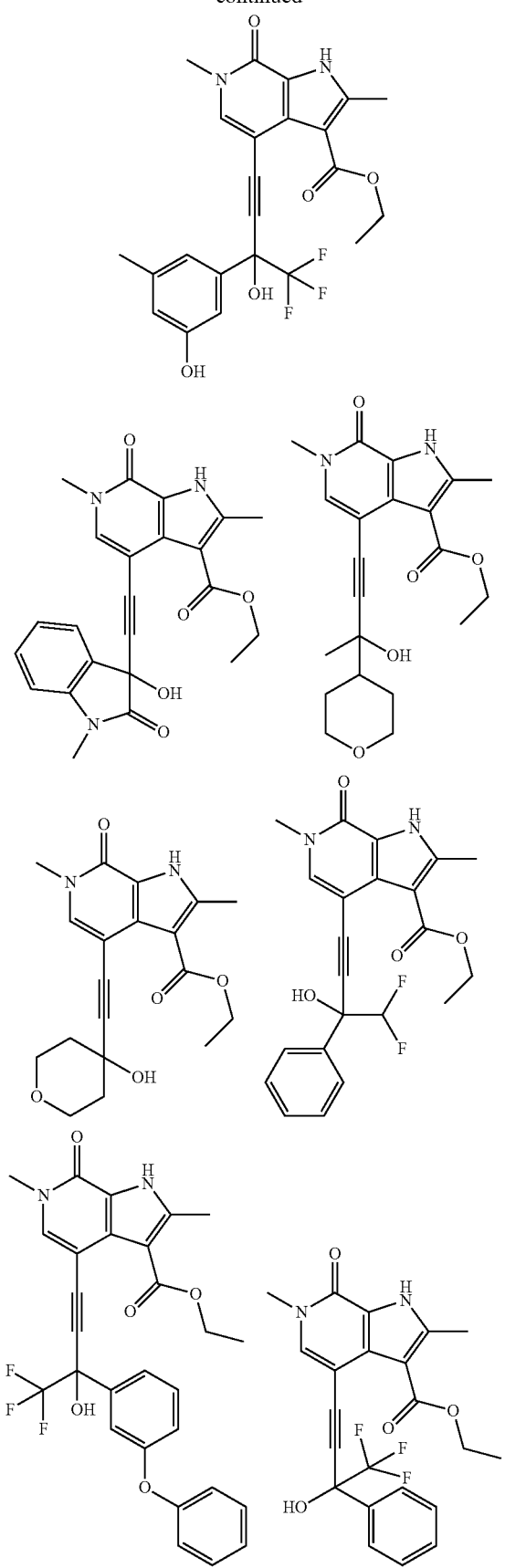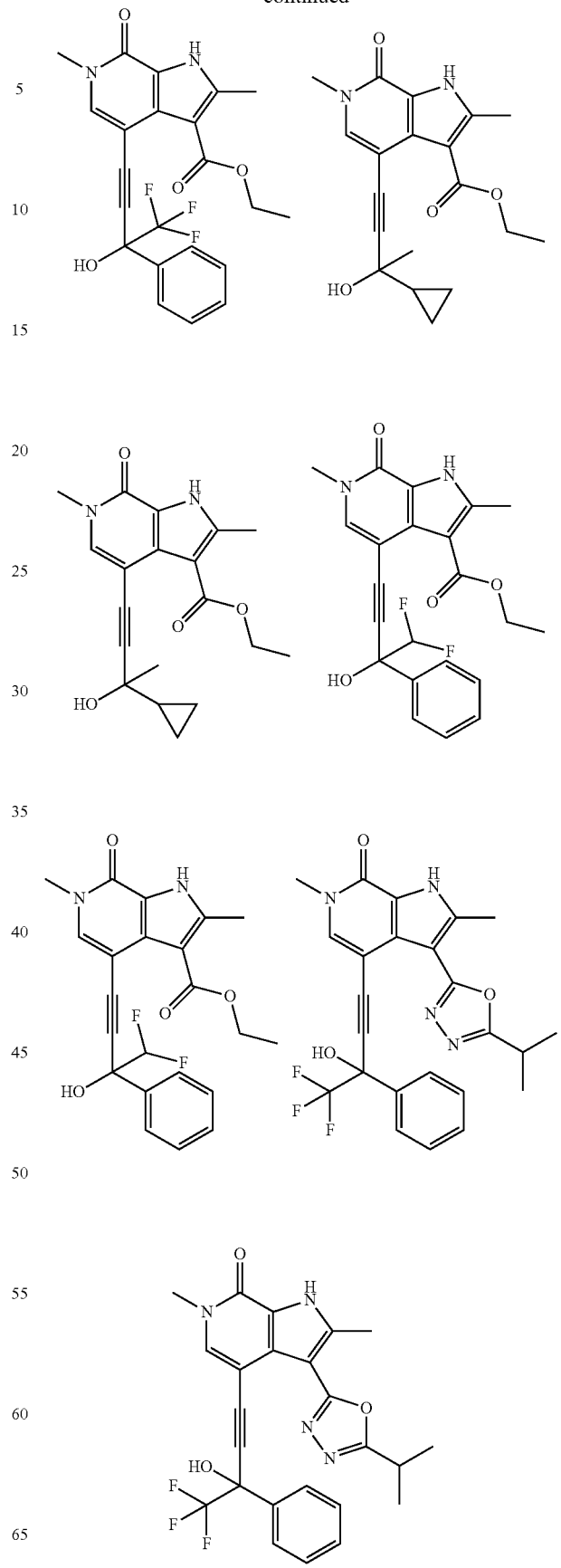

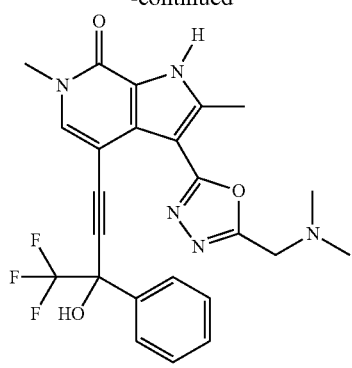
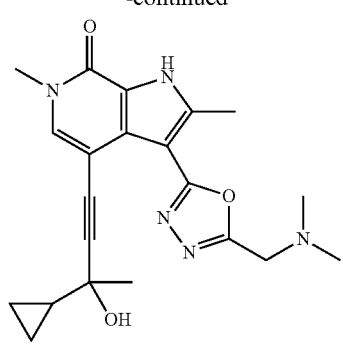
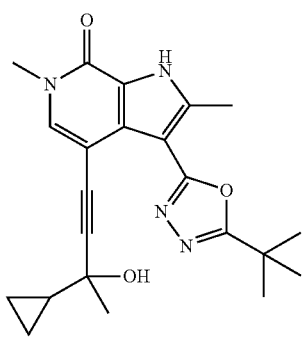
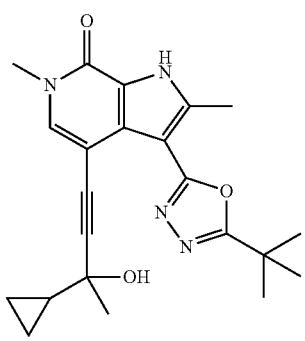
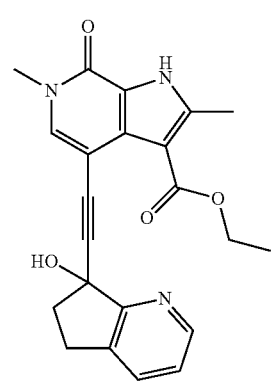

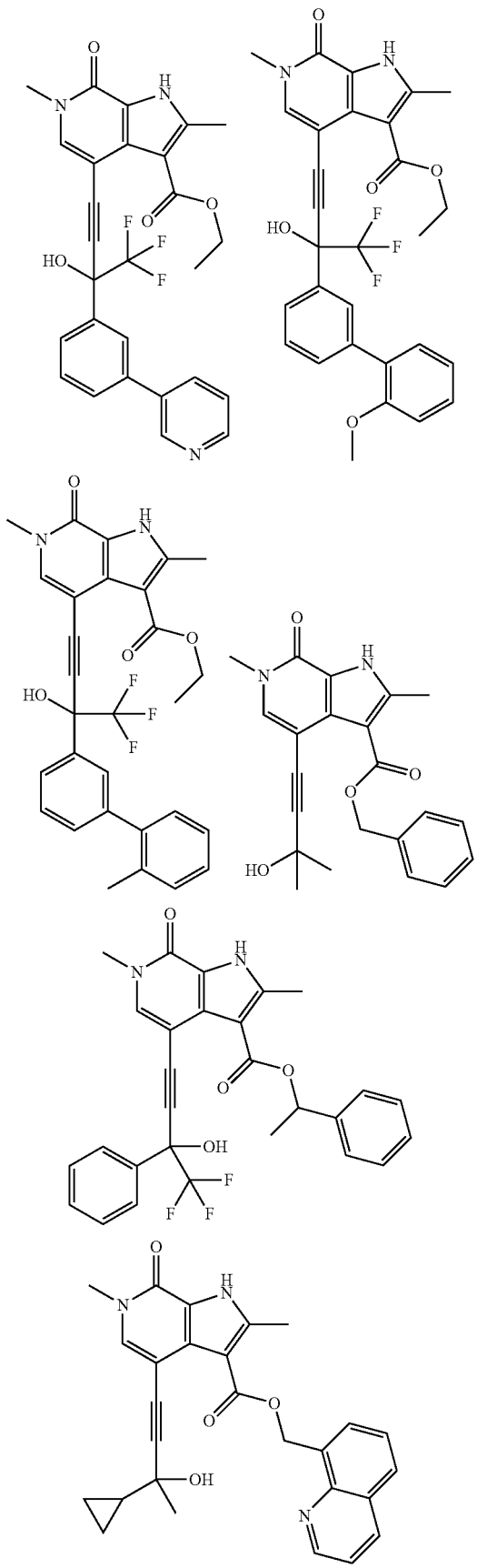
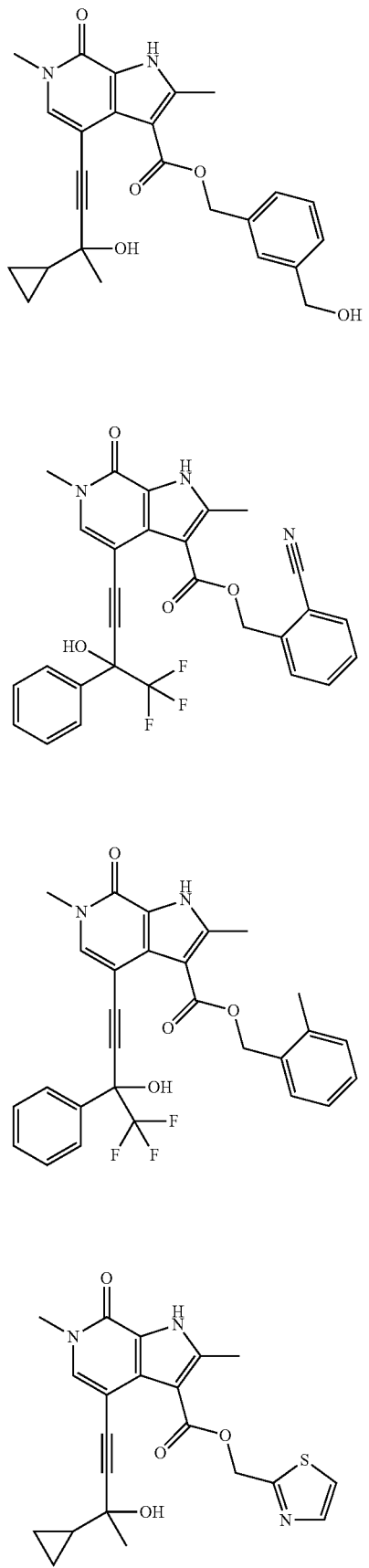

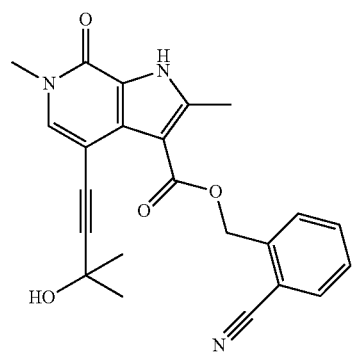
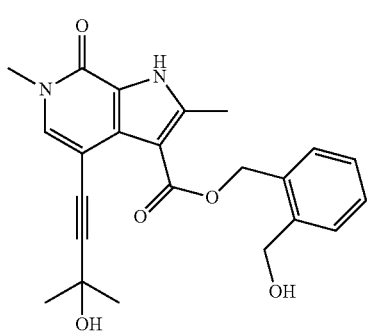
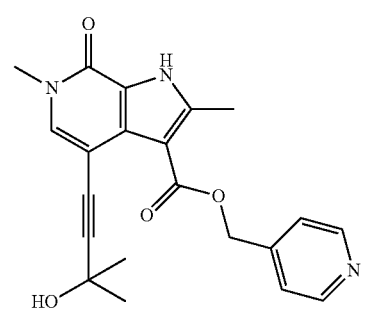
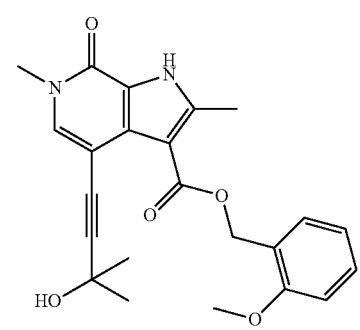
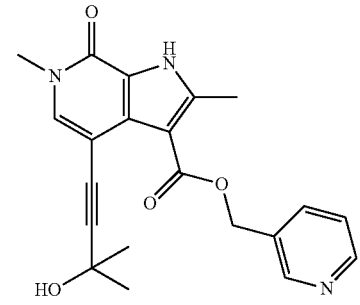
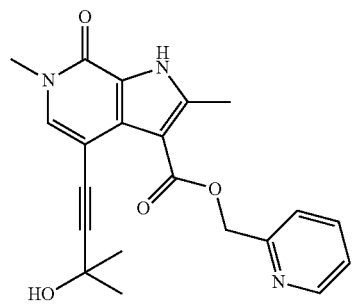
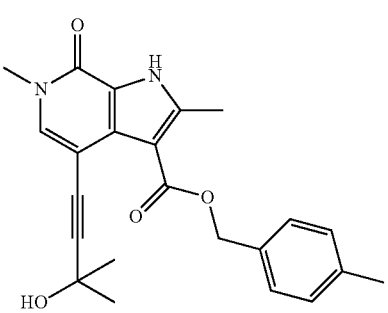
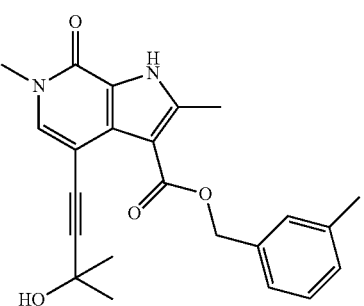
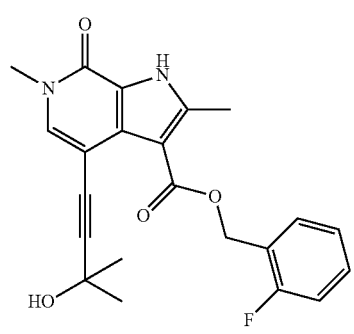

51
-continued
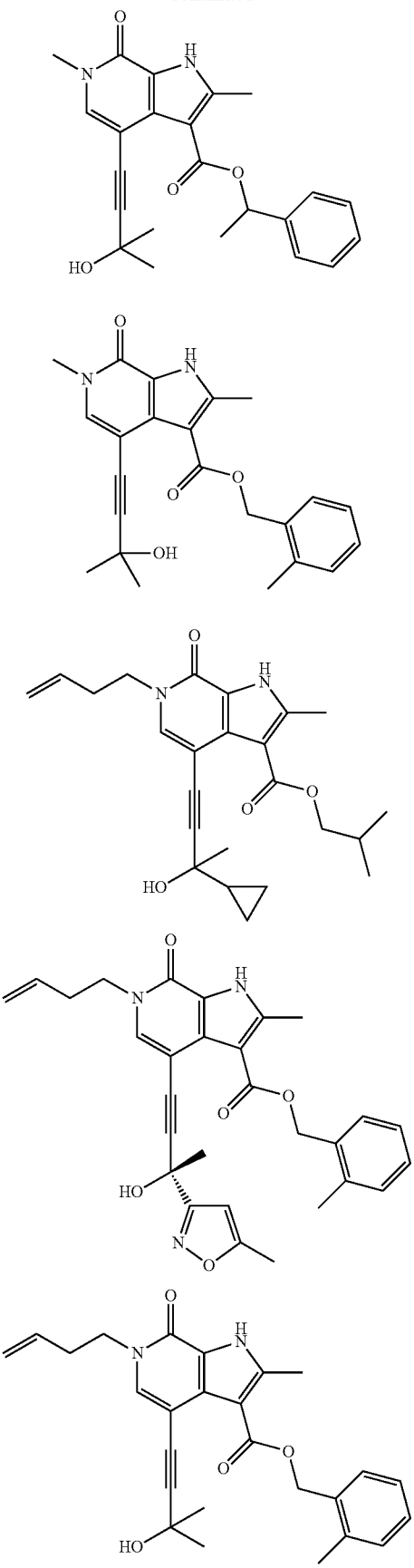
52
-continued
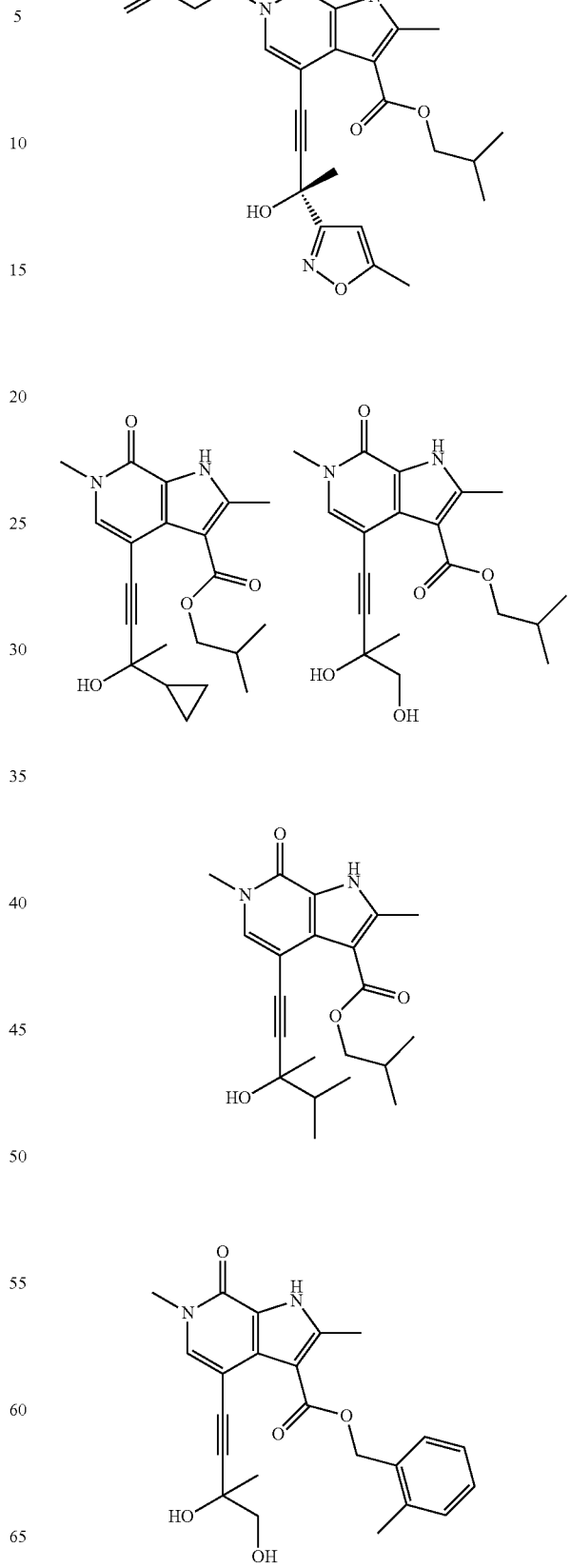

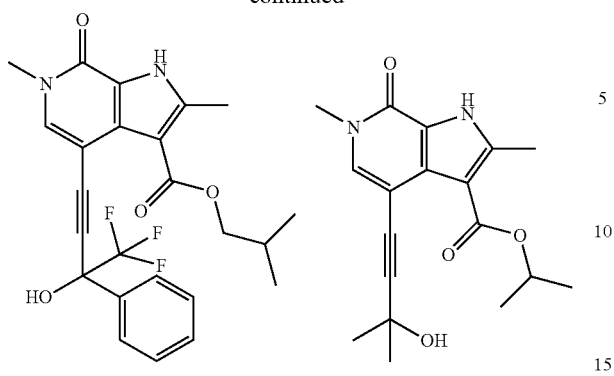
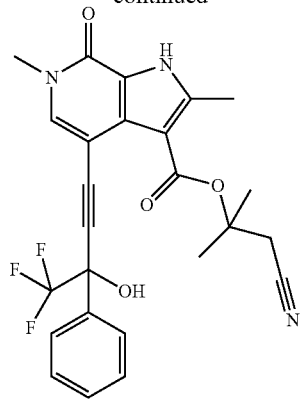
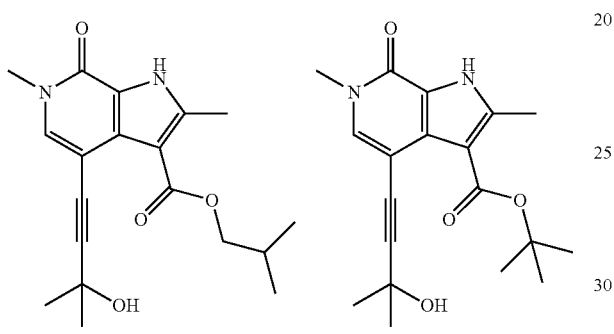
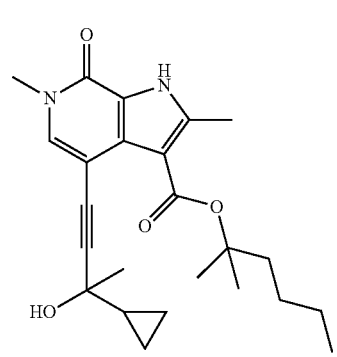
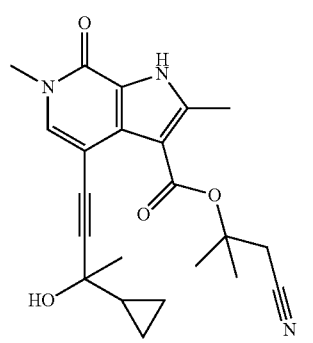
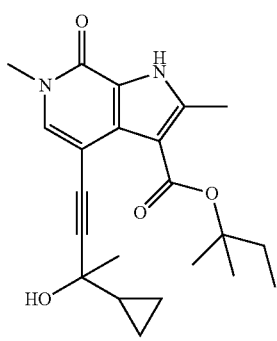
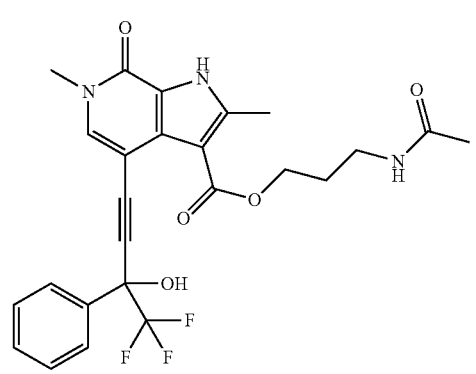
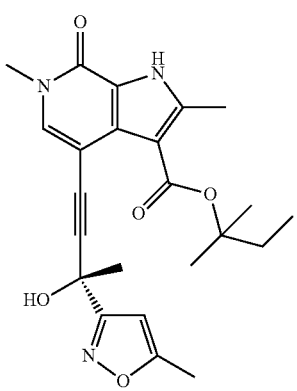

55
-continued
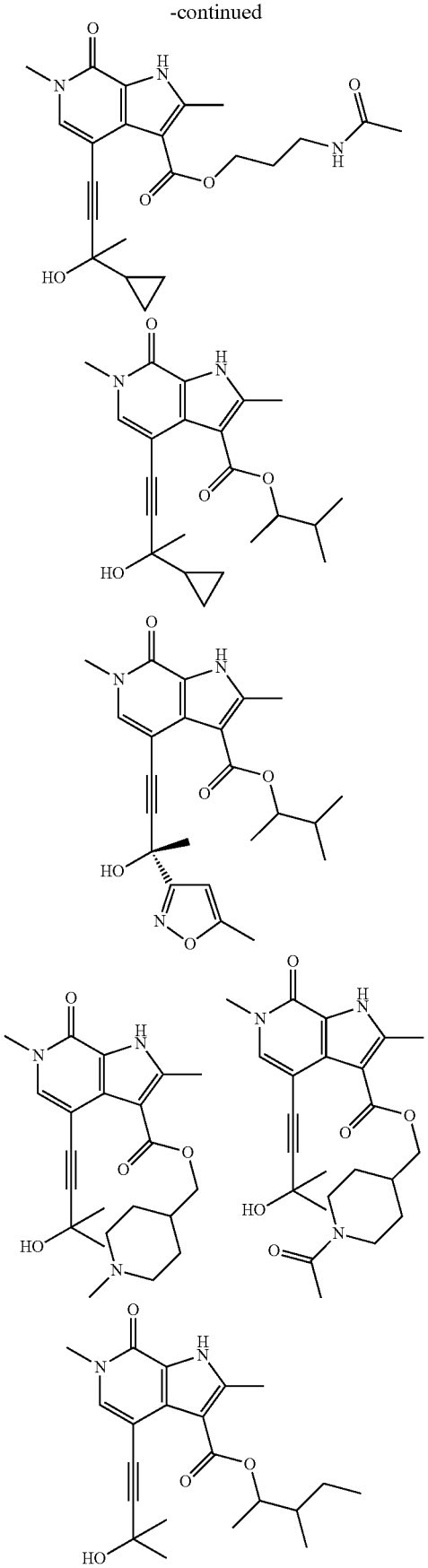
56
-continued
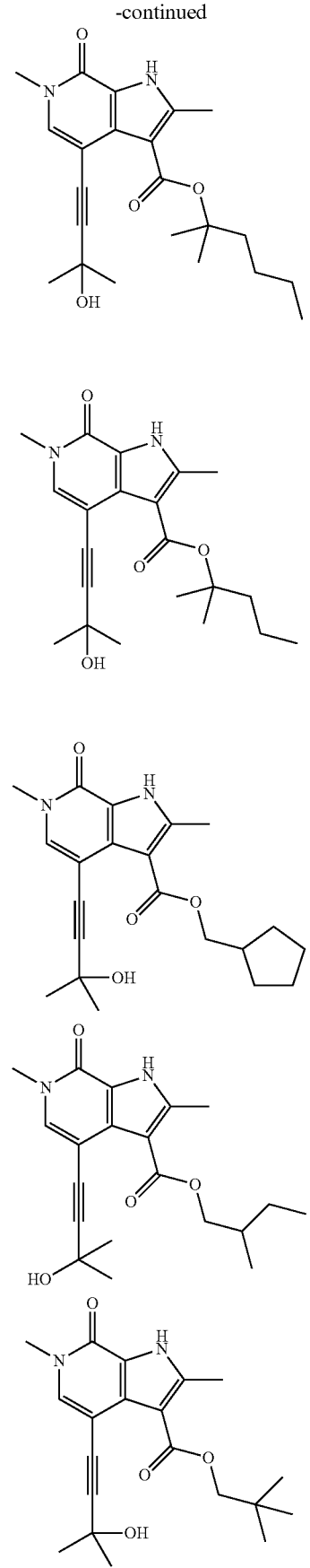

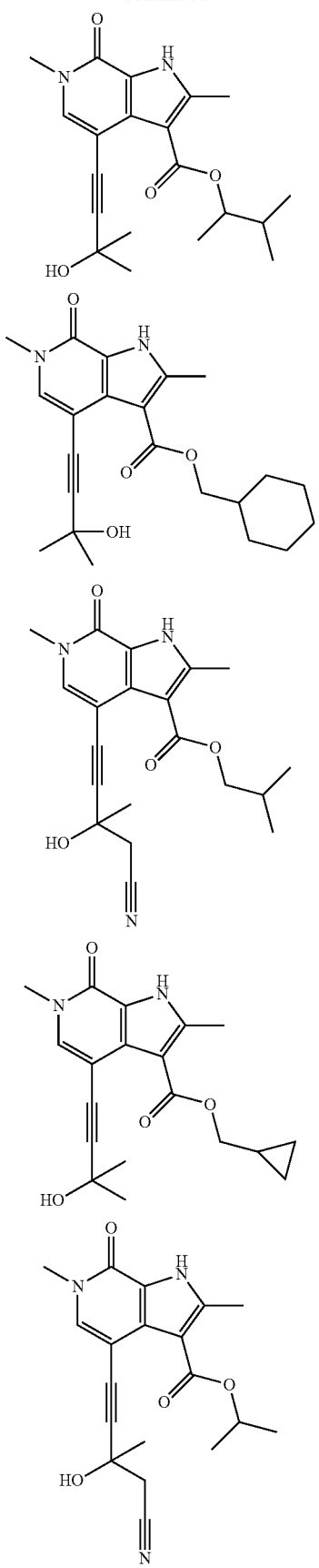
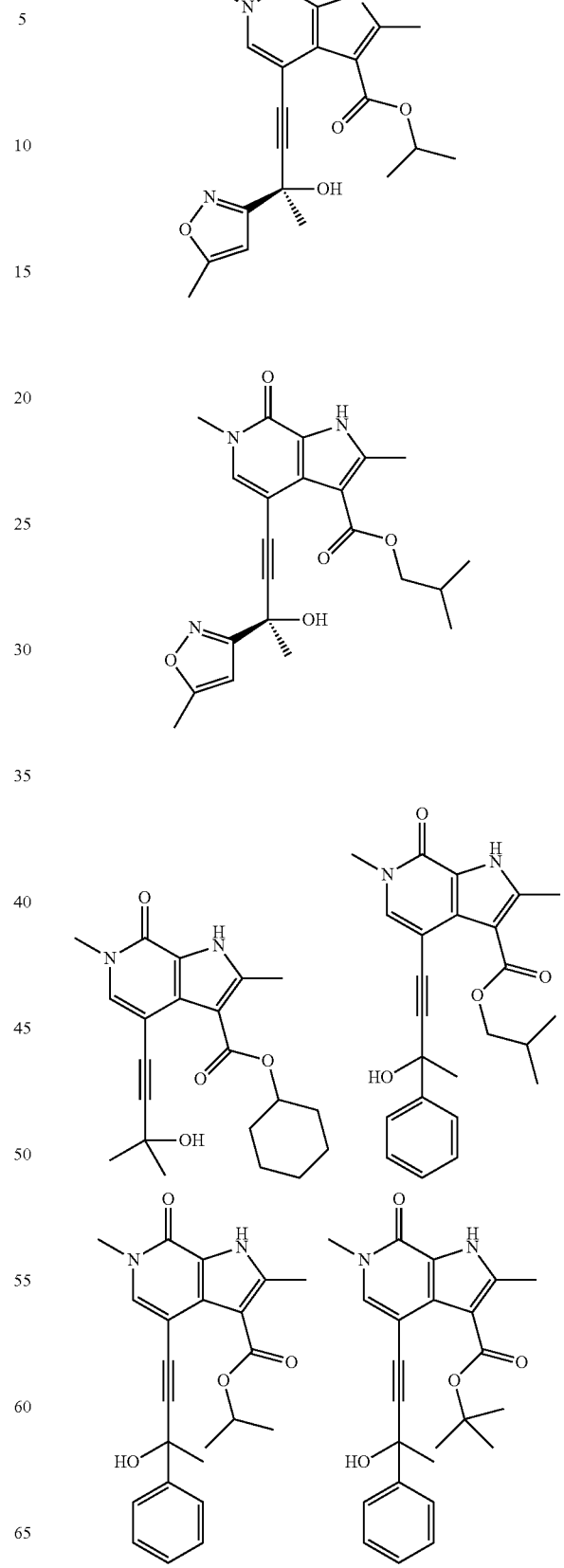

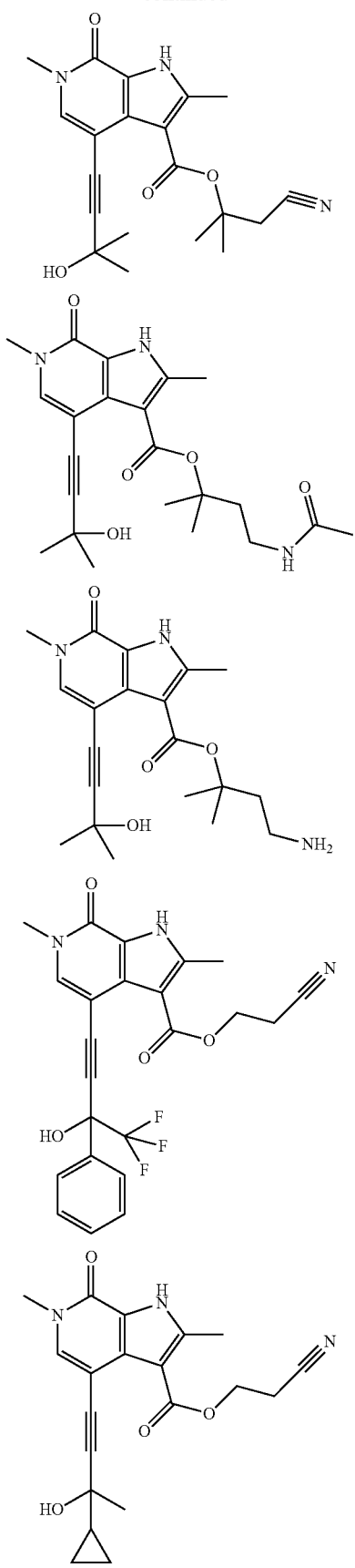
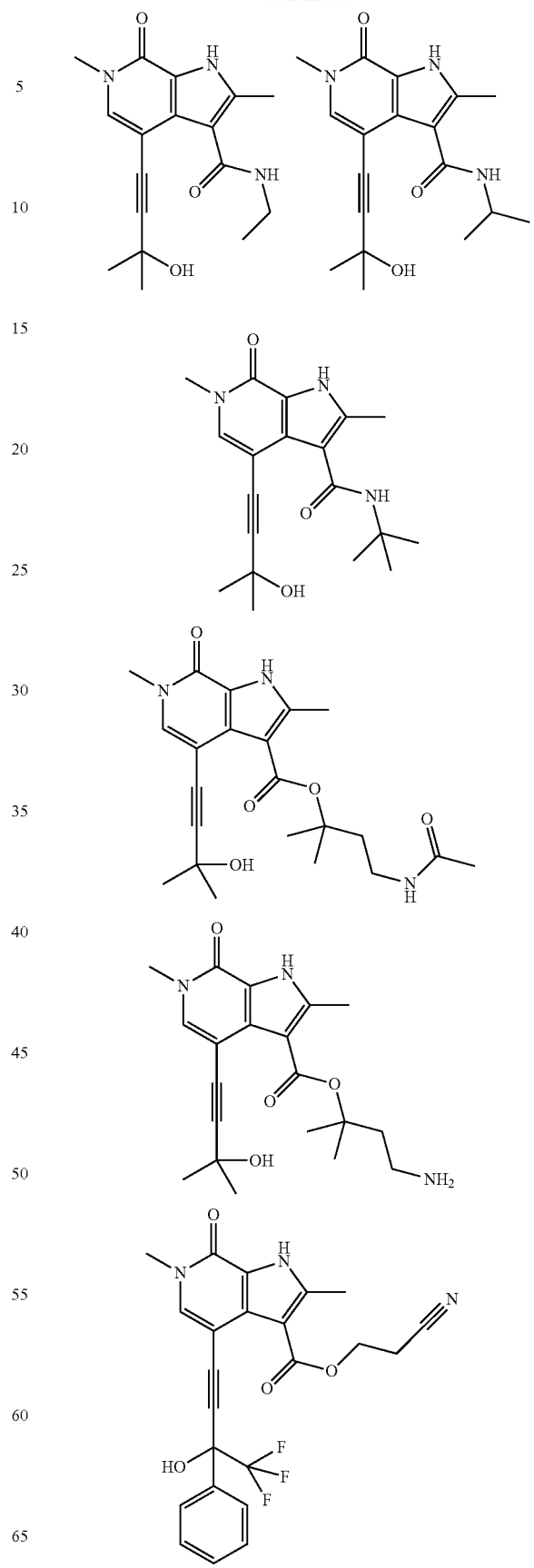

61
-continued
62
-continued
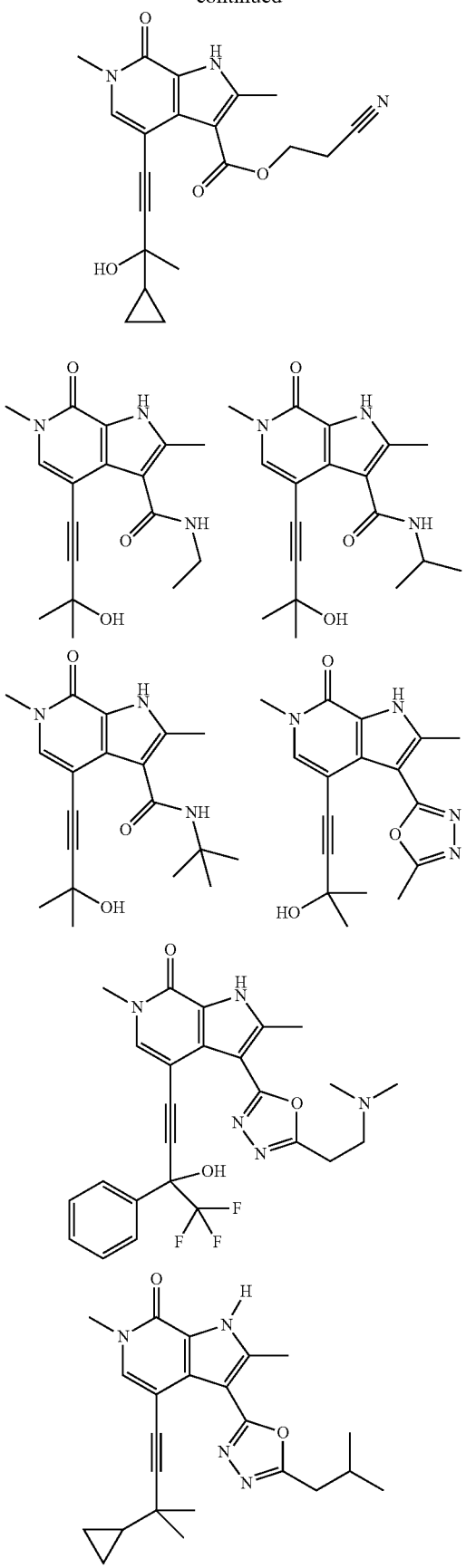
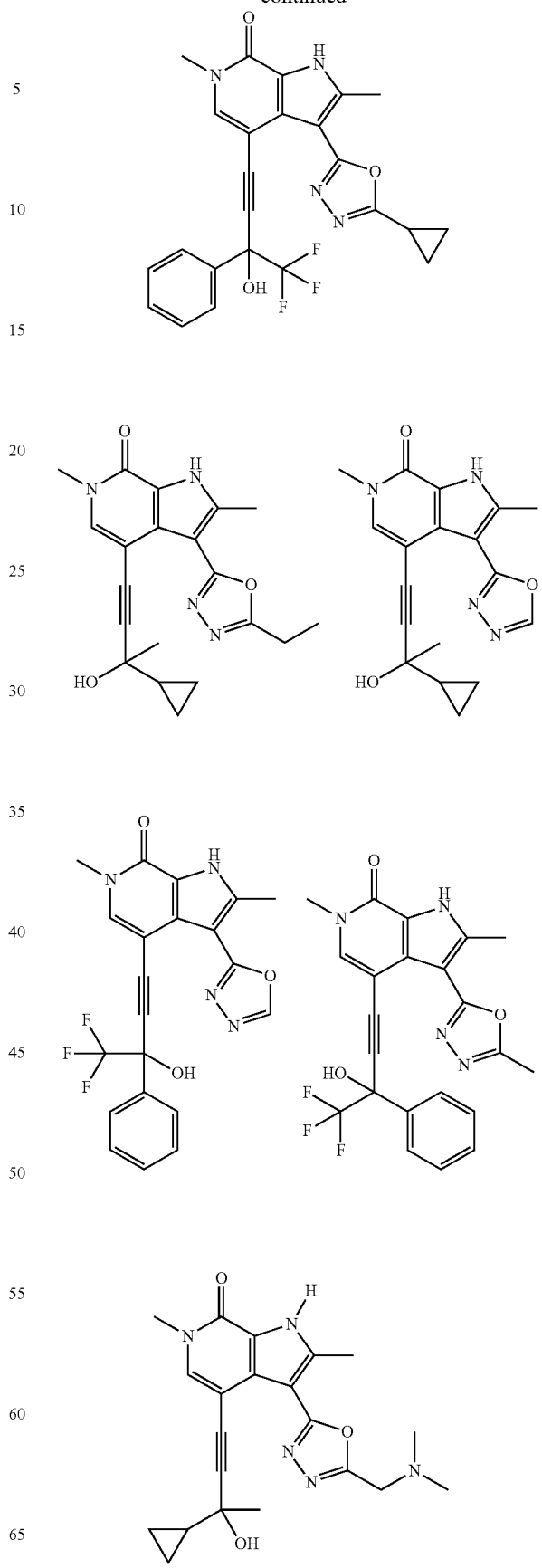

-continued
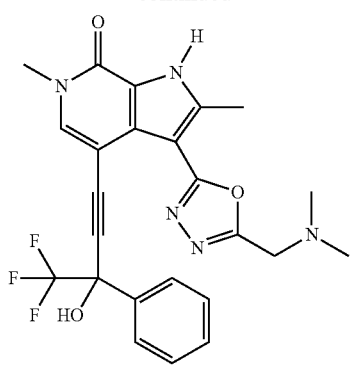
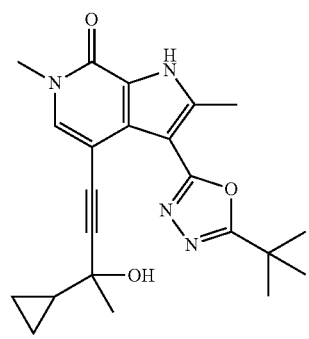
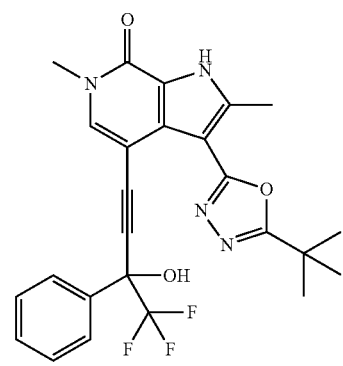
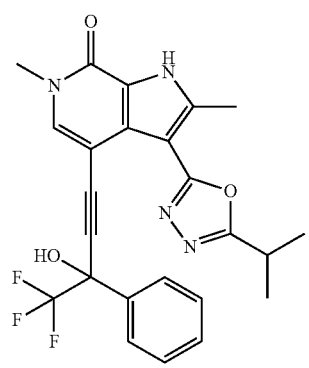
-continued
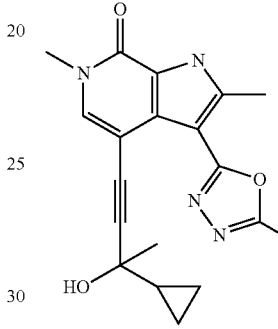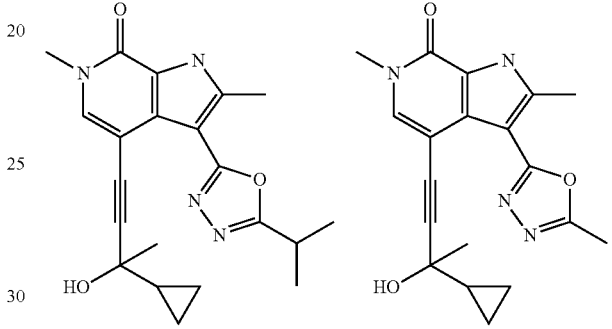
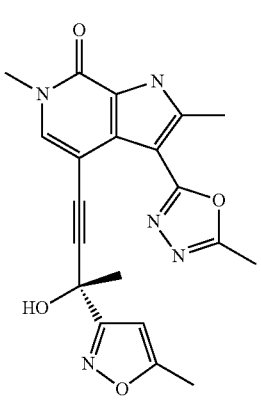
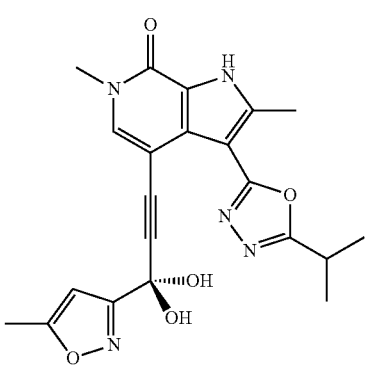

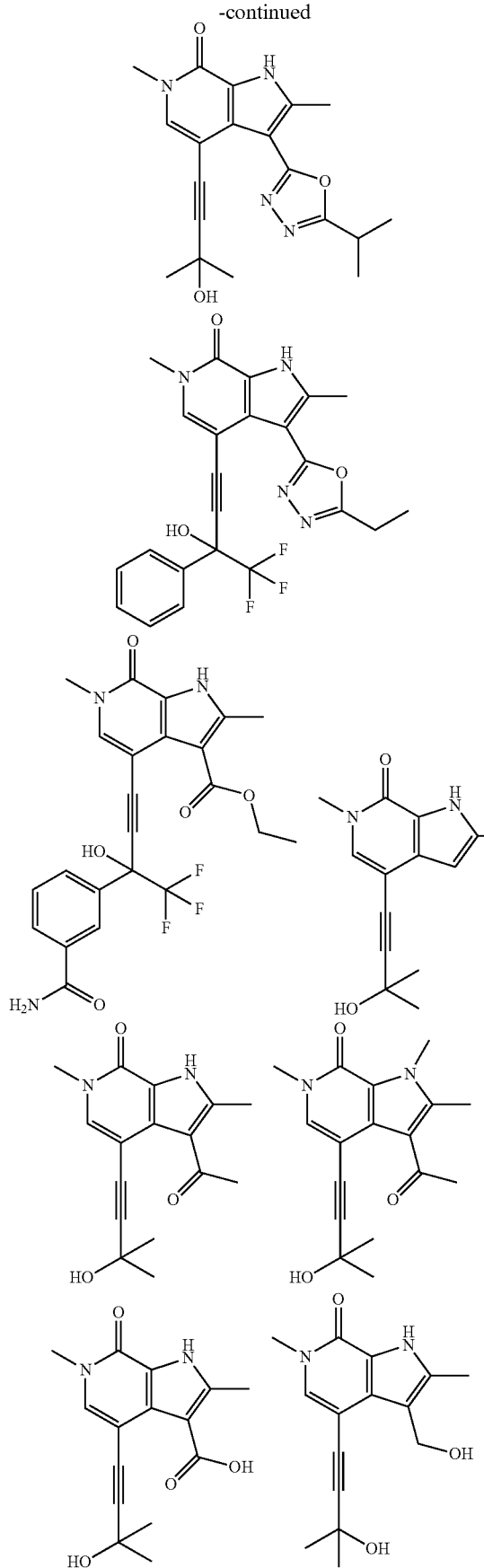
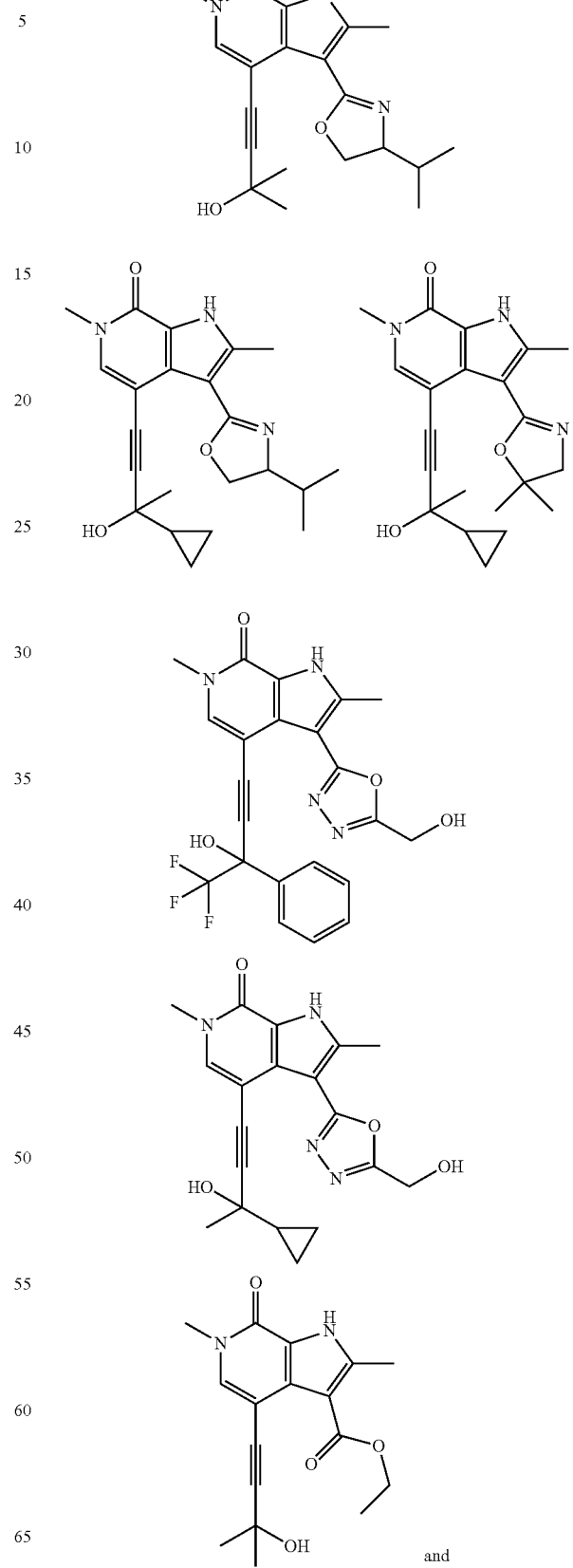

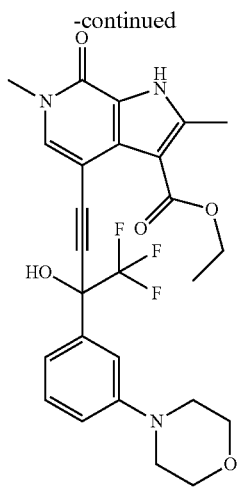

and salts thereof.

One embodiment provides a composition comprising a compound disclosed herein or a pharmaceutically acceptable salt thereof, and a pharmaceutically acceptable adjuvant, carrier, or vehicle.

One embodiment provides a method for treating a TAF1-mediated disorder in an animal comprising administering a disclosed herein or a pharmaceutically acceptable salt thereof to the animal.

One embodiment provides a compound disclosed herein or a pharmaceutically acceptable salt thereof for use in medical therapy.

One embodiment provides a compound disclosed herein or a pharmaceutically acceptable salt thereof for the prophylactic or therapeutic treatment of a TAF1-mediated disorder.

One embodiment provides the use of a compound disclosed herein or a pharmaceutically acceptable salt thereof to prepare a medicament for treating a TAF1-mediated disorder in an animal (e.g. a mammal such as a human).

One embodiment provides synthetic intermediates and synthetic processes disclosed herein that are useful for preparing a compounds disclosed herein or a salt thereof.

Uses, Formulation and Administration

Pharmaceutically Acceptable Compositions

Another aspect includes a pharmaceutical composition comprising a compound of formula (I) or a pharmaceutically acceptable salt thereof or a compound disclosed herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a TAF1 bromodomain. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof or a compound disclosed herein or a pharmaceutically acceptable salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further or a compound disclosed herein or a pharmaceutically acceptable salt thereof comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof or a compound disclosed herein or a pharmaceutically acceptable salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or salt thereof or a compound disclosed herein or a salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I) or a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof or a compound disclosed herein or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I) or the compound disclosed herein.

Example dosage forms for topical or transdermal administration of a compound of formula (I) or a compound disclosed herein include ointments, pastes, creams, lotions, gels, powders, solutions, sprays, inhalants or patches. The compound of formula (I) or a salt thereof or the compound disclosed herein or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof or a compound disclosed herein or a salt thereof may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof or a compound disclosed herein or a salt thereof for the inhibition of TAF1 (in vitro or in vivo).

Another embodiment includes a method for treating a TAF1-mediated disorder in an animal comprising administering a compound of formula (I), or a pharmaceutically acceptable salt thereof or a compound disclosed herein or a pharmaceutically acceptable salt thereof to the animal. TAF1-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or a pharmaceutically acceptable salt thereof or a compound disclosed herein or a pharmaceutically acceptable salt thereof.

Another embodiment includes a method of delaying or preventing development of cancer resistance to a cytotoxic agent in an animal, comprising administering to the animal a compound of formula (I) or a pharmaceutically acceptable salt thereof or a compound disclosed herein or a pharmaceutically acceptable salt thereof.

Another embodiment includes a method of extending the duration of response to a cancer therapy in an animal, comprising administering to an animal undergoing the cancer therapy a compound of formula (I) or a pharmaceutically acceptable salt thereof or a compound disclosed herein or a pharmaceutically acceptable salt thereof, wherein the duration of response to the cancer therapy when the compound of formula (I) or the pharmaceutically acceptable salt or a compound disclosed herein or a pharmaceutically acceptable salt thereof is administered is extended over the duration of response to the cancer therapy in the absence of the administration of the compound of formula (I) or the pharmaceutically acceptable salt thereof or a compound disclosed herein or a pharmaceutically acceptable salt thereof.

Another embodiment includes a method of treating cancer in an individual comprising administering to the individual (a) a compound of formula (I) or a pharmaceutically acceptable salt thereof or a compound disclosed herein or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

TAF1-Mediated Disorders

A "TAF1-mediated disorder" is characterized by the participation TAF1 in the inception, manifestation of one or more symptoms or disease markers, severity, or progression of a disorder.

TAF1-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

TAF1-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

TAF1-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

Co-Administration of Compounds and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARcEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERcEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARcEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-MI prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal antiinflammatory drugs with analgesic, antipyretic and antiinflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; antiinflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCI0-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERcEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid: prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, an adensosine agonist, an antithrombotic agent, acomplement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-10, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERcEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERcEPT™).

A compound of formula (I) or a pharmaceutically acceptable salt thereof can also be co-administered with one or more agents used in the prevention or treatment of AIDS: an HIV reverse transcriptase inhibitor, an HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, repaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof or a compound disclosed herein or a salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) or the compound disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof or a compound disclosed herein or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine,di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof or a compound disclosed herein or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Scheme A (Examples 1-99a/99b)

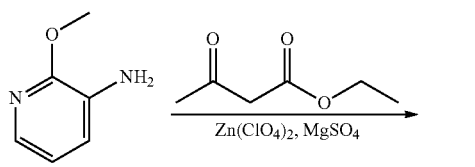

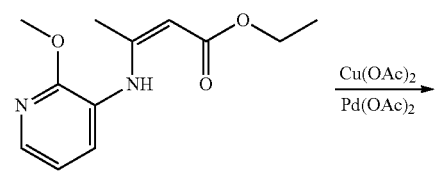

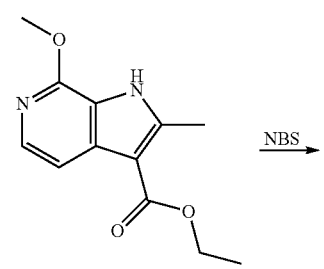

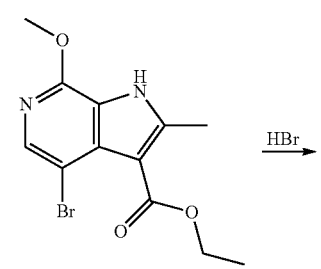

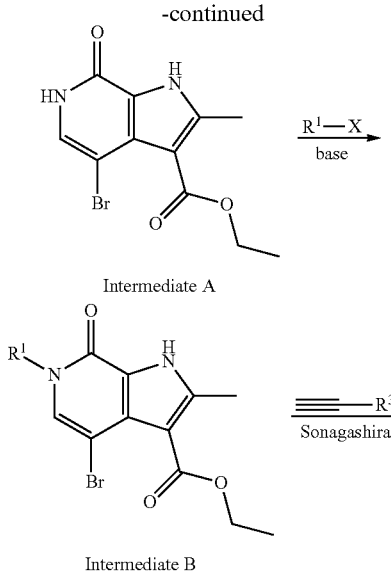

Representative compounds of formula (I) were prepared according to the scheme shown above. Intermediate A (prepared as described below) was alkylated with various $R^1$-halides to yield Intermediate B, which was treated with various $R^3$-alkynes in the presence of various base such as triethylamine or N,N-diisopropylethylamine under Sonagashira conditions to yield compounds of formula (I).

General Scheme B (Examples 103-167)

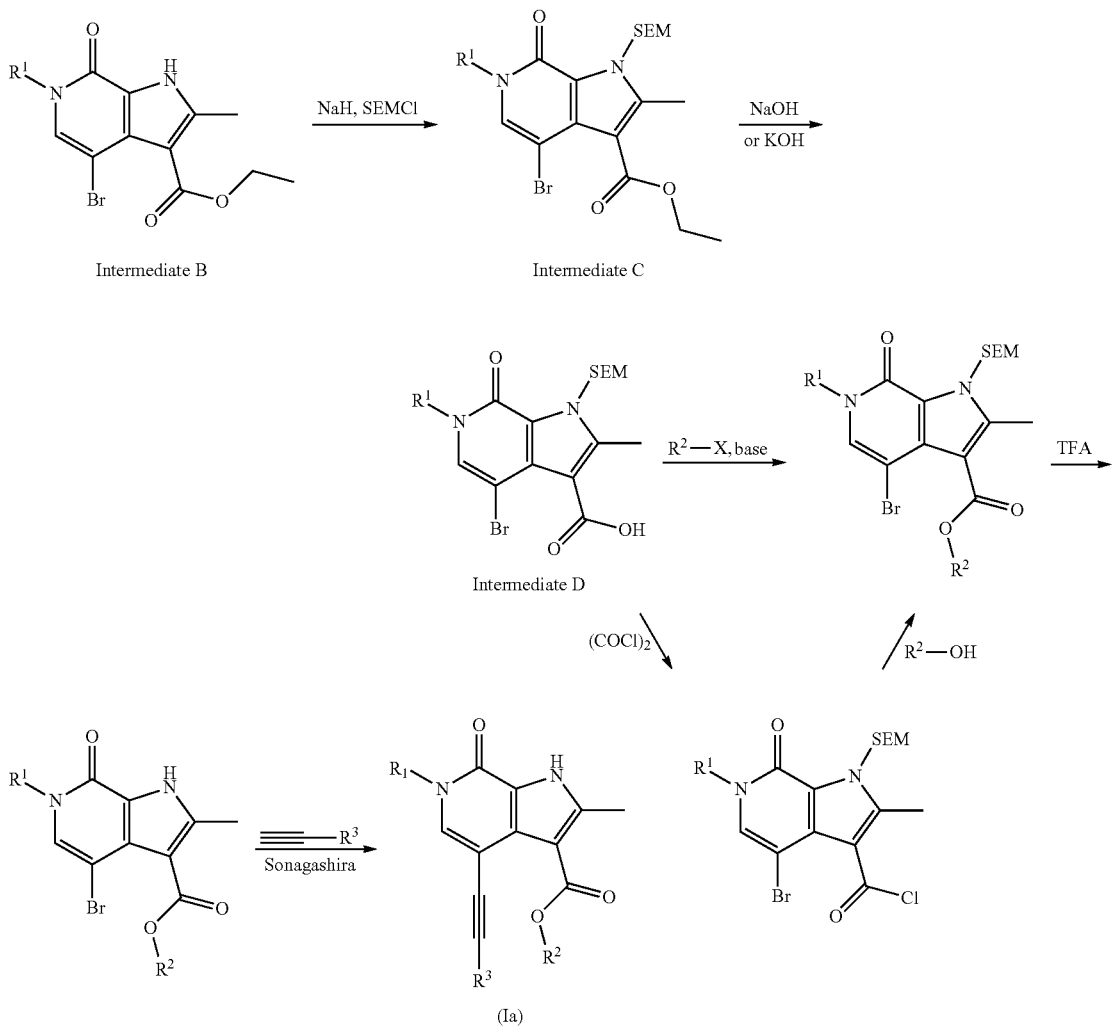

Representative compounds of formula (Ia) were prepared according to the scheme shown above. Various N-substituted derivatives of Intermediate B (prepared as in Generic Scheme A) were treated with 2-(trimethylsilyl)ethoxymethyl chloride under basic conditions. Hydrolysis of the ethyl esters revealed the carboxylic acid, which was treated with various $R^2$-halides to afford the corresponding esters. The esters were alternatively prepared by the treatment of the carboxylic acid chloride with various $R^2$-alcohols, followed by hydrolytic removal of 2-(trimethylsilyl)ethoxymethyl protecting group. The resultant intermediates were treated with various $R^3$-alkynes under Sonagashira conditions to yield compounds of formula (Ia).

General Scheme C (Examples 169-172)

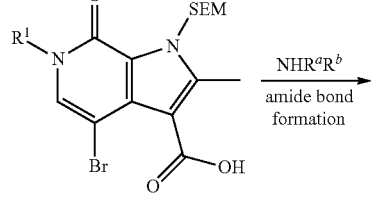

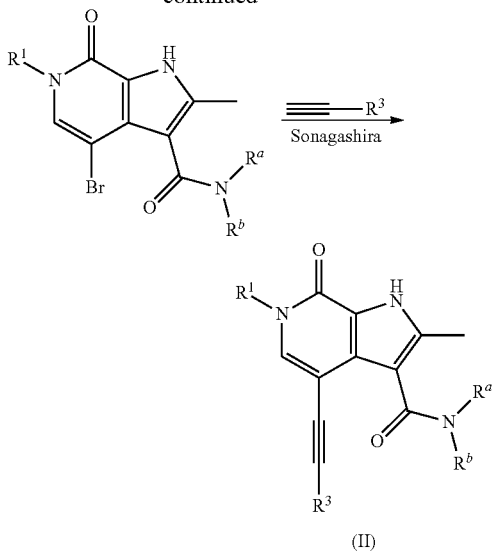

Representative compounds of formula (II) were prepared according to the scheme shown above. Various N-substituted derivatives of Intermediate D (prepared as in Generic Scheme B) were coupled with various amines to afford the corresponding amides, followed by hydrolytic removal of the 2-(trimethylsilyl)ethoxymethyl protecting group. The resultant intermediates were treated with various $R^3$-alkynes under Sonagashira conditions to yield compounds of formula (II).

General Scheme D (Examples 172-196)

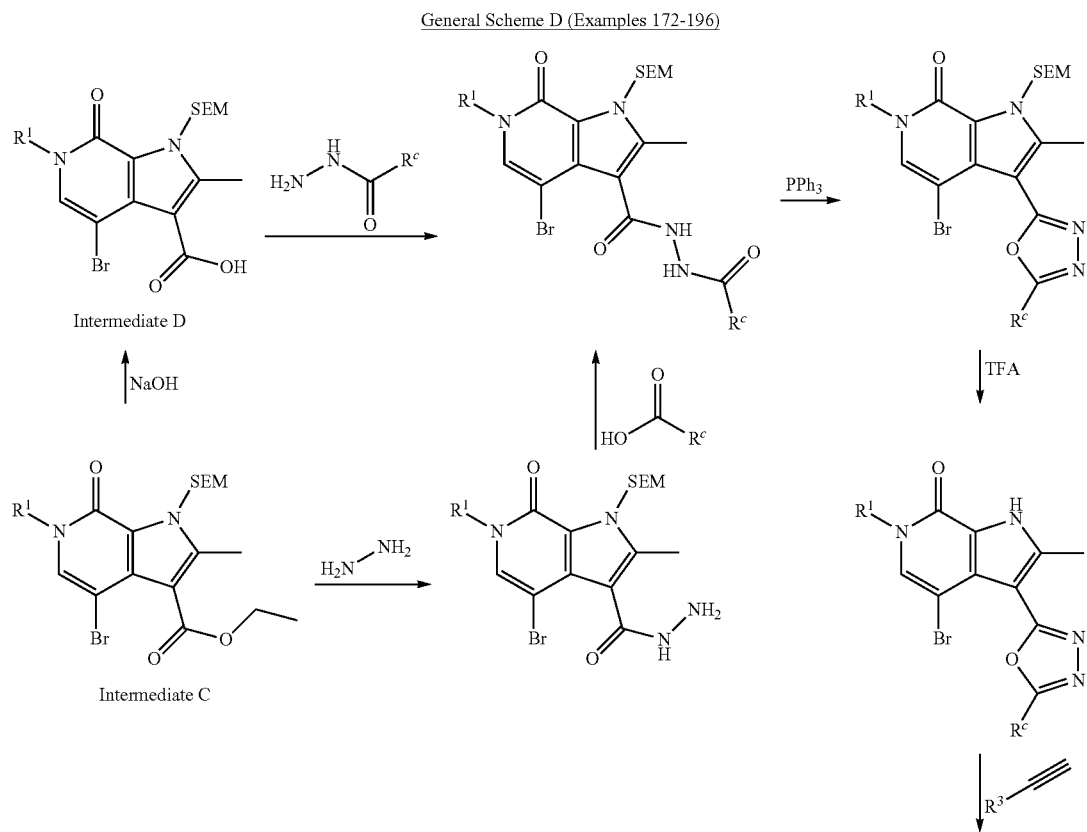

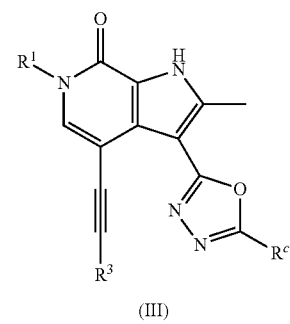

(III)

Representative compounds of formula (III) were prepared according to the scheme shown above. Intermediate C (prepared as in Generic Scheme B) was treated with hydrazine hydrate to give the carbohydrazide intermediate, which was coupled with various carboxylic acids. Cyclization was performed in the presence of triphenylphosphine, followed by hydrolytic removal of the 2-(trimethylsilyl)ethoxymethyl protecting group. The resultant intermediates were treated with various $R^3$-alkynes under Sonagashira conditions to yield compounds of formula (III).

General Procedure for the Preparation of Intermediates A & B & C & D

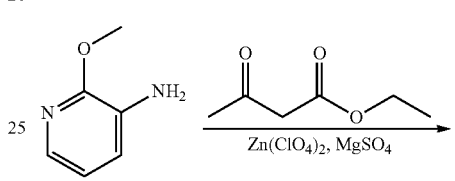

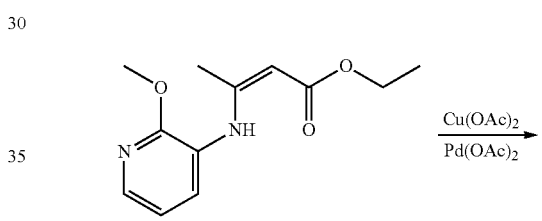

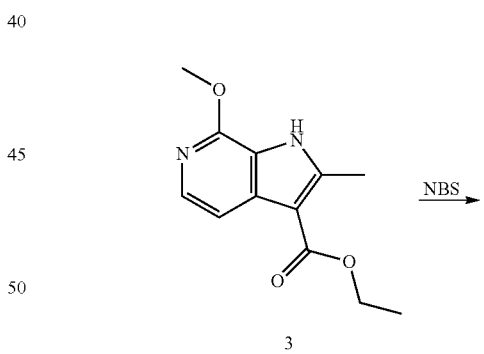

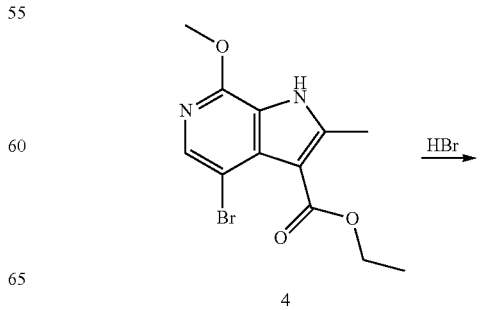

List of Abbreviations

| | |
|---|---|
| ACN | acetonitrile |
| Boc | tert-butoxycarbonyl |
| Br₂ | bromine |
| Cs₂CO₃ | cesium carbonate |
| DCM | dichloromethane |
| DIPEA | N,N-diiopropylethyl amine |
| DMF | N,N-dimethylformamide |
| DMSO | dimethylsulphoxide |
| DMAP | deoxyadenosine monophosphate |
| EDC | N-(3-Dimethylaminopropyl)-N'-ethylcarbodiimide hydrochloride |
| EtOAc | ethyl acetate |
| EtOH | ethanol |
| h | hour(s) |
| HATU | N-[(Dimethylamino)-1H-1,2,3-triazolo-[4,5-b]pyridin-1-ylmethylene]-N-methylmethanaminium hexafluorophosphate N-oxide |
| HCl | hydrogen chloride |
| HPLC | high performance liquid chromatography |
| H₂O | water |
| HOBT | 1-hydroxybenzotriazole |
| K₂CO₃ | potassium carbonate |
| KOH | potassium hydroxide |
| MgSO₄ | magnesium sulfate |
| MeOH | methanol |
| N₂ | nitrogen gas |
| NBS | n-bromosuccinimide |
| NaH | sodium hydride |
| Na₂CO₃ | sodium carbonate |
| Na₂SO₄ | sodium sulfate |
| NaOMe | sodium methoxide |
| NaOH | sodium hydroxide |
| Na₂SO₃ | sodium sulfite |
| NH₄Cl | ammonium chloride |
| NH₄OH | ammonium hydroxide |
| n-BuLi | n-butyllithium |
| PPh₃ | triphenylphosphine |
| SEM-Cl | 2-(trimethylsilyl) ethoxymethyl chloride |
| TBAF | tetra-n-butylammonium fluoride |
| TEA | triethylamine |
| THF | tetrahydrofuran |

-continued

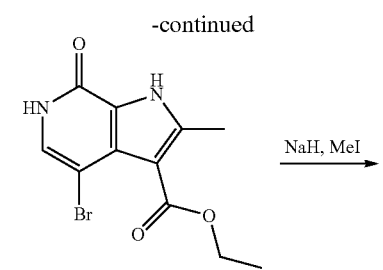

Intermediate A

NaH, MeI

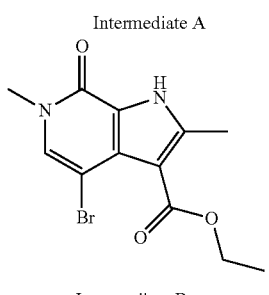

Intermediate B

NaH, SEMCl

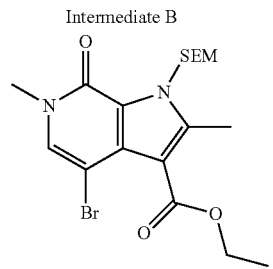

Intermediate C

NaOH, EtOH/H₂O

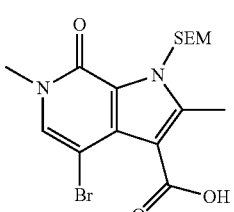

Intermediate D

Step 1

(Z)-ethyl 3-((2-methoxypyridin-3-yl)amino)but-2-enoate

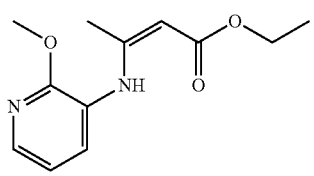 [SMILES: CCOC(=O)/C=C(/C)Nc1cccnc1OC]

A mixture of 2-methoxypyridin-3-amine (100.0 g, 0.80 mol), ethyl 3-oxobutanoate (136.3 g, 1.05 mol), zinc(II) perchlorate hexahydrate (17.9 g, 0.05 mol) and MgSO₄ (290.0 g, 2.42 mol) in DCM (2.0 L) was stirred at ambient temperature for 15 h. After filtration, the filtrate was concentrated under reduced pressure. The crude was purified by column chromatography (petroleum ether:EtOAc=19:1) to give the title compound (113.3 g, 60% yield) as a yellow solid. ¹H NMR (400 MHz, CDCl₃) δ 7.88-7.87 (m, 1H), 7.32-7.29 (m, 1H), 6.84-6.81 (m, 1H), 4.75 (s, 1H), 4.19-4.12 (m, 2H), 4.00 (s, 3H), 2.04 (s, 3H), 1.27 (t, J=7.2 Hz, 3H).

Step 2 ethyl 7-methoxy-2-methyl-1H-pyrrolo[2,3-c]pyridine-3-carboxylate

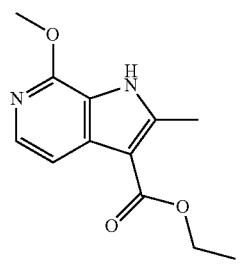 [SMILES: CCOC(=O)c1c(C)[nH]c2c(OC)nccc12]

A mixture of (Z)-ethyl 3-((2-methoxypyridin-3-yl)amino) but-2-enoate (50.0 g, 211.6 mmol), copper(II) acetate (126.8 g, 634.9 mmol), palladium(II) acetate (2.38 g, 10.6 mmol) and K₂CO₃ (67.3 g, 634.9 mmol) in DMF (1.0 L) was heated to 100° C. for 15 h. After cooling to ambient temperature, the reaction mixture was diluted with water (500 mL) and extracted with EtOAc (3×1.0 L). The combined organic layers were dried over anhydrous Na₂SO₄ and concentrated under reduced pressure. The residue was purified by column chromatography (petroleum ether:EtOAc=3:1) to give the title compound (25.0 g, 51% yield) as a yellow solid. ¹H NMR (400 MHz, DMSO-d₆) δ 12.35 (s, 1H), 7.74 (d, J=6.0 Hz, 1H), 7.43 (d, J=5.6 Hz, 1H), 4.28-4.23 (m, 2H), 4.01 (s, 3H), 2.63 (s, 3H), 1.33 (t, J=7.2 Hz, 3H).

Step 3 ethyl 4-bromo-7-methoxy-2-methyl-1H-pyrrolo[2,3-c]pyridine-3-carboxylate

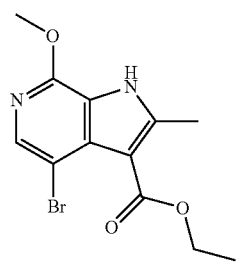 [SMILES: CCOC(=O)c1c(C)[nH]c2c(OC)ncc(Br)c12]

To a solution of ethyl 7-methoxy-2-methyl-1H-pyrrolo[2,3-c]pyridine-3-carboxylate (10.00 g, 42.69 mmol) in DMF (100 mL) at 0° C. was added palladium(II) acetate (48 mg, 0.21 mmol) and NBS (8.36 g, 46.96 mmol). The reaction was stirred at ambient temperature for 15 h and then diluted with water (100 mL). The solution was extracted with EtOAc (3×100 mL). The combined organic layers were dried over anhydrous Na₂SO₄ and concentrated under reduced pressure. The residue was purified by column chromatography (petroleum ether:EtOAc=3:1) to give the title compound (10.71 g, 80% yield) as a yellow solid.

Step 4 ethyl 4-bromo-2-methyl-7-oxo-6,7-dihydro-1H-pyrrolo[2,3-c]pyridine-3-carboxylate

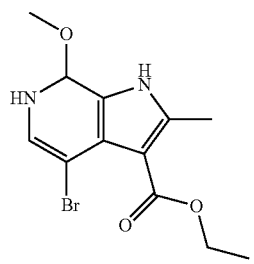 [SMILES: CCOC(=O)c1c(C)[nH]c2c1C(Br)=CNC2OC]

To a solution of ethyl 4-bromo-7-methoxy-2-methyl-1H-pyrrolo[2,3-c]pyridine-3-carboxylate (10.0 g, 31.93 mmol) in EtOH (100 mL) was added hydrogen bromide (40% aq, 25 mL, 184.16 mmol). The reaction was heated at 80° C. for 3 h, then cooled to ambient temperature and evaporated under reduced pressure and the residue was diluted with water (100 mL). The resulting precipitate was collected by filtration to give the crude title compound (Intermediate A) (8.0 g, 84% yield) as a yellow solid. The crude was used in the following reactions without further purification.

Step 5 ethyl 4-bromo-2,6-dimethyl-7-oxo-6,7-dihydro-1H-pyrrolo[2,3-c]pyridine-3-carboxylate

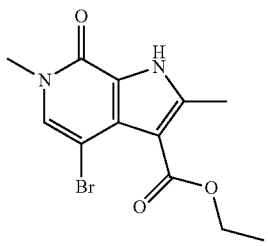 [SMILES: CCOC(=O)c1c(C)[nH]c2c(=O)n(C)cc(Br)c12]

To a solution of ethyl 4-bromo-2-methyl-7-oxo-6,7-dihydro-1H-pyrrolo[2,3-c]pyridine-3-carboxylate (8.0 g, 26.75 mmol) in DMF (100 mL) at 0° C. was added NaH (60% in mineral oil, 1.6 g, 40.13 mmol) portionwise. The reaction was stirred for 30 min before methyl iodide (3.8 g, 26.75 mmol) was added. The reaction was stirred at ambient temperature for 1 h and then poured into water (50 mL) and extracted with EtOAc (3×100 mL). The combined organic layers were dried over anhydrous $Na_2SO_4$ and concentrated under reduced pressure. The residue was purified by column chromatography (petroleum ether:EtOAc=1:1) to give the title compound (Intermediate B) (7.50 g, 90% yield) as a yellow solid. LCMS M/Z (M+H) 312.8, 314.8.

Step 6 ethyl 4-bromo-2,6-dimethyl-7-oxo-1-((2-(trimethylsilyl)ethoxy)methyl)-6,7-dihydro-1H-pyrrolo[2,3-c]pyridine-3-carboxylate

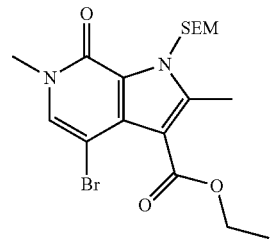 [SMILES: CCOC(=O)c1c(C)n(COCC[Si](C)(C)C)c2c(=O)n(C)cc(Br)c12]

To a solution of ethyl 4-bromo-2,6-dimethyl-7-oxo-6,7-dihydro-1H-pyrrolo[2,3-c]pyridine-3-carboxylate (7.50 g, 23.95 mmol) in DMF (100 mL) at 0° C. was added NaH (60% in mineral oil, 1.50 g, 38.32 mmol). The reaction was stirred for 30 min and SEM-Cl (6.69 g, 40.13 mmol) was added. The reaction was stirred for 1 h at 0° C., then poured into water (50 mL) and extracted with EtOAc (3×100 mL). The combined organic layers were dried over anhydrous $Na_2SO_4$ and concentrated under reduced pressure. The crude was purified by column chromatography (petroleum ether:EtOAc=4:1) to give the title compound (Intermediate C) (7.30 g, 69% yield) as a yellow solid. $^1$H NMR (400 MHz, $CD_3OD$) δ 7.51 (s, 1H), 6.06 (s, 2H), 4.39-4.33 (m, 2H), 3.62-3.60 (m, 2H), 3.57 (s, 3H), 2.54 (s, 3H), 1.43-1.37 (m, 3H), 0.84 (t, J=8.0 Hz, 2H), 0.07 (s, 9H).

Step 7

4-bromo-2,6-dimethyl-7-oxo-1-((2-(trimethylsilyl)ethoxy)methyl)-6,7-dihydro-1H-pyrrolo[2,3-c]pyridine-3-carboxylic acid

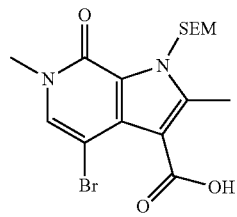

To a solution of ethyl 4-bromo-2,6-dimethyl-7-oxo-1-((2-(trimethylsilyl)ethoxy) methyl)-6,7-dihydro-1H-pyrrolo[2,3-c]pyridine-3-carboxylate (7.00 g, 15.79 mmol) in EtOH (50 mL) was added aqueous NaOH (4 N, 20 mL, 80.00 mmol). The reaction was heated at 80° C. for 15 h. After cooling, the mixture was adjusted to pH 4-5 by the addition of aqueous HCl (1 N). The EtOH was removed under reduced pressure and the aqueous solution was extracted with EtOAc (3×100 mL). The combined organic layers were dried over anhydrous $Na_2SO_4$ and concentrated under reduced pressure to give the crude title compound (Intermediate D) (6.20 g, 94% yield) as a yellow solid. $^1$H NMR (400 MHz, $CD_3OD$) δ 7.51 (s, 1H), 6.08 (s, 2H), 3.63-3.58 (m, 2H), 3.58 (s, 3H), 2.58 (s, 3H), 0.85 (t, J=8.0 Hz, 2H), 0.06 (s, 9H).

General Procedure for the Preparation of Intermediates E1-E4

Ethyl 4-bromo-6-(but-3-en-1-yl)-2-methyl-7-oxo-6,7-dihydro-1H-pyrrolo[2,3-c]pyridine-3-carboxylate

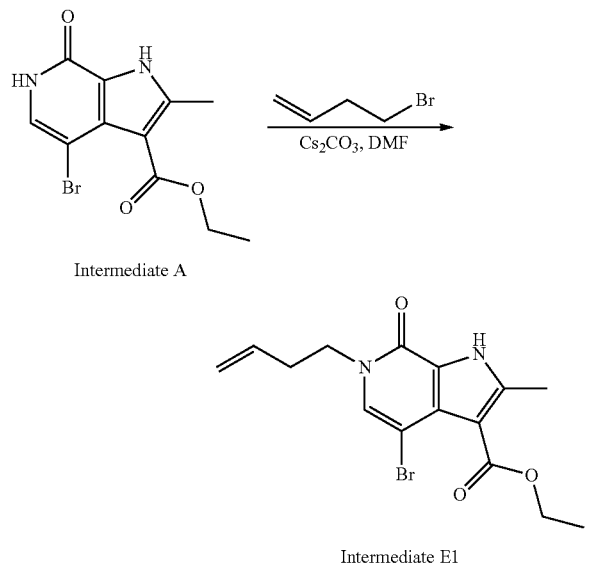

Intermediate A

Intermediate E1

To a solution of ethyl 4-bromo-2-methyl-7-oxo-1,6-dihydropyrrolo[2,3-c]pyridine-3-carboxylate (17.00 g, 56.83 mmol) in DMF (250 mL) was added $Cs_2CO_3$ (27.78 g, 85.25 mmol) and 4-bromobut-1-ene (9.97 g, 73.88 mmol). The reaction was stirred at ambient temperature for 16 h and then filtered. The filtrate was concentrated under reduced pressure. The residue was purified by column chromatography (petroleum ether:EtOAc=2:1) to give the title compound (Intermediate E1) (7.00 g, 35% yield) as a white solid. $^1$H NMR (400 MHz, DMSO-$d_6$) δ 12.69 (s, 1H), 7.57 (s, 1H), 5.85-5.76 (m, 1H), 5.04-4.98 (m, 2H), 4.27-4.21 (m, 2H), 4.05-4.01 (m, 2H), 2.44-2.39 (m, 5H), 1.30 (t, J=7.2 Hz, 3H). LCMS M/Z (M+H) 355.

The following compounds were prepared in a similar fashion to intermediate E1

Examples 2-4

| Example | Structure | Compound Name | m/z |
|---|---|---|---|
| E2 | | ethyl 6-allyl-4-bromo-2-methyl-7-oxo-6,7-dihydro-1H-pyrrolo[2,3-c]pyridine-3-carboxylate | 339 |
| E3 | 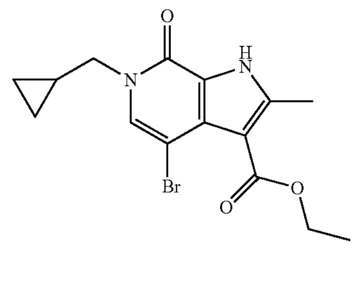 [SMILES: CCOC(=O)c1c(C)[nH]c2c(=O)n(CC3CC3)cc(Br)c12] | ethyl 4-bromo-6-(cyclopropylmethyl)-2-methyl-7-oxo-6,7-dihydro-1H-pyrrolo[2,3-c]pyridine-3-carboxylate | 353 |
| E4 | 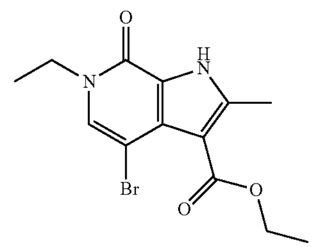 [SMILES: CCOC(=O)c1c(C)[nH]c2c(=O)n(CC)cc(Br)c12] | ethyl 4-bromo-6-ethyl-2-methyl-7-oxo-6,7-dihydro-1H-pyrrolo[2,3-c]pyridine-3-carboxylate | 327 |

General Procedure for the Preparation of Intermediate F

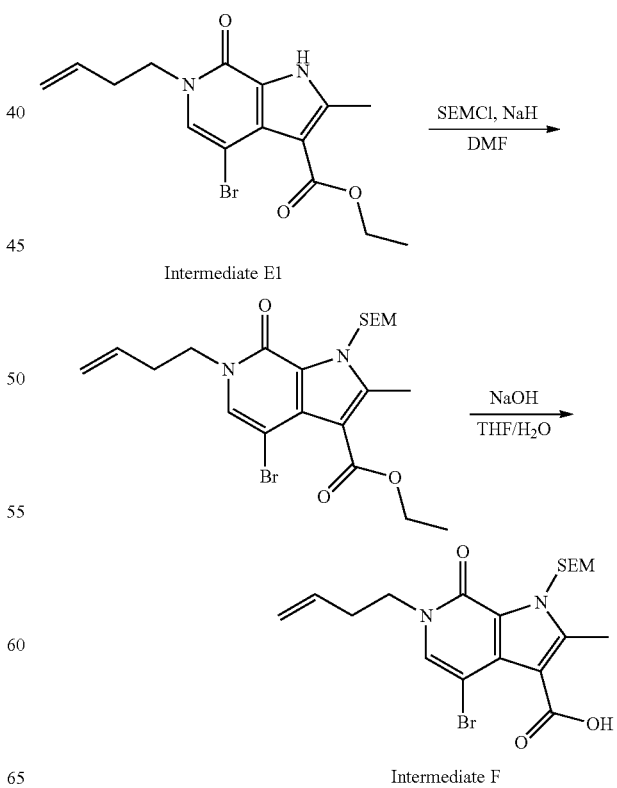

Intermediate E1

Intermediate F

Step 1 ethyl 4-bromo-6-(but-3-en-1-yl)-2-methyl-7-oxo-1-((2-(trimethylsilyl)ethoxy) methyl)-6,7-dihydro-1H-pyrrolo[2,3-c]pyridine-3-carboxylate

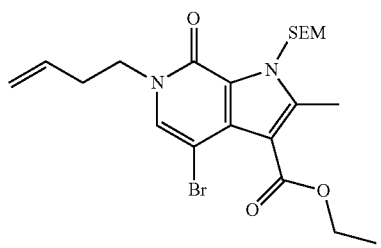 [SMILES: C=CCCn1cc(Br)c2c(C(=O)OCC)c(C)n(COCC[Si](C)(C)C)c2c1=O]

To a solution of ethyl 4-bromo-6-(but-3-en-1-yl)-2-methyl-7-oxo-6,7-dihydro-1H-pyrrolo[2,3-c]pyridine-3-carboxylate (Intermediate E1) (1.0 g, 2.83 mmol) in DMF (10 mL) at 0° C. was added NaH (60% in mineral oil, 170 mg, 4.25 mmol). After stirring for 30 min, SEM-Cl (708 mg, 4.25 mmol) was added. The reaction was stirred at ambient temperature for 1 h and then poured into ice water (10 mL) and extracted with EtOAc (3×10 mL). The combined organic layers were concentrated under reduced pressure. The residue was purified by column chromatography (petroleum ether:EtOAc=4:1) to give the title compound (1.2 g, 88% yield) as a pale yellow solid.

Step 2

4-bromo-6-(but-3-en-1-yl)-2-methyl-7-oxo-1-((2-(trimethylsilyl)ethoxy)methyl)-6,7-dihydro-1H-pyrrolo[2,3-c]pyridine-3-carboxylic acid

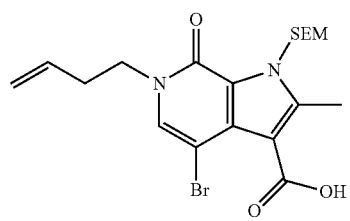 [SMILES: C=CCCn1cc(Br)c2c(C(=O)O)c(C)n(COCC[Si](C)(C)C)c2c1=O]

To a solution of ethyl 4-bromo-6-(but-3-en-1-yl)-2-methyl-7-oxo-1-((2-(trimethylsilyl) ethoxy)methyl)-6,7-dihydro-1H-pyrrolo[2,3-c]pyridine-3-carboxylate (1.20 g, 2.48 mmol) in EtOH/H₂O (10 mL/10 mL) was added NaOH (0.50 g, 12.41 mmol). The reaction was heated at 80° C. for 16 h. The EtOH was evaporated under reduced pressure and the residue was adjusted to pH 5 by the addition of aqueous HCl (1 N). The solution was extracted with EtOAc (3×50 mL). The combined organic layers were dried over anhydrous Na₂SO₄, filtered and concentrated under reduced pressure to give the crude title compound (Intermediate F) (1.00 g, 88% yield) as a white solid.

General Procedure for the Preparation of Intermediates G1-G2

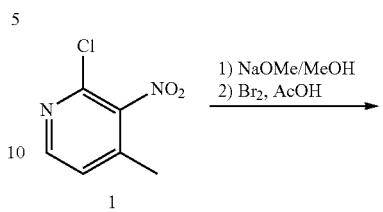

1

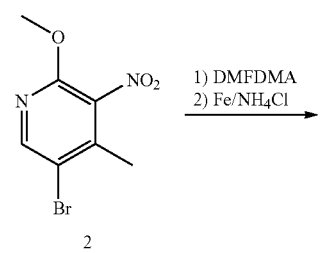

2

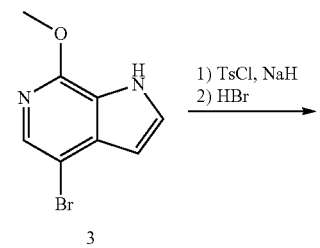

3

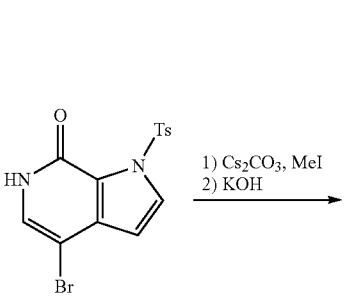

4

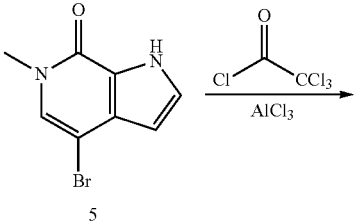

5

-continued

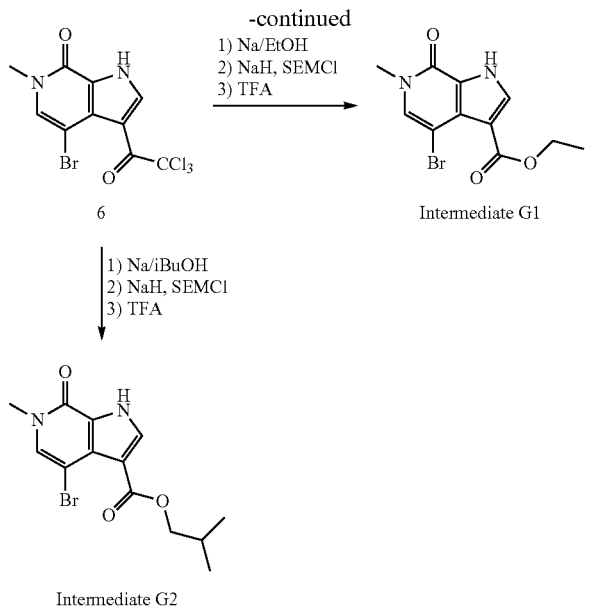

6

Intermediate G1

1) Na/iBuOH
2) NaH, SEMCl
3) TFA

Intermediate G2

Step 1

2-methoxy-4-methyl-3-nitropyridine

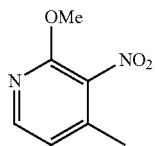

A solution of 2-chloro-4-methyl-3-nitropyridine (250 g, 1.45 mol) in MeOH (1.0 L) was added dropwise over 2 h to a stirred and cooled (0° C.) solution of NaOMe (250 g, 4.63 mol) in MeOH (850 mL). The reaction was heated to reflux temperature for 23 h. The mixture was partially concentrated under reduced pressure and quenched by the addition of water (1.5 L), the resulting solid was collected by filtration, washed with water and dried under vacuum to give the title compound (250 g, 100% yield) as a brown solid. $^1$H NMR (400 MHz, DMSO-$d_6$): δ 8.22 (d, J=5.2 Hz, 1H), 7.10 (d, J=5.6 Hz, 1H), 3.92 (s, 3H), 2.26 (s, 3H).

Step 2

5-bromo-2-methoxy-4-methyl-3-nitropyridine

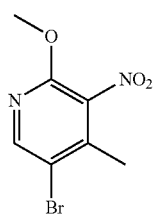

Sodium acetate (365 g, 5.37 mol) was added to a stirred solution of 2-methoxy-4-methyl-3-nitropyridine (250 g, 1.49 mol) in acetic acid (1.5 L) at ambient temperature, then bromine (639 g, 4.00 mol) was added and the reaction was heated at 80° C. for 12 h. The mixture was then quenched by the addition of 10% aqueous NaOH (1.5 L) and saturated aqueous Na$_2$SO$_3$ (1.5 L) at 0° C. The resulting solid was collected by filtration and washed with water, dried under vacuum to give the title compound (302 g, 82.2% yield) as a light yellow solid. $^1$H NMR (400 MHz, DMSO-$d_6$): δ 8.25 (s, 1H), 3.94 (s, 3H), 2.29 (s, 3H).

Step 3

2-(5-bromo-2-methoxy-3-nitropyridin-4-yl)-N,N-dimethylethenamine

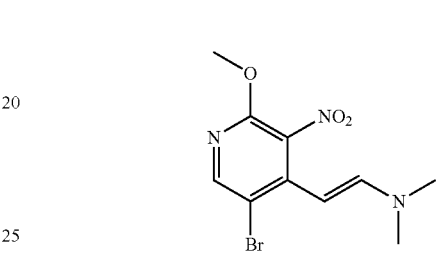

N,N-dimethylformamide dimethyl acetal (600 mL) was slowly added to a stirred and heated (80° C.) solution of 5-bromo-2-methoxy-4-methyl-3-nitropyridine (134 g, 0.54 mol) in DMF (1.1 L). The mixture was heated at 95° C. for 5 h. The reaction was cooled to ambient temperature and poured into ice-cold water (3 L). The resulting red solid was collected by filtration, washed with water and dried under vacuum to give the title compound (167 g, 100% yield) as a reddish solid. $^1$H NMR (400 MHz, DMSO-$d_6$): δ 8.24 (s, 1H), 7.05 (d, J=13.6 Hz, 1H), 7.05 (d, J=13.6 Hz, 1H), 4.80 (d, J=13.2 Hz, 1H), 3.88 (s, 3H), 2.90 (s, 6H).

Step 4

4-bromo-7-methoxy-1H-pyrrolo[2,3-c]pyridine

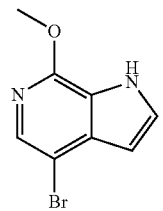

A mixture of 2-(5-bromo-2-methoxy-3-nitropyridin-4-yl)-N,N-dimethylethenamine (50.0 g, 165 mmol), iron powder (50.0 g, 893 mmol) and NH$_4$Cl (50.0 g, 943 mmol) in MeOH/H$_2$O (1900/250 mL) was heated to reflux temperature for 7 h. The reaction was filtered while hot and the filter cake was washed with MeOH (3×200 mL). The combined filtrates were concentrated under reduced pressure, and the resulting residue was purified by column chromatography (petroleum ether:EtOAc=5:1) to give the crude product. The crude was washed with ACN to give the title compound (37.4 g, 99.5% yield) as a light brown solid. LCMS M/Z (M+H) 226.7, 228.7.

Step 5

4-bromo-7-methoxy-1-tosyl-1H-pyrrolo[2,3-c]pyridine

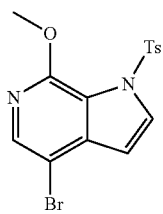 [SMILES: COc1ncc(Br)c2ccn(S(=O)(=O)c3ccc(C)cc3)c12]

A solution of 4-bromo-7-methoxy-1H-pyrrolo[2,3-c]pyridine (34.3 g, 0.15 mol) in THF (700 mL) was added to a stirred and cooled (0° C.) solution of NaH (60%, 19.2 g, 0.48 mol) in THF (700 mL). The reaction was stirred at ambient temperature for 1 h, and then re-cooled to 0° C. before p-toluenesulfonyl chloride (38.0 g, 0.20 mol) in THF (700 mL) was added. The reaction was stirred at ambient temperature for 2 h. The mixture was quenched by the addition of saturated aqueous NH$_4$Cl (1.0 L), and then extracted with EtOAc (3×600 mL). The combined organic layers were dried over anhydrous Na$_2$SO$_4$, filtered and concentrated. The residue was washed with ACN to give the title compound (51.2 g, 88.9% yield) as a brown solid. This crude was used in the next step without further purification.

Step 6

4-bromo-1-tosyl-1H-pyrrolo[2,3-c]pyridin-7(6H)-one

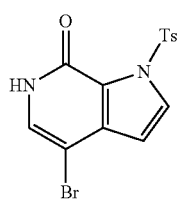

Hydrogen bromide (40% aq, 1.1 L) was added to a solution of 4-bromo-7-methoxy-1-tosyl-1H-pyrrolo[2,3-c]pyridine (102.5 g, 0.27 mol) in EtOH (200 mL). The reaction was heated at 90° C. for 2 h. The mixture was cooled to 0° C. and the resulting white solid was collected by filtration. The solid was washed with water and dried to give the title compound (87.5 g, 88.6% yield) as a light brown solid. $^1$H NMR (400 MHz, DMSO-d$_6$): δ 11.48 (s, 1H), 8.01 (d, J=3.6 Hz, 1H), 8.90 (d, J=8.0 Hz, 2H), 7.38 (d, J=8.0 Hz, 2H), 7.32 (s, 1H), 6.57 (d, J=3.2 Hz, 1H), 2.34 (s, 3H).

Step 7

4-bromo-6-methyl-1-tosyl-1H-pyrrolo[2,3-c]pyridin-7(6H)-one

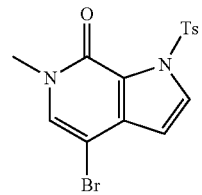 [SMILES: Cc1ccc(S(=O)(=O)n2ccc3c(Br)cn(C)c(=O)c32)cc1]

To a solution of 4-bromo-1-(p-tolylsulfonyl)-6H-pyrrolo[2,3-c]pyridin-7-one (6.00 g, 16.34 mmol) in dioxane (120 mL) was added Cs$_2$CO$_3$ (10.65 g, 32.68 mmol) and methyl iodide (6.15 g, 43.30 mmol). The reaction was stirred at ambient temperature for 1 h and then quenched by the addition of water (300 mL). The resulting precipitate was collected by filtration, washed with water (100 mL) and dried in vacuo to give the crude title compound (6.00 g, 96% yield) as a white solid. LCMS M/Z (M+H) 381.

Step 8

4-bromo-6-methyl-1H-pyrrolo[2,3-c]pyridin-7(6H)-one

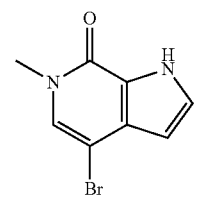

To a solution of 4-bromo-6-methyl-1-(p-tolylsulfonyl)pyrrolo[2,3-c]pyridin-7-one (6.00 g, 15.74 mmol) in MeOH (120 mL) was added a solution of KOH (4.41 g, 78.69 mmol) in water (24 mL). The mixture was heated at 70° C. for 30 min and then concentrated under reduced pressure. The residue was diluted with water (60 mL). The resulting precipitate was collected by filtration, washed with water (50 mL) and dried in vacuo to give the crude title compound (3.57 g, 100% yield) as a white solid. LCMS M/Z (M+H) 229.

Step 9

4-bromo-6-methyl-3-(2,2,2-trichloroacetyl)-1H-pyrrolo[2,3-c]pyridin-7(6H)-one

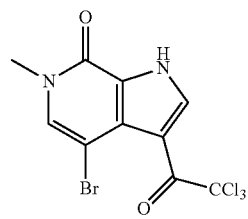

To a solution of 4-bromo-6-methyl-1H-pyrrolo[2,3-c]pyridin-7-one (3.57 g, 15.85 mmol) in DCM (200 mL) was added aluminum chloride (12.68 g, 95.12 mmol) in portions. The reaction was stirred at ambient temperature for 10 min, and 2,2,2-trichloroacetyl chloride (11.54 g, 63.44 mmol) was added. The reaction was heated at 60° C. for 8 h and then cooled to ambient temperature. The mixture was slowly added into ice water (100 mL) and the phases were then separated. The aqueous layer was extracted with DCM (2×30 mL). The combined organic layers were washed with brine (50 mL), dried over anhydrous Na$_2$SO$_4$ and concentrated under reduced pressure to give the title compound (4.00 g, 68% yield) as an off-white solid.

Step 10a ethyl 4-bromo-6-methyl-7-oxo-6,7-dihydro-1H-pyrrolo[2,3-c]pyridine-3-carboxylate

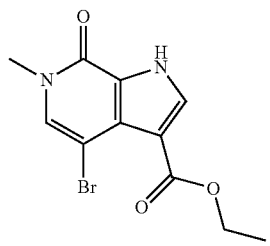 [SMILES: CCOC(=O)c1c[nH]c2c(=O)n(C)cc(Br)c12]

To a solution of sodium ethoxide (from 0.18 g sodium, 8.06 mmol) in EtOH (10 mL) was added 4-bromo-6-methyl-3-(2,2,2-trichloroacetyl)-1H-pyrrolo[2,3-c]pyridine-7-one (1.00 g, 2.69 mmol). The mixture was stirred at ambient temperature for 2 h and then concentrated under reduced pressure. The residue was diluted with water (30 mL) and extracted with EtOAc (3×30 mL). The combined organic layers were dried over anhydrous Na$_2$SO$_4$, filtered and concentrated to give the crude compound as a brown solid.

Step 10b 4-bromo-6-methyl-7-oxo-1-((2-(trimethylsilyl)ethoxy)methyl)-6,7-dihydro-1H-pyrrolo[2,3-c]pyridine3-carboxylate The crude ethyl 4-bromo-6-methyl-7-oxo-6,7-dihydro-1H-pyrrolo[2,3-c]pyridine-3-carboxylate was dissolved in DMF (15 mL) and NaH (60% in mineral oil, 0.19 g, 8.06 mmol) was added. After stirring for 10 min, SEM-Cl (1.34 g, 8.06 mmol) was added dropwise. The reaction was stirred at ambient temperature for 1 h and then quenched by the addition of water (30 mL). The solution was extracted with EtOAc (3×30 mL) and the combined organic layers were dried over anhydrous Na$_2$SO$_4$, filtered and concentrated under reduced pressure. The residue was purified by column chromatography (petroleum ether:EtOAc=4:1) to give ethyl 4-bromo-6-methyl-7-oxo-1-((2-(trimethylsilyl)ethoxy)methyl)-6,7-dihydro-1H-pyrrolo[2,3-c]pyridine3-carboxylate (580 mg, 50% yield over two steps) as a light yellow oil.

Step 10c

Ethyl 4-bromo-6-methyl-7-oxo-1-((2-(trimethylsilyl)ethoxy)methyl)-6,7-dihydro-1H-pyrrolo[2,3-c]pyridine3-carboxylate (200 mg, 0.47 mmol) was dissolved in DCM (3 mL) and 2,2,2-trifluoroacetic acid (3 mL) was added. The reaction was stirred at ambient temperature for 10 h and then concentrated under reduced pressure. The residue was dissolved in THF (20 mL) and K$_2$CO$_3$ (500 mg) was added. The reaction was stirred at ambient temperature for 10 min and filtered. The filtrate was concentrated under reduced pressure. The residue was purified by column chromatography (petroleum ether:EtOAc=4:1) to give the title compound (Intermediate G1) (139 mg, 100% yield) as a brown solid.

The compound G2 was prepared in a similar fashion to Intermediate G1, by replacing sodium ethoxide with sodium isobutoxide in step 10.

Example G2

| Example | Structure | Compound Name | m/z |
|---|---|---|---|
| G2 | 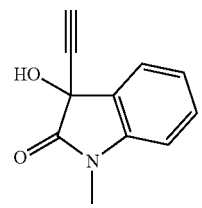 | isobutyl 4-bromo-6-methyl-7-oxo-6,7-dihydro-1H-pyrrolo[2,3-c]pyridine-3-carboxylate | 327 |

General Procedure for the Preparation of Propargyl Alcohol Reagents H1-H44

Example H1:
3-ethynyl-3-hydroxy-1-methylindolin-2-one

To a solution of 1-methylindoline-2,3-dione (1-methylisatin) (0.25 g, 1.54 mmol) in THF (10 mL) at 0° C. was added 0.5 M ethynylmagnesium bromide in THF solution (3.08 mL, 1.54 mmol) dropwise. The reaction was slowly warmed to ambient temperature and stirred overnight. The reaction mixture was poured into saturated aqueous NH$_4$Cl and then extracted with EtOAc (2×100 mL). The combined organic layers were dried over anhydrous Na$_2$SO$_4$, filtered and concentrated under reduced pressure to give the racemic title compound (H1) (213 mg, 74% yield) as an off-white solid. LCMS M/Z (M-OH) 170, (M+Na) 210.

The following compounds were prepared in a similar fashion to Example H1

Examples H2-H24

| Example | Structure | Compound Name | NMR |
|---|---|---|---|
| H2 | 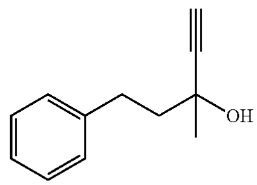 | 3-methyl-5-phenylpent-1-yn-3-ol | $^1$H NMR (400 MHz, DMSO-d$_6$) δ 7.31-7.25 (m, 2 H), 7.21-7.15 (m, 3 H), 5.41 (s, 1 H), 3.29 (s, 1 H), 2.78-2.70 (m, 2 H), 1.84-1.77 (m, 2 H), 1.41 (s, 3 H). |
| H3 | 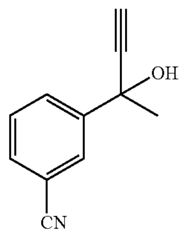 | 3-(2-hydroxybut-3-yn-2-yl)benzonitrile | $^1$H NMR (400 MHz, DMSO-d$_6$) δ 7.93-7.87 (m, 2 H), 7.78-7.74 (m, 1 H), 7.59 (t, J = 7.6 Hz, 1 H), 3.61 (s, 1 H), 2.64 (s, 1 H), 1.64 (s, 3 H). |
| H4 | 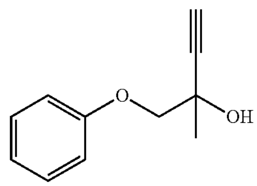 | 2-methyl-1-phenoxybut-3-yn-2-ol | $^1$H NMR (400 MHz, CDCl$_3$) δ 7.34-7.27 (m, 2 H), 7.02-6.93 (m, 3 H), 4.07-4.03 (m, 1 H), 3.96-3.91 (m, 1 H), 3.03 (s, 1 H), 2.50 (s, 1 H), 1.62 (s, 3 H). |
| H5 | 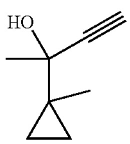 | 2-(1-methylcyclopropyl)but-3-yn-2-ol | $^1$H NMR (400 MHz, CDCl$_3$) δ 2.36 (s, 1 H), 2.04 (s, 1 H), 1.51 (s, 3 H), 1.15 (s, 3 H), 0.85-0.74 (m, 2 H), 0.30-0.26 (m, 2 H). |
| H6 | 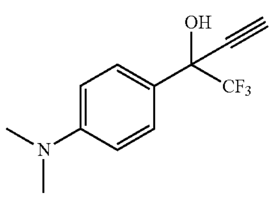 [SMILES: C#CC(O)(c1ccc(N(C)C)cc1)C(F)(F)F] | 2-(4-(dimethylamino)phenyl)-1,1,1-trifluorobut-3-yn-2-ol | $^1$H NMR (400 MHz, CDCl$_3$) δ 7.62-7.57 (m, 2 H), 6.76-6.71 (m, 2 H), 3.15-3.10 (m, 1 H), 2.98 (s, 6 H), 2.81 (s, 1 H). |
| H7 | 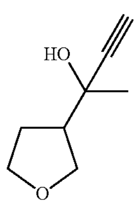 | 2-(tetrahydrofuran-3-yl)but-3-yn-2-ol | $^1$H NMR (400 MHz, CDCl$_3$) δ 3.93-3.75 (m, 4 H), 2.52-2.46 (m, 2 H), 2.04-1.84 (m, 3 H), 1.51-1.46 (m, 3 H). |
| H8 | 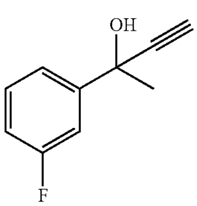 | 2-(3-fluorophenyl)but-3-yn-2-ol | $^1$H NMR (400 MHz, CDCl$_3$) δ 7.45-7.32 (m, 3 H), 7.02-6.98 (m, 1 H), 2.69 (s, 1 H), 2.63 (s, 1 H), 1.77 (s, 3 H). |
| H9 | 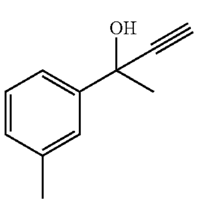 | 2-(m-tolyl)but-3-yn-2-ol | $^1$H NMR (400 MHz, CDCl$_3$) δ 7.47-7.44 (m, 2 H), 7.28-7.23 (m, 1 H), 7.12 (d, J = 7.6 Hz, 1 H), 2.67 (s, 1 H), 2.44 (s, 1 H), 2.38 (s, 3 H), 1.78 (s, 3 H). |

-continued

| Example | Compound Name | NMR |
|---|---|---|
| H10 | 1-ethynylcyclobutanol | no data |
| H11 | 4-ethynyltetrahydro-2H-pyran-4-ol | no data |
| H12 | 2-(tetrahydro-2H-pyran-4-yl)but-3-yn-2-ol | no data |
| H13 | 1,1-difluoro-2-phenylbut-3-yn-2-ol | no data |
| H14 | (R)-2-(pyrimidin-2-yl)but-3-yn-2-ol | described in WO2013120980(A1) |
| H15 | (S)-2-(pyrimidin-2-yl)but-3-yn-2-ol | described in WO2013120980(A1) |
| H16 | (R)-2-(5-methylisoxazol-3-yl)but-3-yn-2-ol | described in WO2013120980(A1) |
| H17 | (S)-2-(5-methylisoxazol-3-yl)but-3-yn-2-ol | described in WO2013120980(A1) |
| H18 | 3-hydroxy-3-methylpent-4-ynenitrile | described in WO2013120980(A1) |
| H19 | 2-methylbut-3-yne-1,2-diol | described in WO2013120980(A1) |
| H20 | (R)-2-(5-methyl-1,3,4-oxadiazol-2-yl)but-3-yn-2-ol | described in WO2013120980(A1) |

| Example | Structure | Compound Name | NMR |
|---|---|---|---|
| H21 | 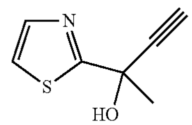 | 2-(thiazol-2-yl)but-3-yn-2-ol | described in WO2013120980(A1) |
| H22 | 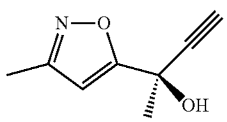 | (R)-2-(3-methylisoxazol-5-yl)but-3-yn-2-ol | described in WO2013120980(A1) |

Example H23: 1,1,1-trifluoro-2-(pyridin-3-yl)but-3-yn-2-ol

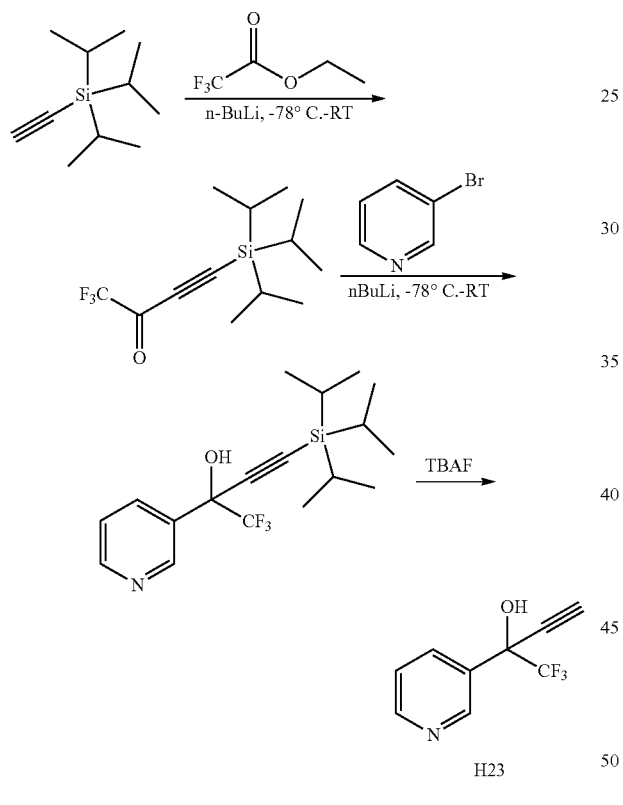

Step 1

1,1,1-trifluoro-4-(triisopropylsilyl)but-3-yn-2-one

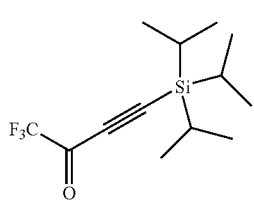 [SMILES: CC(C)[Si](C#CC(=O)C(F)(F)F)(C(C)C)C(C)C]

To a solution of ethynyltriisopropylsilane (4.50 g, 24.67 mmol) in THF (20 mL) at −78° C. was added n-BuLi (2.5 M, 9.9 mL, 24.67 mmol). The mixture was stirred at −78° C. for 1 h before ethyl 2,2,2-trifluoroacetate (5.26 g, 37.01 mmol) was added. The reaction was warmed to ambient temperature and stirred for 16 h. The reaction was quenched by the addition of saturated aqueous NH$_4$Cl (30 mL) and extracted with EtOAc (3×20 mL). The combined organic layers were washed with water (20 mL), brine (20 mL), dried over anhydrous Na$_2$SO$_4$ and concentrated under reduced pressure. The crude was purified by column chromatography (petroleum ether:EtOAc=20:1) to give the title compound (5.00 g, 73% yield) as a colorless oil.

Step 2

1,1,1-trifluoro-2-(pyridin-3-yl)-4-(triisopropylsilyl)but-3-yn-2-ol

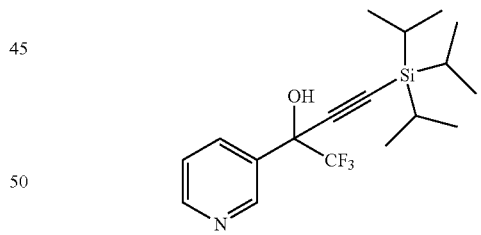

To a solution of 3-bromopyridine (300 mg, 1.90 mmol) in THF (10 mL) at −78° C. was added n-BuLi (2.5 M, 0.8 mL, 2.00 mmol) in THF. The mixture was stirred at −78° C. for 0.5 h before 1,1,1-trifluoro-4-triisopropylsilyl-but-3-yn-2-one (793 mg, 2.85 mmol) in THF (3 mL) was added. The reaction was stirred at ambient temperature for 2 h, then quenched by the addition of saturated aqueous NH$_4$Cl (20 mL). The mixture was extracted with EtOAc (2×20 mL). The combined organic layers were washed with water (20 mL) and brine (20 mL), dried over anhydrous Na$_2$SO$_4$ and concentrated under reduced pressure. The crude was purified by column chromatography (petroleum ether:EtOAc=100:1 to 3:1) to give the title compound (300 mg, 44% yield) as a colorless oil.

113

Step 3

1,1,1-trifluoro-2-(pyridin-3-yl)but-3-yn-2-ol

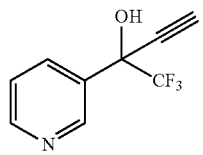

To a solution of 1,1,1-trifluoro-2-(3-pyridyl)-4-triisopropylsilyl-but-3-yn-2-ol (300 mg, 0.84 mmol) in THF (10 mL) was added tetrabutylammonium fluoride (439 mg, 1.68 mmol). The reaction mixture was stirred at ambient temperature for 2 h and then concentrated under reduced pressure. The residue was purified by column chromatography (petroleum ether:EtOAc=1:1) to give the title compound (H23) (120 mg, 71% yield) as a yellow oil.

The following compounds were prepared in a similar fashion to Example H23

Examples H24-H26

| Example | Structure | Compound Name | NMR |
|---|---|---|---|
| H24 | (OH, CF₃, ethynyl phenyl with CH₂OH) | 1,1,1-trifluoro-2-(3-(hydroxymethyl)phenyl)but-3-yn-2-ol | $^1$H NMR (400 MHz, CDCl$_3$) δ 7.74 (s, 1 H), 7.69-7.67 (m, 1 H), 7.43-7.40 (m, 2 H), 4.72 (s, 2 H), 3.89 (s, 1 H), 2.82 (s, 1 H), 2.12-2.08 (m, 1 H). |
| H25 | (OH, CF₃, ethynyl phenyl with NMe₂) | 2-(3-(dimethylamino)phenyl)-1,1,1-trifluorobut-3-yn-2-ol | $^1$H NMR (400 MHz, CDCl$_3$) δ 7.25-7.23 (m, 1 H), 7.06 (d, J = 6.8 Hz, 2 H), 6.77-6.75 (m, 1 H), 3.06 (s, 1 H), 2.95 (s, 6 H), 2.78 (s, 1 H). |
| H26 | (OH, CF₃, ethynyl phenyl with CN) | 3-(1,1,1-trifluoro-2-hydroxybut-3-yn-2-yl)benzonitrile | $^1$H NMR (400 MHz, CDCl$_3$) δ 8.06 (s, 1 H), 8.00 (d, J = 7.6 Hz, 1 H), 7.71 (d, J = 7.6 Hz, 1 H), 7.54 (t, J = 8.0 Hz, 1 H), 4.55 (s, 1 H), 2.88 (s, 1 H). |
| H27 | (F₃C, HO, ethynyl, cyclopropyl) | 2-cyclopropyl-1,1,1-trifluorobut-3-yn-2-ol | no data |

114

Example H28: 2-(3-(1H-pyrazol-4-yl)phenyl)-1,1,1-trifluorobut-3-yn-2-ol

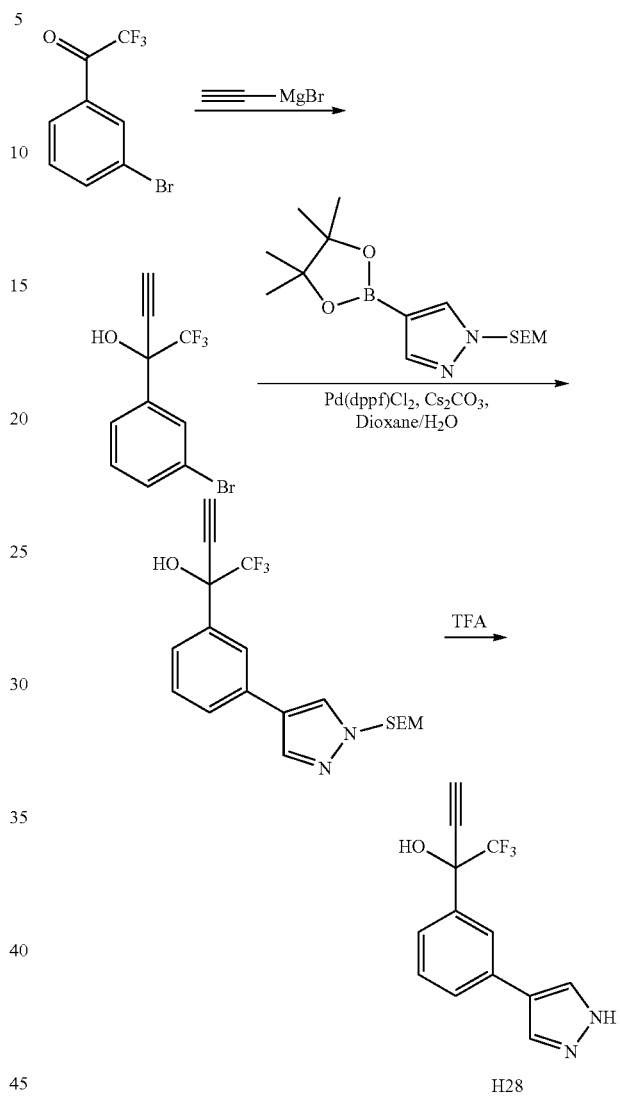

Step 1

2-(3-bromophenyl)-1,1,1-trifluorobut-3-yn-2-ol

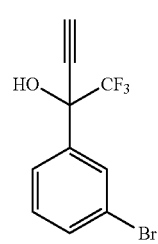

To a solution of 1-(3-bromophenyl)-2,2,2-trifluoroethanone (1.00 g, 3.95 mmol) in THF (10 mL) at 0° C. was added ethynylmagnesium bromide (0.5 M in THF, 19.7 mL, 9.85 mmol). The reaction was stirred at ambient temperature for 16 h and then quenched by the addition of saturated aqueous NH₄Cl (20 mL) and water (10 mL). The mixture was extracted with EtOAc (2×30 mL). The combined organic layers were dried over anhydrous Na₂SO₄, filtered and concentrated under reduced pressure to give the crude title compound (1.00 g, 91% yield) as a brown oil.

Step 2

1,1,1-trifluoro-2-(3-(1-((2-(trimethylsilyl)ethoxy)methyl)-1H-pyrazol-4-yl)phenyl)but-3-yn-2-ol

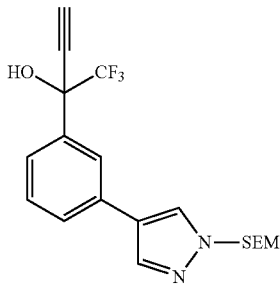 [SMILES: C#CC(O)(c1cccc(-c2cnn(COCC[Si](C)(C)C)c2)c1)C(F)(F)F]

To a solution of 4-(4,4,5,5-tetramethyl-1,3,2-dioxaborolan-2-yl)-1H-pyrazole (1.00 g, 5.15 mmol) in DMF (20 mL) was added K₂CO₃ (1.07 g, 7.73 mmol) and (2-(chloromethoxy)ethyl)trimethylsilane (1.03 g, 6.18 mmol). The reaction was stirred at ambient temperature for 16 h and then diluted with water (20 mL). The mixture was extracted with EtOAc (2×30 mL). The combined organic layers were dried over anhydrous Na₂SO₄ and concentrated under reduced pressure to give the crude 4-(4,4,5,5-tetramethyl-1,3,2-dioxaborolan-2-yl)-1-((2-(trimethylsilyl)ethoxy) methyl)-1H-pyrazole (1.00 g, 60% yield) as a yellow oil.

A mixture of 2-(3-bromophenyl)-1,1,1-trifluorobut-3-yn-2-ol (500 mg, 1.79 mmol), 4-(4,4,5,5-tetramethyl-1,3,2-dioxaborolan-2-yl)-1-((2-(trimethylsilyl)ethoxy)methyl)-1H-pyrazole (872 mg, 2.69 mmol), Cs₂CO₃ (1.17 g, 3.58 mmol) and 1,1'-Bis(diphenylphosphion) ferrocene dichloride palladium(II) (66 mg, 0.09 mmol) in dioxane/H₂O (5 mL/1 mL) was heated at 110° C. for 0.5 h under microwave conditions. The solvent was removed and the crude residue was purified by column chromatography (petroleum ether:EtOAc=4:1) to give the title compound (300 mg, 42% yield) as a colorless oil.

Step 3

2-(3-(1H-pyrazol-4-yl)phenyl)-1,1,1-trifluorobut-3-yn-2-ol

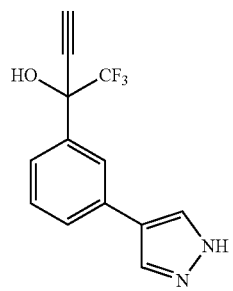 [SMILES: C#CC(O)(c1cccc(-c2cn[nH]c2)c1)C(F)(F)F]

To a solution of 1,1,1-trifluoro-2-(3-(1-((2-(trimethylsilyl)ethoxy)methyl)-1H-pyrazol-4-yl)phenyl)but-3-yn-2-ol (300 mg, 0.76 mmol) in DCM (3 mL) was added 2,2,2-trifluoroacetic acid (1 mL). The reaction was stirred at ambient temperature for 3 h and then concentrated under reduced pressure. The residue was dissolved in MeOH (10 mL) and adjusted to pH 7-8 by the addition of solid K₂CO₃. The solid was removed by filtration and the filtrate was concentrated under reduced pressure to give the crude title compound (H28) (200 mg, 99% yield) as a white solid.

The following compound was prepared in a similar fashion to Example H28

Example H29

| Example | Structure | Compound Name |
|---|---|---|
| H29 | ![structure] | 2-(3-(1H-pyrazol-3-yl)phenyl)-1,1,1-trifluorobut-3-yn-2-ol |

Example H30: (((2-methylbut-3-yn-2-yl)oxy)methyl)benzene

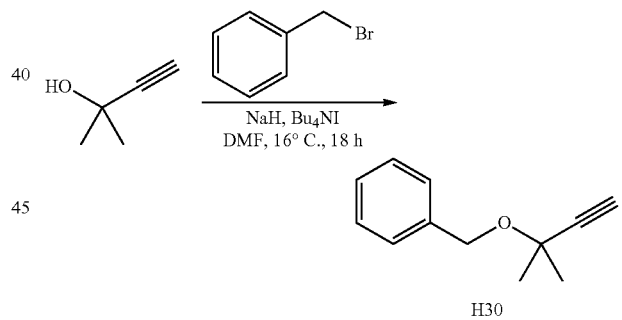

H30

To a solution of 2-methylbut-3-yn-2-ol (2.00 g, 23.78 mmol) in THF (100 mL) at 0° C. was added NaH (60%, 1.05 g, 26.15 mmol). The mixture was stirred at ambient temperature for 1 h before tetrabutylammonium iodide (0.35 g, 0.95 mmol) and benzylbromide (4.88 g, 28.53 mmol) were added. The reaction was stirred at ambient temperature for 18 h and quenched by the addition of saturated aqueous NH₄Cl solution (10 mL). The solvent was evaporated under reduced pressure, and the residue was diluted with EtOAc (100 mL). The solution was washed with water (3×100 mL) and brine (100 mL) and dried over anhydrous Na₂SO₄ and concentrated. The residue was purified by column chromatography (petroleum ether:EtOAc=10:1) to give the title compound (H30) (2.40 g, 57% yield) as a colorless oil. ¹H NMR (400 MHz, CDCl₃) δ 7.39-7.32 (m, 5H), 4.65 (s, 2H), 2.45 (s, 1H), 1.57 (s, 6H).

Example H31: 3-ethynyl-3-methyloxetane

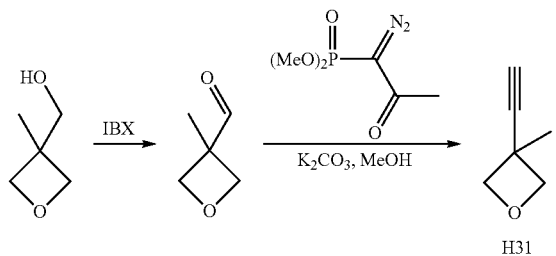

H31

Step 1

3-methyloxetane-3-carbaldehyde

To a solution of (3-methyloxetan-3-yl)methanol (6.00 g, 58.75 mmol) in ACN (300 mL) was added 2-iodyoxybenzoic acid (19.74 g, 70.50 mmol). The reaction was heated to reflux temperature for 2 h. The reaction was cooled to ambient temperature, then diluted with ACN (200 mL) and filtered. The filtrate was concentrated under reduced pressure to give the crude title compound (5.00 g, 85% yield) as a colorless oil. $^1$H NMR (400 MHz, CDCl$_3$) δ 9.93 (s, 1H), 4.86 (d, J=6.4 Hz, 2H), 4.49 (d, J=6.4 Hz, 2H), 1.46 (s, 3H).

Step 2

3-ethynyl-3-methyloxetane

To a solution of 3-methyloxetane-3-carbaldehyde (3.00 g, 29.97 mmol) in MeOH at 0° C. (100 mL) was added K$_2$CO$_3$ (20.71 g, 149.83 mmol) and 1-diazo-1-dimethoxyphosphoryl-propan-2-one (6.04 g, 31.46 mmol). The reaction was stirred at ambient temperature for 2 h and filtered. The filtrate was diluted with water (300 mL) and extracted with tert-butyl methyl ether (3×150 mL). The combined organic layers were concentrated under reduced pressure to give the crude title compound (H31) (700 mg, 24% yield) as a yellow oil. $^1$H NMR (400 MHz, CDCl$_3$) δ 4.82 (d, J=5.2 Hz, 2H), 4.84 (d, J=5.6 Hz, 2H), 2.37 (s, 1H), 1.62 (s, 3H).

Example H32: N-(2-methylbut-3-yn-2-yl)acetamide

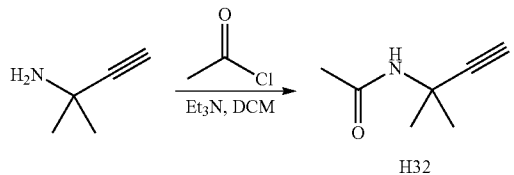

H32

To a solution of 2-methylbut-3-yn-2-amine (500 mg, 6.01 mmol) in DCM (10 mL) at 0° C. was added TEA (910 mg, 9.02 mmol) and acetyl chloride (470 mg, 6.01 mmol). The reaction was stirred at ambient temperature for 0.5 h. The reaction was then diluted with DCM (10 mL) and washed with water (2×10 mL). The organic layer was dried over anhydrous Na$_2$SO$_4$ and concentrated under reduced pressure. The residue was purified by column chromatography (petroleum ether:EtOAc=3:1) to give the title compound (H32) (500 mg, 66% yield) as a white solid.

Example H33: 2,2-dimethylbut-3-ynamide

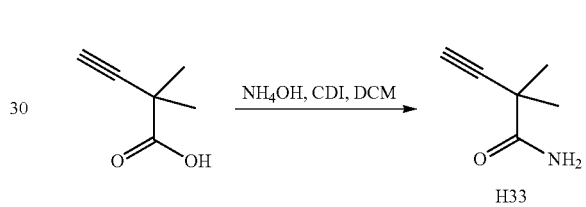

H33

To a solution of 2,2-dimethylbut-3-ynoic acid (0.80 g, 7.14 mmol) in DCM (10 mL) was added 1,1'-Carbonyldiimidazole (1.50 g, 9.28 mmol). The reaction was stirred at ambient temperature for 0.5 h before aqueous ammonia (3 mL) was added. The reaction was stirred for another 3 h and diluted with DCM (15 mL). The organic layer was washed with water (20 mL), dried over anhydrous Na$_2$SO$_4$ and concentrated under reduced pressure to give the crude title compound (H33) (0.50 g, 63% yield) as a colorless oil.

The following compounds were prepared in a similar fashion to Example H33

Examples H34-H35

| Example | Structure | Compound Name |
| --- | --- | --- |
| H34 | 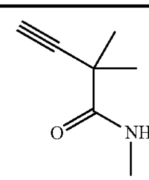 | N,2,2-trimethylbut-3-ynamide |
| H35 | 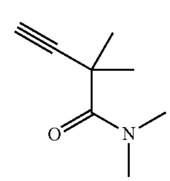 | N,N,2,2-tetramethylbut-3-ynamide |

Example H36: 1-ethynylcyclopropanol

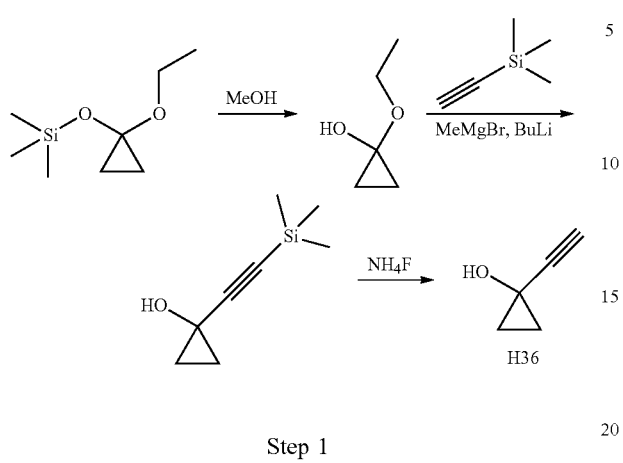

Step 1

1-ethoxycyclopropanol

A solution of (1-ethoxycyclopropyl)oxy-trimethylsilane (12 mL, 59.60 mmol) in MeOH (10 mL) was stirred at ambient temperature for 21 h. The solvent was evaporated under reduced pressure to give the crude title compound (5.60 g, 92% yield) as a colorless oil.

Step 2

1-(((trimethylsilyl)ethynyl)cyclopropanol

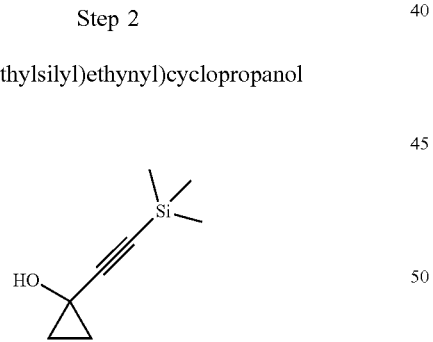

To a solution of methylmagnesium bromide (48 mmol) in THF (60 mL) at 0° C. was added 1-ethoxycyclopropanol (4.90 g, 48 mmol) in THF (30 mL) dropwise. The reaction was stirred for 1 h.

To a solution of (trimethylsilyl)ethyne (5.20 g, 53 mmol) in THF (50 mL) at −78° C. was added n-BuLi (2.5 M, 22 mL, 55 mmol). The resulting [(trimethylsilyl)ethynyl] lithium was added into the solution of bromide magnesium 1-ethoxy cyclopropanolate at 0° C. The reaction was heated at 40° C. for 17 h and then quenched by the addition of saturated aqueous NH₄Cl (60 mL) and was extracted with EtOAc (2×80 mL). The combined organic layers were washed with water (2×80 mL), dried over anhydrous MgSO₄, filtered and concentrated under reduced pressure to give the crude title compound (6.00 g, 74% yield) as a colorless oil.

Step 3

1-ethynylcyclopropanol

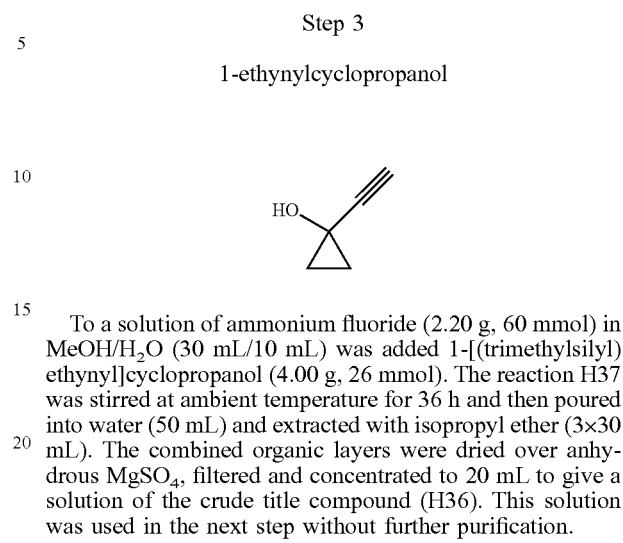

To a solution of ammonium fluoride (2.20 g, 60 mmol) in MeOH/H₂O (30 mL/10 mL) was added 1-[(trimethylsilyl)ethynyl]cyclopropanol (4.00 g, 26 mmol). The reaction H37 was stirred at ambient temperature for 36 h and then poured into water (50 mL) and extracted with isopropyl ether (3×30 mL). The combined organic layers were dried over anhydrous MgSO₄, filtered and concentrated to 20 mL to give a solution of the crude title compound (H36). This solution was used in the next step without further purification.

Example H37: 2-methyl-1-(phenylamino)but-3-yn-2-ol

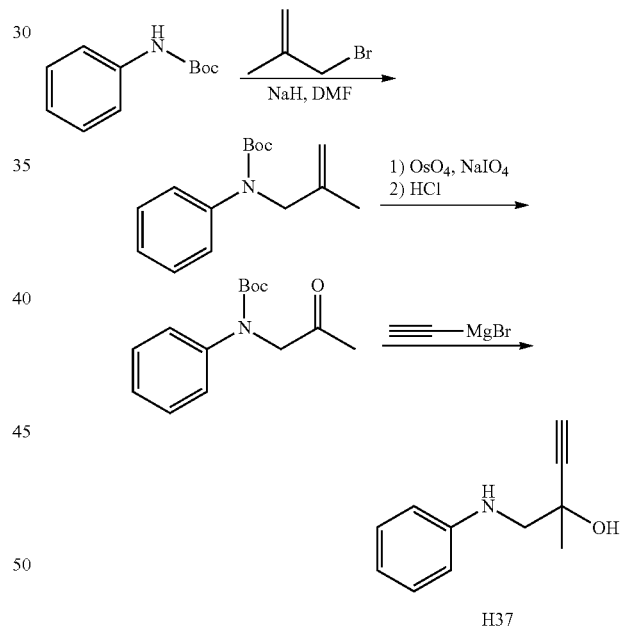

Step 1 tert-butyl (2-methylallyl)(phenyl)carbamate

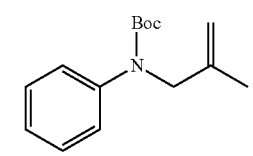 [SMILES: C=C(C)CN(C(=O)OC(C)(C)C)c1ccccc1]

To a solution of tert-butyl phenylcarbamate (5.20 g, 26.91 mmol) in THF (60 mL) at 0° C. was added NaH (60%, 2.15 g, 53.82 mmol). The mixture was stirred for 30 min before 3-bromo-2-methylprop-1-ene (11.00 g, 81.48 mmol) was added. The reaction was stirred at ambient temperature for 12 h. The reaction was quenched by the addition of saturated aqueous NH₄Cl (30 mL) and extracted with EtOAc (3×50 mL). The combined organic layers were concentrated under reduced pressure. The residue was purified by column chromatography (petroleum ether:EtOAc=3:1) to give the title compound (4.60 g, 69% yield) as a white solid.

Step 2 tert-butyl (2-oxopropyl)(phenyl)carbamate

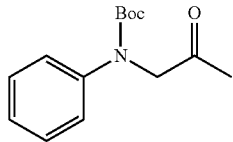 [SMILES: CC(=O)CN(C(=O)OC(C)(C)C)c1ccccc1]

To a solution of tert-butyl (2-methylallyl)(phenyl)carbamate (4.50 g, 18.22 mmol) in dioxane/H₂O (50 mL/20 mL) was added sodium periodate (15.57 g, 72.78 mmol) and Osmium tetroxide (0.19 g, 0.73 mmol). The reaction was stirred at ambient temperature for 12 h and then diluted with water (50 mL). The mixture was extracted with EtOAc (2×100 mL). The combined organic layers were dried over anhydrous Na₂SO₄ and concentrated under reduced pressure. The residue was purified by column chromatography (petroleum ether:EtOAc=3:1) to give the title compound (3.80 g, 84% yield) as a colorless oil. ¹H NMR (400 MHz, CDCl₃) δ 7.34-7.29 (m, 2H), 7.27-7.22 (m, 2H), 7.21-7.16 (m, 1H), 4.34 (s, 2H), 2.17 (s, 3H), 1.43 (s, 9H).

Step 3

1-(phenylamino)propan-2-one

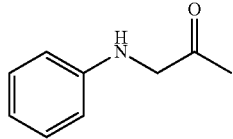

To a solution of tert-butyl (2-oxopropyl)(phenyl)carbamate (3.80 g, 15.26 mmol) in EtOAc (20 mL) at 0° C. was added HCl (4 N in EtOAc, 20 mL). The reaction was stirred at ambient temperature for 2 h and then concentrated under reduced pressure. The residue was diluted with EtOAc (50 mL) and washed with saturated aqueous NaHCO₃ (2×30 mL). The organic layer was dried over anhydrous Na₂SO₄ and concentrated to give the crude title compound (2.20 g, 95% yield) as a yellow solid. This crude was used in the next step immediately without further purification.

Step 4

2-methyl-1-(phenylamino)but-3-yn-2-ol

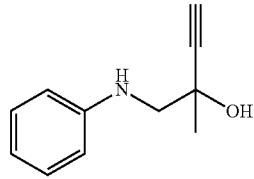

To a solution of 1-(phenylamino)propan-2-one (2.20 g, 14.75 mmol) in THF (40 mL) at 0° C. was added ethynylmagnesium bromide (0.5 M, 44 mL, 22.12 mmol). The reaction was stirred at ambient temperature for 15 h and then quenched by the addition of saturated aqueous NH₄Cl (20 mL). The resulting mixture was extracted with EtOAc (3×40 mL). The combined organic layers were dried over anhydrous Na₂SO₄, filtered and concentrated under reduced pressure. The residue was purified by column chromatography (petroleum ether:EtOAc=7:1) to give the title compound (H37) (420 mg, 18% yield) as a yellow oil. ¹H NMR (400 MHz, CDCl₃) δ 7.26-7.16 (m, 2H), 6.79-6.72 (m, 3H), 3.34-3.30 (m, 2H), 2.50 (s, 1H), 1.57 (s, 3H).

Example H38: 4-ethynylpiperidin-4-ol

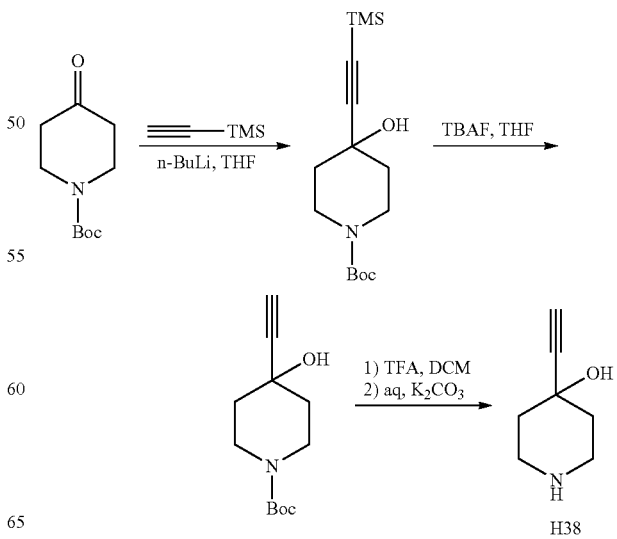

Step 1 tert-butyl 4-hydroxy-4-((trimethylsilyl)ethynyl)piperidine-1-carboxylate

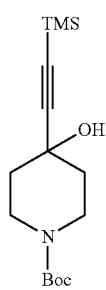

To a solution of ethynyltrimethylsilane (5.42 g, 50.21 mmol) in THF (100 mL) at −78° C. was added n-BuLi (2.5 M, 22.1 mL, 55.25 mmol). After stirring for 1 h at −78° C., tert-butyl 4-oxopiperidine-1-carboxylate (10.00 g, 50.19 mmol) was added. The reaction was stirred at ambient temperature for 3 h and then quenched by the addition of saturated aqueous NH$_4$Cl (100 mL). The mixture was extracted with EtOAc (3×150 mL) and the combined organic layers were concentrated under reduced pressure. The residue was purified by column chromatography (petroleum ether:EtOAc=4:1) to give the title compound (10.00 g, 67% yield) as a white solid. $^1$H NMR (400 MHz, CDCl$_3$) δ 3.75-3.69 (m, 2H), 3.25-3.17 (m, 2H), 2.29 (s, 1H), 1.89-1.83 (m, 2H), 1.71-1.63 (m, 1H), 1.46 (s, 9H), 0.17 (s, 9H).

Step 2 tert-butyl 4-ethynyl-4-hydroxypiperidine-1-carboxylate

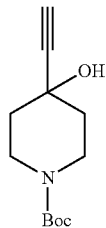 [SMILES: C#CC1(O)CCN(C(=O)OC(C)(C)C)CC1]

To a solution of tert-butyl 4-hydroxy-4-(2-trimethylsilylethynyl)piperidine-1-carboxylate (5.00 g, 16.81 mmol) in THF (150 mL) at 0° C. was added TBAF (5.57 g, 17.65 mmol). The reaction was stirred at 30° C. for 16 h and then concentrated under reduced pressure. The residue was dissolved in water (50 mL) and extracted with EtOAc (2×50 mL). The combined organic layers were concentrated under reduced pressure. The residue was purified by column chromatography (petroleum ether:EtOAc=7:3) to give the title compound (3.00 g, 79% yield) as a white solid.

Step 3

4-ethynylpiperidin-4-ol

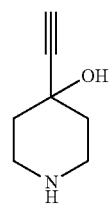

To a solution of tert-butyl 4-ethynyl-4-hydroxypiperidine-1-carboxylate (3.00 g, 13.32 mmol) in EtOAc (15 mL) at 0° C. was added 2,2,2-trifluoroacetic acid (1 mL). The reaction was stirred at ambient temperature for 3 h and then evaporated under reduced pressure. The residue was dissolved in MeOH (15 mL), and adjusted to pH 7-8 with aqueous K$_2$CO$_3$ (4 M). The mixture was diluted with water (15 mL) and extracted with EtOAc (3×20 mL). The combined organic layers were dried over anhydrous Na$_2$SO$_4$ and concentrated under reduced pressure to give the crude title compound (H38) (1.50 g, 90% yield) as a yellow oil. $^1$H NMR (400 MHz, CDCl$_3$) δ 3.07-3.02 (m, 2H), 2.89-2.84 (m, 2H), 2.52 (s, 1H), 1.96-1.91 (m, 2H), 1.71-1.66 (m, 2H).

Example H39: 1-ethyl-4-ethynylpiperidin-4-ol

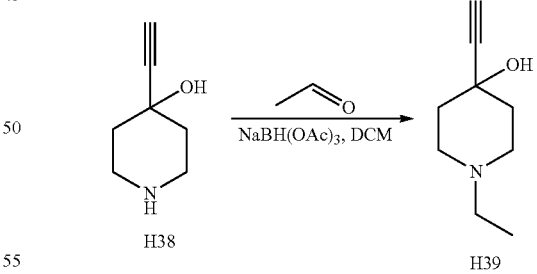

To a solution of 4-ethynylpiperidin-4-ol (H38) (322 mg, 2.57 mmol) in DCM (5 mL) was added acetaldehyde (567 mg, 12.86 mmol). The mixture was stirred at 25° C. for 2 h before sodium triacetylhydroborate (1.09 g, 5.15 mmol) was added. The reaction was stirred for 1 h and then quenched by the addition of saturated aqueous NH$_4$Cl (10 mL) and extracted with DCM (3×20 mL). The combined organic layers were dried over anhydrous Na$_2$SO$_4$, filtered and concentrated under reduced pressure to give the crude title compound (H39) (200 mg, 51% yield) as a yellow oil.

Example H40: 1-(4-ethynyl-4-hydroxypiperidin-1-yl)ethanone

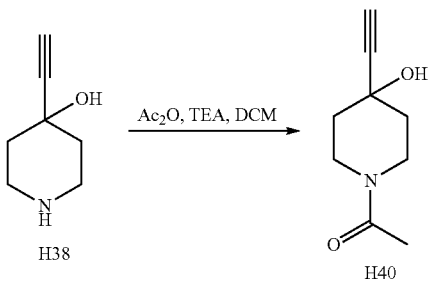

To a solution of 4-ethynylpiperidin-4-ol (H38) (250 mg, 2.00 mmol) in DCM (10 mL) was added acetic anhydride (306 mg, 3.00 mmol) and TEA (404 mg, 3.99 mmol). The reaction was stirred at ambient temperature for 1 h and then quenched by the addition of water (15 mL) and extracted with DCM (3×20 mL). The combined organic layers were dried over anhydrous $Na_2SO_4$ and concentrated under reduced pressure to give the crude title compound (H40) (300 mg, 90% yield) as a yellow oil.

The following compound was prepared in a similar fashion to Example H40

Example H41

| Example | Structure | Compound Name |
|---|---|---|
| H41 | 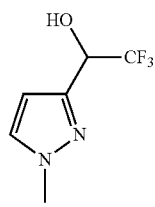 | 1-(4-ethynyl-4-hydroxypiperidin-1-yl)propan-1-one |

Example H42: 2-(1-methyl-1H-pyrazol-3-yl)but-3-yn-2-ol

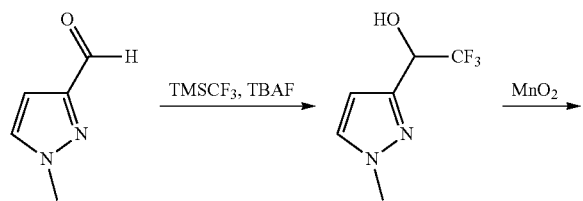

-continued

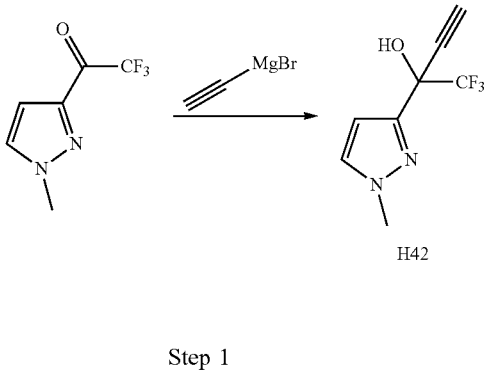

Step 1

2,2,2-trifluoro-1-(1-methyl-1H-pyrazol-3-yl)ethanol

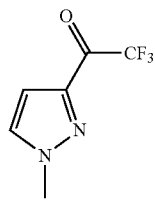

To a solution of 1-methyl-1H-pyrazole-3-carbaldehyde (1.00 g, 9.08 mmol) in THF (10 mL) at 0° C. was added trimethyl(trifluoromethyl)silane (2.58 g, 18.16 mmol) and TBAF (238 mg, 0.91 mmol). The reaction was stirred at ambient temperature for 3 h and then poured into water (10 mL) and extracted with EtOAc (3×10 mL). The combined organic layers were dried over anhydrous $Na_2SO_4$, filtered and concentrated under reduced pressure to give the crude title compound (1.60 g, 98% yield) as a yellow oil.

Step 2

2,2,2-trifluoro-1-(1-methyl-1H-pyrazol-3-yl)ethanone

To a solution of 2,2,2-trifluoro-1-(1-methyl-1H-pyrazol-3-yl)ethanol (1.60 g, 8.83 mmol) in DMF (20 mL) was added manganese dioxide (2.53 g, 29.15 mmol). The reaction was heated at 100° C. for 15 h and filtered. The filtrate was concentrated under reduced pressure. The residue was purified by column chromatography (petroleum ether:EtOAc=9:1) to give the title compound (800 mg, 51% yield) as a yellow oil.

Step 3

2-(1-methyl-1H-pyrazol-3-yl)but-3-yn-2-ol

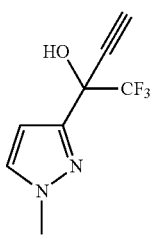

To a solution of 2,2,2-trifluoro-1-(1-methyl-1H-pyrazol-3-yl)ethanone (600 mg, 3.37 mmol) in THF (10 mL) at 0° C. was added ethynylmagnesium bromide (0.5 M, 8.1 mL, 4.04 mmol). The reaction was stirred at ambient temperature for 15 h and then poured into water (10 mL). The solution was extracted with EtOAc (3×10 mL). The combined organic layers were dried over anhydrous $Na_2SO_4$, filtered and concentrated under reduced pressure to give the crude title compound (H42) (500 mg, 73% yield) as a yellow oil. $^1$H NMR (400 MHz, $CDCl_3$) δ 7.39 (d, J=2.4 Hz, 1H), δ 6.44 (s, 1H), δ 4.48 (s, 1H), δ 3.93 (s, 3H), δ 2.70 (s, 1H).

Example H43: 3-methyl-5-(1,1,1-trifluoro-2-hydroxybut-3-yn-2-yl)phenol

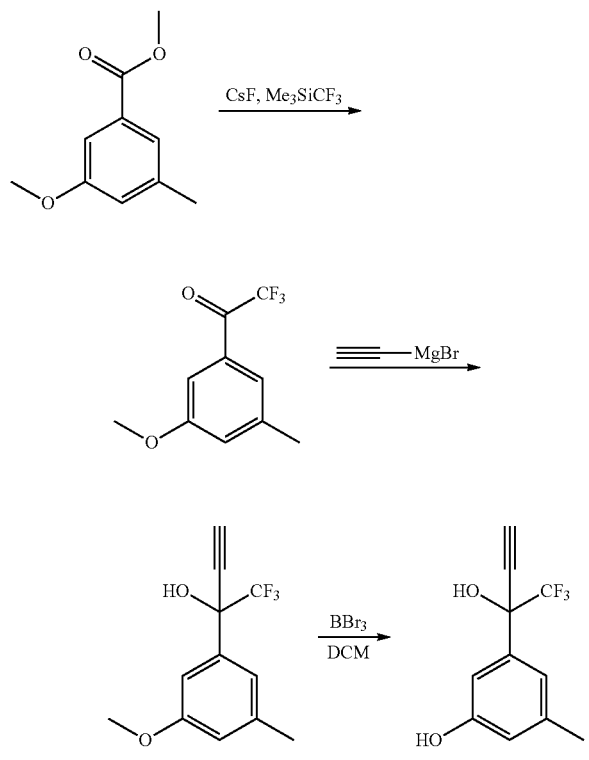

Step 1

2,2,2-trifluoro-1-(3-methoxy-5-methylphenyl)ethan-1-one

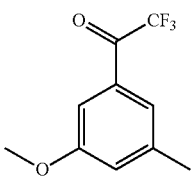

To a vial was added methyl 3-methoxy-5-methylbenzoate (1.0 g, 5.54 mmol), trimethyl(trifluoromethyl)silane (1.08 mL, 7.3 mmol) and cesium fluoride (8.4 mg, 55 μmol). The reaction was stirred at ambient temperature for 48 h then poured into THF (20 mL) and treated with 6N HCl (2 mL). The reaction was stirred for additional 2 h, then neutralized to pH ~7, and extracted with EtOAc (3×). The combined organic layers were dried over anhydrous $Na_2SO_4$, filtered and concentrated. The residue was purified by column chromatography (hexane:EtOAc=8:2) to give the title compound (724 mg, 60% yield) as a colorless oil. LCMS M/Z (M+H) 219.

Step 2

1,1,1-trifluoro-2-(3-methoxy-5-methylphenyl)but-3-yn-2-ol

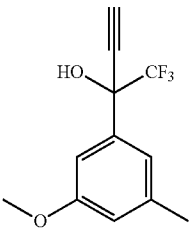

To a solution of 2,2,2-trifluoro-1-(3-methoxy-5-methylphenyl)ethanone (0.724 g, 3.3 mmol) in THF (10 mL) at 0° C. was added ethynylmagnesium bromide (0.5M in THF, 13.2 mL, 6.62 mmol). The reaction was stirred at ambient temperature for 48 h and then quenched with (1:1:1) 1N HCl, water and brine (120 mL). The mixture was extracted with EtOAc (3×) and the combined organic layers were washed with brine and then dried over anhydrous $Na_2SO_4$, filtered and concentrated. The residue was purified by column chromatography (hexane:EtOAc=8.5:1.5) to give the title compound (712 mg, 88% yield) as a pale yellow oil. LCMS M/Z (M+H) 245.

Step 3
3-methyl-5-(1,1,1-trifluoro-2-hydroxybut-3-yn-2-yl) phenol

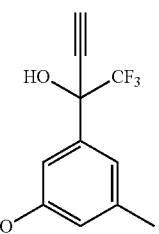

To a solution of 1,1,1-trifluoro-2-(3-methoxy-5-methylphenyl)but-3-yn-2-ol (618 mg, 2.5 mmol) in DCM (10 mL) at 0° C. was added boron tribromide (1M in DCM, 5.56 mL, 5.56 mmol). The reaction was stirred at ambient temperature for 1.5 h and quenched with MeOH (10 mL) and then concentrated. The residue was dissolved in THF (20 mL) and treated with 1N HCl (20 mL) for 1 h. The solution was adjusted to pH ~7 and further diluted with brine and extracted with EtOAc (3×). The combined organic layers were dried over anhydrous $Na_2SO_4$, filtered and concentrated. The residue was purified by column chromatography (hexane:EtOAc=7.5:2.5) to give the title compound (H43) (607.3 mg, 104% yield) as a colorless oil. LCMS M/Z (M+H) 231.

The following compound was prepared in a similar fashion to Example H43

Example H44

| Example | Structure | Compound Name |
|---|---|---|
| H44 | 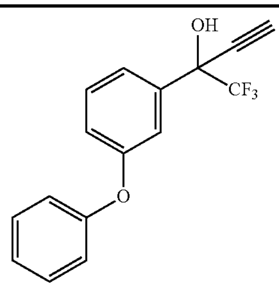 | 1,1,1-trifluoro-2-(3-phenoxyphenyl)but-3-yn-2-ol |

Example 1
ethyl 2,6-dimethyl-7-oxo-4-(4,4,4-trifluoro-3-hydroxy-3-(3-pyridyl) but-1-ynyl)-1H-pyrrolo[2,3-c]pyridine-3-carboxylate

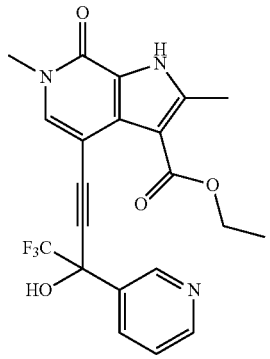 [SMILES: CCOC(=O)c1c(C)[nH]c2c(=O)n(C)cc(C#CC(O)(c3cccnc3)C(F)(F)F)c12]

To a suspension of ethyl 4-bromo-2,6-dimethyl-7-oxo-6,7-dihydro-1H-pyrrolo[2,3-c]pyridine-3-carboxylate (Intermediate B) (100 mg, 0.32 mmol) in DMF (3 mL) and TEA (1 mL) was added 1,1,1-trifluoro-2-(pyridin-3-yl)but-3-yn-2-ol (H23) (129 mg, 0.64 mmol), bis(triphenylphosphine) palladium(II) dichloride (21 mg, 0.03 mmol) and copper(I) iodide (11 mg, 0.06 mmol). The reaction was purged with $N_2$ for 5 min and then stirred at 110° C. for 1 h under microwave conditions. The reaction was concentrated under reduced pressure. The crude product was purified by reverse phase chromatography (ACN 30-60%/0.2% formic acid in water) to give the title compound (19 mg, 14% yield) as a white solid. $^1$H NMR (400 MHz, DMSO-$d_6$) δ 12.72 (br. s, 1H), 8.77 (br. s, 1H), 8.21 (d, J=8.4 Hz, 1H), 8.02 (s, 1H), 7.78 (s, 1H), 7.63-7.48 (m, 1H), 4.20-4.05 (m, 2H), 3.57 (s, 3H), 2.45 (s, 3H), 1.15 (t, J=7.2 Hz, 3H). LCMS M/Z (M+H) 434.

The following compounds were prepared in a similar fashion to Example 1

Examples 2-90

| Example | Compound Name | NMR | m/z |
|---|---|---|---|
| 2 | ethyl 4-[3-(3-aminophenyl)-4,4,4-trifluoro-3-hydroxy-but-1-ynyl]-2,6-dimethyl-7-oxo-1H-pyrrolo[2,3-c]pyridine-3-carboxylate | $^1$H NMR (400 MHz, CD$_3$OD) δ 7.62 (s, 1 H), 7.24 (s, 1 H), 7.17-7.11 (m, 2 H), 6.79-6.72 (m, 1 H), 4.22-4.12 (m, 2 H), 3.65 (s, 3 H), 2.59 (s, 3 H), 1.22 (t, J = 7.2 Hz, 3 H). | 470 (M + Na) |
| 3 | ethyl 4-[3-[4-(dimethylamino)phenyl]-4,4,4-trifluoro-3-hydroxy-but-1-ynyl]-2,6-dimethyl-7-oxo-1H-pyrrolo[2,3-c]pyridine-3-carboxylate | $^1$H NMR (400 MHz, DMSO-$d_6$) δ 12.70 (br. s, 1 H), 7.70 (s, 1 H), 7.56 (d, J = 8.4 Hz, 2 H), 7.37 (s, 1 H), 6.73 (d, J = 8.4 Hz, 2 H), 4.14-4.08 (m, 2 H), 3.57 (s, 3 H), 2.91 (s, 6 H), 2.50 (s, 3 H), 1.14 (t, J = 7.2 Hz, 3 H). | 458 (M − OH) |
| 4 | ethyl 4-[3-hydroxy-3-(1-methylcyclopropyl)but-1-ynyl]-2,6-dimethyl-7-oxo-1H-pyrrolo[2,3-c]pyridine-3-carboxylate | $^1$H NMR (400 MHz, CD$_3$OD) δ 7.42 (s, 1 H), 4.44-4.33 (m, 2 H), 3.61 (s, 3 H), 2.58 (s, 3 H), 1.57 (s, 3 H), 1.39 (t, J = 7.2 Hz, 3 H), 1.21 (s, 3 H), 0.97-0.78 (m, 2 H), 0.31-0.21 (m, 2 H). | 339 (M − OH) |
| 5 | ethyl 4-[(3S)-3-hydroxy-3-pyrimidin-2-yl-but-1-ynyl]- | $^1$H NMR (400 MHz, CD$_3$OD) δ 8.84 (d, J = 4.8 Hz, 2 H), 7.50 (s, | 403 (M + Na) |

| Example | Compound Name | NMR | m/z |
|---|---|---|---|
|  | 2,6-dimethyl-7-oxo-1H-pyrrolo[2,3-c]pyridine-3-carboxylate | 1 H), 7.44 (t, J = 5.2 Hz, 1 H), 4.29-4.20 (m, 2 H), 3.60 (s, 3 H), 2.56 (s, 3 H), 1.95 (s, 3 H), 1.29 (t, J = 7.2 Hz, 3 H). |  |
| 6 | ethyl 4-[(3R)-3-hydroxy-3-pyrimidin-2-yl-but-1-ynyl]-2,6-dimethyl-7-oxo-1H-pyrrolo[2,3-c]pyridine-3-carboxylate | $^1$H NMR (400 MHz, DMSO-$d_6$) δ 12.56 (br. s, 1 H), 8.88-8.85 (m, 2 H), 7.49-7.46 (m, 1 H), 5.89 (s, 1 H), 4.16-4.08 (m, 2 H), 3.50 (s, 3 H), 2.45 (s, 3 H), 1.86 (s, 3 H), 1.16 (t, J = 6.8 Hz, 3 H). | 381 |
| 7 | ethyl 4-(3-hydroxy-3-tetrahydrofuran-3-yl-but-1-ynyl)-2,6-dimethyl-7-oxo-1H-pyrrolo[2,3-c]pyridine-3-carboxylate | $^1$H NMR (400 MHz, CD$_3$OD) δ 7.48-7.46 (m, 1 H), 4.40-4.33 (m, 2 H), 3.97-3.89 (m, 2 H), 3.85-3.74 (m, 2 H), 3.61 (s, 3 H), 2.63-2.57 (m, 4 H), 2.14-1.98 (m, 2 H), 1.57-1.52 (m, 3 H), 1.39 (t, J = 7.2 Hz, 3 H). | 355 (M − OH) |
| 8 | ethyl 4-[2-(1-ethyl-4-hydroxy-4-piperidyl)ethynyl]-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.52 (s, 1 H), 4.32-4.22 (m, 2 H), 3.71-3.42 (m, 9 H), 2.48 (s, 3 H), 1.92-1.90 (m, 2 H), 1.77-1.75 (m, 2 H), 1.29 (t, J = 7.2 Hz, 3 H), 1.03 (t, J = 6.8 Hz, 3 H). | 386 |
| 9 | ethyl 4-[2-(4-hydroxy-1-methyl-4-piperidyl)ethynyl]-2,6-dimethyl-7-oxo-1H-pyrrolo[2,3-c]pyridine-3-carboxylate | $^1$H NMR (400 MHz, DMSO-$d_6$) δ 12.56 (br. s, 1 H), 8.19 (br. s, 1 H), 7.52 (s, 1 H), 5.33 (s, 1 H), 4.32-4.22 (m, 2 H), 3.52 (s, 3 H), 3.42-3.38 (m, 4 H), 2.48 (s, 3 H), 2.22 (s, 3 H), 1.92-1.85 (m, 2 H), 1.77-1.71 (m, 2 H), 1.29 (t, J = 7.2 Hz, 3 H). | 372 |
| 10 | ethyl 4-[2-(4-hydroxy-1-propanoyl-4-piperidyl)ethynyl]-2,6-dimethyl-7-oxo-1H-pyrrolo[2,3-c]pyridine-3-carboxylate | $^1$H NMR (400 MHz, DMSO-$d_6$) δ 12.51 (br. s, 1 H), 7.57 (s, 1 H), 5.58 (s, 1 H), 4.31-4.21 (m, 2 H), 3.84-3.81 (m, 1 H), 3.63-3.60 (m, 1 H), 3.52 (s, 3 H), 3.38-3.30 (m, 2 H), 2.48 (s, 3 H), 2.35-2.30 (m, 2 H), 1.93-1.83 (m, 2 H), 1.68-1.54 (m, 2 H), 1.28 (t, J = 7.2 Hz, 3 H), 0.98 (t, J = 7.6 Hz, 3 H). | 396 (M − OH) |
| 11 | ethyl 4-[2-(1-acetyl-4-hydroxy-4-piperidyl)ethynyl]-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.58 (s, 1 H), 5.59 (s, 1 H), 4.29-4.24 (m, 2 H), 3.84-3.76 (m, 1 H), 3.65-3.58 (m, 1 H), 3.52 (s, 3 H), 3.38-3.30 (m, 2 H), 2.48 (s, 3 H), 2.00 (s, 3 H), 1.94-1.80 (m, 2 H), 1.69-1.54 (m, 2 H), 1.28 (t, J = 7.2 Hz, 3 H). | 382 (M − OH) |
| 12 | ethyl 4-[2-(4-hydroxy-4-piperidyl)ethynyl]-2,6-dimethyl-7-oxo-1H-pyrrolo[2,3-c]pyridine-3-carboxylate | $^1$H NMR (400 MHz, DMSO-$d_6$) δ 12.40 (br. s, 1 H), 7.53 (s, 1 H), 5.31 (br. s, 1 H), 4.30-4.24 (m, 2 H), 3.52 (s, 3 H), 2.84-2.78 (m, 2 H), 2.75-2.60 (m, 2 H), 2.47 (s, 3 H), 1.85-1.78 (m, 2 H), 1.58-1.45 (m, 2 H), 1.28 (t, J = 7.2 Hz, 3 H). | 358 |
| 13 | ethyl 2,6-dimethyl-4-[2-(3-methyloxetan-3-yl)ethynyl]-7-oxo-1H-pyrrolo[2,3-c]pyridine-3-carboxylate | $^1$H NMR (400 MHz, DMSO-$d_6$) δ 12.60 (br. s, 1 H), 7.59 (s, 1 H), 4.78 (d, J = 4.8 Hz, 2 H), 4.42 (d, J = 5.2 Hz, 2 H), 4.28-4.21 (m, 2 H), 3.53 (s, 3 H), 2.50 (s, 3 H), 1.64 (s, 3 H), 1.30 (t, J = 7.2 Hz, 3 H). | 351 (M + Na) |
| 14 | ethyl 4-(4-anilino-3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.40 (s, 1 H), 7.22-7.05 (m, 6 H), 6.80 (br. s, 1 H), 5.94 (s, 1 H), 3.81-3.76 (m, 2 H), 3.44 (s, 3 H), 2.34 (s, 3 H), 2.09 (s, 3 H), 1.23 (s, 3 H), 0.92 (t, J = 7.2 Hz, 3 H). | 390 (M − OH) |
| 15 | ethyl 4-(4-hydroxy-3,3-dimethyl-but-1-ynyl)-2,6- | $^1$H NMR (400 MHz, CD$_3$OD) δ 7.45 (s, 1 H), 4.40-4.34 (m, 2 | 331 |

| Example | Compound Name | NMR | m/z |
|---|---|---|---|
|  | dimethyl-7-oxo-1H-pyrrolo[2,3-c]pyridine-3-carboxylate | H), 3.62 (s, 3 H), 3.50 (s, 2 H), 2.60 (s, 3 H), 1.42 (t, J = 7.2 Hz, 3 H), 1.28 (s, 6 H). |  |
| 16 | ethyl 4-(3-hydroxy-3-methyl-4-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.50 (br. s, 1 H), 7.40 (s, 1 H), 7.34-7.31 (m, 2 H), 7.28-7.25 (m, 2 H), 7.24-7.15 (m, 1 H), 5.33 (br. s, 1 H), 4.25-4.19 (m, 2 H), 3.51 (s, 3 H), 2.99-2.91 (m, 2 H), 2.48 (s, 3 H), 1.41 (s, 3 H), 1.25 (t, J = 7.2 Hz, 3 H). | 415 (M + Na) |
| 17 | ethyl 4-(3-hydroxy-3-methyl-4-phenoxy-but-1-ynyl)-2,6-dimethyl-7-oxo-1H-pyrrolo[2,3-c]pyridine-3-carboxylate | $^1$H NMR (400 MHz, CD$_3$OD) δ 7.40 (s, 1 H), 7.30-7.25 (m, 2 H), 7.02-6.93 (m, 3 H), 4.34-4.28 (m, 2 H), 4.10 (s, 2 H), 3.59 (s, 3 H), 2.58 (s, 3 H), 1.66 (s, 3 H), 1.34 (t, J = 7.2 Hz, 3 H). | 409 |
| 18 | ethyl 4-[2-(1-hydroxycyclopropyl)ethynyl]-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.53 (s, 1 H), 6.10 (s, 1 H), 4.35-4.24 (m, 2 H), 3.50 (s, 3 H), 2.46 (s, 3 H), 1.30 (t, J = 7.2 Hz, 3 H), 0.93 (m, 4 H). | 315 |
| 19 | ethyl 4-[3-(3-cyanophenyl)-3-hydroxy-but-1-ynyl]-2,6-dimethyl-7-oxo-1H-pyrrolo[2,3-c]pyridine-3-carboxylate | $^1$H NMR (400 MHz, CD$_3$OD) δ 8.16-8.14 (m, 1 H), 8.07-8.03 (m, 1 H), 7.67-7.64 (m, 1 H), 7.57-7.53 (m, 2 H), 4.31-4.25 (m, 2 H), 3.62 (s, 3 H), 2.60 (s, 3 H), 1.82 (s, 3 H), 1.32 (t, J = 7.2 Hz, 3 H). | 426 (M + Na) |
| 20 | ethyl 4-[2-(1-hydroxycyclopentyl)ethynyl]-2,6-dimethyl-7-oxo-1H-pyrrolo[2,3-c]pyridine-3-carboxylate | $^1$H NMR (400 MHz, DMSO-$d_6$) δ 12.55 (br. s, 1 H), 7.51 (s, 1 H), 5.11 (s, 1 H), 4.35-4.24 (m, 2 H), 3.51 (s, 3 H), 2.47 (s, 3 H), 1.89-1.86 (m, 4 H), 1.76-1.66 (m, 4 H), 1.29 (t, J = 7.2 Hz, 3 H). | 343 |
| 21 | ethyl 4-[2-(1-hydroxycyclobutyl)ethynyl]-2,6-dimethyl-7-oxo-1H-pyrrolo[2,3-c]pyridine-3-carboxylate | $^1$H NMR (400 MHz, DMSO-$d_6$) δ 12.56 (br. s, 1 H), 7.55 (s, 1 H), 5.67 (s, 1 H), 4.29-4.23 (m, 2 H), 3.56 (s, 3 H), 2.48 (s, 3 H), 2.40-2.37 (m, 2 H), 2.20-2.16 (m, 2 H), 1.80-1.75 (m, 2 H), 1.28 (t, J = 7.2 Hz, 3 H). | 329 |
| 22 | ethyl 4-(3-acetamido-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.28 (br. s, 1 H), 7.91 (s, 1 H), 7.44 (s, 1 H), 4.28-4.22 (m, 2 H), 3.51 (s, 3 H), 2.47 (s, 3 H), 1.80 (s, 3 H), 1.57 (s, 6 H), 1.28 (t, J = 7.2 Hz, 3 H). | 358 |
| 23 | ethyl 4-(3-hydroxy-3-methyl-5-phenyl-pent-1-ynyl)-2,6-dimethyl-7-oxo-1H-pyrrolo[2,3-c]pyridine-3-carboxylate | $^1$H NMR (400 MHz, DMSO-$d_6$) δ 12.56 (s, 1 H), 7.52 (s, 1 H), 7.30-7.22 (m, 4 H), 7.19-7.16 (m, 1 H), 5.28 (s, 1 H), 4.28-4.22 (m, 2 H), 3.53 (s, 3 H), 2.87-2.75 (m, 2 H), 2.48 (s, 3 H), 1.94-1.88 (m, 2 H), 1.50 (s, 3 H), 1.26 (t, J = 7.2 Hz, 3 H). | 407 |
| 24 | ethyl 4-(3-ethyl-3-hydroxy-pent-1-ynyl)-2,6-dimethyl-7-oxo-1H-pyrrolo[2,3-c]pyridine-3-carboxylate | $^1$H NMR (400 MHz, DMSO-$d_6$) δ 12.51 (br. s, 1 H), 7.48 (s, 1 H), 4.85 (s, 1 H), 4.29-4.23 (m, 2 H), 3.52 (s, 3 H), 2.47 (s, 3 H), 1.68-1.56 (m, 4 H), 1.27 (t, J = 7.2 Hz, 3 H), 0.97 (t, J = 7.6 Hz, 6H). | 367 (M + Na) |
| 25 | ethyl 4-(3-benzyloxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.58 (s, 1 H), 7.35-7.24 (m, 5 H), 4.66 (s, 2 H), 4.25-4.18 (m, 2 H), 3.52 (s, 3 H), 2.48 (s, 3 H), 1.56 (s, 6 H), 1.25 (t, J = 7.2 Hz, 3 H). | 407 |
| 26 | ethyl 4-(3-methoxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.59 (br. s, 1 H), 7.58 (s, 1 H), 4.27-4.21 (m, 2 H), 3.52 (s, 3 H), 3.29 (s, 3 H), 2.48 (s, 3 H), 1.45 (s, 6 H), 1.28 (t, J = 7.2 Hz, 3 H). | 353 (M + Na) |

-continued

| Example | Compound Name | NMR | m/z |
|---|---|---|---|
| 27 | ethyl 4-[3-hydroxy-3-(4-pyridyl)but-1-ynyl]-2,6-dimethyl-7-oxo-1H-pyrrolo[2,3-c]pyridine-3-carboxylate | $^1$H NMR (400 MHz, DMSO-d$_6$) δ 12.56 (br. s, 1 H), 8.56-8.54 (m, 2 H), 7.63-7.61 (m, 2 H), 7.59 (s, 1 H), 6.27 (br. s, 1 H), 4.16 (q, J = 7.2 Hz, 2 H), 3.52 (s, 3 H), 2.48 (s, 3 H), 1.71 (s, 3 H), 1.20 (t, J = 7.2 Hz, 3 H). | 402 (M + Na) |
| 28 | ethyl 4-[3-hydroxy-3-(3-pyridyl)but-1-ynyl]-2,6-dimethyl-7-oxo-1H-pyrrolo[2,3-c]pyridine-3-carboxylate | $^1$H NMR (400 MHz, DMSO-d$_6$) δ 12.44 (br. s, 1 H), 8.87 (d, J = 3.2 Hz, 1 H), 8.48 (d, J = 3.2 Hz, 1 H), 8.02-7.99 (m, 1 H), 7.59 (s, 1 H), 7.39-7.36 (m, 1 H), 6.18 (br. s, 1 H), 4.19-4.13 (m, 2 H), 3.52 (s, 3 H), 2.48 (s, 3 H), 1.76 (s, 3 H), 1.20 (t, J = 7.2 Hz, 3 H). | 380 |
| 29 | ethyl 4-[3-hydroxy-3-(m-tolyl)but-1-ynyl]-2,6-dimethyl-7-oxo-1H-pyrrolo[2,3-c]pyridine-3-carboxylate | $^1$H NMR (400 MHz, DMSO-d$_6$) δ 12.59 (br. s, 1 H), 7.55 (s, 1 H), 7.46-7.43 (m, 2 H), 7.22 (t, J = 7.6 Hz, 1 H), 7.06 (d, J = 7.6 Hz, 1 H), 5.92 (s, 1 H), 4.17-4.12 (m, 2 H), 3.53 (s, 3 H), 2.48 (s, 3 H), 2.32 (s, 3 H), 1.70 (s, 3 H), 1.19 (t, J = 7.2 Hz, 3 H). | 375 (M − OH) |
| 30 | ethyl 4-[2-(3-hydroxyoxetan-3-yl)ethynyl]-2,6-dimethyl-7-oxo-1H-pyrrolo[2,3-c]pyridine-3-carboxylate | $^1$H NMR (400 MHz, DMSO-d$_6$) δ 12.64 (br. s, 1 H), 7.65 (s, 1 H), 6.46 (s, 1 H), 4.80-4.77 (m, 2 H), 4.60-4.57 (m, 2 H), 4.28-4.22 (m, 2 H), 3.53 (s, 3 H), 2.50 (s, 3 H), 1.28 (t, J = 7.2 Hz, 3 H). | 353 (M + Na) |
| 31 | ethyl 4-[2-3-hydroxytetrahydrofuran-3-yl)ethynyl]-2,6-dimethyl-7-oxo-1H-pyrrolo[2,3-c]pyridine-3-carboxylate | $^1$H NMR (400 MHz, DMSO-d$_6$) δ 12.59 (br. s, 1 H), 7.57 (s, 1 H), 5.67 (s, 1 H), 4.28-4.23 (m, 2 H), 3.90-3.85 (m, 2 H), 3.82-3.77 (m, 2 H), 3.51 (s, 3 H), 2.48 (s, 3 H), 2.26-2.14 (m, 2 H), 1.29 (t, J = 7.2 Hz, 3 H). | 367 (M + Na) |
| 32 | ethyl 4-[3,3-dimethyl-4-(methylamino)-4-oxo-but-1-ynyl]-2,6-dimethyl-7-oxo-1H-pyrrolo[2,3-c]pyridine-3-carboxylate | $^1$H NMR (400 MHz, DMSO-d$_6$) δ 12.66 (br. s, 1 H), 8.09 (s, 1 H), 7.60 (s, 1 H), 4.30-4.23 (m, 2 H), 3.53 (s, 3 H), 3.34 (s, 3 H), 2.71 (d, J = 4.4 Hz, 3 H), 1.39 (s, 6 H), 1.32-1.29 (m, 3 H). | 358 |
| 33 | ethyl 4-[3-(3-fluorophenyl)-3-hydroxy-but-1-ynyl]-2,6-dimethyl-7-oxo-1H-pyrrolo[2,3-c]pyridine-3-carboxylate | $^1$H NMR (400 MHz, DMSO--d6) δ 12.49 (br. s, 1 H), 7.58 (s, 1 H), 7.55-7.45 (m, 1 H), 7.42-7.38 (m, 2 H), 7.12-7.08 (m, 1 H), 6.15 (s, 1 H), 4.19-4.14 (m, 2 H), 3.53 (s, 3 H), 2.50 (s, 3 H), 1.72 (s, 3 H), 1.20 (t, J = 7.2 Hz, 3H). | 419 (M + Na) |
| 34 | ethyl 4-[(3S)-3-hydroxy-3-(5-methylisoxazol-3-yl)but-1-ynyl]-2,6-dimethyl-7-oxo-1H-pyrrolo[2,3-c]pyridine-3-carboxylate | $^1$H NMR (400 MHz, DMSO-d$_6$) δ 12.59 (br. s, 1 H), 7.55 (s, 1 H), 6.33 (s, 1 H), 6.26 (s, 1 H), 4.24-4.18 (m, 2 H), 3.52 (s, 3 H), 2.48 (s, 3 H), 2.39 (s, 3 H), 1.79 (s, 3 H), 1.23 (t, J = 7.2 Hz, 3 H). | 406 (M + Na) |
| 35 | ethyl 4-(4-cyano-3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.58 (br. s, 1 H), 7.52 (s, 1 H), 6.02 (s, 1 H), 4.28-4.22 (m, 2 H), 3.50 (s, 3 H), 2.92 (s, 2 H), 2.47 (s, 3 H), 1.54 (s, 3 H), 1.27 (t, J = 7.2 Hz, 3 H). | 342 |
| 36 | ethyl 4-[4-(dimethylamino)-3,3-dimethyl-4-oxo-but-1-ynyl]-2,6-dimethyl-7-oxo-1H-pyrrolo[2,3-c]pyridine-3-carboxylate | $^1$H NMR (400 MHz, DMSO-d$_6$, δ 12.27 (br. s, 1 H), 7.45 (s, 1 H), 4.26-4.20 (m, 2 H), 3.52 (s, 3 H), 3.04 (s, 6 H), 2.45 (s, 3 H), 1.49 (s, 6 H), 1.29 (t, J = 7.2 Hz, 3 H). | 394 (M + Na) |
| 37 | ethyl 4-(4-amino-3,3-dimethyl-4-oxo-but-1-ynyl)-2,6-dimethyl-7-oxo-1H-pyrrolo[2,3-c]pyridine-3-carboxylate | $^1$H NMR (400 MHz, DMSO-d$_6$) δ 12.63 (br. s, 1 H), 7.59 (s, 1 H), 7.48 (s, 1 H), 7.28 (s, 1 H), 4.27-4.20 (m, 2 H), 3.51 (s, 3 H), 2.45 (s, 3 H), 1.39 (s, 6 H), 1.28 (t, J = 7.2 Hz, 3 H). | 344 |
| 38 | ethyl 4-[(3R)-3-hydroxy-3-(5-methylisoxazol-3-yl)but-1-ynyl]-2,6- | $^1$H NMR (400 MHz, DMSO-d$_6$) δ 12.56 (br. s, 1 H), 7.53 (s, 1 H), 6.31 (s, 1 H), 6.23 (s, 1 H), | 384 |

| Example | Compound Name | NMR | m/z |
|---|---|---|---|
| | dimethyl-7-oxo-1H-pyrrolo[2,3-c]pyridine-3-carboxylate | 4.22-4.15 (m, 2 H), 3.50 (s, 3 H), 2.45 (s, 3 H), 2.37 (s, 3 H), 1.77 (s, 3 H), 1.21 (t, J = 7.2 Hz, 3 H). | |
| 39 | ethyl 4-[3-[3-(dimethylamino)phenyl]-4,4,4-trifluoro-3-hydroxy-but-1-ynyl]-2,6-dimethyl-7-oxo-1H-pyrrolo[2,3-c]pyridine-3-carboxylate | $^1$H NMR (400 MHz, DMSO-$d_6$) δ 12.40 (br. s, 1 H), 7.68 (s, 1 H), 7.52 (s, 1 H), 7.24-7.20 (m, 1 H), 7.14 (s, 1 H), 7.09-7.07 (m, 1 H), 6.77-6.75 (m, 1 H), 4.12-4.01 (m, 2 H), 3.56 (s, 3 H), 2.90 (s, 6 H), 2.50 (s, 3 H), 1.13 (t, J = 7.2 Hz, 3 H). | 476 |
| 40 | ethyl 4-[3-(3-cyanophenyl)-4,4,4-trifluoro-3-hydroxy-but-1-ynyl]-2,6-dimethyl-7-oxo-1H-pyrrolo[2,3-c]pyridine-3-carboxylate | $^1$H NMR (400 MHz, DMSO-$d_6$) δ 12.80 (br. s, 1 H), 8.27 (s, 1 H), 8.14-8.11 (m, 1 H), 8.08 (s, 1 H), 7.96-7.94 (m, 1 H), 7.76 (s, 1 H), 7.72-7.67 (m, 1 H), 4.17-4.09 (m, 2 H), 3.57 (s, 3 H), 2.50 (s, 3 H), 1.16 (t, J = 7.2 Hz, 3 H). | 458 |
| 41 | ethyl 2,6-dimethyl-7-oxo-4-[4,4,4-trifluoro-3-hydroxy-3-[3-(1H-pyrazol-4-yl)phenyl]but-1-ynyl]-1H-pyrrolo[2,3-c]pyridine-3-carboxylate | $^1$H NMR (400 MHz, DMSO-$d_6$) δ 12.99 (br. s, 1 H), 12.68 (br. s, 1 H), 8.20 (s, 1 H), 8.02 (s, 1 H), 7.92 (s, 1 H), 7.73-7.71 (m, 2 H), 7.67-7.65 (m, 1 H), 7.63-7.61 (m, 1 H), 7.44-7.42 (m, 1 H), 4.10-4.01 (m, 2 H), 3.57 (s, 3 H), 2.50 (s, 3 H), 1.12 (t, J = 7.2 Hz, 3 H). | 499 |
| 42 | ethyl 2,6-dimethyl-7-oxo-4-[4,4,4-trifluoro-3-hydroxy-3-(1-methylpyrazol-3-yl)but-1-ynyl]-1H-pyrrolo[2,3-c]pyridine-3-carboxylate | $^1$H NMR (400 MHz, DMSO-$d_6$) δ 12.66 (br. s, 1 H), 7.71 (s, 1 H), 7.65 (s, 1 H), 7.34 (s, 1 H), 6.45 (s, 1 H), 4.15-4.07 (m, 2 H), 3.85 (s, 3 H), 3.56 (s, 3 H), 2.50 (s, 3 H), 1.16-1.12 (t, J = 7.2 Hz, 3 H). | 437 |
| 43 | ethyl 2,6-dimethyl-7-oxo-4-[4,4,4-trifluoro-3-hydroxy-3-[3-(hydroxymethyl)phenyl]but-1-ynyl]-1H-pyrrolo[2,3-c]pyridine-3-carboxylate | $^1$H NMR (400 MHz, DMSO-$d_6$) δ 12.66 (br. s, 1 H), 7.76 (s, 1 H), 7.72 (s, 1 H), 7.67-7.65 (m, 2 H), 7.41-7.35 (m, 2 H), 5.28 (t, J = 5.2 Hz, 1 H), 4.55 (d, J = 4.8 Hz, 2 H), 4.10-4.02 (m, 2 H), 3.57 (s, 3 H), 2.50 (s, 3 H), 1.12 (t, J = 7.2 Hz, 3 H). | 485 (M + Na) |
| 44 | ethyl 2,6-dimethyl-7-oxo-4-[4,4,4-trifluoro-3-hydroxy-3-[3-(1H-pyrazol-3-yl)phenyl]but-1-ynyl]-1H-pyrrolo[2,3-c]pyridine-3-carboxylate | $^1$H NMR (400 MHz, CD$_3$OD) δ 8.28 (s, 1 H), 7.83-7.80 (m, 2 H), 7.68-7.64 (m, 2 H), 7.50-7.45 (m, 1 H), 6.71 (s, 1 H), 4.15-4.09 (m, 2 H), 3.65 (s, 3 H), 2.59 (s, 3 H), 1.18 (t, J = 7.2 Hz, 3H). | 499 |
| 45 | ethyl 4-(3-cyclopropyl-4,4,4-trifluoro-3-hydroxy-but-1-ynyl)-2,6-dimethyl-7-oxo-1H-pyrrolo[2,3-c]pyridine-3-carboxylate | $^1$H NMR (400 MHz, CD$_3$OD) δ 7.51 (s, 1 H), 4.45-4.32 (m, 2 H), 3.62 (s, 3 H), 2.59 (s, 3 H), 1.45-1.31 (m, 4 H), 0.85-0.81 (m, 1 H), 0.79-0.74 (m, 1 H), 0.62-0.57 (m, 2 H). | 397 |
| 46 | ethyl 6-but-3-enyl-4-(3-cyclopropyl-3-hydroxy-but-1-ynyl)-2-methyl-7-oxo-1H-pyrrolo[2,3-c]pyridine-3-carboxylate | $^1$H NMR (400 MHz, DMSO-$d_6$) δ 12.54 (br. s, 1 H), 7.44 (s, 1 H), 5.88-5.71 (m, 1 H), 5.08 (s, 1 H), 5.07-4.98 (m, 2 H), 4.32-4.20 (m, 2 H), 4.06 (t, J = 6.8 Hz, 2 H), 2.47 (s, 3 H), 2.44-2.38 (m, 2 H), 1.49 (s, 3 H), 1.28 (t, J = 7.2 Hz, 3 H), 1.10-1.01 (m, 1 H), 0.52-0.46 (m, 2 H), 0.38-0.34 (m, 2 H). | 405 (M + Na) |
| 47 | ethyl 6-but-3-enyl-4-(4-hydroxy-3,3-dimethyl-but-1-ynyl)-2-methyl-7-oxo-1H-pyrrolo[2,3-c]pyridine-3-carboxylate | $^1$H NMR (400 MHz, CDCl$_3$) δ 12.04 (br. s, 1 H), 7.24 (s, 1 H), 5.85-5.77 (m, 1 H), 5.15-5.05 (m, 2 H), 4.39-4.25 (m, 3 H), 4.14-4.09 (m, 2 H), 3.52-3.50 (m, 2 H), 2.70 (s, 3 H), 2.60-2.53 (m, 2 H), 1.39 (t, J = 7.2 Hz, 3 H), 1.29 (s, 6 H). | 371 |
| 48 | ethyl 4-(4-amino-3,3-dimethyl-4-oxo-but-1-ynyl)-6-but-3-enyl-2-methyl-7-oxo-1H-pyrrolo[2,3-c]pyridine-3- | $^1$H NMR (400 MHz, CDCl$_3$) δ 11.95 (br. s, 1 H), 8.20 (s, 1 H), 7.25 (s, 1 H), 5.87-5.78 (m, 1 H), 5.48 (s, 1 H), 5.14-5.08 (m, 2 H), 4.32 (q, J = 7.2 Hz, 2 H), | 384 |

-continued

| Example | Compound Name | NMR | m/z |
|---|---|---|---|
| | carboxylate | 4.15-4.11 (m, 2 H), 2.71 (s, 3 H), 2.60-2.54 (m, 2 H), 1.57 (s, 6 H), 1.40 (t, J = 7.2 Hz, 3 H). | |
| 49 | ethyl 6-but-3-enyl-4-(3-hydroxy-3-methyl-but-1-ynyl)-2-methyl-7-oxo-1H-pyrrolo[2,3-c]pyridine-3-carboxylate | $^1$H NMR (400 MHz, CDCl$_3$) δ 11.87 (br. s, 1 H), 7.20 (s, 1 H), 5.86-5.74 (m, 1 H), 5.12-5.07 (m, 2 H), 4.36 (q, J = 7.2 Hz, 2 H), 4.11 (t, J = 7.2 Hz, 2 H), 3.42 (s, 1 H), 2.70 (s, 3 H), 2.60-2.51 (m, 2 H), 1.60 (s, 6 H), 1.39 (t, J = 7.2 Hz, 3 H). | 379 (M + Na) |
| 50 | ethyl 6-ethyl-4-(3-hydroxy-3-methyl-but-1-ynyl)-2-methyl-7-oxo-1H-pyrrolo[2,3-c]pyridine-3-carboxylate | $^1$H NMR (400 MHz, DMSO-d$_6$) δ 7.47 (s, 1 H), 4.30-4.24 (m, 2 H), 4.03-3.96 (m, 2 H), 2.46 (s, 3 H), 1.45 (s, 6 H), 1.28 (t, J = 7.2 Hz, 3 H), 1.22 (t, J = 7.2 Hz, 3H). | 331 |
| 51 | ethyl 6-allyl-4-(3-hydroxy-3-methyl-but-1-ynyl)-2-methyl-7-oxo-1H-pyrrolo[2,3-c]pyridine-3-carboxylate | $^1$H NMR (400 MHz, CD$_3$OD) δ 7.37 (s, 1 H), 6.04-5.94 (m, 1 H), 5.25-5.22 (m, 1 H), 5.16-5.11 (m, 1 H), 4.66 (d, J = 5.6 Hz, 2 H), 4.41-4.35 (m, 2 H), 2.59 (s, 3 H), 1.56 (s, 6 H), 1.39 (t, J = 7.2 Hz, 3 H). | 343 |
| 52 | ethyl 6-(cyclopropylmethyl)-4-(3-hydroxy-3-methyl-but-1-ynyl)-2-methyl-7-oxo-1H-pyrrolo[2,3-c]pyridine-3-carboxylate | $^1$H NMR (400 MHz, DMSO-d$_6$) δ 12.54 (br. s, 1 H), 7.52 (s, 1 H), 5.24 (s, 1 H), 4.33-4.25 (m, 2 H), 3.87-3.84 (m, 2 H), 2.47 (s, 3 H), 1.46 (s, 6 H), 1.29 (t, J = 7.2 Hz, 3 H), 1.24-1.20 (m, 1 H), 0.47-0.38 (m, 4 H). | 339 (M − OH) |
| 53 | ethyl 4-(3-hydroxy-3-methyl-but-1-ynyl)-6-methyl-7-oxo-1H-pyrrolo[2,3-c]pyridine-3-carboxylate | $^1$HNMR (400 MHz, CD$_3$OD) δ 7.91 (s, 1 H), 7.50 (s, 1 H), 4.63 (s, 1 H), 4.40-4.30 (m, 2 H), 3.64 (s, 3 H), 1.60 (s, 6 H), 1.39 (t, J = 7.2 Hz, 3 H) | 303 |
| 54 | isobutyl 4-[(3R)-3-hydroxy-3-(5-methylisoxazol-3-yl)but-1-ynyl]-6-methyl-7-oxo-1H-pyrrolo[2,3-c]pyridine-3-carboxylate | $^1$HNMR (400 MHz, DMSO-d$_6$) δ 7.92 (s, 1 H), 7.59 (s, 1 H), 6.40 (s, 1 H), 4.06 (d, J = 6.8 Hz, 2 H), 3.64 (s, 3 H), 2.45 (s, 3 H), 2.15-2.00 (m, 1 H), 1.92 (s, 3 H), 1.02 (d, J = 7.2 Hz, 6 H). | 398 |
| 55 | ethyl 2,6-dimethyl-7-oxo-4-(2-phenylethynyl)-1H-pyrrolo[2,3-c]pyridine-3-carboxylate | $^1$H NMR (400 MHz, DMSO-d$_6$) δ 7.75 (s, 1H), 7.54-7.46 (m, 2H), 7.46-7.31 (m, 3H), 4.21 (q, J = 7.1 Hz, 2H), 3.55 (s, 3H), 2.51 (s, 3H), 1.21 (t, J = 7.1 Hz, 3H). | 335 |
| 56 | ethyl 2,6-dimethyl-4-[2-(3-methylimidazol-4-yl)ethynyl]-7-oxo-1H-pyrrolo[2,3-c]pyridine-3-carboxylate | $^1$H NMR (400 MHz, DMSO-d$_6$) δ 12.67 (s, 1H), 7.79 (s, 2H), 4.18 (q, J = 7.1 Hz, 2H), 3.70 (s, 3H), 3.55 (s, 3H), 2.50 (s, 3H), 1.21 (t, J = 7.1 Hz, 3H). | 339 |
| 57 | ethyl 2,6-dimethyl-7-oxo-4-[2-[2-(trifluoromethoxy)phenyl]ethynyl]-1H-pyrrolo[2,3-c]pyridine-3-carboxylate | $^1$H NMR (400 MHz, DMSO-d$_6$) δ 12.67 (s, 1H), 7.74-7.66 (m, 2H), 7.55-7.41 (m, 3H), 4.17 (q, J = 7.1 Hz, 2H), 3.64-3.51 (m, 3H), 2.50 (s, 3H), 1.17 (t, J = 7.1 Hz, 3H). | 419 |
| 58 | ethyl 4-[2-(4-methoxyphenyl)ethynyl]-2,6-dimethyl-7-oxo-1H-pyrrolo[2,3-c]pyridine-3-carboxylate | $^1$H NMR (400 MHz, DMSO-d$_6$) δ 12.62 (s, 1H), 7.70 (s, 1H), 7.48-7.39 (m, 2H), 7.02-6.93 (m, 2H), 4.20 (q, J = 7.1 Hz, 2H), 3.85-3.74 (m, 3H), 3.54 (s, 3H), 3.41-3.22 (m, 37H), 2.50 (s, 3H), 1.25-1.16 (m, 3H). | 365 |
| 59 | ethyl 4-[2-(2-fluorophenyl)ethynyl]-2,6-dimethyl-7-oxo-1H-pyrrolo[2,3-c]pyridine-3-carboxylate | no data | 353 |
| 60 | ethyl 4-[2-(3-aminophenyl)ethynyl]-2,6-dimethyl-7-oxo-1H-pyrrolo[2,3-c]pyridine-3-carboxylate | $^1$H NMR (400 MHz, DMSO-d$_6$) δ 12.61 (s, 1H), 7.69 (s, 1H), 7.02 (t, J = 7.8 Hz, 1H), 6.71-6.60 (m, 2H), 6.55 (ddd, J = 8.1, 2.3, 1.0 Hz, 1H), 5.19 (s, 2H), 4.22 (q, | 350 |

| Example | Compound Name | NMR | m/z |
|---|---|---|---|
| | | J = 7.1 Hz, 2H), 3.62-3.45 (m, 3H), 2.50 (s, 3H), 1.25-1.17 (m, 3H). | |
| 61 | ethyl 2,6-dimethyl-7-oxo-4-[2-(3-pyridyl)ethynyl]-1H-pyrrolo[2,3-c]pyridine-3-carboxylate | $^1$H NMR (400 MHz, DMSO-$d_6$) δ 12.67 (s, 1H), 8.71 (dd, J = 2.1, 0.9 Hz, 1H), 8.54 (dd, J = 4.9, 1.7 Hz, 1H), 7.89 (ddd, J = 7.9, 2.2, 1.7 Hz, 1H), 7.82 (s, 1H), 7.45 (ddd, J = 7.9, 4.9, 0.9 Hz, 1H), 4.22 (q, J = 7.1 Hz, 2H), 3.56 (s, 3H), 2.52 (s, 3H), 1.22 (t, J = 7.1 Hz, 3H). | 336 |
| 62 | ethyl 2,6-dimethyl-7-oxo-4-[2-(3-thienyl)ethynyl]-1H-pyrrolo[2,3-c]pyridine-3-carboxylate | $^1$H NMR (400 MHz, DMSO-$d_6$) δ 12.63 (s, 1H), 7.76-7.69 (m, 2H), 7.62 (dd, J = 5.0, 3.0 Hz, 1H), 7.24-7.17 (m, 1H), 4.21 (q, J = 7.1 Hz, 2H), 3.59-3.49 (m, 4H), 2.51 (s, 6H), 1.20 (t, J = 7.1 Hz, 3H). | 341 |
| 63 | ethyl 4-[2-(3-hydroxyphenyl)ethynyl]-2,6-dimethyl-7-oxo-1H-pyrrolo[2,3-c]pyridine-3-carboxylate | $^1$H NMR (400 MHz, DMSO-$d_6$) δ 9.65 (s, 1H), 7.73 (s, 1H), 7.19 (t, J = 7.9 Hz, 1H), 6.96-6.85 (m, 2H), 6.76 (ddd, J = 8.2, 2.5, 1.0 Hz, 1H), 4.22 (q, J = 7.1 Hz, 2H), 3.55 (s, 3H), 2.50 (s, 3H), 1.22 (t, J = 7.1 Hz, 3H). | 351 |
| 64 | ethyl 4-[(3R)-3-hydroxy-3-(5-methyl-1,3,4-oxadiazol-2-yl)but-1-ynyl]-2,6-dimethyl-7-oxo-1H-pyrrolo[2,3-c]pyridine-3-carboxylate | $^1$H NMR (400 MHz, DMSO-$d_6$) δ 12.58 (s, 1H), 7.60 (s, 1H), 4.38-4.03 (m, 2H), 3.52 (s, 3H), 2.52 (s, 3H), 2.48 (s, J = 0.8 Hz, 3H), 1.90 (s, 3H), 1.23 (t, J = 7.1 Hz, 3H). | 385 |
| 65 | ethyl 4-(3-hydroxy-3-methyl-pent-1-ynyl)-2,6-dimethyl-7-oxo-1H-pyrrolo[2,3-c]pyridine-3-carboxylate | $^1$H NMR (400 MHz, DMSO-$d_6$) δ 12.69 (s, 1H), 7.60 (s, 1H), 5.44 (s, 1H), 4.26 (dq, J = 13.3, 7.1 Hz, 2H), 3.52 (s, 3H), 2.47 (s, 3H), 1.57 (dd, J = 7.4, 4.8 Hz, 2H), 1.41 (s, 3H), 1.35-1.24 (m, 3H), 1.02-0.95 (m, 3H). | 313 (M − OH) |
| 66 | ethyl 4-(3,4-dihydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 7.52 (s, 1H), 5.11 (s, 1H), 4.71 (t, J = 6.5 Hz, 1H), 4.29 (q, J = 7.1 Hz, 2H), 3.52 (s, 3H), 3.47-3.36 (m, 2H), 2.49-2.47 (m, 3H), 1.38 (s, 3H), 1.32-1.27 (m, 3H). | 315 (M − OH) |
| 67 | ethyl 4-(3-amino-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 7.46 (s, 1H), 4.26 (q, J = 7.1 Hz, 2H), 3.51 (s, 3H), 2.47 (s, 3H), 1.39 (s, 6H), 1.30 (m, 3H). | 299 (M − OH) |
| 68 | ethyl 4-(3-hydroxy-3-thiazol-2-yl-but-1-ynyl)-2,6-dimethyl-7-oxo-1H-pyrrolo[2,3-c]pyridine-3-carboxylate | $^1$H NMR (400 MHz, DMSO-$d_6$) δ 7.74 (d, J = 3.3 Hz, 1H), 7.66-7.64 (m, 1H), 7.55 (s, 1H), 6.77 (s, 1H), 4.18 (q, J = 7.1 Hz, 2H), 3.52 (s, 3H), 2.48 (s, 3H), 1.88 (s, 3H), 1.21 (t, J = 7.1 Hz, 3H). | 368 (M − OH) |
| 69 | ethyl 4-[(3R)-3-hydroxy-3-(3-methylisoxazol-5-yl)but-1-ynyl]-2,6-dimethyl-7-oxo-1H-pyrrolo[2,3-c]pyridine-3-carboxylate | $^1$H NMR (400 MHz, DMSO-$d_6$) δ 12.61 (s, 1H), 7.60 (s, 1H), 6.46 (s, 1H), 6.37 (d, J = 0.4 Hz, 1H), 4.22 (q, J = 7.1 Hz, 2H), 3.53 (s, 3H), 2.22 (s, 3H), 1.79 (s, 3H), 1.31-1.19 (m, 3H). | 384 |
| 70 | ethyl 4-(3-hydroxy-3,4-dimethyl-pent-1-ynyl)-2,6-dimethyl-7-oxo-1H-pyrrolo[2,3-c]pyridine-3-carboxylate | $^1$H NMR (400 MHz, DMSO-$d_6$) δ 12.52 (s, 1H), 7.48 (s, 1H), 5.08-4.80 (m, 1H), 4.39-4.18 (m, 2H), 3.52 (s, 3H), 2.47 (s, 3H), 1.76 (p, J = 6.7 Hz, 1H), 1.38 (s, 3H), 1.32-1.25 (m, 3H), 0.98 (dd, J = 14.1, 6.7 Hz, 6H). | 345 |
| 71 | ethyl 6-but-3-enyl-4-[(3S)-3-hydroxy-3-(5-methylisoxazol-3-yl)but-1-ynyl]-2-methyl-7-oxo-1H-pyrrolo[2,3-c]pyridine-3-carboxylate | 1H NMR (400 MHz, DMSO-$d_6$) δ 12.57 (s, 1H), 7.52 (s, 1H), 6.46 (s, 1H), 6.20 (s, 1H), 5.91-5.68 (m, 1H), 5.15-4.89 (m, 2H), 4.26-4.16 (m, 2H), 4.06 (t, J = 7.0 Hz, 2H), 2.48 (d, J = 0.6 Hz, 3H), 2.42 (m, J = 7.1, 0.5 Hz, 2H), 2.39 (d, J = 0.9 Hz, 3H), 1.80 (s, 3H), 1.29-1.19 (m, 3H). | 424 |

-continued

| Example | Compound Name | NMR | m/z |
|---|---|---|---|
| 72 | ethyl 6-but-3-enyl-4-(4-cyano-3-hydroxy-3-methyl-but-1-ynyl)-2-methyl-7-oxo-1H-pyrrolo[2,3-c]pyridine-3-carboxylate | 1H NMR (400 MHz, DMSO-$d_6$) δ 12.58 (s, 1H), 7.52 (s, 1H), 6.02 (s, 1H), 5.80 (ddt, J = 17.1, 10.3, 6.8 Hz, 1H), 5.18-4.84 (m, 2H), 4.28 (q, J = 7.1 Hz, 2H), 4.06 (t, J = 7.0 Hz, 2H), 2.95 (s, 3H), 2.42 (m, J = 7.0 Hz, 2H), 1.57 (s, 3H), 1.30 (t, J = 7.1 Hz, 3H). | 382 (M − OH) |
| 73 | ethyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1$H NMR (400 MHz, DMSO-$d_6$) δ 12.68 (s, 1H), 7.85-7.77 (m, 2H), 7.73 (s, 1H), 7.66 (s, 1H), 7.50-7.39 (m, 3H), 4.16-3.96 (m, 2H), 3.57 (s, 3H), 1.22-1.03 (m, 3H). | 433 |
| 74 | ethyl 4-[2-(3-hydroxy-1-methyl-2-oxo-pyrrolidin-3-yl)ethynyl]-2,6-dimethyl-7-oxo-1H-pyrrolo[2,3-c]pyridine-3-carboxylate | $^1$H NMR (400 MHz, DMSO-$d_6$) δ 12.50 (s, J = 79.7 Hz, 1H), 7.54 (s, 1H), 6.10 (s, J = 49.8 Hz, 1H), 4.27 (q, J = 7.1 Hz, 2H), 3.52 (s, 3H), 3.30-3.40 (m, 2H), 2.79 (s, 3H), 2.46 (s, 3H), 2.10-2.25 (m, 2H), 1.32-1.16 (m, 3H). | 372 |
| 75 | ethyl 4-(3-hydroxy-3-phenyl-pent-1-ynyl)-2,6-dimethyl-7-oxo-1H-pyrrolo[2,3-c]pyridine-3-carboxylate | $^1$H NMR (400 MHz, DMSO-$d_6$) δ 12.58 (s, 1H), 7.66-7.61 (m, 2H), 7.57 (s, 1H), 7.37-7.31 (m, 2H), 7.28-7.22 (m, 1H), 5.81 (s, 1H), 4.32-3.99 (m, 2H), 3.54 (s, 3H), 2.49 (s, 3H), 1.90 (dd, J = 7.4, 1.6 Hz, 2H), 1.18 (t, J = 7.1 Hz, 3H), 0.92-0.80 (m, 3H). | 393 |
| 76 | ethyl 4-(3,3-dimethylbut-1-ynyl)-2,6-dimethyl-7-oxo-1H-pyrrolo[2,3-c]pyridine-3-carboxylate | $^1$H NMR (400 MHz, DMSO-$d_6$) δ 12.48 (s, 1H), 7.43 (s, 1H), 4.24 (q, J = 7.1 Hz, 2H), 3.50 (s, 3H), 2.46 (s, 3H), 1.28 (d, J = 11.8 Hz, 12H). | 315 |
| 77 | ethyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (s, 1H), 7.47 (s, 1H), 5.05 (s, 1H), 4.29 (q, J = 7.1 Hz, 2H), 3.52 (s, 3H), 2.47 (s, 3H), 1.49 (s, 3H), 1.34-1.24 (m, 3H), 1.10 (tt, J = 8.2, 5.1 Hz, 1H), 0.58-0.32 (m, 4H). | 325 (M − OH) |
| 78 | ethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (br. s., 1 H), 7.49 (s, 1 H), 5.22 (s, 1 H), 4.28 (q, J = 7.1 Hz, 2 H), 3.51 (s, 3 H), 2.47 (s, 3 H), 1.45 (s, 6 H), 1.33-1.26 (m, 3 H) | 317 |
| 79 | ethyl 4-(2-cyclohexylethynyl)-2,6-dimethyl-7-oxo-1H-pyrrolo[2,3-c]pyridine-3-carboxylate | $^1$H NMR (400 MHz, DMSO-$d_6$) δ 12.54-12.48 (m, 1 H), 7.47 (s, 1 H), 4.23 (t, J = 7.3 Hz, 2 H), 3.50 (d, J = 1.0 Hz, 3 H), 2.55 (s, 3 H), 2.46 (s, 1 H), 1.86-1.77 (m, 2 H), 1.75-1.65 (m, 2 H), 1.54-1.40 (m, 2 H), 1.34-1.20 (m, 7 H) | 341 |
| 80 | ethyl 4-(3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.59 (br. s., 1 H), 7.68-7.52 (m, 3 H), 7.37-7.31 (m, 2 H), 7.28-7.22 (m, 1 H), 5.96 (s, 1 H), 4.16 (q, J = 6.8 Hz, 2 H), 3.53 (s, 3 H), 2.48 (s, 3 H), 1.72 (s, 3 H), 1.20 (t, J = 7.1 Hz, 3 H) | 379 |
| 81 | ethyl 4-[2-(1-hydroxycyclohexyl)ethynyl]-2,6-dimethyl-7-oxo-1H-pyrrolo[2,3-c]pyridine-3-carboxylate | $^1$H NMR (400 MHz, DMSO-$d_6$) δ 12.55 (br. s., 1 H), 7.50 (s, 1 H), 5.16 (s, 1 H), 4.33-4.23 (m, 2 H), 3.55-3.49 (m, 3 H), 2.47 (s, 3 H), 1.90-1.79 (m, 2 H), 1.66-1.39 (m, 7 H), 1.32-1.16 (m, 4 H) | 357 |
| 82 | ethyl 4-(4-hydroxybut-1-ynyl)-2,6-dimethyl-7-oxo-1H-pyrrolo[2,3-c]pyridine-3-carboxylate | $^1$H NMR (400 MHz, DMSO-$d_6$) δ 12.56 (br. s, 1 H), 7.51 (s, 1 H), 4.23 (q, J = 7.1 Hz, 2 H), 3.60-3.47 (m, 6 H), 2.55-2.52 (m, 2 H), 2.47 (s, 3 H), 1.29 (t, J = 7.1 Hz, 3 H) | 303 |
| 83 | ethyl 4-[2-(2-hydroxycyclopentyl)ethynyl]-2,6-dimethyl-7-oxo-1H- | $^1$H NMR (400 MHz, DMSO-$d_6$) δ 12.53 (br. s, 1 H), 7.47 (s, 1 H), 4.87 (d, J = 4.4 Hz, 1 H), 4.23 (q, | 343 |

| Example | Compound Name | NMR | m/z |
|---|---|---|---|
| | pyrrolo[2,3-c]pyridine-3-carboxylate | J = 7.1 Hz, 2 H), 4.09 (dd, J = 4.5, 5.7 Hz, 1 H), 3.53-3.48 (m, 3 H), 2.70-2.63 (m, 1 H), 2.46 (s, 3 H), 1.72-1.60 (m, 3 H), 1.53-1.44 (m, 3 H), 1.32-1.27 (m, 3 H) | |
| 84 | ethyl 4-[2-(2-hydroxycyclohexyl)ethynyl]-2,6-dimethyl-7-oxo-1H-pyrrolo[2,3-c]pyridine-3-carboxylate | $^1$H NMR (400 MHz, DMSO-$d_6$) δ 12.55 (br. s, 1 H), 7.50 (s, 1 H), 4.71 (d, J = 3.9 Hz, 1 H), 4.28-4.19 (m, 3 H), 3.52-3.49 (m, 3 H), 3.46 (d, J = 5.1 Hz, 1 H), 2.48-2.46 (m, 3 H), 1.87 (d, J = 3.7 Hz, 2 H), 1.62 (d, J = 12.0 Hz, 2 H), 1.56-1.37 (m, 2 H), 1.32-1.26 (m, 3 H), 1.25 (d, J = 7.1 Hz, 2H) | 357 |
| 85 | ethyl 2,6-dimethyl-7-oxo-4-[4,4,4-trifluoro-3-hydroxy-3-(3-hydroxy-5-methyl-phenyl)but-1-ynyl]-1H-pyrrolo[2,3-c]pyridine-3-carboxylate | $^1$H NMR (400 MHz, DMSO-$d_6$) δ 12.68 (s, 1 H), 9.39 (s, 1 H), 7.68 (s, 1 H), 7.50 (s, 1 H), 7.04 (s, 1 H), 7.00 (s, 1 H), 6.61 (s, 1 H), 4.12-4.02 (m, 2 H), 3.57 (s, 3 H), 2.50 (s, 3 H), 2.26 (s, 3 H), 1.12 (t, J = 7.1 Hz, 3 H). | 463 |
| 86 | ethyl 4-[2-(3-hydroxy-1-methyl-2-oxo-indolin-3-yl)ethynyl]-2,6-dimethyl-7-oxo-1H-pyrrolo[2,3-c]pyridine-3-carboxylate | $^1$H NMR (400 MHz, DMSO-$d_6$) δ 12.53-12.65 (m, 1H), 7.58 (s, 1H), 7.46-7.52 (m, 1H), 7.33-7.40 (m, 1H), 7.08-7.14 (m, 1H), 7.01-7.06 (m, 1H), 6.90 (s, 1H), 3.98-4.13 (m, 2H), 3.51 (s, 3H), 3.15 (s, 3H), 2.46 (s, 3H), 1.06-1.19 (m, 3H). | 419 |
| 87 | ethyl 4-(3-hydroxy-3-tetrahydropyran-4-yl-but-1-ynyl)-2,6-dimethyl-7-oxo-1H-pyrrolo[2,3-c]pyridine-3-carboxylate | $^1$H NMR (400 MHz, DMSO-$d_6$) δ 12.54 (br. s, 1H), 7.48 (s, 1H), 5.07 (s, 1H), 4.27 (q, J = 7.08 Hz, 2H), 3.82-3.95 (m, 2H), 3.51 (s, 3H), 3.25 (t, J = 10.86 Hz, 2H), 2.46 (s, 3H), 1.77 (d, J = 12.70 Hz, 1H), 1.55-1.67 (m, 2H), 1.44 (td, J = 3.69, 12.39 Hz, 2H), 1.39 (s, 3H), 1.27 (t, J = 7.08 Hz, 3H). | 387 |
| 88 | ethyl 4-[2-(4-hydroxytetrahydropyran-4-yl)ethynyl]-2,6-dimethyl-7-oxo-1H-pyrrolo[2,3-c]pyridine-3-carboxylate | $^1$H NMR (400 MHz, DMSO-$d_6$) δ 12.56 (br. s, 1H), 7.55 (s, 1H), 5.48 (s, 1H), 4.25 (q, J = 7.08 Hz, 2H), 3.68-3.78 (m, 2H), 3.59 (ddd, J = 2.93, 8.73, 11.54 Hz, 2H), 3.50 (s, 3H), 2.44-2.47 (m, 3H), 1.87 (d, J = 13.43 Hz, 2H), 1.66 (ddd, J = 3.91, 8.91, 12.82 Hz, 2H), 1.27 (t, J = 7.08 Hz, 3H). | 359 |
| 89 | ethyl 4-(4,4-difluoro-3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.66 (br. s, 1H), 7.71 (d, J = 6.84 Hz, 2H), 7.68 (s, 1H), 7.30-7.51 (m, 3H), 6.95 (s, 1H), 6.07 (t, J = 55.70 Hz, 1H), 3.89-4.35 (m, 2H), 3.56 (s, 3H), 2.50 (s, 3H), 1.16 (t, J = 7.08 Hz, 3H). | 415 |
| 90 | ethyl 2,6-dimethyl-7-oxo-4-[4,4,4-trifluoro-3-hydroxy-3-(3-phenoxyphenyl)but-1-ynyl]-1H-pyrrolo[2,3-c]pyridine-3-carboxylate | $^1$H NMR (400 MHz, DMSO-$d_6$) δ 12.71 (s, 1H), 7.79 (s, 1H), 7.69 (s, 1H), 7.58 (d, J = 8.1 Hz, 1H), 7.41-7.49 (m, 2H), 7.35-7.41 (m, 2H), 7.11-7.17 (m, 1H), 7.07 (ddd, J = 8.1, 2.4, 1.0 Hz, 1H), 6.97-7.05 (m, 2H), 3.97-4.13 (m, 2H), 3.56 (s, 3H), 2.49 (s, 3H), 1.12 (t, J = 7.1 Hz, 3H). | 525 |

Examples 91a and 91b ethyl 2,6-dimethyl-7-oxo-4-(4,4,4-trifluoro-3-hydroxy-3-phenyl-but-1-ynyl)-1H-pyrrolo[2,3-c]pyridine-3-carboxylate (91a/91b)

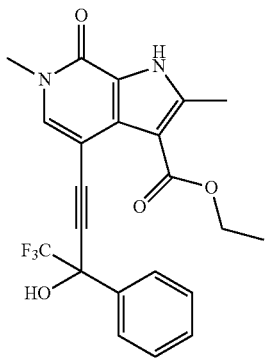 [SMILES: CCOC(=O)c1c(C)[nH]c2c(=O)n(C)cc(C#CC(O)(c3ccccc3)C(F)(F)F)c12]

Ethyl 2,6-dimethyl-7-oxo-4-(4,4,4-trifluoro-3-hydroxy-3-phenyl-but-1-ynyl)-1H-pyrrolo[2,3-c]pyridine-3-carboxylate was prepared in a similar fashion as Example 1. The racemic (50 mg) were separated by supercritical fluid chromatography (SFC) to give the title compound 91a (22 mg, 43% yield) as an off-white solid and the compound 91b (21 mg, 42% yield) as an off-white solid. The stereochemistry of both enantiomers was arbitrarily assigned. SFC conditions: PIC-100, Column: Cellulose-3 (21.2×150 mm, 5 um), Flow: 70 ml/min, Mobile Phase A: Carbon Dioxide, Mobile Phase B: MeOH with 0.1% $NH_4OH$, Method: Isocratic 20% B, 100 bars, 40° C.

Compound 91a: chiral HPLC retention time 0.584 min; $^1$H NMR (400 MHz, DMSO-$d_6$) δ 12.67 (s, 1H), 7.80 (dd, J=7.3, 2.4 Hz, 2H), 7.72 (s, 1H), 7.66 (s, 1H), 7.52-7.36 (m, 3H), 4.14-4.00 (m, 2H), 3.57 (s, 3H), 1.12 (t, J=7.1 Hz, 3H). LCMS M/Z (M+H) 433.

Compound 91b: chiral HPLC retention time 0.825 min, $^1$H NMR (400 MHz, DMSO-$d_6$) δ 12.67 (s, 1H), 7.80 (dd, J=7.3, 2.5 Hz, 2H), 7.72 (s, 1H), 7.66 (s, 1H), 7.48-7.39 (m, 3H), 4.06 (t, J=7.0 Hz, 2H), 3.57 (s, 3H), 1.12 (t, J=7.1 Hz, 3H). LCMS M/Z (M+H) 433.

The following compounds were prepared in a similar fashion to Example 91a/92b:

Examples 92a/92b-99a/99b

| Example | Compound Name | NMR | m/z | Rt |
|---|---|---|---|---|
| 92a | ethyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (s, 1H), 7.46 (s, 1H), 5.05 (s, 1H), 4.29 (q, J = 7.1 Hz, 2H), 3.52 (s, 3H), 2.47 (s, 3H), 1.49 (s, 3H), 1.29 (t, J = 7.1 Hz, 3H), 1.17-1.01 (m, 1H), 0.56-0.28 (m, 4H). | 325 (M − OH) | 0.86 |
| 92b | ethyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (s, 1H), 7.47 (s, 1H), 5.05 (s, 1H), 4.29 (q, J = 7.1 Hz, 2H), 3.52 (s, 3H), 2.47 (s, 3H), 1.49 (s, 3H), 1.29 (t, J = 7.1 Hz, 3H), 1.15-1.02 (m, 1H), 0.60-0.29 (m, 4H). | 325 (M − OH) | 1.09 |
| 93a | ethyl 4-(4,4-difluoro-3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.65 (s, 1H), 7.74-7.70 (m, 2H), 7.68 (s, 1H), 7.44-7.34 (m, 2H), 6.95 (s, 1H), 6.07 (t, J = 56.0 Hz, 1H), 4.18-4.06 (m, 2H), 3.56 (s, 3H), 2.49 (s, 1H), 1.16 (t, J = 7.1 Hz, 3H). | 415 | 0.65 |
| 93b | ethyl 4-(4,4-difluoro-3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.65 (s, 1H), 7.74-7.69 (m, 2H), 7.68 (s, 1H), 7.44-7.34 (m, 2H), 6.94 (s, 1H), 6.07 (t, J = 56.0 Hz, 1H), 4.30-3.92 (m, 2H), 3.56 (s, 3H), 2.49 (s, 1H), 1.16 (t, J = 7.1 Hz, 3H). | 415 | 0.83 |
| 94a | 3-(5-isopropyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, DMSO-$d_6$) δ 12.85 (s, 1H), 7.82 (s, 1H), 7.73 (s, 1H), 7.61 (dd, J = 7.2, 2.3 Hz, 2H), 7.43-7.40 (m, 2H), 3.60 (s, 3H), 2.84 (p, J = 6.9 Hz, 1H), 2.47-2.40 (m, 3H), 1.19 (d, J = 6.9 Hz, 3H), 1.08-1.01 (m, 3H). | 471 | 0.75 |
| 94b | 3-(5-isopropyl-1,3,4-oxadiazol-2-yl)-2,6-dimethyl-4-(4,4,4-trifluoro-3-hydroxy-3-phenyl-but-1-ynyl)-1H-pyrrolo[2,3- | $^1$H NMR (400 MHz, DMSO-$d_6$) δ 12.85 (s, 1H), 7.82 (s, 1H), 7.72 (s, 1H), 7.61 (dd, J = 7.5, 2.2 Hz, 2H), 7.44-7.40 (m, 2H), 3.60 (s, 3H), 2.84 (m, J = 7.0 Hz, 1H), | 471 | 0.92 |

| Example | Compound Name | NMR | m/z | Rt |
|---|---|---|---|---|
| | c]pyridin-7-one | 2.44 (d, J = 0.6 Hz, 3H), 1.19 (d, J = 6.9 Hz, 3H), 1.10-1.01 (m, 3H). | | |
| 95a | 3-[5-[(dimethylamino)methyl]-1,3,4-oxadiazol-2-yl]-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, DMSO-$d_6$) δ 12.90 (s, 1H), 7.98 (s, 1H), 7.87 (s, 1H), 7.66 (dd, J = 7.0, 2.8 Hz, 2H), 7.46-7.38 (m, 3H), 3.60 (s, 3H), 3.53-3.38 (m, 2H), 2.47 (s, 3H), 2.12 (s, 6H). | 486 | 0.51 |
| 95b | 3-[5-[(dimethylamino)methyl]-1,3,4-oxadiazol-2-yl]-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, DMSO-$d_6$) δ 12.90 (s, 1H), 7.98 (s, 1H), 7.87 (s, 1H), 7.66 (dd, J = 6.9, 2.7 Hz, 2H), 7.47-7.38 (m, 3H), 3.60 (s, 3H), 3.53-3.38 (m, 2H), 2.47 (s, 3H), 2.12 (s, 6H). | 486 | 0.57 |
| 96a | 4-(3-cyclopropyl-3-hydroxy-but-1-ynyl)-2,6-dimethyl-3-(5-tetrahydrofuran-3-yl-1,3,4-oxadiazol-2-yl)-1H-pyrrolo[2,3-c]pyridin-7-one | $^1$H NMR (400 MHz, DMSO-$d_6$) δ 12.74 (s, 1H), 7.54 (s, 1H), 5.09 (d, J = 1.3 Hz, 1H), 4.13-3.73 (m, 4H), 3.54 (s, 3H), 2.39 (s, 3H), 2.38-2.20 (m, 2H), 1.31 (s, 3H), 1.06-0.95 (m, 1H), 0.42-0.19 (m, 4H). | 391 (M − OH) | 1.38 |
| 96b | 4-(3-cyclopropyl-3-hydroxy-but-1-ynyl)-2,6-dimethyl-3-(5-tetrahydrofuran-3-yl-1,3,4-oxadiazol-2-yl)-1H-pyrrolo[2,3-c]pyridin-7-one | $^1$H NMR (400 MHz, DMSO-$d_6$) δ 12.74 (s, 1H), 7.54 (s, 1H), 5.10 (s, 1H), 4.09-3.72 (m, 4H), 3.54 (s, 3H), 2.39 (s, 3H), 2.36-2.22 (m, 2H), 1.30 (s, 3H), 1.15-0.86 (m, 1H), 0.41-0.22 (m, 4H). | 391 (M − OH) | 1.73 |
| 97a | 4-(3-cyclopropyl-3-hydroxy-but-1-ynyl)-3-[5-[(dimethylamino)methyl]-1,3,4-oxadiazol-2-yl]-2,6-dimethyl-1H-pyrrolo[2,3-c]pyridin-7-one | $^1$H NMR (400 MHz, DMSO-$d_6$) δ 12.77 (s, 1H), 7.55 (s, 1H), 5.31 (s, 1H), 3.94-3.73 (m, 2H), 3.54 (s, 3H), 2.44-2.37 (m, 3H), 2.26 (s, 6H), 1.32 (s, 3H), 1.01 (s, 1H), 0.44-0.19 (m, 4H). | 396 | 1.56 |
| 97b | 4-(3-cyclopropyl-3-hydroxy-but-1-ynyl)-3-[5-[(dimethylamino)methyl]-1,3,4-oxadiazol-2-yl]-2,6-dimethyl-1H-pyrrolo[2,3-c]pyridin-7-one | $^1$H NMR (400 MHz, DMSO-$d_6$) δ 12.77 (s, 1H), 7.55 (s, 1H), 5.31 (s, 1H), 3.84 (d, J = 0.9 Hz, 2H), 3.54 (s, 3H), 2.41 (s, 3H), 2.27 (s, 6H), 1.32 (s, 3H), 1.12-0.90 (m, 1H), 0.31 (m, J = 13.0, 5.1, 4.1, 2.5 Hz, 4H). | 396 | 1.73 |
| 98a | 3-(5-tert-butyl-1,3,4-oxadiazol-2-yl)-4-(3-cyclopropyl-3-hydroxy-but-1-ynyl)-2,6-dimethyl-1H-pyrrolo[2,3-c]pyridin-7-one | $^1$H NMR (400 MHz, DMSO-$d_6$) δ 12.71 (s, 1H), 7.51 (s, 1H), 4.90 (s, 1H), 3.54 (s, 3H), 2.37-2.28 (m, 3H), 1.46-1.37 (m, 9H), 1.29 (s, 3H), 0.98 (m, 1H), 0.47-0.18 (m, 4H). | 378 (M − OH) | 1.43 |
| 98b | 3-(5-tert-butyl-1,3,4-oxadiazol-2-yl)-4-(3-cyclopropyl-3-hydroxy-but-1-ynyl)-2,6-dimethyl-1H-pyrrolo[2,3-c]pyridin-7-one | $^1$H NMR (400 MHz, DMSO-$d_6$) δ 12.71 (s, 1H), 7.51 (s, 1H), 4.90 (s, 1H), 3.54 (s, 3H), 2.32 (s, 3H), 1.43-1.39 (m, 9H), 1.29 (s, 3H), 1.03-0.90 (m, 1H), 0.44-0.21 (m, 4H). | 378 (M − OH) | 1.86 |
| 99a | ethyl 4-[2-(7-hydroxy-5,6-dihydrocyclopenta[b]pyridin-7-yl)ethynyl]-2,6-dimethyl-7-oxo-1H-pyrrolo[2,3-c]pyridine-3-carboxylate | $^1$H NMR (400 MHz, DMSO-$d_6$) δ 12.56 (s, 1H), 8.42 (m, J = 4.7, 2.4, 1.6, 0.8 Hz, 1H), 7.70 m, J = 6.8, 3.3, 1.6, 0.8 Hz, 1H), 7.50 (s, 1H), 7.26 (m, J = 10.1, 7.6, 4.8 Hz, 1H), 5.94 (s, 1H), 4.15 (q, J = 7.1 Hz, 2H), 3.58-3.45 (s, 3H), 3.02-2.79 (m, 2H), 2.46 (s, 3H), 2.37-2.24 (m, 2H), 1.18 (t, J = 7.1 Hz, 3H). | 392 | 0.60 |

-continued

| Example | Compound Name | NMR | m/z | Rt |
|---|---|---|---|---|
| 99b | ethyl 4-[2-(7-hydroxy-5,6-dihydrocyclopenta[b]pyridin-7-yl)ethynyl]-2,6-dimethyl-7-oxo-1H-pyrrolo[2,3-c]pyridine-3-carboxylate | $^1$H NMR (400 MHz, DMSO-d$_6$) δ 12.56 (s, 1H), 8.42 (m, J = 3.9, 1.6, 0.8 Hz, 1H), 7.81-7.62 (m, 1H), 7.50 (s, 1H), 7.26 (m, J = 10.1, 7.6, 4.8 Hz, 1H), 5.94 (s, 1H), 4.15 (q, J = 7.1 Hz, 2H), 3.58-3.47 (s, 3H), 3.03-2.81 (m, 2H), 2.46 (s, 3H), 2.37-2.24 (m, 2H), 1.18 (t, J = 7.1 Hz, 3H). | 392 | 0.80 |

Example 100 ethyl 2,6-dimethyl-7-oxo-4-[4,4,4-trifluoro-3-hydroxy-3-[3-(3-pyridyl) phenyl]but-1-ynyl]-1H-pyrrolo[2,3-c]pyridine-3-carboxylate

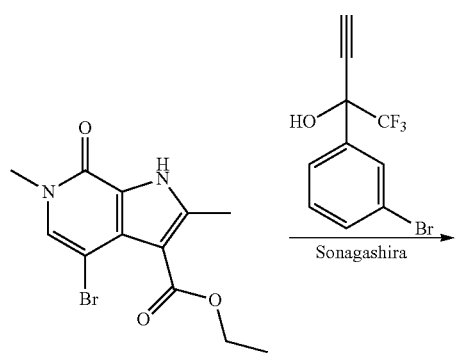

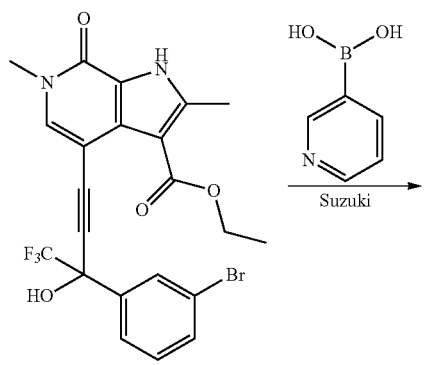

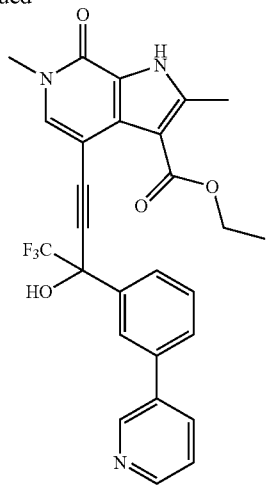

Ethyl 4-(3-(3-bromophenyl)-4,4,4-trifluoro-3-hydroxybut-1-yn-1-yl)-2,6-dimethyl-7-oxo-6,7-dihydro-1H-pyrrolo[2,3-c]pyridine-3-carboxylate was prepared in a similar fashion as Example 1.

To a solution of ethyl 4-(3-(3-bromophenyl)-4,4,4-trifluoro-3-hydroxybut-1-yn-1-yl)-2,6-dimethyl-7-oxo-6,7-dihydro-1H-pyrrolo[2,3-c]pyridine-3-carboxylate (90 mg, 0.18 mmol) in dioxane (2 mL) and Na$_2$CO$_3$ aqueous solution (1M, 0.44 mL, 0.44 mmol) was added pyridin-3-ylboronic acid (28 mg, 0.23 mmol) and tetrakistriphenylphosphinepalladium(0) (10.1 mg, 8 μmol). The reaction was heated at 90° C. for 12 h and concentrated under reduced pressure. The crude product was purified by reverse phase chromatography to give the title compound (20 mg, 22% yield) as a white solid. $^1$H NMR (400 MHz, DMSO-d$_6$) δ 12.70 (s, 1H), 8.97 (br. s., 1H), 8.67 (d, J=4.4 Hz, 1H), 8.24 (d, J=8.1 Hz, 1H), 8.17 (s, 1H), 7.92-7.81 (m, 2H), 7.74 (s, 1H), 7.67-7.59 (m, 2H), 4.05-3.95 (m, 3H), 3.57 (s, 3H), 2.50 (br. s., 3H), 1.10 (t, J=7.1 Hz, 3H). LCMS M/Z (M+H) 510.

The following compounds were prepared in a similar fashion to Example 100:

Examples 101-102

| Example | Compound Name | NMR | m/z |
|---|---|---|---|
| 101 | ethyl 2,6-dimethyl-7-oxo-4-[4,4,4-trifluoro-3-hydroxy-3-[3-(2-methoxyphenyl)phenyl]but-1-ynyl]-1H-pyrrolo[2,3-c]pyridine-3-carboxylate | $^1$H NMR (400 MHz, DMSO-d$_6$) δ 12.68 (s, 1 H), 7.94-7.00 (m, 10 H), 3.99 (dd, J = 7.1, 10.0 Hz, 2 H), 3.71 (s, 3 H), 3.56 (s, 3 H), 2.49 (s, 3 H), 1.09 (t, J = 7.1 Hz, 3 H) | 539 |

| Example | Compound Name | NMR | m/z |
|---|---|---|---|
| 102 | ethyl 2,6-dimethyl-7-oxo-4-[4,4,4-trifluoro-3-hydroxy-3-[3-(o-tolyl)phenyl]but-1-ynyl]-1H-pyrrolo[2,3-c]pyridine-3-carboxylate | $^1$H NMR (400 MHz, DMSO-$d_6$) δ 12.68 (s, 1 H), 7.82-7.19 (m, 10 H), 3.95 (dd, J = 7.1, 17.1 Hz, 2 H), 3.56 (s, 3 H), 2.49 (s, 3 H), 2.21 (s, 3 H), 1.07 (t, J = 7.1 Hz, 3 H) | 523 |

Example 103

Benzyl 4-(3-hydroxy-3-methyl-but-1-ynyl)-2,6-dimethyl-7-oxo-1H-pyrrolo[2,3-c]pyridine-3-carboxylate

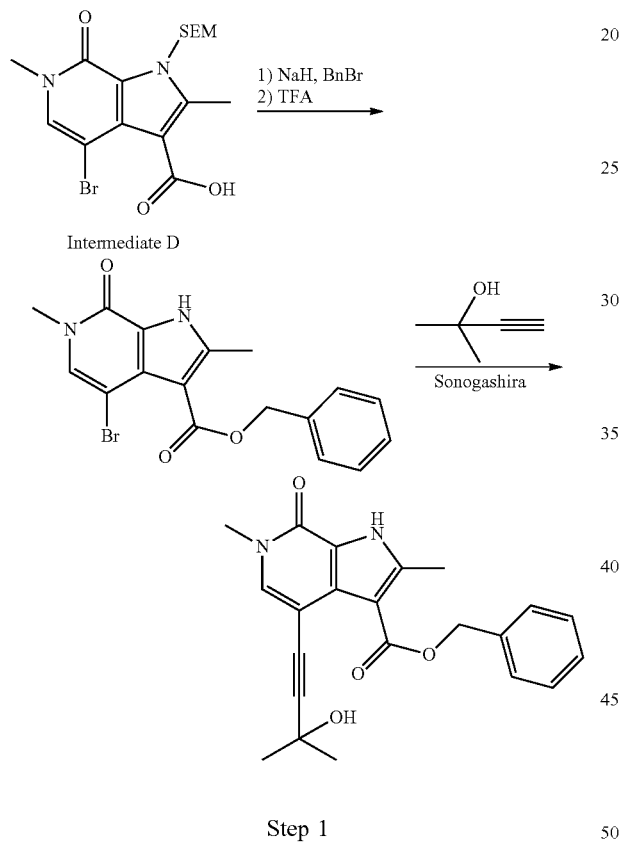

Step 1

Benzyl 4-bromo-2,6-dimethyl-7-oxo-1-((2-(trimethylsilyl)ethoxy)methyl)-6,7-dihydro-1H-pyrrolo[2,3-c]pyridine-3-carboxylate

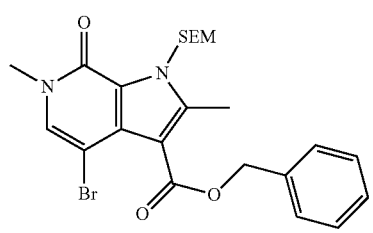 [SMILES: Cc1c(C(=O)OCc2ccccc2)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carboxylic acid (Intermediate D) (207 mg, 0.50 mmol) in DMF (10 mL) at 0° C. was added NaH (60% in mineral oil, 40 mg, 1.00 mmol). After stirring for 15 min, benzyl bromide (170 mg, 1.00 mmol) was added. The reaction was stirred at ambient temperature for 2 h and then quenched by the addition of water (20 mL). The mixture was extracted with EtOAc (3×20 mL) and the combined organic layers were dried over anhydrous $Na_2SO_4$, filtered and concentrated under reduced pressure. The residue was purified by column chromatography (petroleum ether:EtOAc=4:1) to give the title compound (200 mg, 79% yield) as a yellow solid.

Step 2 benzyl 4-bromo-2,6-dimethyl-7-oxo-6,7-dihydro-1H-pyrrolo[2,3-c]pyridine-3-carboxylate To a solution of benzyl 4-bromo-2,6-dimethyl-7-oxo-1-((2-(trimethylsilyl)ethoxy) methyl)-6,7-dihydro-1H-pyrrolo[2,3-c]pyridine-3-carboxylate (200 mg, 0.40 mmol) in DCM (10 mL) was added 2,2,2-trifluoroacetic acid (1 mL). The reaction was stirred at 25° C. for 2 h and then concentrated under reduced pressure. The residue was dissolved in MeOH (5 mL) and adjusted to pH 8 by the addition of $K_2CO_3$. The suspension was diluted with water (20 mL) and extracted with EtOAc (3×20 mL). The combined organic layers were concentrated under reduced pressure. The residue was purified by column chromatography (DCM:MeOH=9:1) to give the title compound (100 mg, 67% yield) as a yellow solid.

Step 3 benzyl 4-(3-hydroxy-3-methyl-but-1-ynyl)-2,6-dimethyl-7-oxo-1H-pyrrolo[2,3-c]pyridine-3-carboxylate

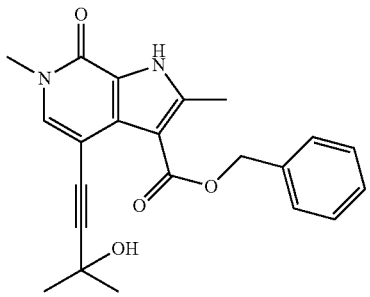 [SMILES: Cc1[nH]c2c(=O)n(C)cc(C#CC(C)(C)O)c2c1C(=O)OCc1ccccc1]

To a suspension of benzyl 4-bromo-2,6-dimethyl-7-oxo-6,7-dihydro-1H-pyrrolo[2,3-c]pyridine-3-carboxylate (100 mg, 0.27 mmol) in DMF (3 mL) and TEA (1 mL) was added 2-methylbut-3-yn-2-ol (109 mg, 1.30 mmol), copper(I) iodide (11 mg, 0.06 mmol) and bis(triphenylphosphine)palladium(II) dichloride (21 mg, 0.03 mmol). The reaction was purged with $N_2$ for 5 min and then stirred at 110° C. for 1 h under microwave conditions. The reaction mixture was concentrated under reduced pressure. The crude product was purified by reverse phase chromatography (ACN 43-73%/0.1% $NH_4OH$ in water) to give the title compound (13 mg, 13% yield) as a white solid. $^1H$ NMR (400 MHz, DMSO-$d_6$) δ 12.47 (br. s, 1H), 7.52 (s, 1H), 7.43 (d, J=7.2 Hz, 2H), 7.38-7.35 (m, 2H), 7.31-7.27 (m, 1H), 5.36 (s, 2H), 5.26 (s, 1H), 3.52 (s, 3H), 2.46 (s, 3H), 1.45 (s, 6H). LCMS M/Z (M+Na) 401.

The following compounds were prepared in a similar fashion to Example 103

Examples 104-133

| Example | Compound Name | NMR | m/z |
|---|---|---|---|
| 104 | 1-phenylethyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1H$ NMR (400 MHz, CD$_3$OD) δ 7.93-7.80 (m, 2 H), 7.62-7.61 (m, 1 H), 7.45-7.29 (m, 8 H), 5.97-5.94 (m, 1 H), 3.63 (s, 3 H), 2.60 (d, J = 7.2 Hz, 3 H), 1.62-1.59 (m, 3 H). | 531 (M + Na) |
| 105 | 8-quinolylmethyl 4-(3-cyclopropyl-3-hydroxy-but-1-ynyl)-2,6-dimethyl-7-oxo-1H-pyrrolo[2,3-c]pyridine-3-carboxylate | $^1H$ NMR (400 MHz, CD$_3$OD) δ 8.94-8.93 (m, 1 H), 8.36 (d, J = 6.8 Hz, 1 H), 7.93-7.86 (m, 2 H), 7.62-7.55 (m, 2 H), 7.45 (s, 1 H), 6.08 (s, 2 H), 3.62 (s, 3 H), 2.50 (s, 3 H), 1.50 (s, 3 H), 1.10-1.08 (m, 1 H), 0.64-0.62 (m, 1 H), 0.53-0.51 (m, 1 H), 0.41-0.36 (m, 2 H). | 478 (M + Na) |
| 106 | [3-(hydroxymethyl)phenyl]methyl 4-(3-cyclopropyl-3-hydroxy-but-1-ynyl)-2,6-dimethyl-7-oxo-1H-pyrrolo[2,3-c]pyridine-3-carboxylate | $^1H$ NMR (400 MHz, DMSO-$d_6$) δ 12.62 (br. s, 1 H), 7.50 (s, 1 H), 7.37 (s, 1 H), 7.32-7.25 (m, 3 H), 5.36 (s, 2 H), 5.20 (t, J = 5.6 Hz, 1 H), 5.14 (s, 1 H), 4.48 (d, J = 5.6 Hz, 2 H), 3.52 (s, 3 H), 2.46 (s, 3 H), 1.48 (s, 3 H), 1.11-1.08 (m, 1 H), 0.53-0.51 (m, 1 H), 0.46-0.42 (m, 1 H), 0.36-0.29 (m, 2 H). | 457 (M + Na) |
| 107 | (2-cyanophenyl)methyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1H$ NMR (400 MHz, DMSO-$d_6$) δ 12.80 (br. s, 1 H), 7.85-7.83 (m, 1 H), 7.81-7.77 (m, 3 H), 7.71 (s, 1 H), 7.64-7.61 (m, 1 H), 7.50-7.46 (m, 2 H), 7.42-7.39 (m, 3 H), 5.33-5.25 (m, 2 H), 3.58 (s, 3 H), 2.48 (s, 3 H). | 520 |
| 108 | o-tolylmethyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1H$ NMR (400 MHz, CD$_3$OD) δ 7.85-7.80 (m, 2 H), 7.65 (s, 1 H), 7.39-7.37 (m, 3 H), 7.26-7.24 (m, 1 H), 7.20-7.05 (m, 3 H), 5.20-5.15 (m, 2 H), 3.65 (s, 3 H), 2.52 (s, 3 H), 2.28 (s, 3 H). | 531 (M + Na) |
| 109 | thiazol-2-ylmethyl 4-(3-cyclopropyl-3-hydroxy-but-1-ynyl)-2,6-dimethyl-7-oxo-1H-pyrrolo[2,3-c]pyridine-3-carboxylate | $^1H$ NMR (400 MHz, CD$_3$OD) δ 7.80 (d, J = 3.2 Hz, 1 H), 7.64 (d, J = 3.2 Hz, 1 H), 7.45 (s, 1 H), 5.69 (s, 2 H), 3.61 (s, 3 H), 2.61 (s, 3 H), 1.58 (s, 3 H), 1.19-1.16 (m, 1 H), 0.64-0.62 (m, 1 H), 0.55-0.44 (m, 3 H). | 434 (M + Na) |
| 110 | (2-cyanophenyl)methyl 4-(3-hydroxy-3-methyl-but-1-ynyl)-2,6-dimethyl-7- | $^1H$ NMR (400 MHz, DMSO-$d_6$) δ 12.66 (br. s, 1 H), 7.88 (d, J = 7.6 Hz, 1 H), 7.75-7.66 | 386 (M − OH) |

| Example | Compound Name | NMR | m/z |
|---|---|---|---|
| | oxo-1H-pyrrolo[2,3-c]pyridine-3-carboxylate | (m, 2 H), 7.55-7.52 (m, 2 H), 5.50 (s, 2 H), 5.23 (s, 1 H), 3.52 (s, 3 H), 2.47 (s, 3 H), 1.39 (s, 6 H). | |
| 111 | [2-(hydroxymethyl)phenyl]methyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.48-7.41 (m, 3 H), 7.33-7.27 (m, 2 H), 5.50 (s, 2 H), 4.77 (s, 2 H), 3.59 (s, 3 H), 2.51 (s, 3 H), 1.50 (s, 6 H). | 391 (M − OH) |
| 112 | 4-pyridylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CDCl$_3$) δ 11.94 (br. s, 1 H), 8.64-8.60 (m, 2 H), 7.44-7.27 (m, 3 H), 6.28 (s, 1 H), 5.22 (s, 2 H), 3.72 (s, 3 H), 2.72 (s, 3 H), 2.06 (s, 3H), 1.89 (s, 3 H). | 402 (M + Na) |
| 113 | (2-methoxyphenyl)methyl-4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.56 (br. s, 1 H), 7.51 (s, 1 H), 7.34-7.28 (m, 2 H), 7.03 (d, J = 8.0 Hz, 1 H), 6.94 (d, J = 7.6 Hz, 1 H), 5.30 (s, 2 H), 5.22 (s, 1 H), 3.81 (s, 3 H), 3.51 (s, 3 H), 2.44 (s, 3 H), 1.39 (s, 6 H). | 391 (M − OH) |
| 114 | 3-pyridylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.62 (br. s, 1 H), 8.66 (s, 1 H), 8.53-8.51 (m, 1 H), 7.86 (d, J = 8.0 Hz, 1 H), 7.53 (s, 1 H), 7.42-7.38 (m, 1 H), 5.40 (s, 2 H), 5.28 (s, 1 H), 3.52 (s, 3 H), 2.46 (s, 3 H), 1.42 (s, 6 H). | 362 (M − OH) |
| 115 | 2-pyridylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.65 (br. s, 1 H), 8.54 (d, J = 4.4 Hz, 1 H), 7.82-7.80 (m, 1 H), 7.53 (s, 1 H), 7.42 (d, J = 7.6 Hz, 1 H), 7.34-7.31 (m, 1 H), 5.41 (s, 2 H), 5.33 (s, 1 H), 3.52 (s, 3 H), 2.50 (s, 3 H), 1.36 (s, 6 H). | 402 (M + Na) |
| 116 | [2-(trifluoromethyl)phenyl]methyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.57 (br. s, 1 H), 7.77 (d, J = 7.6 Hz, 1 H), 7.70-7.66 (m, 2 H), 7.56-7.52 (m, 2 H), 5.54 (s, 2 H), 5.22 (s, 1 H), 3.52 (s, 3 H), 2.46 (s, 3 H), 1.35 (s, 6 H). | 429 (M − OH) |
| 117 | p-tolylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.60 (br. s, 1 H), 7.52 (s, 1 H), 7.32 (d, J = 7.6 Hz, 2 H), 7.17 (d, J = 8.0 Hz, 2 H), 5.30 (s, 2 H), 5.27 (s, 1 H), 3.51 (s, 3 H), 2.44 (s, 3 H), 2.29 (s, 3 H), 1.43 (s, 6 H). | 375 (M − OH) |
| 118 | m-tolylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.50 (br. s, 1 H), 7.53 (s, 1 H), 7.25-7.21 (m, 3 H), 7.13-7.10 (m, 1 H), 5.32 (s, 2 H), 5.26 (s, 1 H), 3.52 (s, 3 H), 2.46 (s, 3 H), 2.29 (s, 3 H), 1.43 (s, 6 H). | 375 (M − OH) |
| 119 | (2-fluorophenyl)methyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.54 (br. s, 1 H), 7.52-7.49 (m, 2 H), 7.41-7.38 (m, 1 H), 7.25-7.19 (m, 2 H), 5.39 (s, 2 H), 5.24 (s, 1 H), 3.51 (s, 3 H), 2.44 (s, 3 H), 1.41 (s, 6 H). | 379 (M − OH) |
| 120 | 1-phenylethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.54 (br. s, 1 H), 7.47 (s, 1 H), 7.42 (d, J = 7.6 Hz, 2 H), 7.37-7.33 (m, 2 H), 7.28-7.24 (m, 1 H), 5.98-5.93 (m, 1 H), 5.09 (s, 1 H), 3.49 (s, 3 H), 2.47 (s, 3 H), 1.58 (d, J = | 375 (M − OH) |

| Example | Compound Name | NMR | m/z |
|---|---|---|---|
| | | 6.8 Hz, 3 H), 1.36 (s, 3 H), 1.32 (s, 3 H). | |
| 121 | o-tolylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.50 (br. s, 1 H), 7.49 (s, 1 H), 7.36-7.34 (m, 1 H), 7.21-7.16 (m, 3 H), 5.36 (s, 2 H), 5.24 (br. s, 1 H), 3.51 (s, 3 H), 2.44 (s, 3 H), 2.34 (s, 3 H), 1.41 (s, 6 H). | 393 |
| 122 | isobutyl 6-but-3-enyl-4-(3-cyclopropyl-3-hydroxy-but-1-ynyl)-2-methyl-7-oxo-1H-pyrrolo[2,3-c]pyridine-3-carboxylate | $^1$H NMR (400 MHz, DMSO-$d_6$) δ 12.50 (br. s, 1 H), 7.44 (s, 1 H), 5.84-5.76 (m, 1 H), 5.10-4.98 (m, 3 H), 4.10-3.95 (m, 4 H), 2.48 (s, 3 H), 2.44-2.38 (m, 2 H), 2.05-1.97 (m, 1 H), 1.48 (s, 3 H), 1.12-1.09 (m, 1 H), 0.93 (d, J = 6.8 Hz, 6 H), 0.52-0.46 (m, 2 H), 0.36-0.33 (m, 2 H). | 393 (M − OH) |
| 123 | o-tolylmethyl 6-but-3-enyl-4-[(3R)-3-hydroxy-3-(5-methylisoxazol-3-yl)but-1-ynyl]-2-methyl-7-oxo-1H-pyrrolo[2,3-c]pyridine-3-carboxylate | $^1$H NMR (400 MHz, DMSO-$d_6$) δ 12.64 (br. s, 1 H), 7.55 (s, 1 H), 7.30-7.28 (m, 1 H), 7.21-7.14 (m, 3 H), 6.29-6.28 (m, 2 H), 5.83-5.76 (m, 1 H), 5.28 (s, 2 H), 5.04-4.98 (m, 2 H), 4.08-4.04 (m, 2 H), 2.44-2.39 (m, 5 H), 2.36 (s, 3 H), 2.31 (s, 3 H), 1.76 (s, 3 H). | 500 |
| 124 | o-tolylmethyl 6-but-3-enyl-4-(3-hydroxy-3-methyl-but-1-ynyl)-2-methyl-7-oxo-1H-pyrrolo[2,3-c]pyridine-3-carboxylate | $^1$H NMR (400 MHz, DMSO-$d_6$) δ 12.58 (br. s, 1 H), 7.48 (s, 1 H), 7.36-7.34 (m, 1 H), 7.24-7.17 (m, 3 H), 5.83-5.76 (m, 1 H), 5.36 (s, 2 H), 5.24 (s, 1 H), 5.04-4.98 (m, 2 H), 4.06 (t, J = 6.8 Hz, 2 H), 2.44-2.39 (m, 5 H), 2.34 (s, 3 H), 1.42 (s, 6 H). | 455 (M + Na) |
| 125 | isobutyl 6-but-3-enyl-4-[(3R)-3-hydroxy-3-(5-methylisoxazol-3-yl)but-1-ynyl]-2-methyl-7-oxo-1H-pyrrolo[2,3-c]pyridine-3-carboxylate | $^1$H NMR (400 MHz, DMSO-$d_6$) δ 12.59 (br. s, 1 H), 7.53 (s, 1 H), 6.34 (s, 1 H), 6.23 (s, 1 H), 5.83-5.76 (m, 1 H), 5.04-4.98 (m, 2 H), 4.06 (t, J = 7.2 Hz, 2 H), 3.96-3.93 (m, 2 H), 2.48 (s, 3 H), 2.46-2.36 (m, 5 H), 1.97-1.94 (m, 1 H), 1.79 (s, 3 H), 0.90 (d, J = 6.8 Hz, 6 H). | 452 |
| 126 | isobutyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (s, 1H), 7.46 (s, 1H), 5.01 (s, 1H), 4.04 (d, J = 6.6 Hz, 2H), 3.52 (s, 3H), 2.49 (s, 3H), 2.01 (dt, J = 13.3, 6.7 Hz, 1H), 1.49 (s, 3H), 1.16-1.02 (m, 1H), 0.94 (d, J = 6.7 Hz, 6H), 0.56-0.43 (m, 2H), 0.41-0.28 (m, 2H). | 353 (M − OH) |
| 127 | isobutyl 4-(3,4-dihydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.58 (s, 1H), 7.52 (s, 1H), 5.08 (s, 1H), 4.80-4.49 (m, 1H), 4.03 (d, J = 6.6 Hz, 2H), 3.52 (s, 3H), 2.49 (s, 3H), 2.10-1.93 (m, 2H), 1.38 (s, 3H), 0.94 (d, J = 6.7 Hz, 6H). | 361 |
| 128 | isobutyl 4-(3-hydroxy-3,4-dimethyl-pent-1-ynyl)-2,6-dimethyl-7-oxo-1H-pyrrolo[2,3-c]pyridine-3-carboxylate | $^1$H NMR (400 MHz, DMSO-$d_6$) δ 12.54 (br, s, 1H), 7.48 (s, 1H), 4.92 (s, 1H), 4.03 (d, J = 6.6 Hz, 2H), 3.52 (s, 3H), 2.49 (s, 3H), 2.07-1.94 (m, 1H), 1.85-1.68 (m, 1H), 1.38 (s, 3H), 0.98 (dd, J = 13.8, 6.8 Hz, 6H), 0.93 (d, J = 6.7 Hz, 6H). | 373 |
| 129 | o-tolylmethyl 4-(3,4-dihydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 7.54 (s, 1H), 7.36 (dt, J = 7.5, 1.1 Hz, 1H), 7.29-7.13 (m, 3H), 5.37 (s, 3H), 5.12 (s, 1H), 4.71 (t, J = 6.5 Hz, 1H), 3.52 (s, 2H), 3.40 (dd, J = 6.5, | 391 (M − OH) |

-continued

| Example | Compound Name | NMR | m/z |
|---|---|---|---|
| 130 | isobutyl 2,6-dimethyl-7-oxo-4-(4,4,4-trifluoro-3-hydroxy-3-phenyl-but-1-ynyl)-1H-pyrrolo[2,3-c]pyridine-3-carboxylate | 4.6 Hz, 2H), 2.46-2.43 (s, 3H), 2.35 (s, 3H), 1.36 (s, 3H). $^1$H NMR (400 MHz, DMSO-$d_6$) δ 12.67 (s, 1H), 7.81 (dd, J = 6.6, 2.9 Hz, 2H), 7.71 (s, 1H), 7.63 (s, 1H), 7.47-7.39 (m, 2H), 3.83 (d, J = 6.7 Hz, 2H), 3.57 (s, 3H), 2.46 (s, 3H), 0.83 (d, J = 6.7, 4.6 Hz, 6H). | 461 |
| 131 | isopropyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.49 (br. s, 1 H), 7.48 (s, 1 H), 5.54 (s, 1 H), 5.10-5.01 (m, 1 H), 3.51 (s, 3 H), 2.46 (s, 3 H), 1.45 (s, 6 H), 1.31 (d, J = 6.1 Hz, 6 H) | 331 |
| 132 | isobutyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.55 (br. s., 1 H), 7.49 (s, 1 H), 5.18 (s, 1 H), 4.03 (d, J = 6.6 Hz, 2 H), 3.51 (s, 3 H), 2.48 (br. s., 3 H), 2.01 (s, 1 H), 1.45 (s, 6 H), 0.94 (d, J = 6.8 Hz, 6 H) | 345 |
| 133 | tert-butyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.44 (br. s., 1 H), 7.46 (s, 1 H), 5.14 (s, 1 H), 3.51 (s, 3 H), 2.46 (s, 3 H), 1.53 (s, 9 H), 1.45 (s, 6 H) | 345 |

Example 134

(2-cyano-1,1-dimethyl-ethyl)-4-(3-cyclopropyl-3-hydroxy-but-1-ynyl)-2,6-dimethyl-7-oxo-1H-pyrrolo[2,3-c]pyridine-3-carboxylate

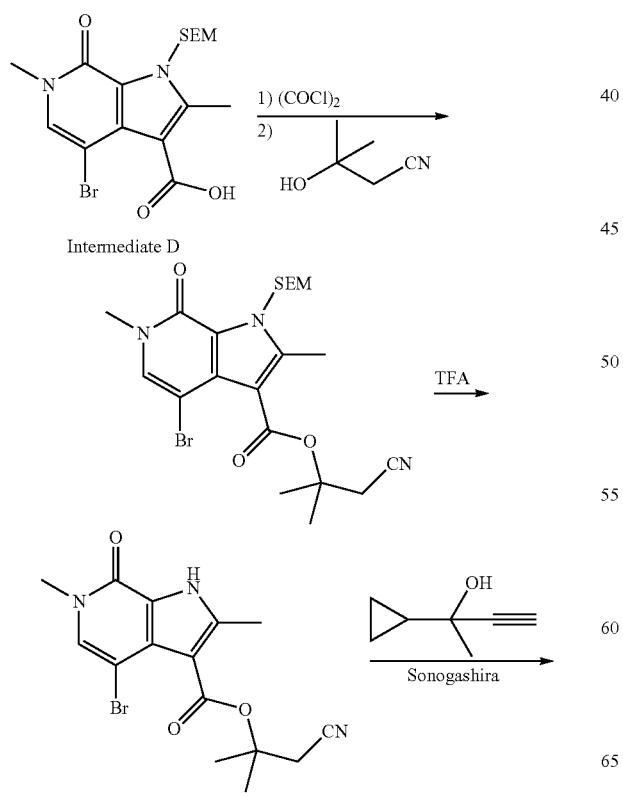

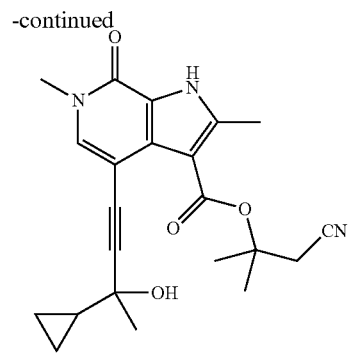

Step 1

4-bromo-2,6-dimethyl-7-oxo-1-((2-(trimethylsilyl)ethoxy)methyl)-6,7-dihydro-1H-pyrrolo[2,3-c]pyridine-3-carbonyl chloride To a solution of 4-bromo-2,6-dimethyl-7-oxo-1-((2-(trimethylsilyl)ethoxy)methyl)-6,7-dihydro-1H-pyrrolo[2,3-c]pyridine-3-carboxylic acid (Intermediate D) (207 mg, 0.50 mmol) in DCM (10 mL) was added oxalyl dichloride (1 mL). The reaction was stirred at ambient temperature for 2 h and then concentrated under reduced pressure to give the crude title compound (217 mg, 100% yield) as a yellow oil.

Step 2

1-cyano-2-methylpropan-2-yl-4-bromo-2,6-dimethyl-7-oxo-1-((2-(trimethylsilyl)ethoxy)methyl)-6,7-dihydro-1H-pyrrolo[2,3-c]pyridine-3-carboxylate

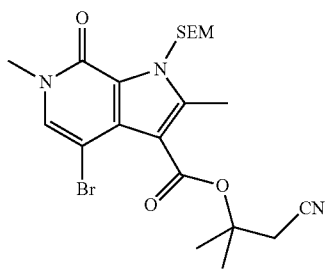 [SMILES: Cc1c(C(=O)OC(C)(C)CC#N)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carbonyl chloride (217 mg, 0.50 mmol) in toluene (20 mL) was added 3-hydroxy-3-methylbutanenitrile (99 mg, 1.00 mmol). The reaction was heated at 100° C. for 3 h. After cooling to ambient temperature, the reaction was quenched by the addition of water (20 mL) and then extracted with EtOAc (3×20 mL). The combined organic layers were dried over anhydrous $Na_2SO_4$ and concentrated under reduced pressure. The residue was purified by column chromatography (petroleum ether:EtOAc=4:1) to give the title compound (150 mg, 61% yield) as a yellow solid.

Step 3

1-cyano-2-methylpropan-2-yl-4-bromo-2,6-dimethyl-7-oxo-6,7-dihydro-1H-pyrrolo[2,3-c]pyridine-3-carboxylate

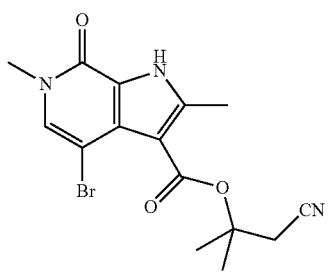 [SMILES: Cc1[nH]c2c(=O)n(C)cc(Br)c2c1C(=O)OC(C)(C)CC#N]

To a solution of 1-cyano-2-methylpropan-2-yl 4-bromo-2,6-dimethyl-7-oxo-1-((2-(trimethylsilyl)ethoxy)methyl)-6,7-dihydro-1H-pyrrolo[2,3-c]pyridine-3-carboxylate (150 mg, 0.30 mmol) in DCM (10 mL) was added 2,2,2-trifluoroacetic acid (1 mL). The reaction was stirred at ambient temperature for 2 h and then concentrated under reduced pressure. The residue was diluted with MeOH (5 mL) and adjusted to pH 8 by the addition of $K_2CO_3$. The suspension was diluted with water (20 mL) and extracted with EtOAc (3×20 mL). The combined organic layers were concentrated under reduced pressure. The residue was purified by column chromatography (DCM:MeOH=9:1) to give the title compound (100 mg, 90% yield) as a yellow solid.

Step 4

(2-cyano-1,1-dimethyl-ethyl)-4-(3-cyclopropyl-3-hydroxy-but-1-ynyl)-2,6-dimethyl-7-oxo-1H-pyrrolo[2,3-c]pyridine-3-carboxylate

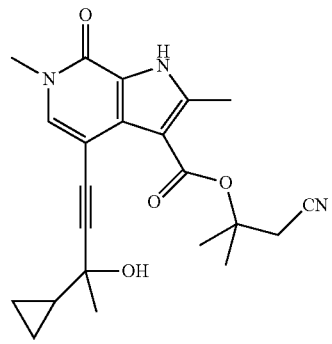 [SMILES: Cc1[nH]c2c(=O)n(C)cc(C#CC(C)(O)C3CC3)c2c1C(=O)OC(C)(C)CC#N]

To a suspension of 1-cyano-2-methylpropan-2-yl 4-bromo-2,6-dimethyl-7-oxo-6,7-dihydro-1H-pyrrolo[2,3-c]pyridine-3-carboxylate (100 mg, 0.27 mmol) in DMF (3 mL) and TEA (1 mL) was added 2-cyclopropylbut-3-yn-2-ol (150 mg, 1.37 mmol), copper(I) iodide (11 mg, 0.06 mmol) and bis(triphenylphosphine)palladium(II) dichloride (21 mg, 0.03 mmol). The solution was purged with $N_2$ for 5 min and then stirred at 110° C. for 1 h under microwave conditions. The reaction mixture was concentrated under reduced pressure. The crude product was purified by reverse phase chromatography (ACN 30-60%/0.1% $NH_4OH$ in water) to give the title compound (20 mg, 19% yield) as a white solid. $^1$H NMR (400 MHz, $CD_3OD$) δ 7.43 (s, 1H), 3.61 (s, 3H), 3.24 (s, 2H), 2.63 (s, 3H), 1.73 (s, 6H), 1.63 (s, 3H), 1.19-1.15 (m, 1H), 0.72-0.71 (m, 1H), 0.62-0.60 (m, 1H), 0.49-0.46 (m, 2H). LCMS M/Z (M-OH) 378.

The following compounds were prepared in a similar fashion to Example 134

Examples 135-167

| Example | Compound Name | NMR | m/z |
|---|---|---|---|
| 135 | 3-acetamidopropyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1$H NMR (400 MHz, DMSO-$d_6$) δ 12.69 (br. s, 1 H), 7.87-7.77 (m, 3 H), 7.73 (s, 1 H), 7.67 (s, 1 H), 7.50-7.40 (m, 3 H), 4.10-3.98 (m, 2 H), 3.57 (s, 3 H), 3.06-2.99 (m, 2 H), 2.51 (s, 3 H), 1.77 (s, 3 H), 1.73-1.65 (m, 2 H). | 526 (M + Na) |

-continued

| Example | Compound Name | NMR | m/z |
|---|---|---|---|
| 136 | (2-cyano-1,1-dimethyl-ethyl) 2,6-dimethyl-7-oxo-4-(4,4,4-trifluoro-3-hydroxy-3-phenyl-but-1-ynyl)-1H-pyrrolo[2,3-c]pyridine-3-carboxylate | $^1$H NMR (400 MHz, CD$_3$OD) δ 7.91-7.89 (m, 2 H), 7.62 (s, 1 H), 7.42-7.39 (m, 3 H), 3.63 (s, 3 H), 3.11 (d, J = 3.6 Hz, 2 H), 2.63 (s, 3 H), 1.62 (s, 6 H). | 486 |
| 137 | 1,1-dimethylpentyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, CD$_3$OD) δ 7.42 (s, 1 H), 3.60 (s, 3 H), 2.58 (s, 3 H), 1.98-1.94 (m, 2 H), 1.62 (s, 3 H), 1.59 (s, 6 H), 1.45-1.35 (m, 4 H), 1.18-1.14 (m, 1 H), 0.94 (t, J = 7.2 Hz, 3 H), 0.70-0.67 (m, 1 H), 0.62-0.58 (m, 1 H), 0.46-0.44 (m, 2 H). | 435 (M + Na) |
| 138 | 1,1-dimethylpropyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, CD$_3$OD) δ 7.41 (s, 1 H), 3.60 (s, 3 H), 2.58 (s, 3 H), 2.03-1.97 (m, 2 H), 1.61 (s, 3 H), 1.58 (s, 6 H), 1.17-1.15 (m, 1 H), 0.99 (t, J = 7.6 Hz, 3 H), 0.70-0.68 (m, 1 H), 0.61-0.59 (m, 1 H), 0.47-0.44 (m, 2 H). | 367 (M − OH) |
| 139 | 1,1-dimethylpropyl 4-[(3R)-3-hydroxy-3-(5-methylisoxazol-3-yl)but-1-ynyl]-2,6-dimethyl-7-oxo-1H-pyrrolo[2,3-c]pyridine-3-carboxylate | $^1$H NMR (400 MHz, CD$_3$OD) δ 7.51 (s, 1 H), 6.38 (s, 1 H), 3.61 (s, 3 H), 2.58 (s, 3 H), 2.42 (s, 3 H), 1.99-1.93 (m, 2 H), 1.89 (s, 3 H), 1.55 (s, 6 H), 0.96 (t, J = 7.6 Hz, 3 H). | 426 |
| 140 | 3-acetamidopropyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, CD$_3$OD) δ 7.42 (s, 1 H), 4.37 (t, J = 6.4 Hz, 2 H), 3.60 (s, 3 H), 3.34-3.33 (m, 2 H), 2.59 (s, 3 H), 2.00-1.91 (m, 5 H), 1.60 (s, 3 H), 1.18-1.14 (m, 1 H), 0.68-0.65 (m, 1 H), 0.55-0.52 (m, 1 H), 0.52-0.45 (m, 2 H). | 396 (M − OH) |
| 141 | 1,2-dimethylpropyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, DMSO-d$_6$) δ 12.18 (br. s, 1 H), 7.46 (s, 1 H), 4.98 (s, 1 H), 4.90-4.83 (m, 1 H), 3.51 (s, 3 H), 2.49 (s, 3 H), 1.89-1.85 (m, 1 H), 1.49 (s, 3 H), 1.22 (d, J = 6.4 Hz, 3 H), 1.08-1.06 (m, 1 H), 0.93 (d, J = 6.8 Hz, 6 H), 0.53-0.47 (m, 2 H), 0.33-0.31 (m, 2 H). | 407 (M + Na) |
| 142 | 1,2-dimethylpropyl 4-[3-hydroxy-3-(5-methylisoxazol-3-yl)but-1-ynyl]-2,6-dimethyl-7-oxo-1H-pyrrolo[2,3-c]pyridine-3-carboxylate | $^1$H NMR (400 MHz, DMSO-d$_6$) δ 12.40 (br. s, 1 H), 7.54 (s, 1 H), 6.36 (s, 1 H), 4.85-4.81 (m, 1 H), 3.51 (s, 3 H), 2.50 (s, 3 H), 2.38 (s, 3 H), 1.89-1.86 (m, 1 H), 1.79 (s, 3 H), 1.21-1.18 (m, 3 H), 0.93-0.90 (m, 6 H). | 408 (M − OH) |
| 143 | (1-methyl-4-piperidyl)methyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.45 (s, 1 H), 4.24 (d, J = 6.4 Hz, 2 H), 3.61 (s, 3 H), 3.06-3.02 (m, 2 H), 2.59 (s, 3 H), 2.40 (s, 3 H), 2.30-2.24 (m, 2 H), 1.92-1.85 (m, 3 H), 1.57 (s, 6 H), 1.49-1.46 (m, 1 H), 1.44-1.29 (m, 1 H). | 400 |
| 144 | (1-acetyl-4-piperidyl)methyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.40 (br. s, 1 H), 7.49 (s, 1 H), 5.23 (br. s, 1 H), 4.39-4.35 (m, 1 H), 4.12 (d, J = 6.4 Hz, 2 H), 3.83-3.79 (m, 2 H), 3.51 (s, 3 H), 3.03-2.96 (m, 2 H), 2.47 (s, 3 H), 1.97 (s, 3 H), 1.74-1.65 (m, 2 H), 1.45 (s, 6 H), 1.22- | 410 (M − OH) |

| Example | Compound Name | NMR | m/z |
|---|---|---|---|
| | | 1.17 (m, 1 H), 1.07-1.02 (m, 1 H). | |
| 145 | 1,2-dimethylbutyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.49 (br. s, 1 H), 7.48 (s, 1 H), 5.17 (s, 1 H), 5.01-4.95 (m, 1 H), 3.50 (s, 3 H), 2.50-2.48 (m, 4 H), 1.62-1.58 (m, 2 H), 1.46-1.42 (m, 6 H), 1.24-1.19 (m, 4 H), 0.94-0.88 (m, 5 H). | 355 (M − OH) |
| 146 | 1,1-dimethylpentyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.45 (s, 1 H), 3.62 (s, 3 H), 2.59 (s, 3 H), 2.10-1.95 (m, 2 H), 1.61 (s, 6 H), 1.59 (s, 6 H), 1.46-1.35 (m, 4 H), 0.95 (t, J = 7.2 Hz, 3 H). | 387 |
| 147 | 1,1-dimethylbutyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.43 (s, 1 H), 4.63 (s, 1 H), 3.60 (s, 3 H), 2.57 (s, 3 H), 1.96-1.91 (m, 2 H), 1.59 (s, 6 H), 1.57 (s, 6 H), 1.52-1.48 (m, 2 H), 0.96 (t, J = 7.2 Hz, 3 H). | 395 (M + Na) |
| 148 | cyclopentylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.50 (br. s, 1 H), 7.46 (s, 1 H), 5.19 (br. s, 1 H), 4.11 (d, J = 6.8 Hz, 2 H), 3.50 (s, 3 H), 2.47 (s, 3 H), 2.30-2.28 (m, 1 H), 1.74-1.71 (m, 2 H), 1.60-1.50 (m, 4 H), 1.44 (s, 6 H), 1.30-1.26 (m, 2 H). | 393 (M + Na) |
| 149 | 2-methylbutyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.56 (br. s, 1 H), 7.49 (s, 1 H), 5.21 (s, 1 H), 4.16-4.05 (m, 2 H), 3.51 (s, 3 H), 2.48 (s, 3 H), 1.83-1.77 (m, 1 H), 1.47-1.43 (m, 7 H), 1.24-1.15 (m, 1 H), 0.93-0.87 (m, 6 H). | 341 (M − OH) |
| 150 | 2,2-dimethylpropyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.44 (s, 1 H), 4.05 (s, 2 H), 3.61 (s, 3 H), 2.62 (s, 3 H), 1.56 (s, 6 H), 1.05 (s, 9 H). | 359 |
| 151 | 1,1-dimethylpropyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.44 (s, 1 H), 3.60 (s, 3 H), 2.58 (s, 3 H), 2.03-1.97 (m, 2 H), 1.59 (s, 6 H), 1.57 (s, 6 H), 0.99 (t, J = 7.4 Hz, 3 H). | 381 (M + Na) |
| 152 | 1,2-dimethylpropyl 4-(3-hydroxy-3-methyl-but-1-ynyl)-2,6-dimethyl-7-oxo-1H-pynolo[2,3-c]pyridine-3-carboxylate | $^1$H NMR (400 MHz, DMSO-d$_6$) δ 12.51 (br. s, 1 H), 7.48 (s, 1 H), 5.15 (s, 1 H), 4.89-4.83 (m, 1 H), 3.51 (s, 3 H), 2.49 (s, 3 H), 1.94-1.86 (m, 1 H), 1.45 (s, 6 H), 1.22 (d, J = 6.4 Hz, 3 H), 0.93 (d, J = 6.4 Hz, 6 H). | 341 (M − OH) |
| 153 | cyclohexylmethyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.44 (s, 1 H), 4.15 (d, J = 4.4 Hz, 2 H), 3.61 (s, 3 H), 2.59 (s, 3 H), 1.85-1.69 (m, 5 H), 1.57 (s, 6 H), 1.34-1.24 (m, 4 H), 1.13-1.07 (m, 2 H). | 407 (M + Na) |
| 154 | isobutyl 4-(4-cyano-3-hydroxy-3-methyl-but-1-ynyl)-2,6-dimethyl-7-oxo-1H-pyrrolo[2,3-c]pyridine-3-carboxylate | $^1$H NMR (400 MHz, DMSO-d$_6$) δ 12.62 (br. s, 1 H), 7.55 (s, 1 H), 6.02 (s, 1 H), 4.02 (d, J = 6.4 Hz, 2 H), 3.52 (s, 3 H), 2.94 (s, 2 H), 2.50 (s, 3 H), 2.04-1.97 (m, 1 H), 1.55 (s, 3 H), 0.95 (d, J = 6.8 Hz, 6 H). | 392 (M + Na) |
| 155 | cyclopropylmethyl 4-(3-hydroxy-3-methyl-but-1- | $^1$H NMR (400 MHz, DMSO-d$_6$) δ 12.56 (br. s, 1 H), 7.50 | 325 (M − OH) |

| Example | Compound Name | NMR | m/z |
|---|---|---|---|
| | ynyl)-2,6-dimethyl-7-oxo-1H-pyrrolo[2,3-c]pyridine-3-carboxylate | (s, 1 H), 5.22 (s, 1 H), 4.09 (d, J = 7.6 Hz, 2 H), 3.51 (s, 3 H), 2.49 (s, 3 H), 1.44 (s, 6 H), 1.24-1.19 (m, 1 H), 0.55-0.51 (m, 2 H), 0.34-0.31 (m, 2 H). | |
| 156 | isopropyl 4-(4-cyano-3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.55 (s, 1 H), 6.01 (s, 1 H), 5.12-5.06 (m, 1 H), 3.51 (s, 3 H), 2.96 (s, 2 H), 2.49 (s, 3 H), 1.57 (s, 3 H), 1.32 (d, J = 6.0 Hz, 6 H). | 378 (M + Na) |
| 157 | isopropyl 4-[(3R)-3-hydroxy-3-(5-methylisoxazol-3-yl)but-1-ynyl]-2,6-dimethyl-7-oxo-1H-pyrrolo[2,3-c]pyridine-3-carboxylate | $^1$H NMR (400 MHz, DMSO-$d_6$) δ 12.54 (br. s, 1 H), 7.54 (s, 1 H), 6.36 (s, 1 H), 6.19 (s, 1 H), 5.04-4.99 (m, 1 H), 3.51 (s, 3 H), 2.47 (s, 3 H), 2.38 (s, 3 H), 1.80 (s, 3 H), 1.30-1.27 (m, 6 H). | 420 (M + Na) |
| 158 | isobutyl 4-[(3R)-3-hydroxy-3-(5-methylisoxazol-3-yl)but-1-ynyl]-2,6-dimethyl-7-oxo-1H-pyrrolo[2,3-c]pyridine-3-carboxylate | $^1$H NMR (400 MHz, DMSO-$d_6$) δ 12.60 (br. s, 1 H), 7.55 (s, 1 H), 6.34 (s, 1 H), 6.22 (s, 1 H), 3.96-3.91 (m, 2 H), 3.52 (s, 3 H), 2.50 (s, 3 H), 2.38 (s, 3 H), 1.99-1.93 (m, 1 H), 1.78 (s, 3 H), 0.90 (d, J = 6.8 Hz, 6 H). | 434 (M + Na) |
| 159 | cyclohexyl 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.20 (br. s, 1 H), 7.47 (s, 1 H), 5.16 (br. s, 1 H), 4.87-4.83 (m, 1 H), 3.50 (s, 3 H), 2.48 (s, 3 H), 1.92-1.88 (m, 2 H), 1.72-1.68 (m, 2 H), 1.59-1.51 (m, 3 H), 1.50-1.25 (m, 9 H). | 393 (M + Na) |
| 160 | isobutyl 4-(3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.60 (br. s, 1 H), 7.66 (d, J = 7.2 Hz, 2 H), 7.56 (s, 1 H), 7.34 (t, J = 7.6 Hz, 2 H), 7.27-7.23 (m, 1 H), 5.95 (s, 1 H), 3.92 (d, J = 6.8 Hz, 2 H), 3.52 (s, 3 H), 2.50 (s, 3 H), 1.96-1.90 (m, 1 H), 1.71 (s, 3 H), 0.88 (d, J = 3.2 Hz, 3 H), 0.86 (d, J = 3.2 Hz, 3 H). | 429 (M + Na) |
| 161 | isopropyl 4-(3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.41 (br. s, 1 H), 7.68 (d, J = 7.2 Hz, 2 H), 7.53 (s, 1 H), 7.33 (t, J = 7.6 Hz, 2 H), 7.26-7.22 (m, 1 H), 5.91 (s, 1 H), 5.08-5.01 (m, 1 H), 3.51 (s, 3 H), 2.49 (s, 3 H), 1.72 (s, 3 H), 1.32-1.25 (m, 6 H). | 375 (M − OH) |
| 162 | tert-butyl 4-(3-hydroxy-3-phenyl-but-1-ynyl)-2,6-dimethyl-7-oxo-1H-pyrrolo[2,3-c]pyridine-3-carboxylate | $^1$H NMR (400 MHz, DMSO-$d_6$) δ 12.50 (br. s, 1 H), 7.70 (d, J = 7.6 Hz, 2 H), 7.51 (s, 1H), 7.32 (t, J = 7.6 Hz, 2 H), 7.24 (t, J = 7.2 Hz, 1 H), 5.90 (s, 1 H), 3.51 (s, 3 H), 2.50 (s, 3 H), 1.72 (s, 3 H), 1.52 (s, 9 H). | 429 (M + Na) |
| 163 | (2-cyano-1,1-dimethyl-ethyl) 4-(3-hydroxy-3-methyl-but-1-ynyl)-2,6-dimethyl-7-oxo-1H-pyrrolo[2,3-c]pyridine-3-carboxylate | $^1$H NMR (400 MHz, DMSO-$d_6$) δ 12.57 (br. s, 1 H), 7.50 (s, 1 H), 5.21 (s, 1 H), 3.51 (s, 3 H), 3.24 (s, 2 H), 2.50 (s, 3 H), 1.63 (s, 6 H), 1.46 (s, 6 H). | 392 (M + Na) |
| 164 | (3-acetamido-1,1-dimethyl-propyl) 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.44 (s, 1 H), 3.60 (s, 3 H), 3.36-3.31 (m, 2 H), 2.59 (s, 3 H), 2.18 (t, J = 7.8 Hz, 2 H), 1.87 (s, 3 H), 1.63 (s, 6 H), 1.58 (s, 6 H). | 438 (M + Na) |

-continued

| Example | Compound Name | NMR | m/z |
|---|---|---|---|
| 165 | (3-amino-1,1-dimethyl-propyl) 4-(3-hydroxy-3-methyl-but-1-ynyl)-2,6-dimethyl-7-oxo-1H-pyrrolo[2,3-c]pyridine-3-carboxylate | $^1$H NMR (400 MHz, CD$_3$OD) δ 7.47 (s, 1 H), 3.63 (s, 3 H), 3.13-3.08 (m, 2 H), 2.60 (s, 3 H), 2.38-2.33 (m, 2 H), 1.68 (s, 6 H), 1.61 (s, 6 H). | 374 |
| 166 | 2-cyanoethyl 2,6-dimethyl-7-oxo-4-(4,4,4-trifluoro-3-hydroxy-3-phenyl-but-1-ynyl)-1H-pyrrolo[2,3-c]pyridine-3-carboxylate | $^1$H NMR (400 MHz, DMSO-d$_6$) δ 12.50 (br. s, 1 H), 7.81-7.76 (m, 4 H), 7.46-7.44 (m, 2 H), 4.24-4.15 (m, 2 H), 3.57 (s, 3 H), 2.88-2.85 (m, 2 H), 2.53 (s, 3 H). | 458 |
| 167 | 2-cyanoethyl 4-(3-cyclopropyl-3-hydroxy-but-1-ynyl)-2,6-dimethyl-7-oxo-1H-pyrrolo[2,3-c]pyridine-3-carboxylate | $^1$H NMR (400 MHz, CD$_3$OD) δ 7.44 (s, 1 H), 4.55-4.49 (m, 2 H), 3.61 (s, 3 H), 3.00-2.95 (m, 2 H), 2.63 (s, 3 H), 1.61-1.60 (m, 3 H), 1.17-1.15 (m, 1 H), 0.70-0.67 (m, 1 H), 0.57-0.47 (m, 3 H). | 390 (M + Na) |

Example 168

N-ethyl-4-(3-hydroxy-3-methyl-but-1-ynyl)-2,6-dimethyl-7-oxo-1H-pyrrolo[2,3-c]pyridine-3-carboxamide

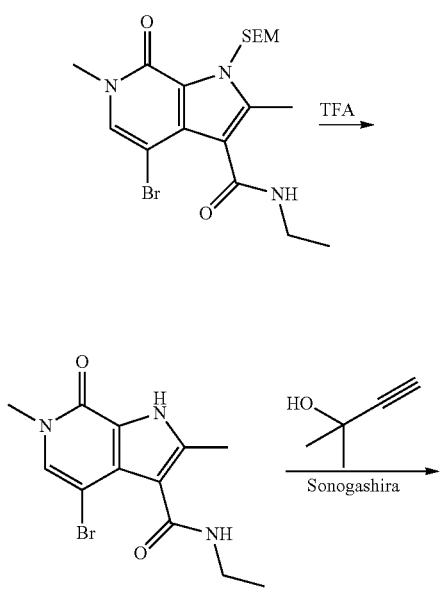

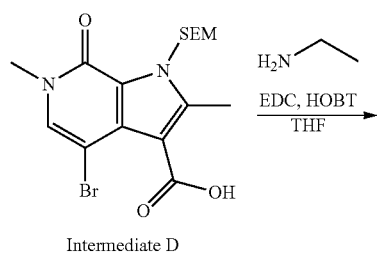

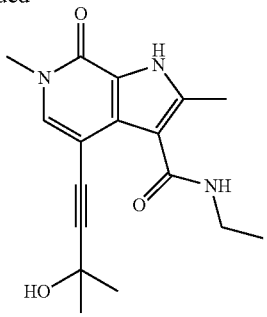

Step 1

4-bromo-N-ethyl-2,6-dimethyl-7-oxo-1-((2-(trimethylsilyl)ethoxy)methyl)-6,7-dihydro-1H-pyrrolo[2,3-c]pyridine-3-carboxamide To a solution of 4-bromo-2,6-dimethyl-7-oxo-1-2-(trimethylsilyl)ethoxy)methyl)-6,7-dihydro-1H-pyrrolo[2,3-c]pyridine-3-carboxylic acid (Intermediate D) (211 mg, 0.51 mmol) in THF (5 mL) was added HOBT (80 mg, 0.56 mmol), ethylamine (2M in THF, 0.28 mL, 0.56 mmol) and EDC (110 mg, 0.56 mmol). The reaction was stirred at ambient temperature for 12 h and then concentrated under reduced pressure. The residue was purified by column chromatography (hexane:EtOAc=5:5) to give the title compound (201.4 mg, 88%) as a white solid. LCMS M/Z (M+H) 442, 444.

Step 2

4-bromo-N-ethyl-2,6-dimethyl-7-oxo-6,7-dihydro-1H-pyrrolo[2,3-c]pyridine-3-carboxamide

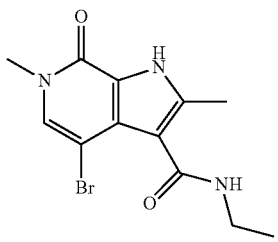 [SMILES: CCNC(=O)c1c(C)[nH]c2c(=O)n(C)cc(Br)c12]

To a solution of 4-bromo-N-ethyl-2,6-dimethyl-7-oxo-1-((2-(trimethylsilyl)ethoxy)methyl)-6,7-dihydro-1H-pyrrolo[2,3-c]pyridine-3-carboxamide (201.4 mg, 0.45 mmol) was added 2,2,2-trifluoroacetic acid (4 mL). The reaction was stirred at ambient temperature for 1 h and MeOH (1 mL) was added. The reaction was concentrated under reduced pressure. The residue was purified by column chromatography (50% DCM:MeOH:NH$_4$OH=90:10:1 in DCM) to give the title compound (133.0 mg, 95%) as an off-white solid. LCMS M/Z (M+H) 312, 314.

Step 3

N-ethyl-4-(3-hydroxy-3-methyl-but-1-ynyl)-2,6-dimethyl-7-oxo-1H-pyrrolo[2,3-c]pyridine-3-carboxamide

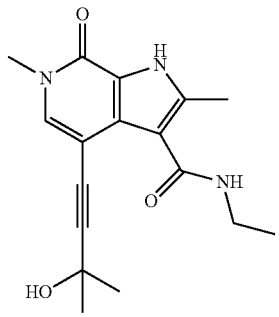 [SMILES: CCNC(=O)c1c(C)[nH]c2c(=O)n(C)cc(C#CC(C)(C)O)c12]

To a solution of 4-bromo-N-ethyl-2,6-dimethyl-7-oxo-6,7-dihydro-1H-pyrrolo[2,3-c]pyridine-3-carboxamide (133 mg, 0.43 mmol)) in DMF (2 mL) and DIPEA (0.74 mL, 4.26 mmol) was added 2-methylbut-3-yn-2-ol (83 uL, 0.85 mmol), copper(I) iodide (16 mg, 0.09 mmol) and bis(triphenylphosphine)palladium(II) dichloride (15 mg, 0.021 mmol). The reaction was purged with N$_2$ for 5 min and then stirred at 100° C. overnight. The reaction mixture was concentrated under reduced pressure. The crude product was purified by column chromatography (0-65% DCM:MeOH:NH$_4$OH=90:10:1 in DCM) to give the title compound (84 mg, 63% yield) as an off-white solid. $^1$H NMR (400 MHz, DMSO-d$_6$) δ 12.14 (s, 1H), 7.82 (t, J=5.4 Hz, 1H), 7.43 (s, 1H), 5.20 (s, 1H), 3.52-3.47 (m, 3H), 3.31-3.22 (m, 2H), 2.33 (s, 3H), 1.43 (s, 6H), 1.11 (t, J=7.2 Hz, 3H). LCMS M/Z (M+H) 316.

The following compounds were prepared in a similar fashion to Example 168:

Examples 169-171

| Example | Compound Name | NMR | m/z |
|---|---|---|---|
| 169 | 4-(3-hydroxy-3-methyl-but-1-ynyl)-N-isopropyl-2,6-dimethyl-7-oxo-1H-pyrrolo[2,3-c]pyridine-3-carboxamide | $^1$H NMR (400 MHz, DMSO-d$_6$) δ 11.60 (br. s, 1 H), 7.77-7.57 (m, 1 H), 7.14-7.00 (m, 1 H), 6.15 (s, 2 H), 4.32 (d, J = 4.9 Hz, 3 H), 4.16 (dd, J = 7.1, 10.3 Hz, 1 H), 3.84 (s, 3 H), 2.60 (s, 3 H), 2.23-2.14 (m, 6 H), 1.53 (d, J = 7.1 Hz, 3 H) | 330 |
| 170 | N-tert-butyl-4-(3-hydroxy-3-methyl-but-1-ynyl)-2,6-dimethyl-7-oxo-1H-pyrrolo[2,3-c]pyridine-3-carboxamide | $^1$H NMR (400 MHz, DMSO-d$_6$) δ 12.07 (s, 1 H), 7.39 (s, 1 H), 7.36 (s, 1 H), 5.15 (s, 1 H), 3.50 (s, 3 H), 2.34 (s, 3 H), 1.44 (s, 6 H), 1.39-1.33 (m, 9 H) | 344 |
| 171 | 4-(3-hydroxy-3-methyl-but-1-ynyl)-N,N,6-trimethyl-7-oxo-1H-pyrrolo[2,3-c]pyridine-3-carboxamide | 1H NMR (400 MHz, DMSO-d$_6$) δ 12.43 (br. s, 1 H), 7.49 (s, 1 H), 7.39 (d, J = 2.9 Hz, 1 H), 5.27 (br. s., 1 H), 3.51 (s, 3 H), 3.00 (s, 3 H), 2.85 (s, 3 H), 1.46-1.40 (m, 6 H) | 284 (M − OH) |

Example 172

4-(3-cyclopropyl-3-hydroxy-but-1-ynyl)-3-(5-(1-hydroxy-1-methyl-ethyl)-1,3,4-oxadiazol-2-yl)-2,6-dimethyl-1H-pyrrolo[2,3-c]pyridin-7-one

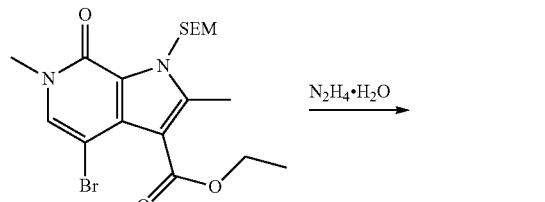

Intermediate C

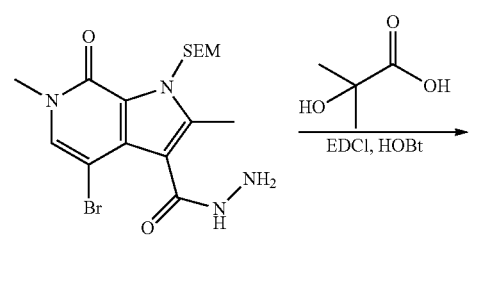

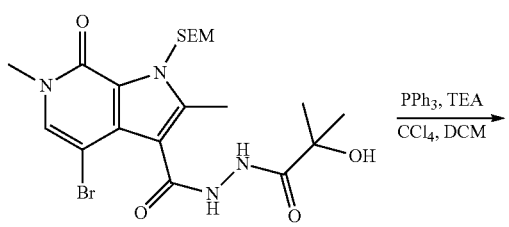

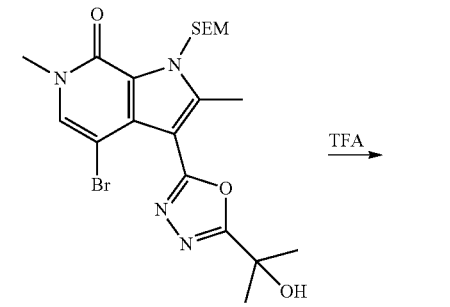

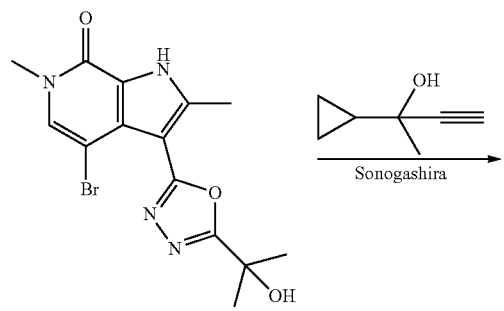

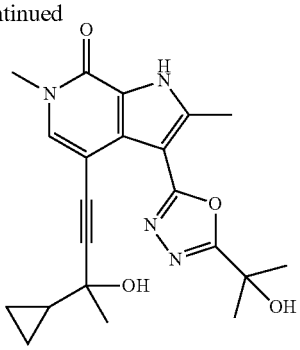

Step 1

4-bromo-2,6-dimethyl-7-oxo-1-((2-(trimethylsilyl)ethoxy)methyl)-6,7-dihydro-1H pyrrolo[2,3-c]pyridine-3-carbohydrazide

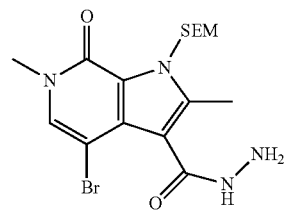 [SMILES: Cc1c(C(=O)NN)c2c(Br)cn(C)c(=O)c2n1COCC[Si](C)(C)C]

To a solution of ethyl 4-bromo-2,6-dimethyl-7-oxo-1-((2-(trimethylsilyl)ethoxy) methyl)-6,7-dihydro-1H-pyrrolo[2,3-c]pyridine-3-carboxylate (Intermediate C) (500 mg, 1.13 mmol) in ethane-1,2-diol (15 mL) and EtOH (5 mL) was added hydrazine hydrate (20 mL). The reaction mixture was heated at 100° C. for 48 h. After cooling to ambient temperature, the solution was diluted with water (30 mL). The resulting precipitate was collected by filtration, washed with water (10 mL) and dried in vacuo to give the crude title compound (300 mg, 62% yield) as a white solid.

Step 2

4-bromo-N'-(2-hydroxy-2-methylpropanoyl)-2,6-dimethyl-7-oxo-1-((2-(trimethylsilyl) ethoxy)methyl)-6,7-dihydro-1H-pyrrolo[2,3-c]pyridine-3-carbohydrazide

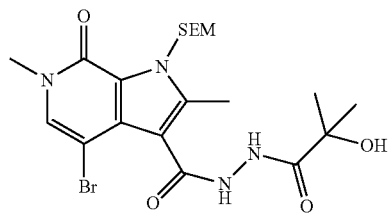 [SMILES: Cc1c(C(=O)NNC(=O)C(C)(C)O)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carbohydrazide (300 mg, 0.70 mmol) in DMF (10 mL) was added EDC (267 mg, 1.40 mmol), HOBT (189 mg, 1.40 mmol) and 2-hydroxy-2-methylpropanoic acid (146 mg, 1.40 mmol). The reaction was stirred at ambient temperature for 16 h and then quenched by the addition of water (20 mL). The mixture was extracted with EtOAc (2×20 mL). The combined organic layers were washed with water (2×20 mL) and brine (2×20 mL), dried over anhydrous $Na_2SO_4$ and concentrated under reduced pressure to give the crude title compound (250 mg, 69% yield) as a yellow solid.

Step 3

4-bromo-3-(5-(2-hydroxypropan-2-yl)-1,3,4-oxadiazol-2-yl)-2,6-dimethyl-1-((2-(trimethylsilyl)ethoxy)methyl)-1H-pyrrolo[2,3-c]pyridin-7(6H)-one

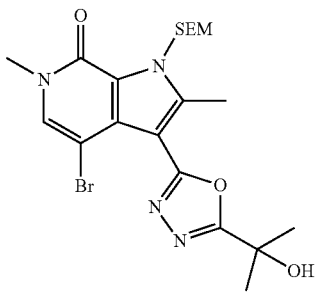 [SMILES: Cc1c(-c2nnc(C(C)(C)O)o2)c2c(Br)cn(C)c(=O)c2n1COCC[Si](C)(C)C]

To a solution of 4-bromo-N-(2-hydroxy-2-methylpropanoyl)-2,6-dimethyl-7-oxo-1-((2-(trimethylsilyl)ethoxy)methyl)-6,7-dihydro-1H-pyrrolo[2,3-c]pyridine-3-carbohydrazide (250 mg, 0.49 mmol) in DCM (20 mL) was added TEA (247 mg, 2.45 mmol), triphenylphosphine (257 mg, 0.98 mmol) and carbon tetrachloride (372 mg, 2.45 mmol). The reaction was heated at 50° C. for 16 h and then concentrated under reduced pressure. The residue was purified by column chromatography (petroleum ether:EtOAc=1:1) to give the title compound (160 mg, 66% yield) as a yellow solid.

Step 4

4-bromo-3-(5-(2-hydroxypropan-2-yl)-1,3,4-oxadiazol-2-yl)-2,6-dimethyl-1H-pyrrolo[2,3-c]pyridin-7(6H)-one

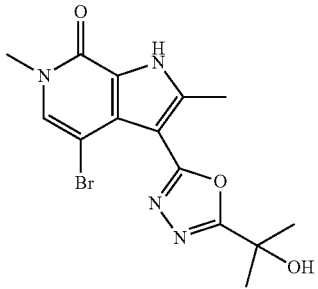 [SMILES: Cc1[nH]c2c(=O)n(C)cc(Br)c2c1-c1nnc(C(C)(C)O)o1]

To a solution of 4-bromo-3-(5-(2-hydroxypropan-2-yl)-1,3,4-oxadiazol-2-yl)-2,6-dimethyl-1-((2-(trimethylsilyl)ethoxy)methyl)-1H-pyrrolo[2,3-c]pyridin-7(6H)-one (160 mg, 0.32 mmol) in DCM (5 mL) was added 2,2,2-trifluoroacetic acid (1 mL). The reaction was stirred at ambient temperature for 2 h and concentrated under reduced pressure. The residue was diluted with MeOH (5 mL) and adjusted to pH 8 by the addition of $K_2CO_3$. The suspension was diluted with water (20 mL) and extracted with DCM (3×20 mL). The combined organic layers were dried over anhydrous $Na_2SO_4$, filtered and concentrated under reduced pressure to give the crude title compound (100 mg, 85% yield) as a yellow solid.

Step 5

4-(3-cyclopropyl-3-hydroxy-but-1-ynyl)-3-(5-(1-hydroxy-1-methyl-ethyl)-1,3,4-oxadiazol-2-yl)-2,6-dimethyl-1H-pyrrolo[2,3-c]pyridin-7-one

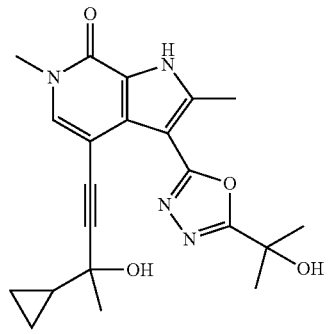 [SMILES: Cc1[nH]c2c(=O)n(C)cc(C#CC(C)(O)C3CC3)c2c1-c1nnc(C(C)(C)O)o1]

To a suspension of 4-bromo-3-(5-(2-hydroxypropan-2-yl)-1,3,4-oxadiazol-2-yl)-2,6-dimethyl-1H-pyrrolo[2,3-c]pyridin-7(6H)-one (100 mg, 0.27 mmol) in DMF (3 mL) and TEA (1 mL) was added 2-methylbut-3-yn-2-ol (154 mg, 1.40 mmol), copper(I) iodide (11 mg, 0.06 mmol) and bis(triphenylphosphine)palladium(II) dichloride (21 mg, 0.03 mmol). The reaction was purged with $N_2$ for 5 min and then stirred at 110° C. for 1 h under microwave conditions. The reaction mixture was concentrated under reduced pressure. The crude product was purified by reverse phase chromatography (ACN 30-60%/0.1% $NH_4OH$ in water) to give the title compound (20 mg, 18% yield) as a white solid.
$^1$H NMR (400 MHz, $CD_3OD$) δ 7.47 (s, 1H), 3.63 (s, 3H), 2.49 (s, 3H), 1.72 (s, 6H), 1.46 (s, 3H), 1.11-1.06 (m, 1H), 0.46-0.36 (m, 4H). LCMS M/Z (M-OH) 379.

The following compounds were prepared in a similar fashion to Example 172

Examples 173-179

| Example | Compound Name | NMR | m/z |
|---|---|---|---|
| 173 | N-[[5-[2,6-dimethyl-7-oxo-4-(4,4,4-trifluoro-3-hydroxy-3-phenyl-but-1-ynyl)-1H-pyrrolo[2,3-c]pyridin-3-yl]-1,3,4- | $^1$H NMR (400 MHz, $CD_3OD$) δ 7.72-7.63 (m, 3 H), 7.45-7.29 (m, 3 H), 4.24-4.13 (m, 2 H), 3.67 (s, 3 H), 2.51 (s, 3 H), 1.97 (s, 3 H). | 500 |

| Example | Compound Name | NMR | m/z |
|---|---|---|---|
| | oxadiazol-2-yl]methyl]acetamide | | |
| 174 | N-[[5-[4-(3-cyclopropyl-3-hydroxy-but-1-ynyl)-2,6-dimethyl-7-oxo-1H-pyrrolo[2,3-c]pyridin-3-yl]-1,3,4-oxadiazol-2-yl]methyl]acetamide | $^1$H NMR (400 MHz, DMSO-$d_6$) δ 12.76 (br. s, 1 H), 8.59 (t, J = 5.6 Hz, 1 H), 7.56 (s, 1 H), 5.25 (s, 1 H), 4.65-4.55 (m, 2 H), 3.54 (s, 3 H), 2.39 (s, 3 H), 1.88 (s, 3 H), 1.33 (s, 3 H), 1.03-0.98 (s, 1 H), 0.35-0.28 (m, 4 H). | 392 (M − OH) |
| 175 | 4-(3-cyclopropyl-3-hydroxy-but-1-ynyl)-2,6-dimethyl-3-(5-tetrahydrofuran-3-yl-1,3,4-oxadiazol-2-yl)-1H-pyrrolo[2,3-c]pyridin-7-one | $^1$H NMR (400 MHz, DMSO-$d_6$) δ 12.76 (br. s, 1 H), 7.54 (s, 1 H), 5.12 (s, 1 H), 4.05-4.00 (m, 1 H), 3.98-3.92 (m, 2 H), 3.90-3.83 (m, 1 H), 3.82-3.78 (m, 1 H), 3.54 (s, 3 H), 2.38 (s, 3 H), 2.36-2.21 (m, 2 H), 1.30 (s, 3 H), 1.01-0.97 (m, 1 H), 0.34-0.27 (m, 4 H). | 391 (M − OH) |
| 176 | 4-(3-cyclopropyl-3-hydroxy-but-1-ynyl)-2,6-dimethyl-3-[5-(1-methyl-2-morpholino-ethyl)-1,3,4-oxadiazol-2-yl]-1H-pyrrolo[2,3-c]pyridin-7-one | $^1$H NMR (400 MHz, CD$_3$OD) δ 7.47 (s, 1 H), 3.63-3.60 (m, 7 H), 3.32-3.30 (m, 1 H), 2.85-2.79 (m, 1 H), 2.64-2.46 (m, 8 H), 1.46-1.44 (m, 6 H), 1.10-1.06 (m, 1 H), 0.47-0.36 (m, 4 H). | 448 (M − OH) |
| 177 | 4-(3-hydroxy-3-methyl-but-1-ynyl)-2,6-dimethyl-3-(5-methyl-1,3,4-oxadiazol-2-yl)-1H-pyrrolo[2,3-c]pyridin-7-one | $^1$H NMR (400 MHz, DMSO-$d_6$) δ 12.40 (br. s, 1 H), 7.55 (s, 1 H), 5.29 (br. s, 1 H), 3.53 (s, 3 H), 2.58 (s, 3 H), 2.37 (s, 3 H), 1.29 (s, 6 H). | 349 (M + Na) |
| 178 | 3-[5-[2-(dimethylamino)ethyl]-1,3,4-oxadiazol-2-yl]-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, CD$_3$OD) δ 7.72 (s, 1 H), 7.66-7.64 (m, 2 H), 7.42-7.40 (m, 3 H), 3.68 (s, 3 H), 2.82-2.70 (m, 2 H), 2.68-2.55 (m, 2 H), 2.53 (s, 3 H), 2.22 (s, 6 H). | 500 |
| 179 | 4-(3-cyclopropyl-3-hydroxy-but-1-ynyl)-3-(5-isobutyl-1,3,4-oxadiazol-2-yl)-2,6-dimethyl-1H-pyrrolo[2,3-c]pyridin-7-one | $^1$H NMR (400 MHz, DMSO-$d_6$) δ 12.74 (br. s, 1 H), 7.54 (s, 1 H), 5.12 (s, 1 H), 3.54 (s, 3 H), 2.87 (d, J = 7.2 Hz, 2 H), 2.38 (s, 3 H), 2.16-2.06 (m, 1 H), 1.31 (s, 3 H), 1.00-0.96 (m, 7 H), 0.38-0.28 (m, 4 H). | 377 (M − OH) |

Example 180

3-(5-cyclopropyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one

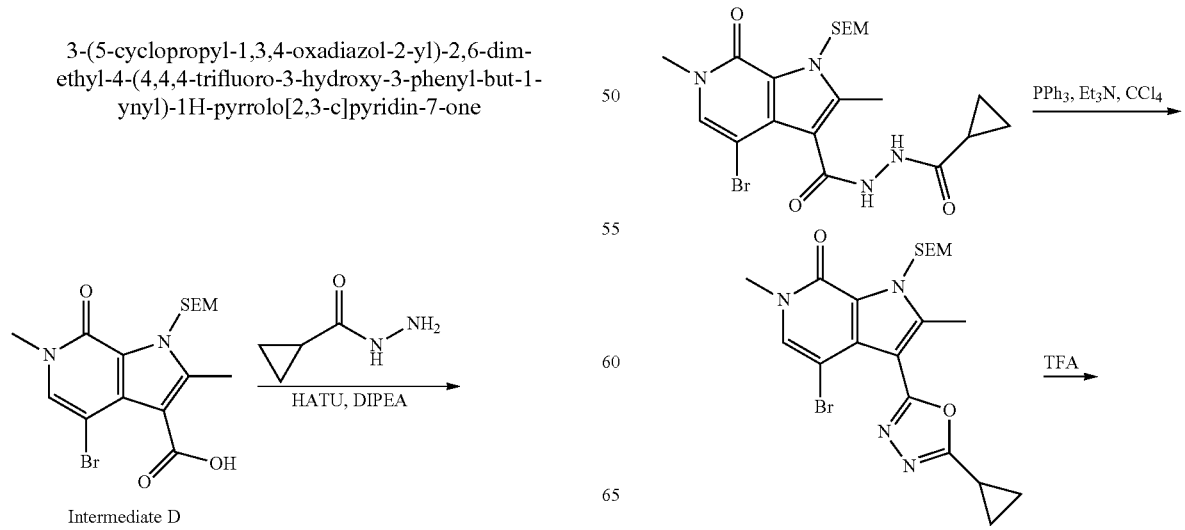

181
-continued

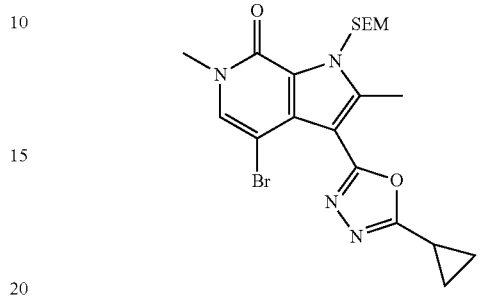

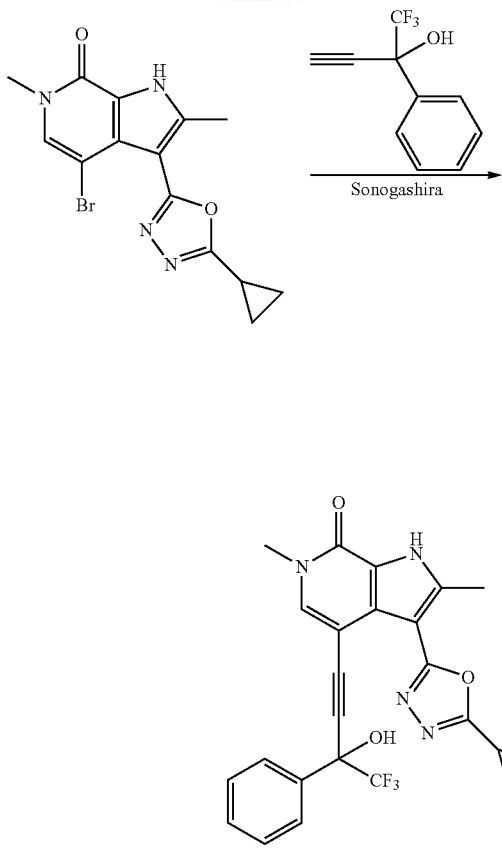

Step 1

4-bromo-N'-(cyclopropanecarbonyl)-2,6-dimethyl-7-oxo-1-((2-(trimethylsilyl)ethoxy)methyl)-6,7-dihydro-1H-pyrrolo[2,3-c]pyridine-3-carbohydrazide

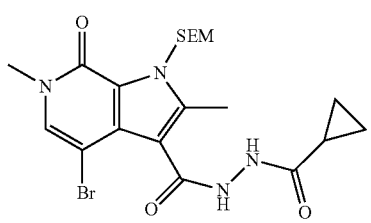 [SMILES: Cc1c(C(=O)NNC(=O)C2CC2)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carboxylic acid (Intermediate D) (500 mg, 1.20 mmol) in DMF (15 mL) was added TEA (243.63 mg, 2.41 mmol), HATU (549 mg, 1.44 mmol) and cyclopropanecarbohydrazide (180 mg, 1.81 mmol). The reaction was stirred at ambient temperature for 16 h and then diluted with water (20 mL). The mixture was extracted with EtOAc (3×20 mL). The combined organic layers were washed with water (25 mL), brine (25 mL), dried over anhydrous Na₂SO₄ and concentrated under reduced pressure to give the title compound (500 mg, 84% yield) as a yellow solid.

182

Step 2

4-bromo-3-(5-cyclopropyl-1,3,4-oxadiazol-2-yl)-2,6-dimethyl-1-((2-(trimethylsily) ethoxy)methyl)-1H-pyrrolo[2,3-c]pyridin-7(6H)-one

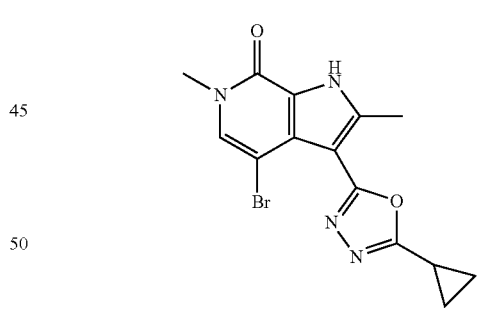

To a solution of 4-bromo-N'-(cyclopropanecarbonyl)-2,6-dimethyl-7-oxo-1-((2-(trimethylsilyl)ethoxy)methyl)-6,7-dihydro-1H-pyrrolo[2,3-c]pyridine-3-carbohydrazide (400 mg, 0.80 mmol) in DCM (20 mL) was added TEA (244, 2.41 mmol), triphenylphosphine (316 mg, 1.21 mmol) and carbon tetrachloride (2 mL). The reaction was heated at 50° C. for 6 h and then concentrated under reduced pressure. The residue was purified by column chromatography (petroleum ether:EtOAc=1:1) to give the title compound (280 mg, 73% yield) as a yellow solid.

Step 3

4-bromo-3-(5-cyclopropyl-1,3,4-oxadiazol-2-yl)-2,6-dimethyl-1H-pyrrolo[2,3-c]pyridin-7(6H)-one To a solution of 4-bromo-3-(5-cyclopropyl-1,3,4-oxadiazol-2-yl)-2,6-dimethyl-1-((2-(trimethylsilyl)ethoxy)methyl)-1H-pyrrolo[2,3-c]pyridin-7(6H)-one (280 mg, 0.58 mmol) in DCM (10 mL) was added 2,2,2-trifluoroacetic acid (1 mL). The reaction was stirred at ambient temperature for 2 h and then concentrated under reduced pressure. The residue was diluted with MeOH (15 mL) and adjusted to pH 8 by the addition of K₂CO₃. The suspension was diluted with water (20 mL) and extracted with EtOAc (3×20 mL). The combined organic layers were dried over anhydrous Na₂SO₄, filtered and concentrated under reduced pressure to give the crude title compound (150 mg, 90% yield) as a yellow solid.

Step 4

3-(5-cyclopropyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one

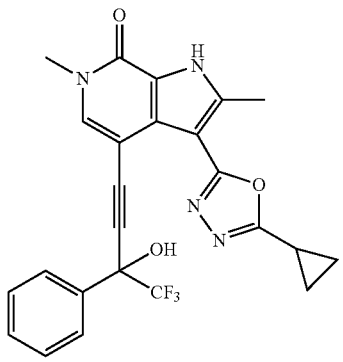 [SMILES: Cc1[nH]c2c(=O)n(C)cc(C#CC(O)(c3ccccc3)C(F)(F)F)c2c1-c1nnc(C2CC2)o1]

To a solution of 4-bromo-3-(5-cyclopropyl-1,3,4-oxadiazol-2-yl)-2,6-dimethyl-1H-pyrrolo[2,3-c]pyridin-7(6H)-one (100 mg, 0.29 mmol) in DMF (2.5 mL) and TEA (290 mg, 2.86 mmol) was added 1,1,1-trifluoro-2-phenyl-but-3-yn-2-ol (115 mg, 0.57 mmol), copper(I) iodide (11 mg, 0.06 mmol) and bis(triphenylphosphine)palladium(II) dichloride (20 mg, 0.03 mmol). The solution was purged with $N_2$ for 5 min and then stirred at 110° C. for 1 h under microwave conditions. The reaction mixture was concentrated under reduced pressure. The crude product was purified by reverse phase chromatography (ACN 30-60%/0.1% $NH_4OH$ in water) to give the title compound (50 mg, 37% yield) as a white solid. $^1$H NMR (400 MHz, DMSO-$d_6$) δ 12.87 (br. s, 1H), 7.81 (s, 1H), 7.73 (s, 1H), 7.61-7.58 (m, 2H), 7.41-7.39 (m, 3H), 3.59 (s, 3H), 2.41 (s, 3H), 1.93-1.88 (m, 1H), 0.91-0.75 (m, 4H). LCMS M/Z (M+H) 469.

The following compounds were prepared in a similar fashion to Example 180

Examples 181-196

| Example | Compound Name | NMR | m/z |
|---|---|---|---|
| 181 | 4-(3-cyclopropyl-3-hydroxy-but-1-ynyl)-3-(5-ethyl-1,3,4-oxadiazol-2-yl)-2,6-dimethyl-1H-pyrrolo[2,3-c]pyridin-7-one | $^1$H NMR (400 MHz, DMSO-$d_6$) δ 12.72 (br. s, 1 H), 7.54 (s, 1 H), 5.16 (s, 1 H), 3.53 (s, 3 H), 3.03-2.93 (m, 2 H), 2.38 (s, 3 H), 1.30 (t, J = 7.2 Hz, 3 H), 1.29 (s, 3 H), 0.99-0.97 (m, 1 H), 0.35-0.27 (m, 4 H). | 349 (M − OH) |
| 182 | 4-(3-cyclopropyl-3-hydroxy-but-1-ynyl)-2,6-dimethyl-3-(1,3,4-oxadiazol-2-yl)-1H-pyrrolo[2,3-c]pyridin-7-one | $^1$H NMR (400 MHz, DMSO-$d_6$) δ 12.79 (br. s, 1 H), 9.23 (s, 1 H), 7.55 (s, 1 H), 5.09 (s, 1 H), 3.53 (s, 3 H), 2.42 (s, 3 H), 1.31 (s, 3 H), 1.00-0.98 (m, 1 H), 0.37-0.35 (m, 1 H), 0.31-0.27 (m, 3 H). | 361 (M + Na) |
| 183 | 2,6-dimethyl-3-(1,3,4-oxadiazol-2-yl)-4-(4,4,4-trifluoro-3-hydroxy-3-phenyl-but-1-ynyl)-1H-pyrrolo[2,3-c]pyridin-7-one | no data | 429 |
| 184 | 2,6-dimethyl-3-(5-methyl-1,3,4-oxadiazol-2-yl)-4-(4,4,4-trifluoro-3-hydroxy-3-phenyl-but-1-ynyl)-1H-pyrrolo[2,3-c]pyridin-7-one | $^1$H NMR (400 MHz, DMSO-$d_6$) δ 12.85 (br. s, 1 H), 7.84 (s, 1 H), 7.81 (s, 1 H), 7.62-7.55 (m, 2 H), 7.45-7.32 (m, 3 H), 3.59 (s, 3 H), 2.44 (s, 3 H), 2.19 (s, 3 H). | 443 |
| 185 | 4-(3-cyclopropyl-3-hydroxy-but-1-ynyl)-3-[5-[(dimethylamino)methyl]-1,3,4-oxadiazol-2-yl]-2,6-dimethyl-1H-pyrrolo[2,3-c]pyridin-7-one | $^1$H NMR (400 MHz, CD$_3$OD) δ 7.47 (s, 1 H), 3.95 (s, 2 H), 3.63 (s, 3 H), 2.52 (s, 3 H), 2.41 (s, 6 H), 1.46 (s, 3 H), 1.12-1.05 (m, 1 H), 0.46-0.37 (m, 4 H). | 378 (M − OH) |
| 186 | 3-[5-[(dimethylamino)methyl]-1,3,4-oxadiazol-2-yl]-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, CD$_3$OD) δ 7.74 (s, 1 H), 7.70-7.67 (m, 2 H), 7.41-7.39 (m, 3 H), 3.68 (s, 3 H), 3.51-3.45 (m, 2 H), 2.55 (s, 3 H), 2.23 (s, 6 H). | 486 |
| 187 | 3-(5-tert-butyl-1,3,4-oxadiazol-2-yl)-4-(3-cyclopropyl-3-hydroxy-but-1-ynyl)-2,6-dimethyl-1H-pyrrolo[2,3-c]pyridin-7-one | $^1$H NMR (400 MHz, DMSO-$d_6$) δ 12.70 (br. s, 1 H), 7.51 (s, 1 H), 4.93 (s, 1 H), 3.53 (s, 3 H), 2.32 (s, 3 H), 1.40 (s, 9 H), 1.28 (s, 3 H), 1.02-0.93 (m, 1 H), 0.39-0.33 (m, 1 H), 0.28-0.25 (m, 3 H). | 377 (M − OH) |

-continued

| Example | Compound Name | NMR | m/z |
|---|---|---|---|
| 188 | 3-(5-tert-butyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, DMSO-d$_6$) δ 7.76 (s, 1 H), 7.62-7.56 (m, 2 H), 7.45-7.36 (m, 3 H), 3.59 (s, 3 H), 2.39 (s, 3 H), 1.24 (s, 9 H). | 485 |
| 189 | 3-(5-isopropyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, CD$_3$OD) δ 7.71 (s, 1 H), 7.64 (d, J = 8.0 Hz, 2 H), 7.40-7.36 (m, 3 H), 3.68 (s, 3 H), 2.86-2.79 (m, 1 H), 2.51 (s, 3 H), 1.24 (d, J = 6.8 Hz, 3 H), 1.10 (d, J = 7.2 Hz, 3 H). | 471 |
| 190 | 3-(5-cyclopropyl-1,3,4-oxadiazol-2-yl)-4-[(3R)-3-hydroxy-3-(5-methylisoxazol-3-yl)but-1-ynyl]-2,6-dimethyl-1H-pyrrolo[2,3-c]pyridin-7-one | $^1$H NMR (400 MHz, DMSO-d$_6$) δ 12.76 (br. s, 1 H), 7.61 (s, 1 H), 6.25 (s, 1 H), 6.19 (s, 1 H), 3.54 (s, 3 H), 2.38 (s, 3 H), 2.36 (s, 3 H), 2.22-2.16 (m, 1 H), 1.62 (s, 3 H), 1.07-0.99 (m, 4 H). | 420 |
| 191 | 4-(3-cyclopropyl-3-hydroxy-but-1-ynyl)-3-(5-isopropyl-1,3,4-oxadiazol-2-yl)-2,6-dimethyl-1H-pyrrolo[2,3-c]pyridin-7-one | $^1$H NMR (400 MHz, DMSO-d$_6$) δ 12.75 (br. s, 1 H), 7.53 (s, 1 H), 5.08 (s, 1 H), 3.54 (s, 3 H), 2.37 (s, 3 H), 1.40 (d, J = 7.2 Hz, 6 H), 1.29 (s, 3 H), 1.02-0.94 (m, 1 H), 0.41-0.33 (m, 1 H), 0.33-0.22 (m, 3 H). | 363 (M − OH) |
| 192 | 4-(3-cyclopropyl-3-hydroxy-but-1-ynyl)-2,6-dimethyl-3-(5-methyl-1,3,4-oxadiazol-2-yl)-1H-pyrrolo[2,3-c]pyridin-7-one | $^1$H NMR (400 MHz, CD$_3$OD) δ 7.46 (s, 1 H), 3.63 (s, 3 H), 2.67 (s, 3 H), 2.48 (s, 3 H), 1.44 (s, 3 H), 1.11-1.07 (m, 1 H), 0.51-0.37 (m, 4 H). | 335 (M − OH) |
| 193 | 4-[(3R)-3-hydroxy-3-(5-methylisoxazol-3-yl)but-1-ynyl]-2,6-dimethyl-3-(5-methyl-1,3,4-oxadiazol-2-yl)-1H-pyrrolo[2,3-c]pyridin-7-one | $^1$H NMR (400 MHz, CD$_3$OD) δ 7.58 (s, 1 H), 6.14 (s, 1 H), 3.63 (s, 3 H), 2.55 (s, 3 H), 2.49 (s, 3 H), 2.42 (s, 3 H), 1.73 (s, 3 H). | 376 (M − OH) |
| 194 | 4-[(3R)-3-hydroxy-3-(5-methylisoxazol-3-yl)but-1-ynyl]-3-(5-isopropyl-1,3,4-oxadiazol-2-yl)-2,6-dimethyl-1H-pyrrolo[2,3-c]pyridin-7-one | $^1$H NMR (400 MHz, DMSO-d$_6$) δ 12.77 (br. s, 1 H), 7.62 (s, 1 H), 6.26 (s, 1 H), 6.18 (s, 1 H), 3.54 (s, 3 H), 3.25-3.16 (m, 1 H), 2.39 (s, 3 H), 2.38 (s, 3 H), 1.60 (s, 3 H), 1.33-1.25 (m, 6 H). | 404 (M − OH) |
| 195 | 4-(3-hydroxy-3-methyl-but-1-ynyl)-3-(5-isopropyl-1,3,4-oxadiazol-2-yl)-2,6-dimethyl-1H-pyrrolo[2,3-c]pyridin-7-one | $^1$H NMR (400 MHz, DMSO-d$_6$) δ 12.72 (br. s, 1 H), 7.55 (s, 1 H), 5.24 (s, 1 H), 3.53 (s, 3 H), 3.37-3.32 (m, 1 H), 2.35 (s, 3 H), 1.34 (d, J = 6.8 Hz, 6 H), 1.27 (s, 3 H), 1.23 (s, 3 H). | 337 (M − OH) |
| 196 | 3-(5-ethyl-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one | $^1$H NMR (400 MHz, DMSO-d$_6$) δ 12.60 (br. s, 1 H), 7.84 (s, 1 H), 7.79 (s, 1 H), 7.62-7.58 (m, 2 H), 7.42-7.37 (m, 3 H), 3.60 (s, 3 H), 2.60-2.54 (m, 2 H), 2.44 (s, 3 H), 1.07 (t, J = 7.6 Hz, 3 H). | 479 (M + Na) |

Example 197 ethyl 4-[3-(3-carbamoylphenyl)-4,4,4-trifluoro-3-hydroxy-but-1-ynyl]-2,6-dimethyl-7-oxo-1H-pyrrolo[2,3-c]pyridine-3-carboxylate

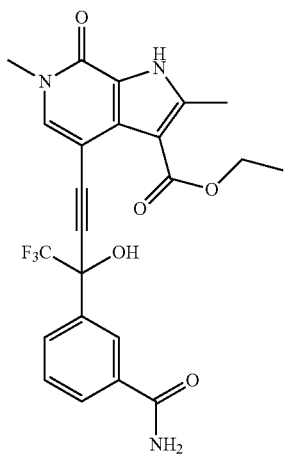 [SMILES: CCOC(=O)c1c(C)[nH]c2c(=O)n(C)cc(C#CC(O)(c3cccc(C(N)=O)c3)C(F)(F)F)c12]

A mixture of ethyl 4-(3-(3-cyanophenyl)-4,4,4-trifluoro-3-hydroxybut-1-yn-1-yl)-2,6-dimethyl-7-oxo-6,7-dihydro-1H-pyrrolo[2,3-c]pyridine-3-carboxylate (Example 40) (60 mg, 0.13 mmol), potassium hydroxide (74 mg, 1.31 mmol) and hydrogen peroxide (30% aq., 0.2 mL, 6.53 mmol) in DMSO (2 mL) was stirred at ambient temperature for 1 h. The solution was neutralized by the addition of 2 M aqueous HCl and then diluted with water (10 mL). The reaction was extracted with EtOAc (2×10 mL). The combined organic layers were dried over anhydrous $Na_2SO_4$ and concentrated under reduced pressure. The crude product was purified by reverse phase chromatography (ACN 23-53%/0.05% $NH_4OH$ in water) to give the title compound (33 mg, 53% yield) as a white solid. $^1$H NMR (400 MHz, DMSO-$d_6$) δ 12.40 (br. s, 1H), 8.30 (s, 1H), 8.05 (s, 1H), 7.96-7.92 (m, 2H), 7.83 (s, 1H), 7.74 (s, 1H), 7.55-7.51 (m, 1H), 7.47 (s, 1H), 4.04 (q, J=6.8 Hz, 2H), 3.57 (s, 3H), 2.50 (s, 3H), 1.10 (t, J=7.2 Hz, 3H). LCMS M/Z (M+H) 476.

Example 198

4-(3-hydroxy-3-methyl-but-1-ynyl)-2,6-dimethyl-1H-pyrrolo[2,3-c]pyridin-7-one

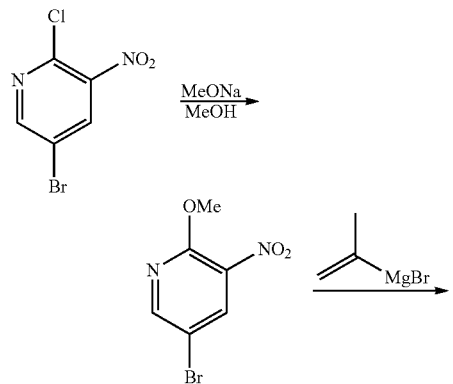

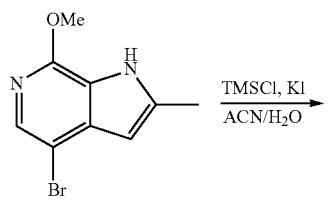

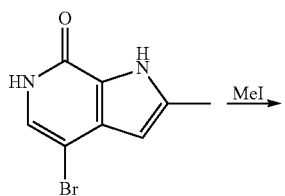

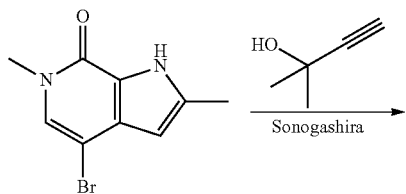

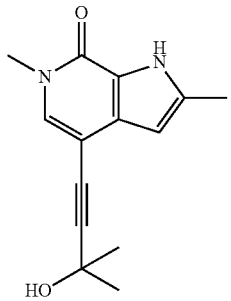

Step 1

5-bromo-2-methoxy-3-nitropyridine

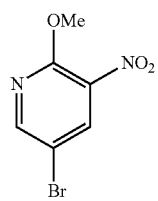 [SMILES: COc1ncc(Br)cc1[N+](=O)[O-]]

Sodium methoxide (17.2 g, 318.4 mmol) was added to a stirred solution of 5-bromo-2-chloro-3-nitropyridine (15.0 g, 64.2 mmol) in MeOH (125 mL). The reaction was heated at reflux temperature for 2 h and then concentrated under reduced pressure. The residue was diluted with water (200 mL). The resulting precipitate was collected by filtration, washed with water, and dried under reduced pressure to give the title compound (12.0 g, 81.5% yield) as a brown solid. $^1$H NMR (400 MHz, CDCl$_3$): δ 8.43 (d, J=2.4 Hz, 1H), 8.38 (d, J=2.0 Hz, 1H), 4.09 (s, 3H).

Step 2

4-bromo-7-methoxy-2-methyl-1H-pyrrolo[2,3-c]pyridine

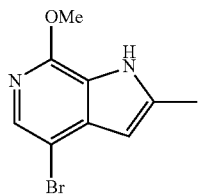

Isopropenyl magnesium bromide (0.5 M in THF, 105.0 mL, 55.0 mmol) was added dropwise to a stirred solution of 5-bromo-2-methoxy-3-nitropyridine (4.0 g, 17.1 mmol) in THF (40 mL) at −78° C. The reaction was allowed to warm to ambient temperature gradually and stirred for an additional 3 h. The reaction mixture was quenched by the addition of 1 M aqueous NH$_4$Cl (150 mL), and then extracted with EtOAc (3×100 mL). The combined organic extracts were dried over anhydrous Na$_2$SO$_4$ and concentrated under reduced pressure. The residue was purified by column chromatography (petroleum ether:EtOAc=10:1) to give the title compound (1.65 g, 39.9% yield) as a brown oil. LCMS M/Z (M+H) 240.1, 242.1.

Step 3

4-bromo-2-methyl-1H-pyrrolo[2,3-c]pyridin-7(6H)-one

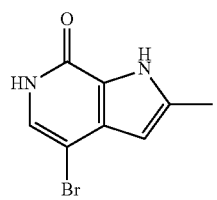

To a solution of 4-bromo-7-methoxy-2-methyl-1H-pyrrolo[2,3-c]pyridine (1.65 g, 6.8 mmol) (1.65 g, 6.8 mmol) in ACN (10 mL) and water (10 mL) was added chlorotrimethylsilane (1.4 g, 13.6 mmol) and potassium iodide (2.5 g, 15.0 mmol). The reaction was heated at 90° C. for 16 h and then concentrated under reduced pressure. The residue was purified by column chromatography (DCM:MeOH=9:1) to give the title compound (0.9 g, 59% yield) as a brown solid. $^1$H NMR (400 MHz, DMSO-d$_6$): δ 12.06 (s, 1H), 11.00 (s, 1H), 7.03 (s, 1H), 5.97 (s, 1H), 2.29 (s, 3H). LCMS M/Z (M+H) 226.8, 228.8.

Step 4

4-bromo-2,6-dimethyl-1H-pyrrolo[2,3-c]pyridin-7(6H)-one

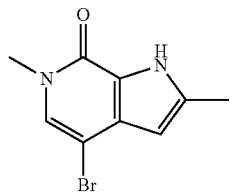

Methyl iodide (112 mg, 0.79 mmol) was added to a stirred mixture of 4-bromo-2-methyl-1H-pyrrolo[2,3-c]pyridin-7(6H)-one (300 mg, 1.32 mmol) and K$_2$CO$_3$ (274 mg, 1.98 mmol) in DMF (15 mL) dropwise at ambient temperature. The reaction was stirred at 70° C. for 15 h, then quenched by the addition of water (25 mL) and extracted with EtOAc (20 mL×2). The combined organic layers were dried over anhydrous Na$_2$SO$_4$ and concentrated under reduced pressure. The crude product was purified by preparative TLC (DCM:MeOH=15:1) to give the title compound (82 mg, 26%) as a brown solid. $^1$H NMR (400 MHz, CD3OD): δ 7.33 (s, 1H), 6.07 (s, 1H), 3.58 (s, 3H), 2.39 (s, 3H).

Step 5

4-(3-hydroxy-3-methyl-but-1-ynyl)-2,6-dimethyl-1H-pyrrolo[2,3-c]pyridin-7-one

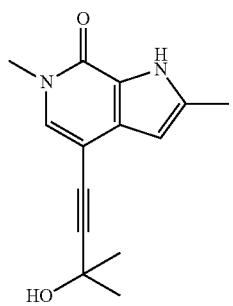

To a solution of 4-bromo-2,6-dimethyl-1H-pyrrolo[2,3-c]pyridin-7(6H)-one (100 mg, 0.4 mmol) in ACN (3 mL) and TEA (1 mL) was added 2-methylbut-3-yn-2-ol (70 mg, 0.8 mmol), copper(I) iodide (8 mg, 0.04 mmol) and bis(triphenylphosphine)palladium(II) dichloride (30 mg, 0.04 mmol). The reaction was purged with N$_2$ for 5 min and then the reaction was heated at 90° C. for 3 h and concentrated under reduced pressure. The crude product was purified by reverse phase chromatography (ACN 0-85%/0.1% NH$_4$OH in water) to give the title compound (9 mg, 9% yield) as an off-white solid. $^1$H NMR (400 MHz, CD$_3$OD) δ 11.87 (s, 1H), 7.39 (s, J=1.4 Hz, 1H), 6.04 (s, 1H), 5.36 (s, 1H), 3.47 (s, 3H), 2.32 (s, 3H), 1.47 (s, 6H). LCMS M/Z (M+H) 245.

Examples 199a & 199b 3-acetyl-4-(3-hydroxy-3-methyl-but-1-ynyl)-2,6-dimethyl-1H-pyrrolo[2,3-c]pyridin-7-one (199a) and 3-acetyl-4-(3-hydroxy-3-methyl-but-1-ynyl)-1,2-dimethyl-6H-pyrrolo[2,3-c]pyridin-7-one (199b)

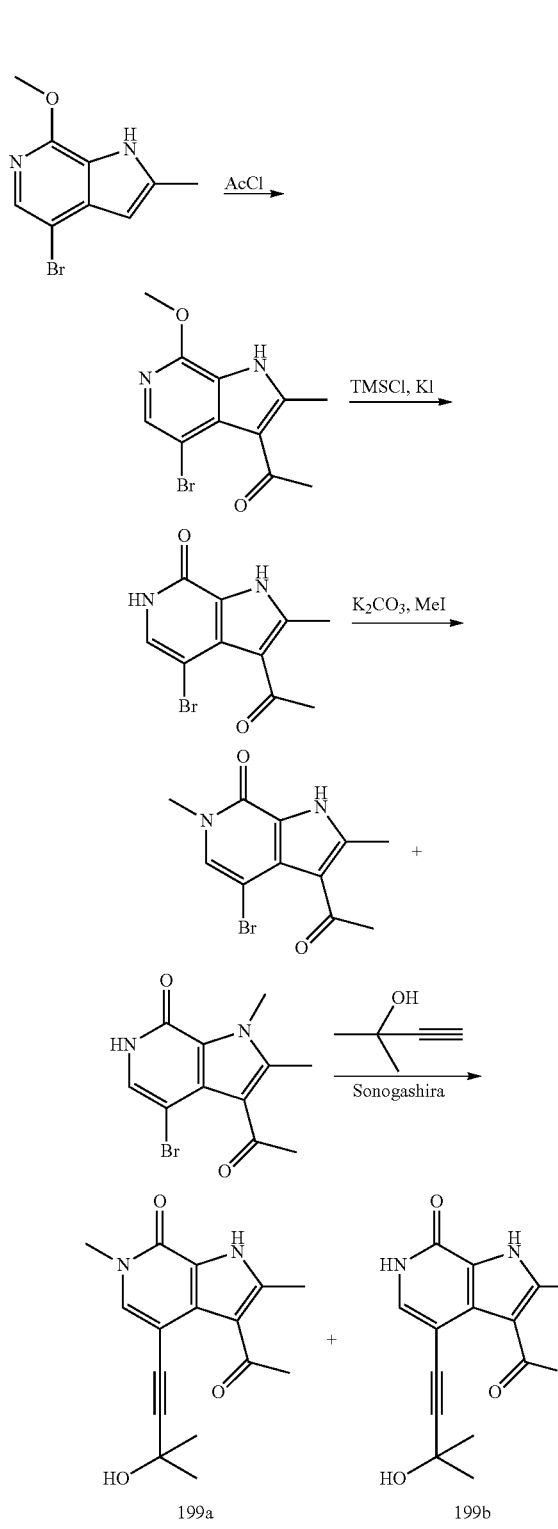

Step 1

1-(4-bromo-7-methoxy-2-methyl-1H-pyrrolo[2,3-c]pyridin-3-yl)ethanone

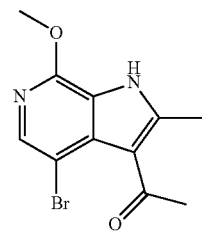 [SMILES: COc1ncc(Br)c2c(C(C)=O)c(C)[nH]c12]

To a solution of 4-bromo-7-methoxy-2-methyl-1H-pyrrolo[2,3-c]pyridine (1.20 g, 5.00 mmol) in DCM (50 mL) was added acetyl chloride (1.17 g, 15.00 mmol) and aluminum trichloride (1.98 g, 15.00 mmol). The reaction was stirred at ambient temperature for 3 h and then slowly quenched by the addition of water (20 mL). The mixture was extracted with DCM (3×30 mL). The combined organic layers were dried over anhydrous $Na_2SO_4$, filtered and concentrated under reduced pressure. The residue was purified by column chromatography (petroleum ether:EtOAc=4:1) to give the title compound (1.00 g, 71% yield) as a yellow oil.

Step 2

3-acetyl-4-bromo-2-methyl-1H-pyrrolo[2,3-c]pyridin-7(6H)-one

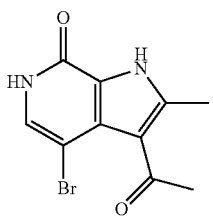

To a solution of 1-(4-bromo-7-methoxy-2-methyl-1H-pyrrolo[2,3-c]pyridin-3-yl) ethanone (800 mg, 2.84 mmol) in ACN (10 mL) and water (10 mL) was added chlorotrimethylsilane (613 mg, 5.68 mmol) and potassium iodide (943 mg, 5.68 mmol). The reaction was heated at 80° C. for 16 h and then concentrated under reduced pressure. The residue was purified by column chromatography (DCM:MeOH=9:1) to give the title compound (450 mg, 59% yield) as a yellow solid.

Step 3

3-acetyl-4-bromo-2,6-dimethyl-1H-pyrrolo[2,3-c]pyridin-7(6H)-one and 3-acetyl-4-bromo-1,2-dimethyl-1H-pyrrolo[2,3-c]pyridin-7(6H)-one

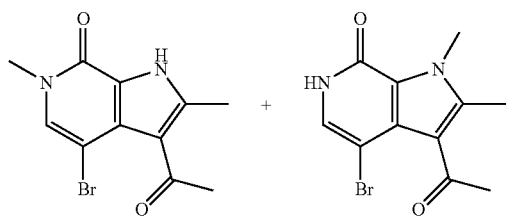

To a solution of 3-acetyl-4-bromo-2-methyl-1H-pyrrolo[2,3-c]pyridin-7(6H)-one (268 mg, 1.00 mmol) in DMF (10 mL) was added $K_2CO_3$ (414 mg, 3.00 mmol) and methyl iodide (142 mg, 1.00 mmol). The reaction was stirred at ambient temperature for 2 h and then concentrated under reduced pressure. The residue was purified by column chromatography (DCM:MeOH=9:1) to give a mixture of the title compounds (70 mg, 25% yield) as a yellow solid.

Step 4

3-acetyl-4-(3-hydroxy-3-methyl-but-1-ynyl)-2,6-dimethyl-1H-pyrrolo[2,3-c]pyridin-7-one (199a) and 3-acetyl-4-(3-hydroxy-3-methyl-but-1-ynyl)-1,2-dimethyl-6H-pyrrolo[2,3-c]pyridin-7-one (199b)

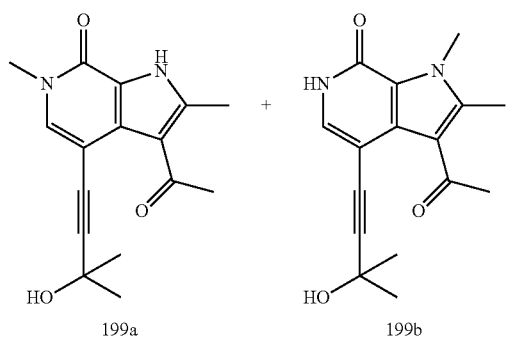

To a suspension of 3-acetyl-4-bromo-2,6-dimethyl-1H-pyrrolo[2,3-c]pyridin-7(6H)-one and 3-acetyl-4-bromo-1,2-dimethyl-1H-pyrrolo[2,3-c]pyridin-7(6H)-one (70 mg, 0.25 mmol) in DMF (3 mL) and TEA (1 mL) was added 2-methylbut-3-yn-2-ol (105 mg, 1.25 mmol), copper(I) iodide (11 mg, 0.06 mmol) and bis(triphenylphosphine)palladium(II) dichloride (21 mg, 0.03 mmol). The reaction was purged with $N_2$ for 5 min and then stirred at 110° C. for 1 h under microwave conditions. The reaction mixture was concentrated under reduced pressure. The crude product was purified by reverse phase chromatography (ACN 10-40%/0.1% $NH_4OH$ in water) to give the title compounds.

199a (5.0 mg, 7% yield) as a white solid: $^1$H NMR (400 MHz, $CD_3OD$) δ 7.53 (s, 1H), 3.64 (s, 3H), 2.71 (s, 3H), 2.53 (s, 3H), 1.57 (s, 6H). LCMS M/Z (M-OH) 269.

199b (6.0 mg, 8% yield) as a white solid: $^1$H NMR (400 MHz, $CD_3OD$) δ 7.22 (s, 1H), 4.12 (s, 3H), 2.68 (s, 3H), 2.44 (s, 3H), 1.56 (s, 6H). LCMS M/Z (M+Na) 309.

Example 200

4-(3-hydroxy-3-methyl-but-1-ynyl)-2,6-dimethyl-7-oxo-1H-pyrrolo[2,3-c]pyridine-3-carboxylic acid

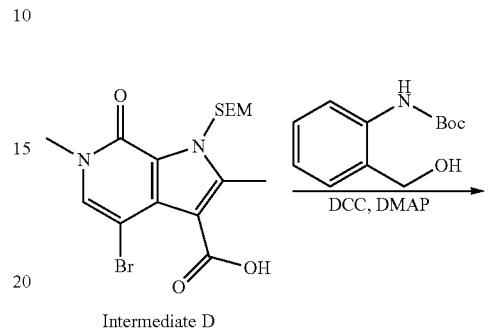

Intermediate D

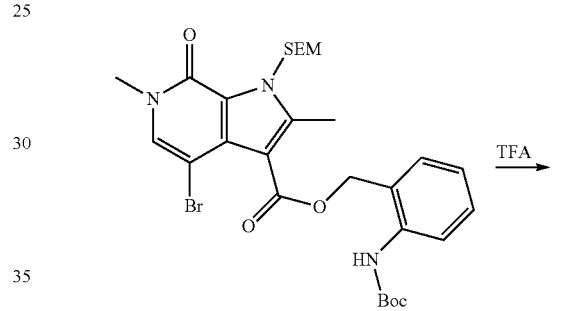

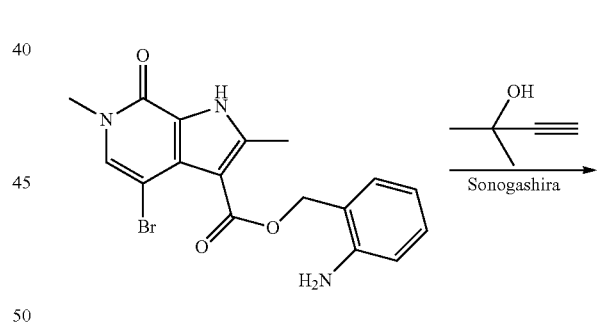

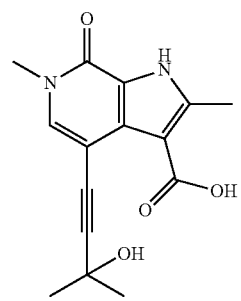

Obtained as BP

Step 1

2-((tert-butoxycarbonyl)amino)benzyl 4-bromo-2,6-dimethyl-7-oxo-1-((2-(trimethyl silyl)ethoxy)methyl)-6,7-dihydro-1H-pyrrolo[2,3-c]pyridine-3-carboxylate

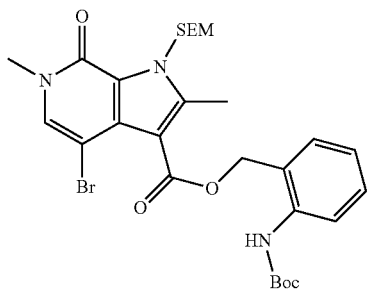 [SMILES: Cc1c(C(=O)OCc2ccccc2NC(=O)OC(C)(C)C)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carboxylic acid (207 mg, 0.50 mmol) in DCM (10 mL) was added tert-butyl (2-(hydroxymethyl)phenyl)carbamate (134 mg, 0.60 mmol), N,N'-Dicyclohexylcarbodiimide (205 mg, 1.00 mmol) and DMAP (122 mg, 1.00 mmol). The mixture was heated at 40° C. for 16 h. After cooling to ambient temperature, the reaction was diluted with water (20 mL) and extracted with DCM (3×20 mL). The combined organic layers were dried over anhydrous Na$_2$SO$_4$ and concentrated under reduced pressure. The residue was purified by column chromatography (petroleum ether:EtOAc=4:1) to give the title compound (280 mg, 90% yield) as a yellow solid.

Step 2

2-aminobenzyl 4-bromo-2,6-dimethyl-7-oxo-6,7-dihydro-1H-pyrrolo[2,3-c]pyridine-3-carboxylate

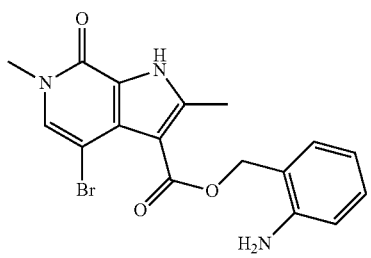 [SMILES: Cc1[nH]c2c(=O)n(C)cc(Br)c2c1C(=O)OCc1ccccc1N]

To a solution of benzyl 2-((tert-butoxycarbonyl)amino) benzyl 4-bromo-2,6-dimethyl-7-oxo-1-((2-(trimethylsilyl)ethoxy)methyl)-6,7-dihydro-1H-pyrrolo[2,3-c]pyridine-3-carboxylate (300 mg, 0.48 mmol) in DCM (10 mL) was added 2,2,2-trifluoroacetic acid (1 mL). The reaction was stirred at ambient temperature for 2 h and concentrated under reduced pressure. The residue was diluted with MeOH (5 mL) and adjusted to pH 8 by the addition of K$_2$CO$_3$. The suspension was diluted with water (20 mL) and extracted with EtOAc (3×20 mL). The combined organic layers were concentrated under reduced pressure. The residue was purified by column chromatography (DCM:MeOH=9:1) to give the title compound (150 mg, 78% yield) as a yellow solid.

Step 3

4-(3-hydroxy-3-methyl-but-1-ynyl)-2,6-dimethyl-7-oxo-1H-pyrrolo[2,3-c]pyridine-3-carboxylic acid

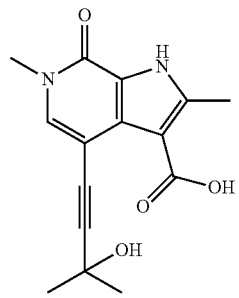

To a suspension of 2-aminobenzyl 4-bromo-2,6-dimethyl-7-oxo-6,7-dihydro-1H-pyrrolo[2,3-c]pyridine-3-carboxylate (150 mg, 0.39 mmol) in DMF (3 mL) and TEA (1 mL) was added 2-methylbut-3-yn-2-ol (168 mg, 2.00 mmol), copper(I) iodide (15 mg, 0.08 mmol) and bis(triphenylphosphine)palladium(II) dichloride (28 mg, 0.04 mmol). The reaction was purged with N$_2$ for 5 min and then stirred at 110° C. for 1 h under microwave conditions. The reaction mixture was concentrated under reduced pressure. The crude product was purified by reverse phase chromatography (ACN 16-46%/0.1% NH$_4$OH in water) to afford the title compound (by product, 10 mg, 6.5% yield) as a white solid. $^1$H NMR (400 MHz, DMSO-d$_6$) δ 12.50 (br. s, 1H), 12.10 (br. s, 1H), 7.47 (s, 1H), 5.12 (s, 1H), 3.51 (s, 3H), 2.48 (s, 3H), 1.44 (s, 6H). LCMS M/Z (M-OH) 271.

Example 201

3-(hydroxymethyl)-4-(3-hydroxy-3-methyl-but-1-ynyl)-2,6-dimethyl-1H-pyrrolo [2,3-c]pyridin-7-one

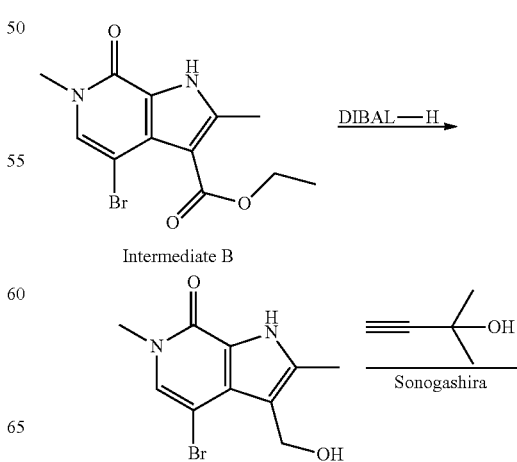

-continued

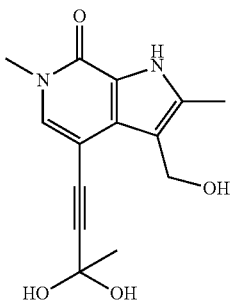

Step 1

4-bromo-3-(hydroxymethyl)-2,6-dimethyl-1H-pyrrolo[2,3-c]pyridin-7(6H)-one

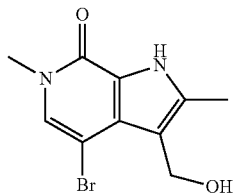

To a solution of ethyl 4-bromo-2,6-dimethyl-7-oxo-6,7-dihydro-1H-pyrrolo[2,3-c]pyridine-3-carboxylate (Intermediate B) (200 mg, 0.64 mmol) in THF (20 mL) at 0° C. was added diisobutylaluminum hydride (1.0 M, 1.8 mL, 1.80 mmol). The reaction was stirred at ambient temperature for 16 h and then quenched by the addition of saturated aqueous NH₄Cl (10 mL). The mixture was extracted with EtOAc (3×20 mL). The combined organic layers were washed with water (10 mL), brine (10 mL), dried over anhydrous Na₂SO₄ and concentrated under reduced pressure. The residue was purified by column chromatography (DCM:MeOH=9:1) to give the title compound (160 mg, 92% yield) as a white solid.

Step 2

3-(hydroxymethyl)-4-(3-hydroxy-3-methyl-but-1-ynyl)-2,6-dimethyl-1H-pyrrolo[2,3-c]pyridin-7-one

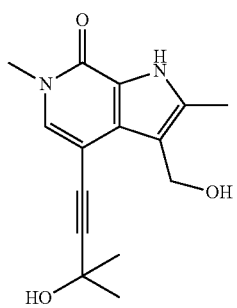

To a solution of 4-bromo-3-(hydroxymethyl)-2,6-dimethyl-1H-pyrrolo[2,3-c]pyridine-7(6H)-one (160 mg, 0.59 mmol) in DMF (3 mL) and TEA (1 mL) was added 2-methylbut-3-yn-2-ol (252 mg, 3.00 mmol), copper(I) iodide (23 mg, 0.12 mmol) and bis(triphenylphosphine)palladium(II) dichloride (42 mg, 0.06 mmol). The reaction was purged with N₂ for 5 min and then stirred at 110° C. for 1 h under microwave conditions. The reaction mixture was concentrated under reduced pressure. The crude product was purified by reverse phase chromatography (ACN 13-29%/0.1% NH₄OH in water) to give the title compound (5 mg, 3% yield) as a white solid. ¹H NMR (400 MHz, CD₃OD) δ 7.35 (s, 1H), 4.95-4.91 (m, 2H), 3.60 (s, 3H), 2.44 (s, 3H), 1.60 (s, 6H). LCMS M/Z (M+H) 275.

Example 202

4-(3-hydroxy-3-methyl-but-1-ynyl)-3-(4-isopropyl-4,5-dihydrooxazol-2-yl)-2,6-dimethyl-1H-pyrrolo[2,3-c]pyridin-7-one

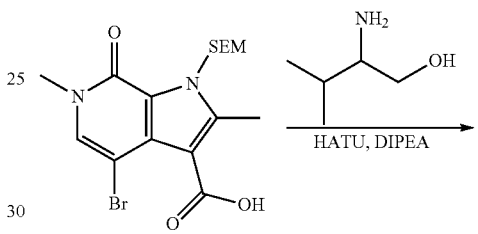

Intermediate D

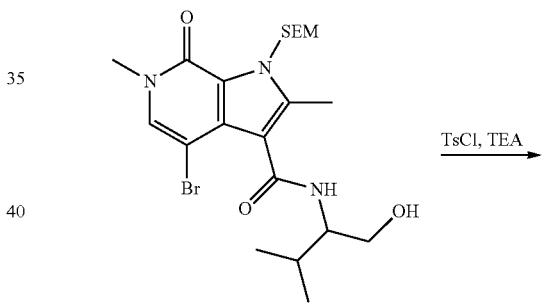

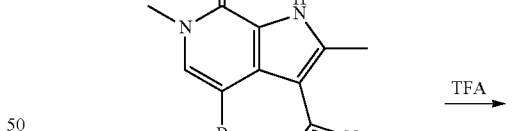

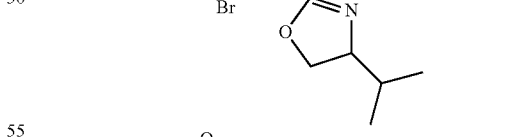

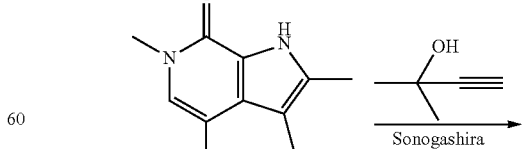

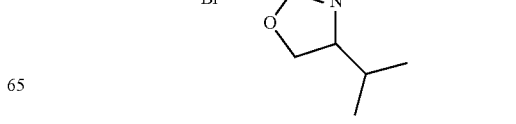

-continued

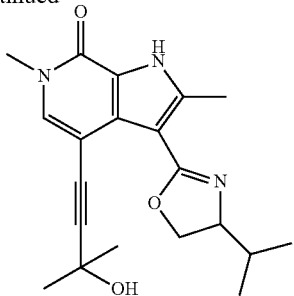

Step 1

4-bromo-N-(1-hydroxy-3-methylbutan-2-yl)-2,6-dimethyl-7-oxo-1-((2-(trimethylsilyl) ethoxy) methyl)-6,7-dihydro-1H-pyrrolo[2,3-c]pyridine-3-carboxamide

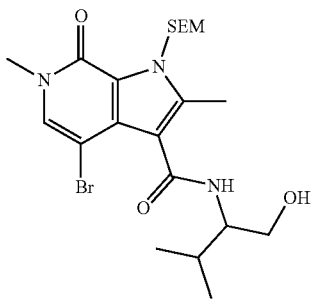 [SMILES: Cc1c(C(=O)NC(CO)C(C)C)c2c(Br)cn(C)c(=O)c2n1COCC[Si](C)(C)C]

To a solution of 4-bromo-2,6-dimethyl-7-oxo-1-((2-(trimethylsilyl)ethoxy)methyl)-6,7-dihydro-1H-pyrrolo[2,3-c]pyridine-3-carboxylic acid (Intermediate D) (207 mg, 0.50 mmol) in DMF (10 mL) was added N-ethyl-N-isopropyl-propan-2-amine (129 mg, 1.00 mmol), HATU (380 mg, 1.00 mmol) and 2-amino-3-methylbutan-1-ol (103 mg, 1.00 mmol). The reaction was stirred at ambient temperature for 16 h and then diluted with water (20 mL). The mixture was extracted with EtOAc (3×20 mL) and the combined organic layers were washed with water (20 mL), brine (20 mL), dried over anhydrous Na$_2$SO$_4$, filtered and concentrated under reduced pressure to give the crude title compound (200 mg, 80% yield) as a yellow solid.

Step 2

4-bromo-3-(4-isopropyl-4,5-dihydrooxazol-2-yl)-2,6-dimethyl-1-((2-(trimethylsilyl) ethoxy)methyl)-1H-pyrrolo[2,3-c]pyridin-7(6H)-one

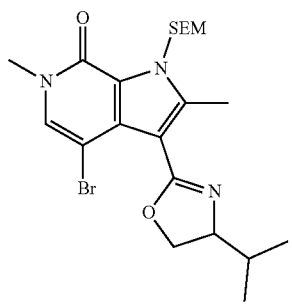 [SMILES: Cc1c(C2=NC(C(C)C)CO2)c2c(Br)cn(C)c(=O)c2n1COCC[Si](C)(C)C]

To a solution of 4-bromo-N-(1-hydroxy-3-methylbutan-2-yl)-2,6-dimethyl-7-oxo-1-((2-(trimethylsilyl)ethoxy)methyl)-6,7-dihydro-1H-pyrrolo[2,3-c]pyridine-3-carboxamide (200 mg, 0.40 mmol) in DCM (10 mL) and DMF (10 mL) was added 4-methylbenzene-1-sulfonyl chloride (152 mg, 0.80 mmol) and TEA (124 mg, 1.20 mmol). The reaction was heated at 40° C. for 6 h and concentrated under reduced pressure. The residue was purified by column chromatography (petroleum ether:EtOAc=1:1) to give the title compound (120 mg, 62% yield) as a yellow solid.

Step 3

4-bromo-3-(4-isopropyl-4,5-dihydrooxazol-2-yl)-2,6-dimethyl-1H-pyrrolo[2,3-c]pyridin-7(6H)-one

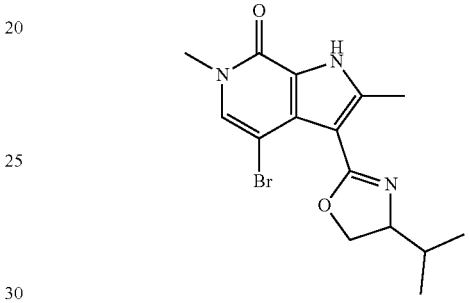

To a solution of 4-bromo-3-(4-isopropyl-4,5-dihydrooxazol-2-yl)-2,6-dimethyl-1-((2-(trimethylsilyl)ethoxy)methyl)-1H-pyrrolo[2,3-c]pyridin-7(6H)-one (120 mg, 0.25 mmol) in DCM (5 mL) was added 2,2,2-trifluoroacetic acid (1 mL). The reaction was stirred at ambient temperature for 2 h and concentrated under reduced pressure. The residue was diluted with MeOH (5 mL) and adjusted to pH 8 by the addition of K$_2$CO$_3$. The suspension was diluted with water (20 mL) and extracted with DCM (3×20 mL). The combined organic layers were dried over anhydrous Na$_2$SO$_4$, filtered and concentrated under reduced pressure to give the crude title compound (70 mg, 80% yield) as a yellow solid.

Step 4

4-(3-hydroxy-3-methyl-but-1-ynyl)-3-(4-isopropyl-4,5-dihydrooxazol-2-yl)-2,6-dimethyl-1H-pyrrolo[2,3-c]pyridin-7-one

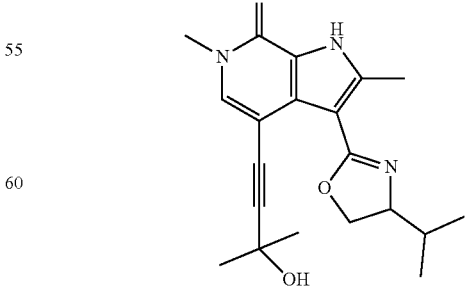

To a suspension of 4-bromo-3-(4-isopropyl-4,5-dihydrooxazol-2-yl)-2,6-dimethyl-1H-pyrrolo[2,3-c]pyridin-7

(6H)-one (70 mg, 0.20 mmol) in DMF (3 mL) and TEA (1 mL) was added 2-methylbut-3-yn-2-ol (84 mg, 1.00 mmol), copper(I) iodide (8 mg, 0.04 mmol) and bis(triphenylphosphine)palladium(II) dichloride (14 mg, 0.02 mmol). The reaction was purged with $N_2$ for 5 min and then stirred at 110° C. for 1 h under microwave conditions. The reaction was concentrated under reduced pressure. The crude product was purified by reverse phase chromatography (ACN 23-53%/0.1% $NH_4OH$ in water) to give the title compound (8 mg, 11% yield) as a white solid. $^1H$ NMR (400 MHz, $CD_3OD$) δ 7.42 (s, 1H), 4.66-4.61 (m, 1H), 4.28-4.24 (m, 1H), 4.16-4.11 (m, 1H), 3.61 (s, 3H), 2.51 (s, 3H), 1.92-1.86 (m, 1H), 1.57 (s, 6H), 1.06 (d, J=6.8 Hz, 3H), 1.00 (d, J=6.8 Hz, 3H). LCMS M/Z (M+H) 356.

The following compound was prepared in a similar fashion to Example 202

Example 203

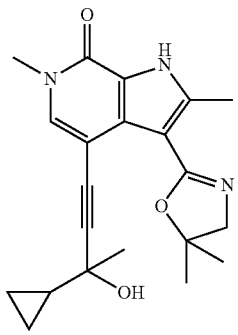

| Example | Compound Name | NMR | m/z |
|---------|---------------|-----|-----|
| 203 | 4-(3-cyclopropyl-3-hydroxy-but-1-ynyl)-3-(4-isopropyl-4,5-dihydrooxazol-2-yl)-2,6-dimethyl-1H-pyrrolo[2,3-c]pyridin-7-one | $^1H$ NMR (400 MHz, $CD_3OD$) δ 7.41 (s, 1 H), 4.69-4.64 (m, 1 H), 4.29-4.25 (m, 1 H), 4.19-4.17 (m, 1 H), 3.61 (s, 3 H), 2.52 (s, 3 H), 1.91-1.89 (m, 1 H), 1.62-1.59 (m, 3 H), 1.20-1.18 (m, 1 H), 1.06-0.96 (m, 6 H), 0.67-0.65 (m, 1 H), 0.50-0.48 (m, 3 H). | 382 |

Example 204

4-(3-cyclopropyl-3-hydroxy-but-1-ynyl)-3-(5,5-dimethyl-4H-oxazol-2-yl)-2,6-dimethyl-1H-pyrrolo[2,3-c]pyridin-7-one

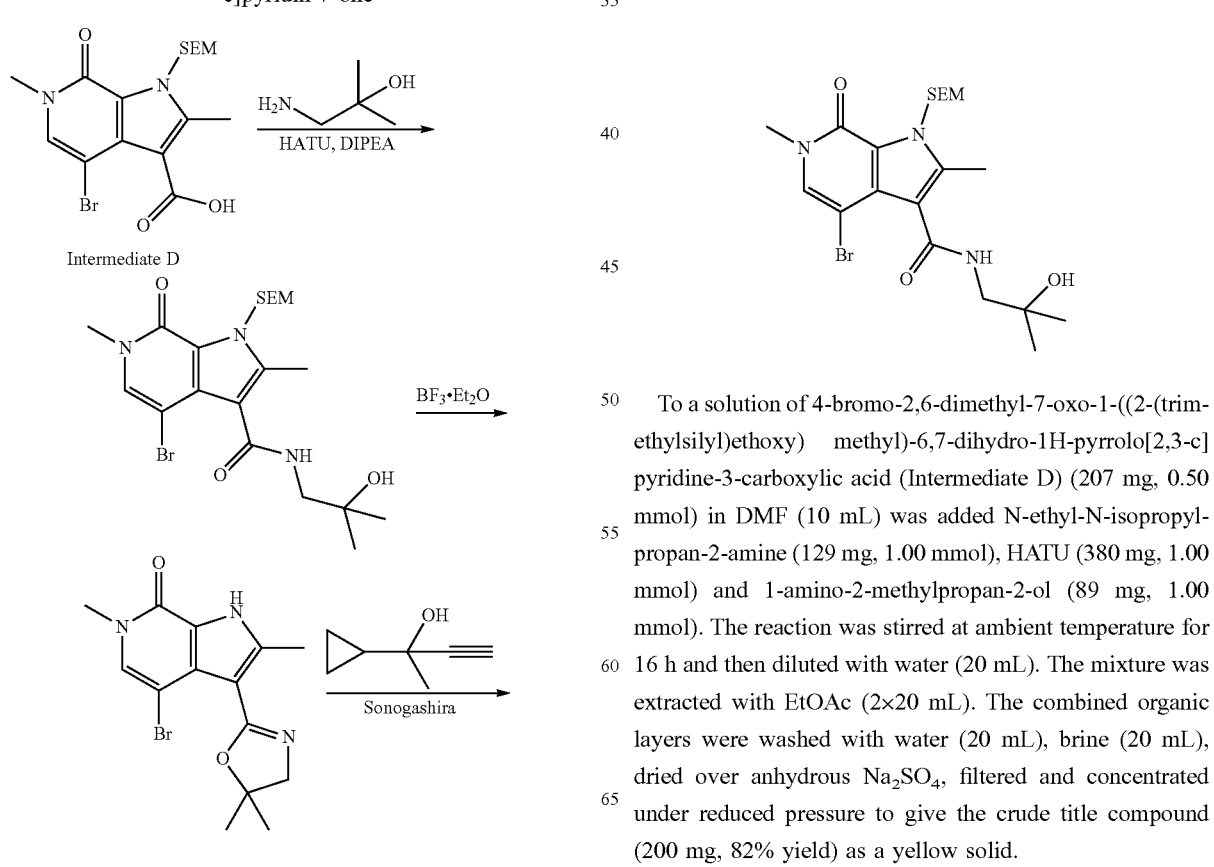

Step 1

4-bromo-N-(2-hydroxy-2-methylpropyl)-2,6-dimethyl-7-oxo-1-((2-(trimethylsilyl) ethoxy)methyl)-6,7-dihydro-1H-pyrrolo[2,3-c]pyridine-3-carboxamide To a solution of 4-bromo-2,6-dimethyl-7-oxo-1-((2-(trimethylsilyl)ethoxy) methyl)-6,7-dihydro-1H-pyrrolo[2,3-c] pyridine-3-carboxylic acid (Intermediate D) (207 mg, 0.50 mmol) in DMF (10 mL) was added N-ethyl-N-isopropylpropan-2-amine (129 mg, 1.00 mmol), HATU (380 mg, 1.00 mmol) and 1-amino-2-methylpropan-2-ol (89 mg, 1.00 mmol). The reaction was stirred at ambient temperature for 16 h and then diluted with water (20 mL). The mixture was extracted with EtOAc (2×20 mL). The combined organic layers were washed with water (20 mL), brine (20 mL), dried over anhydrous $Na_2SO_4$, filtered and concentrated under reduced pressure to give the crude title compound (200 mg, 82% yield) as a yellow solid.

Step 2

4-bromo-3-(5,5-dimethyl-4,5-dihydrooxazol-2-yl)-2,6-dimethyl-1H-pyrrolo[2,3-c]pyridin-7(6H)-one

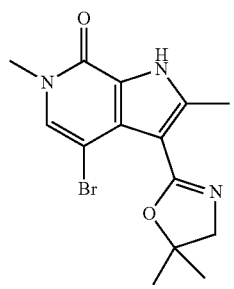

To a solution of 4-bromo-N-(2-hydroxy-2-methylpropyl)-2,6-dimethyl-7-oxo-1-((2-(trimethylsilyl)ethoxy)methyl)-6,7-dihydro-1H-pyrrolo[2,3-c]pyridine-3-carboxamide (200 mg, 0.41 mmol) in THF (10 mL) was added boron trifluoride etherate (1 N, 2.0 mL, 2.00 mmol). The reaction was heated at 65° C. for 16 h and then concentrated under reduced pressure. The residue was purified by column chromatography (DCM:MeOH=9:1) to give the title compound (100 mg, 72% yield) as a yellow solid.

Step 3

4-(3-cyclopropyl-3-hydroxy-but-1-ynyl)-3-(5,5-dimethyl-4H-oxazol-2-yl)-2,6-dimethyl-1H-pyrrolo[2,3-c]pyridin-7-one

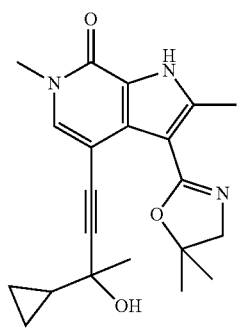 [SMILES: Cc1[nH]c2c(=O)n(C)cc(C#CC(C)(O)C3CC3)c2c1C1=NCC(C)(C)O1]

To a suspension of 4-bromo-3-(5,5-dimethyl-4,5-dihydrooxazol-2-yl)-2,6-dimethyl-1H-pyrrolo[2,3-c]pyridin-7(6H)-one (100 mg, 0.30 mmol) in DMF (3 mL) and TEA (1 mL) was added 2-cyclopropylbut-3-yn-2-ol (165 mg, 1.50 mmol), copper(I) iodide (11 mg, 0.06 mmol) and bis(triphenylphosphine)palladium(II) dichloride (21 mg, 0.03 mmol). The reaction was purged with $N_2$ for 5 min and then stirred at 110° C. for 1 h under microwave conditions. The reaction mixture was concentrated under reduced pressure.

The crude product was purified by reverse phase chromatography (ACN 35-65%/0.1% formic acid in water) to afford the title compound (5 mg, 5% yield) as a white solid. $^1$H NMR (400 MHz, $CD_3OD$) δ 7.39 (s, 1H), 3.82 (s, 2H), 3.61 (s, 3H), 2.49 (s, 3H), 1.59 (s, 3H), 1.54 (s, 6H), 1.18-1.16 (m, 1H), 0.67-0.65 (m, 1H), 0.55-0.47 (m, 3H). LCMS M/Z (M+H) 368.

Example 205

3-(5-(hydroxymethyl)-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one

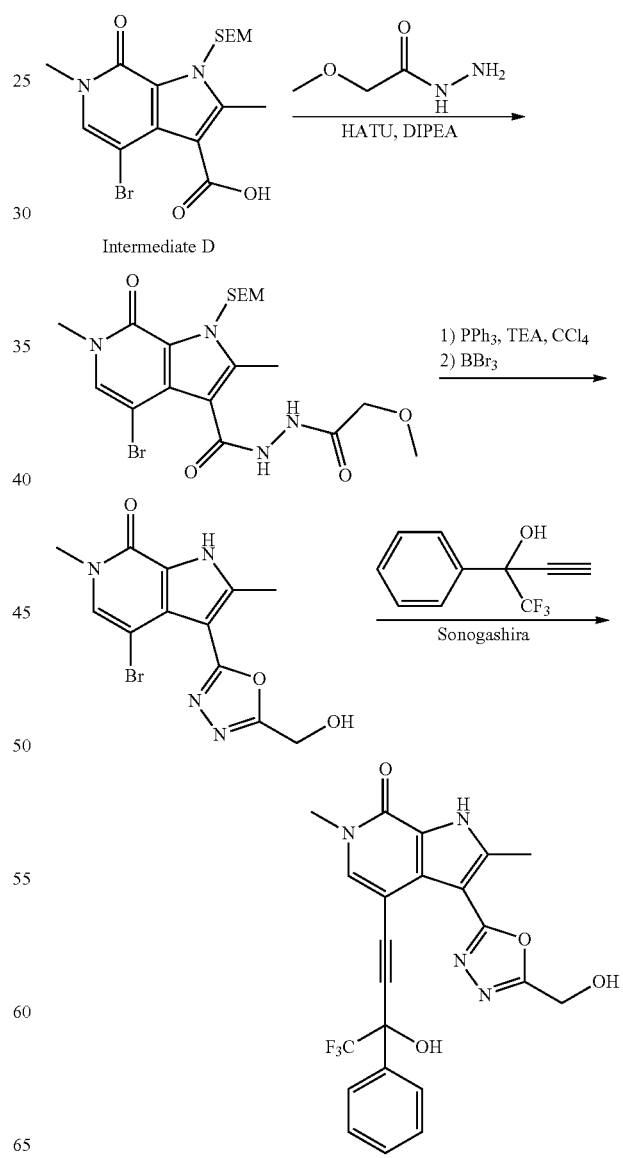

205

Step 1

4-bromo-N'-(2-methoxyacetyl)-2,6-dimethyl-7-oxo-1-((2-(trimethylsilyl)ethoxy) methyl)-6,7-dihydro-1H-pyrrolo[2,3-c]pyridine-3-carbohydrazide

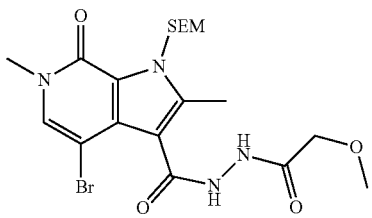

To a solution of 4-bromo-2,6-dimethyl-7-oxo-1-((2-(trimethylsilyl)ethoxy) methyl)-6,7-dihydro-1H-pyrrolo[2,3-c]pyridine-3-carboxylic acid (Intermediate D) (414 mg, 1.00 mmol) in DMF (15 mL) was added N-ethyl-N-isopropylpropan-2-amine (258 mg, 2.00 mmol), HATU (570 mg, 1.50 mmol) and 2-methoxyacetohydrazide (208 mg, 2.00 mmol). The reaction was stirred at ambient temperature for 16 h and diluted with water (20 mL). The mixture was extracted with EtOAc (3×20 mL). The combined organic layers were washed with water (20 mL), brine (20 mL), dried over anhydrous Na$_2$SO$_4$ and concentrated under reduced pressure to give the crude title compound (500 mg, 83% yield) as a yellow solid.

Step 2

4-bromo-3-(5-(methoxymethyl)-1,3,4-oxadiazol-2-yl)-2,6-dimethyl-1-((2-(trimethylsilyl)ethoxy) methyl)-1H-pyrrolo[2,3-c]pyridin-7(6H)-one

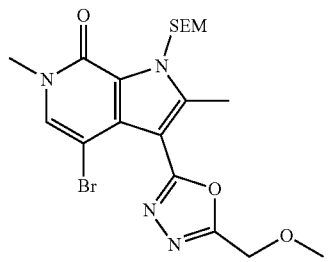

To a solution of 4-bromo-N'-(2-methoxyacetyl)-2,6-dimethyl-7-oxo-1-((2-(trimethyl silyl)ethoxy)methyl)-6,7-dihydro-1H-pyrrolo[2,3-c]pyridine-3-carbohydrazide (500 mg, 1.00 mmol) in DCM (20 mL) and carbon tetrachloride (2 mL) was added triphenylphosphine (524 mg, 2.00 mmol) and TEA (515 mg, 5.00 mmol). The reaction was heated at 60° C. for 6 h and then concentrated under reduced pressure. The residue was purified by column chromatography (petroleum ether:EtOAc=1:1) to give the title compound (300 mg, 62% yield) as a yellow solid.

206

Step 3

4-bromo-3-(5-(hydroxymethyl)-1,3,4-oxadiazol-2-yl)-2,6-dimethyl-1H-pyrrolo[2,3-c]pyridin-7(6H)-one

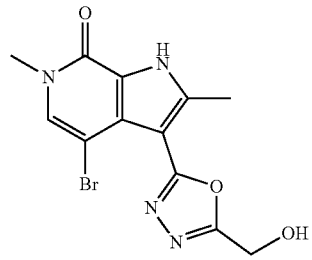 [SMILES: Cc1[nH]c2c(=O)n(C)cc(Br)c2c1-c1nnc(CO)o1]

To a solution of 4-bromo-3-(5-(methoxymethyl)-1,3,4-oxadiazol-2-yl)-2,6-dimethyl-1-((2-(trimethylsilyl)ethoxy) methyl)-1H-pyrrolo[2,3-c]pyridin-7(6H)-one (300 mg, 0.62 mmol) in DCM (20 mL) at −78° C. was added boron tribromide (0.5 mL). The reaction was stirred at ambient temperature for 30 min and then quenched by the addition of water (20 mL). The mixture was extracted with DCM (3×20 mL). The combined organic layers were dried over anhydrous Na$_2$SO$_4$, filtered and concentrated under reduced pressure to give the crude title compound (100 mg, 48% yield) as a yellow solid.

Step 4

3-(5-(hydroxymethyl)-1,3,4-oxadiazol-2-yl)-2,6-dimethyl-4-(4,4,4-trifluoro-3-hydroxy-3-phenyl-but-1-ynyl)-1H-pyrrolo[2,3-c]pyridin-7-one

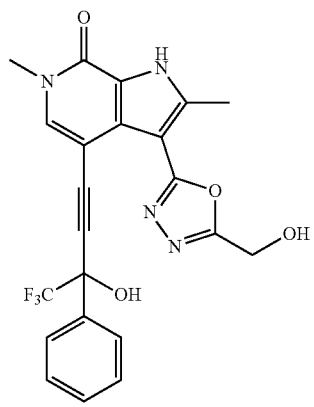 [SMILES: Cc1[nH]c2c(=O)n(C)cc(C#CC(O)(c3ccccc3)C(F)(F)F)c2c1-c1nnc(CO)o1]

To a suspension of 4-bromo-3-(5-(hydroxymethyl)-1,3,4-oxadiazol-2-yl)-2,6-dimethyl-1H-pyrrolo[2,3-c]pyridin-7(6H)-one in DMF (3 mL) and TEA (1 mL) was added 1,1,1-trifluoro-2-phenylbut-3-yn-2-ol (96 mg, 0.48 mmol), copper(I) iodide (11 mg, 0.06 mmol) and bis(triphenylphosphine)palladium(II) dichloride (21 mg, 0.03 mmol). The reaction was purged with N$_2$ for 5 min and then stirred at 110° C. for 1 h under microwave conditions. The reaction mixture was concentrated under reduced pressure. The crude product was purified by reverse phase chromatography (ACN 23-53%/0.1% NH$_4$OH in water) to give the title compound (40 mg, 37% yield) as a white solid. $^1$H NMR (400 MHz, DMSO-d$_6$) δ 12.89 (br. s, 1H), 7.87 (s, 1H), 7.60 (d, J=7.2 Hz, 2H), 7.42-7.40 (m, 3H), 4.41-4.28 (m, 2H), 3.59 (s, 3H), 2.45 (s, 3H). LCMS M/Z (M+H) 459.

The following compound was prepared in a similar fashion to Example 205

Example 206

| Example | Compound Name | NMR | m/z |
|---|---|---|---|
| 206 | 4-(3-cyclopropyl-3-hydroxy-but-1-ynyl)-3-[5-(hydroxymethyl)-1,3,4-oxadiazol-2-yl]-2,6-dimethyl-1H-pyrrolo[2,3-c]pyridin-7-one | 1H NMR (400 MHz, DMSO-$d_6$) δ 12.80 (br. s, 1 H), 7.57 (s, 1 H), 5.91 (t, J = 6.4 Hz, 1 H), 5.20 (s, 1 H), 4.76 (d, J = 6.4 Hz, 2 H), 3.54 (s, 3 H), 2.41 (s, 3 H), 1.31 (s, 3 H), 1.04-0.99 (m, 1 H), 0.34-0.27 (m, 4 H). | 351 (M − OH) |

Example 207 ethyl 2-cyclopropyl-4-(3-hydroxy-3-methyl-but-1-ynyl)-6-methyl-7-oxo-1H-pyrrolo[2,3-c]pyridine-3-carboxylate

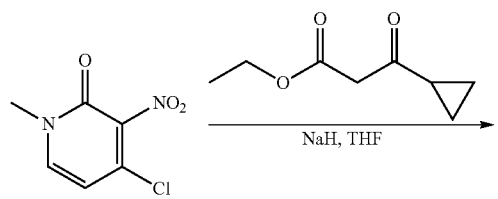

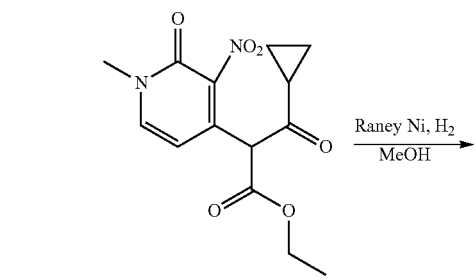

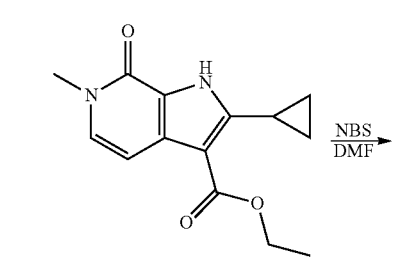

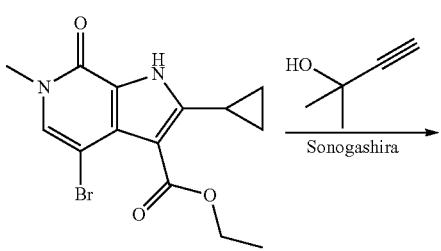

-continued

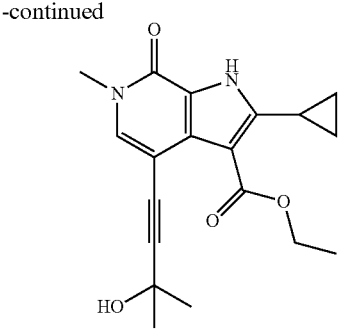

Step 1 ethyl 3-cyclopropyl-2-(1-methyl-3-nitro-2-oxo-1,2-dihydropyridin-4-yl)-3-oxopropanoate

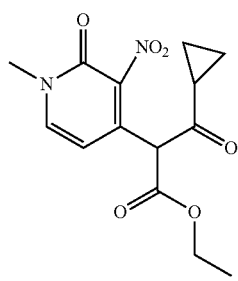 [SMILES: CCOC(=O)C(C(=O)C1CC1)c1ccn(C)c(=O)c1[N+](=O)[O-]]

To a solution of ethyl 3-cyclopropyl-3-oxopropanoate (2.34 ml, 15.9 mmol) in THF (70 mL) at 0° C. was added NaH (60% in mineral oil, 800 mg, 19.9 mmol) portionwise. The mixture was stirred at 0° C. for 0.5 h before 4-chloro-1-methyl-3-nitropyridin-2(1H)-one (2.5 g, 13.3 mmol) in THF (20 mL) was added. The reaction was heated at 50° C. for 12 h and quenched with 5 mL 1N HCl, then poured into brine and extracted with EtOAc (3×). The combined organic layer was dried over anhydrous $Na_2SO_4$, filtered and concentrated. The residue was purified by column chromatography (hexane:EtOAc=3:7) to give the title compound (3.471 g, 85% yield) as a yellow oil. LCMS M/Z (M+H) 309.

Step 2 ethyl 2-cyclopropyl-6-methyl-7-oxo-6,7-dihydro-1H-pyrrolo[2,3-c]pyridine-3-carboxylate

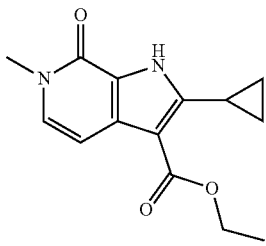 [SMILES: CCOC(=O)c1c(C2CC2)[nH]c2c(=O)n(C)ccc12]

To a solution of ethyl 3-cyclopropyl-2-(1-methyl-3-nitro-2-oxo-1,2-dihydropyridin-4-yl)-3-oxopropanoate (1.7 g, 5.51 mmol) in MeOH (20 mL) was added raney nickel (2 mL). The reaction was purged with $N_2$ for 15 min and then stirred at ambient temperature under hydrogen atmosphere for 12 h. The reaction was diluted with DCM (30 mL), filtered through celite and washed with 1:1 DCM:MeOH and concentrated. The residue was purified by column chromatography (0-40% gradient of 90:10:1 DCM:MeOH:$NH_4OH$ in DCM) to give the title compound (1.27 g, 84% yield) as a tan solid. LCMS M/Z (M+H) 261.

Step 3 ethyl 4-bromo-2-cyclopropyl-6-methyl-7-oxo-6,7-dihydro-1H-pyrrolo[2,3-c]pyridine-3-carboxylate

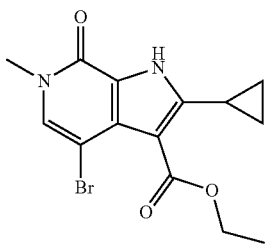 [SMILES: CCOC(=O)c1c(C2CC2)[nH]c2c(=O)n(C)cc(Br)c12]

To a solution of ethyl 2-cyclopropyl-6-methyl-7-oxo-6,7-dihydro-1H-pyrrolo[2,3-c]pyridine-3-carboxylate (1.27 g, 4.87 mmol) in DMF (13 mL) was added NBS (1.43 g, 8.03 mmol). The reaction was stirred at ambient temperature for 1 h. and then poured into water (175 mL) and extracted with EtOAc (3×). The organic layer was washed with brine, dried over anhydrous $Na_2SO_4$, filtered and concentrated. The residue was purified by column chromatography (hexane:EtOAc=4:6 to 8:2) to give the title compound (763.4 mg, 46% yield) as a purple solid. LCMS M/Z (M+H) 339/341.

Step 4 ethyl 2-cyclopropyl-4-(3-hydroxy-3-methyl-but-1-ynyl)-6-methyl-7-oxo-1H-pyrrolo[2,3-c]pyridine-3-carboxylate

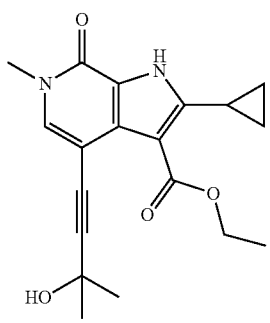 [SMILES: CCOC(=O)c1c(C2CC2)[nH]c2c(=O)n(C)cc(C#CC(C)(C)O)c12]

To a solution of ethyl 4-bromo-2-cyclopropyl-6-methyl-7-oxo-6,7-dihydro-1H-pyrrolo[2,3-c]pyridine-3-carboxylate (100 mg, 0.29 mmol) in DMF (2 mL) and DIPEA (0.51 mL, 2.9 mmol) was added 2-methylbut-3-yn-2-ol (57 µL, 0.59 mmol), copper(I) iodide (11.1 mg, 59 µmol) and bis(triphenylphosphine)palladium(II) dichloride (10.3 mg, 14.7 µmol). The reaction was purged with $N_2$ for 5 min and then stirred at 100° C. for 16 h. The reaction was concentrated under reduced pressure. The crude product was purified by column chromatography (hexane:EtOAc=30:70 to 0:100) to give the title compound (46 mg, 46% yield) as a tan solid. $^1H$ NMR (400 MHz, DMSO-$d_6$) δ 11.97 (s, 1H), 7.49 (s, 1H), 5.24 (s, 1H), 4.31 (q, J=7.1 Hz, 2H), 3.50 (s, 3H), 2.48-2.43 (m, 1H), 1.45 (s, 6H), 1.30 (t, J=7.1 Hz, 3H), 1.06 (td, J=2.8, 5.4 Hz, 2H), 0.99 (td, J=2.9, 8.5 Hz, 2H). LCMS M/Z (M+H) 343.

Example 208 ethyl 2,6-dimethyl-7-oxo-4-[4,4,4-trifluoro-3-hydroxy-3-(3-morpholinophenyl)but-1-ynyl]-1H-pyrrolo[2,3-c]pyridine-3-carboxylate

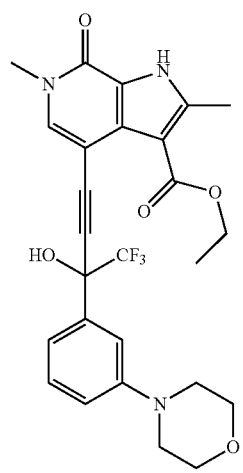 [SMILES: CCOC(=O)c1c(C)[nH]c2c(=O)n(C)cc(C#CC(O)(c3cccc(N4CCOCC4)c3)C(F)(F)F)c12]

To a solution of ethyl 4-(3-(3-bromophenyl)-4,4,4-trifluoro-3-hydroxybut-1-yn-1-yl)-2,6-dimethyl-7-oxo-6,7-dihydro-1H-pyrrolo[2,3-c]pyridine-3-carboxylate (75 mg, 0.15 mmol) in dioxane (2 mL) was added sodium tert-butoxide (49 mg, 0.51 mmol), ruphos precatalyst G3 (6 mg, 7 µmol) and morpholine (25.4 mL, 0.29 mmol). The reaction was purged with $N_2$ and then heated at 100° C. for 16 h. The reaction was concentrated under reduced pressure. The crude product was purified by reverse phase HPLC to give the title compound (3 mg, 4% yield) as a tan solid. LCMS M/Z (M+H) 518.

Example 209

Biological Assays $IC_{50}$ Measurements for Inhibitors Using TAF1-BD2 TR-FRET Binding Assay His/Flag epitope tagged TAF1-BD2$_{1504-1635}$ was cloned, expressed, and purified to homogeneity. TAF1-BD2 binding and inhibition was assessed by monitoring the engagement of a biotinylated small molecule compound 1000 with the target using the TR-FRET assay technology (Perkin-Elmer). Specifically, in a 384 well ProxiPlate, TAF1-BD2 (0.012 uM final) in 50 mM HEPES (pH 7.5; final), 50 mM NaCl (final), 1 mM TCEP (final), 0.1 mg/mL BSA (final), and 0.069 mM Brij-35 (final) was added either in the presence of DMSO (final 0.2% DMSO) or compound dilution series in DMSO. After a 10 minute incubation at room temperature, biotin-ligand (0.04 uM final) was added. After 10 minutes incubation at room temperature, a mixture Eu-W1024 Anti-6× His antibody (Perkin Elmer AD0110) and SureLight™ Streptavidin-Allophycocyanin (SA-APC, Perkin Elmer CR130-100) were added to a final concentration of 0.2 nM antibody and 0.025 uM SA-APC, respectively. After forty minutes of equilibration at room temperature, the plates were read on an Envision instrument and $IC_{50}$s calculated using a four parameter logistic model (XLFIT). Compound 1000 and the TAF1-BD2 TR-FRET Binding Assay described above represent additional embodiments of the invention.

$IC_{50}$ Measurements for Inhibitors Using TAF1-BD1 TR-FRET Binding Assay

His/Flag epitope tagged TAF1-BD1$_{1381-1497}$ was cloned, expressed, and purified to homogeneity. TAF1-BD binding and inhibition was assessed by monitoring the engagement of a biotinylated small molecule compound 1000 with the target using the TR-FRET assay technology (Perkin-Elmer). Specifically, in a 384 well ProxiPlate, TAF1-BDI (0.08 uM final) in 50 mM HEPES (pH 7.5; final), 50 mM NaCl (final), 1 mM TCEP (final), 0.1 mg/mL BSA (final), and 0.069 mM Brij-35 (final) was added either in the presence of DMSO (final 0.2% DMSO) or compound dilution series in DMSO. After a 10 minute incubation at room temperature, biotin-ligand (0.08 uM final) was added. After 10 minutes incubation at room temperature, a mixture Eu-W1024 Anti-6× His antibody (Perkin Elmer ADO 110) and SureLight™ Streptavidin-Allophycocyanin (SA-APC, Perkin Elmer CR130-100) were added to final concentrations of 0.2 nM antibody and 0.05 uM SA-APC, respectively. After forty minutes of equilibration at room temperature, the plates were read on an Envision instrument and $IC_{50}$s calculated using a four parameter logistic model (XLFIT). The TAF1-BD1 TR-FRET Binding Assay described above represents an additional embodiment of the invention.

Example 210

Synthesis of Compound 1000

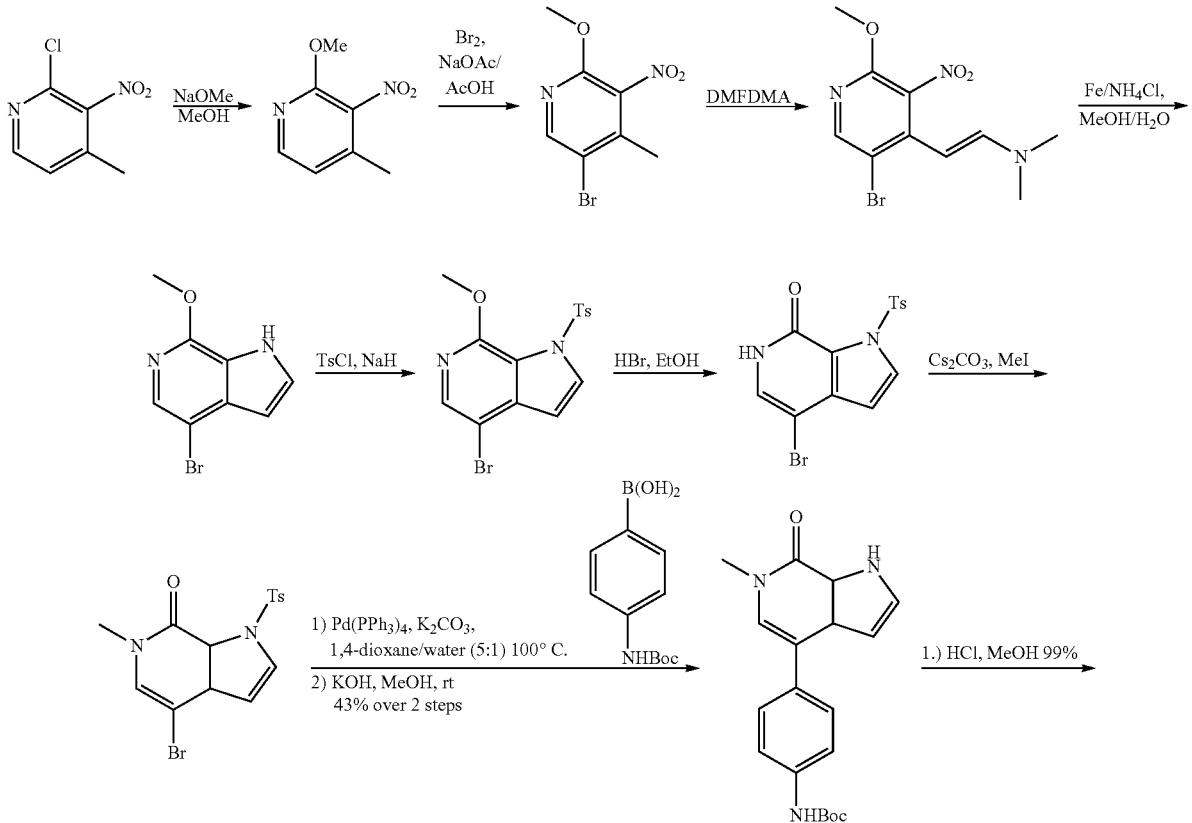

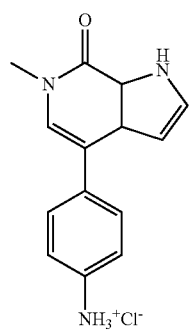
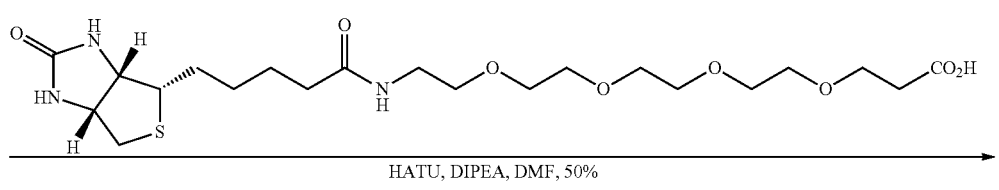

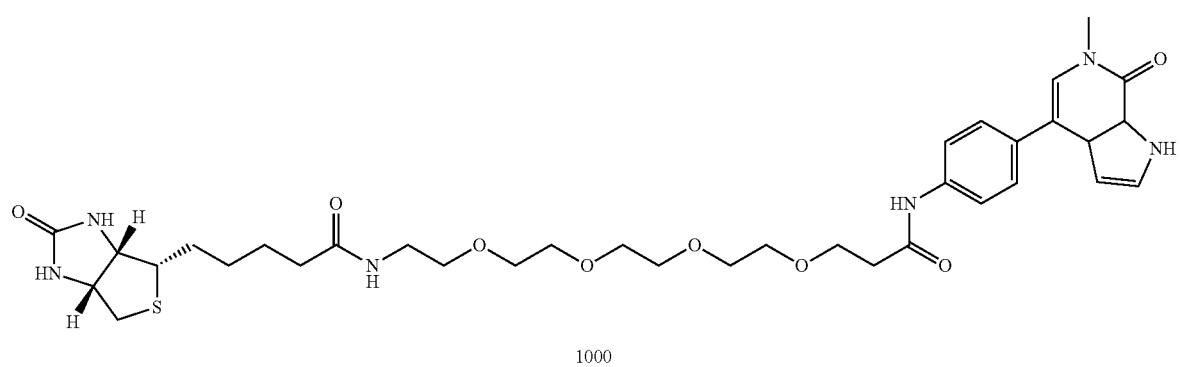

1000

Step 1

2-methoxy-4-methyl-3-nitropyridine

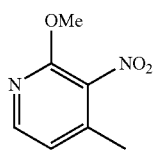

A solution of 2-chloro-4-methyl-3-nitropyridine (250 g, 1.45 mol) in methanol (1.0 L) was added dropwise (2 h) to a stirred and cooled (0° C.) solution of sodium methoxide (250 g, 4.63 mol) in methanol (850 mL). After addition, the mixture was heated to reflux for 23 h, at which time TLC indicated the reaction had gone to completion. The mixture was concentrated under reduced pressure to a volume of approximately 900 mL, and quenched by addition of water (1.5 L). The resulting solid was collected by filtration, washed with water and dried under reduced pressure to give the title compound (250 g, 100% yield) as a brown solid. $^1$H NMR (400 MHz, DMSO-d6): δ 8.22 (d, J=5.2 Hz, 1H), 7.10 (d, J=5.6 Hz, 1H), 3.92 (s, 3H), 2.26 (s, 3H).

Step 2

5-bromo-2-methoxy-4-methyl-3-nitropyridine

Sodium acetate (365 g, 5.37 mol) was added to a stirred solution of 2-methoxy-4-methyl-3-nitropyridine (250 g, 1.49 mol) in acetic acid (1.5 L) at ambient temperature and then Br$_2$ (639 g, 4.00 mol) was added dropwise (30 min). After addition, the mixture was heated at 80° C. for 12 h, at which time TLC indicated the reaction had gone to completion. The mixture was cooled (0° C.) and quenched by sequential addition of 10% aqueous (1.5 L) and saturated aqueous Na$_2$SO$_3$ (1.5 L). The resulting solid was collected by filtration washed with water, and dried under reduced pressure to give the title compound (302 g, 82.2% yield) as a light yellow solid. $^1$H NMR (400 MHz, DMSO-d6): δ 8.25 (s, 1H), 3.94 (s, 3H), 2.29 (s, 3H).

Step 3

(E)-2-(5-bromo-2-methoxy-3-nitro-4-pyridyl)-N,N-dimethyl-ethenamine

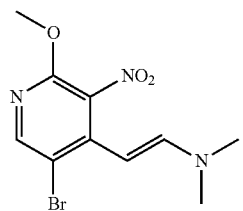 [SMILES: COc1ncc(Br)c(/C=C/N(C)C)c1[N+](=O)[O-]]

DMF-DMA (600 mL) was slowly added to a stirred and heated (80° C.) solution of 5-bromo-2-methoxy-4-methyl-3-nitropyridine (134 g, 0.54 mol) in DMF (1.1 L). After addition, the mixture was heated at 95° C. for 5 h, at which time TLC indicated the reaction had gone to completion. The mixture was cooled to room temperature and poured into ice-cold water (3 L). The resulting red solid was collected by filtration, washed with water, and dried under reduced pressure to give the title compound (167 g, 100% yield) as red solid. $^1$H NMR (400 MHz, DMSO-d6): δ 8.24 (s, 1H), 7.05 (d, J=13.6 Hz, 1H), 7.05 (d, J=13.6 Hz, 1H), 4.80 (d, J=13.2 Hz, 1H), 3.88 (s, 3H), 2.90 (s, 6H).

Step 4

4-bromo-7-methoxy-1H-pyrrolo[2,3-c]pyridine

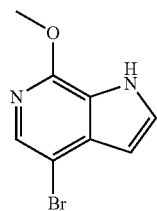

A mixture of 2-(5-bromo-2-methoxy-3-nitropyridin-4-yl)-N,N-dimethylethenamine (50.0 g, 165 mmol), Fe (50.0 g, 893 mmol) and NH$_4$Cl (50.0 g, 943 mmol) in methanol/H$_2$O (1900/250 mL) was heated at reflux for 7 h, at which time LCMS indicated that the reaction had gone to completion. The mixture was filtered while hot and the cake was washed with methanol (3×200 mL). The combined filtrate was concentrated under reduced pressure, and the resulting residue was purified by silica gel chromatography (petroleum ether:Ethyl acetate=5:1) to give the crude product. This crude material was triturated with acetonitrile to give the title compound (37.4 g, 99.5% yield) as a light brown solid. LCMS M/Z (M+H) 226.7, 228.7.

Step 5

4-bromo-7-methoxy-1-(p-tolylsulfonyl)pyrrolo[2,3-c]pyridine

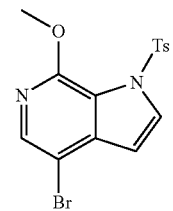 [SMILES: COc1ncc(Br)c2ccn(S(=O)(=O)c3ccc(C)cc3)c12]

A solution of 4-bromo-7-methoxy-1H-pyrrolo[2,3-c]pyridine (34.3 g, 0.15 mol) in THF (700 mL) was added dropwise to a stirred and cooled (0° C.) solution of sodium hydride (60%, 19.2 g, 0.48 mol) in THF (700 mL). After addition, the mixture was stirred at room temperature for 1 h, and then cooled again to 0° C. Tosyl chloride (38.0 g, 0.20 mol) in THF (700 mL) was added dropwise and the resulting mixture was stirred at ambient temperature for 2 h. The reaction was quenched by addition of saturated aqueous ammonium chloride (1.0 L), and then extracted with ethyl acetate (3×600 mL). The combined organic extracts were dried over Na$_2$SO$_4$ and concentrated under reduced pressure. The residue was triturated with acetonitrile to give the title compound (51.2 g, 88.9% yield) as a brown solid. This crude material was used in the next step without further purification.

Step 6

4-bromo-1-(p-tolylsulfonyl)-6H-pyrrolo[2,3-c]pyridin-7-one

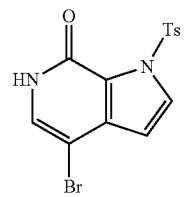 [SMILES: Cc1ccc(S(=O)(=O)n2ccc3c(Br)c[nH]c(=O)c32)cc1]

HBr (40% aqueous, 1.1 L) was added to a solution of 4-bromo-7-methoxy-1-(p-tolylsulfonyl)pyrrolo[2,3-c]pyridine (102.5 g, 0.27 mol) in ethanol (200 mL). After addition, the mixture was heated at 90° C. for 2 h, at which time TLC indicated that the reaction had gone to completion. The mixture was cooled to 0° C. and the resulting white solid was collected by filtration. This solid was washed with water and dried under vacuum to give the title compound (87.5 g, 88.6% yield) as a light brown solid. $^1$H NMR (400 MHz, DMSO-d6): δ 11.48 (s, 1H), 8.01 (d, J=3.6 Hz, 1H), 8.90 (d, J=8.0 Hz, 2H), 7.38 (d, J=8.0 Hz, 2H), 7.32 (s, 1H), 6.57 (d, J=3.2 Hz, 1H), 2.34 (s, 3H).

Step 7

4-bromo-6-methyl-1-(p-tolylsulfonyl)pyrrolo[2,3-c]pyridin-7-one

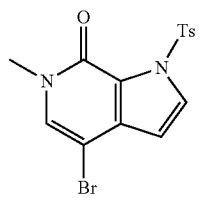 [SMILES: Cc1ccc(S(=O)(=O)n2ccc3c(Br)cn(C)c(=O)c32)cc1]

Methyl iodide (24.5 g, 172.8 mmol) was added dropwise to a stirred suspension of 4-bromo-1-tosyl-1H-pyrrolo[2,3-c]pyridin-7(6H)-one (Intermediate A) (16.7 g, 45.5 mmol) and cesium carbonate (17.8 g, 54.6 mmol) in dioxane (250 mL). After addition, the reaction mixture was stirred at room temperature for 18 h, at which time LCMS indicated the reaction had gone to completion. The solvent was evaporated under reduced pressure, and the residue was diluted with water (200 mL). The mixture was extracted with EtOAc (3×200 mL). The combined organic extracts were dried over sodium sulfate, filtered and concentrated under reduced pressure. The residue was purified by silica gel chromatography (petroleum ether/ethyl acetate=3:1) to give the title compound (14.0 g, 81.4% yield) as a brown solid. $^1$H NMR (400 MHz, DMSO-d6): δ 8.03 (d, J=3.6 Hz, 1H), 7.92 (d, J=8.4 Hz, 2H), 7.78 (s, 1H), 7.39 (d, J=8.4 Hz, 2H), 6.57 (d, J=3.6 Hz, 1H), 3.35 (s, 3H), 2.35 (s, 3H).

Step 8

A 50 mL vial was charged with a magnetic stir bar, 4-bromo-6-methyl-1-tosyl-1H-pyrrolo[2,3-c]pyridin-7(6H)-one (0.281 g, 0.737 mmol), 1,4-dioxane (3.69 ml, 0.737 mmol), water (0.5 ml, 27.8 mmol), $K_2CO_3$ (0.306 g, 2.211 mmol), 4-(tertbutoxycarbonylamino)phenylboronic acid (0.227 g, 0.958 mmol), and $Pd(PPh_3)_4$ (0.085 g, 0.074 mmol). The vial was purged, placed under an atmosphere of nitrogen and heated to 95° C. with stirring for 12 h before being allowed to cool to room temperature. The reaction was then diluted with water (20 ml). A precipitate formed which was collected via vacuum filtration using a Buchner funnel. The solids were washed with additional water (2×25 mL), dried, and collected. This material was suspended in methanol (~5 mL) and treated with KOH (200 mg). After 2 h the MeOH was removed in vacuo and the crude material was suspended in water (~20 mL) and the resulting solids were collected via vacuum filtration using a Buchner funnel. The solids were washed with additional water, were collected, and dried in vacuo to afford tert-butyl 4-(6-methyl-7-oxo-6,7-dihydro-1H-pyrrolo[2,3-c]pyridin-4-yl)phenylcarbamate (362 mg, 0.907 mmol) as a light yellow solid. LCMS M/Z (M+H) 494.

Step 9

A 50 mL round bottom flask was charged with a magnetic stir bar, tert-butyl 4-(6-methyl-7-oxo-6,7-dihydro-1H-pyrrolo[2,3-c]pyridin-4-yl)phenylcarbamate (350 mg, 1.031 mmol), MeOH (2.062 mL, 1.031 mmol), and HCl (1.031 mL, 4.12 mmol) (4N in dioxane). The reaction was then allowed to stir at rt for 4 h before being diluted with dioxane (25 mL). A precipitate formed which was collected via vacuum filtration using a Buchner funnel, washed with additional dioxane, and dried in vacuo to afford 4-(4-aminophenyl)-6-methyl-1H-pyrrolo[2,3-c]pyridin-7(6H)-one (188 mg, 0.786 mmol, 76% yield) as a white solid. LCMS M/Z (M+H) 240.

Step 10

A 25 mL vial was charged with a magnetic stir bar, 4-(4-aminophenyl)-6-methyl-1Hpyrrolo[2,3-c]pyridin-7(6H)-one (0.038 g, 0.159 mmol), anhydrous DMF (0.794 ml, 0.159 mmol), DIPEA (0.139 ml, 0.794 mmol), 17-oxo-21-((3aS,4S,6aR)-2-oxohexahydro-1Hthieno[3,4-d]imidazol-4-yl)-4,7,10,13-tetraoxa-16-azahenicosan-1-oic acid (0.078 g, 0.159 mmol), and HATU (0.075 g, 0.199 mmol). The crude reaction mixture was directly purified via reverse phase HPLC to afford N-(4-(6-methyl-7-oxo-6,7-dihydro-1H-pyrrolo[2,3-c]pyridin-4-yl)phenyl)-1-(5-((3aS,4S,6aR)-2-oxohexahydro-1H-thieno[3,4-d]imidazol-4-yl)pentanamido)-3,6,9,12-tetraoxapentadecan-15-amide (31 mg, 0.041 mmol, 26.0% yield). LCMS M/Z (M+2H)/2 357.

| Example | Structure | TAF1-BD2 HTRF IC50 uM | TAF1-BD1 HTRF IC50 uM |
|---|---|---|---|
| 1 | 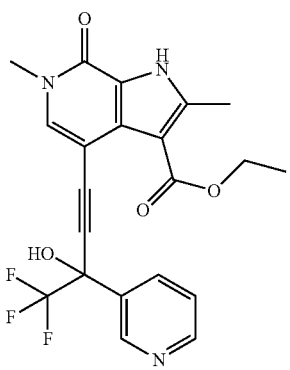 [SMILES: CCOC(=O)c1c(C)[nH]c2c(=O)n(C)cc(C#CC(O)(c3cccnc3)C(F)(F)F)c12] | 0.0804 | 0.312 |

-continued

| Example | Structure | TAF1-BD2 HTRF IC50 uM | TAF1-BD1 HTRF IC50 uM |
|---------|-----------|----------------------|----------------------|
| 2 | 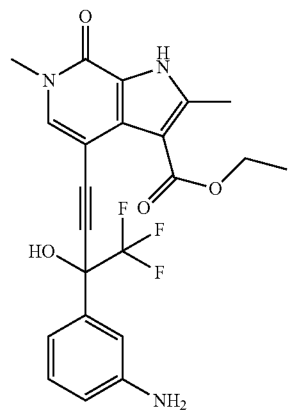 [SMILES: CCOC(=O)c1c(C)[nH]c2c(=O)n(C)cc(C#CC(O)(c3cccc(N)c3)C(F)(F)F)c12] | 0.0453 | 0.249 |
| 3 | 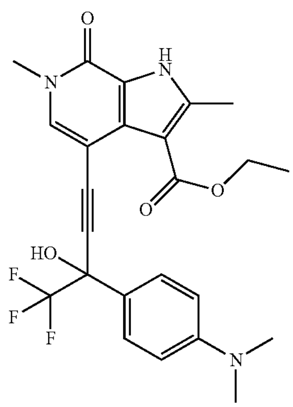 [SMILES: CCOC(=O)c1c(C)[nH]c2c(=O)n(C)cc(C#CC(O)(c3ccc(N(C)C)cc3)C(F)(F)F)c12] | 0.0863 | 0.209 |
| 4 | 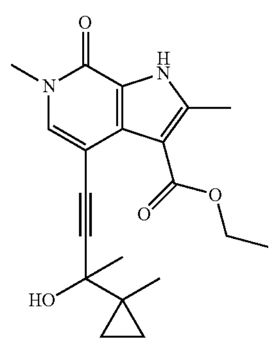 [SMILES: CCOC(=O)c1c(C)[nH]c2c(=O)n(C)cc(C#CC(C)(O)C3(C)CC3)c12] | 0.0727 | 0.352 |
| 5 | 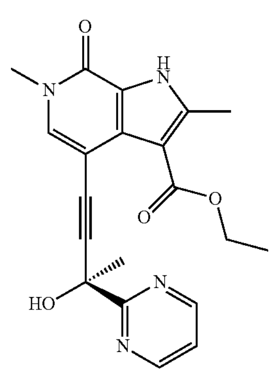 [SMILES: CCOC(=O)c1c(C)[nH]c2c(=O)n(C)cc(C#C[C@](C)(O)c3ncccn3)c12] | 1.63 | 8.35 |

-continued

| Example | Structure | TAF1-BD2 HTRF IC50 uM | TAF1-BD1 HTRF IC50 uM |
|---|---|---|---|
| 6 | 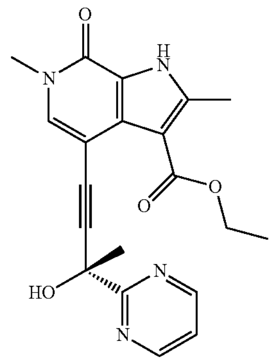 [SMILES: CCOC(=O)c1c(C)[nH]c2c(=O)n(C)cc(C#C[C@@](C)(O)c3ncccn3)c12] | 0.147 | 0.989 |
| 7 | 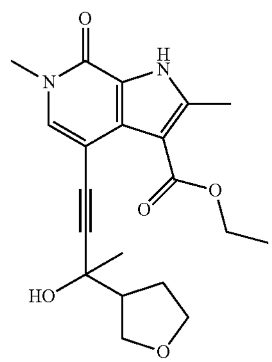 [SMILES: CCOC(=O)c1c(C)[nH]c2c(=O)n(C)cc(C#CC(C)(O)C3CCOC3)c12] | 0.181 | 0.607 |
| 8 | 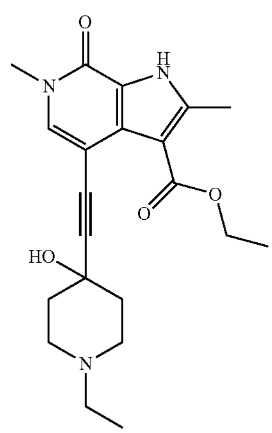 [SMILES: CCOC(=O)c1c(C)[nH]c2c(=O)n(C)cc(C#CC3(O)CCN(CC)CC3)c12] | 0.425 | 7.85 |
| 9 | 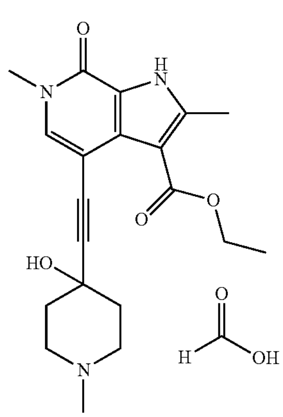 | 0.815 | 14.5 |

-continued

| Example | Structure | TAF1-BD2 HTRF IC50 uM | TAF1-BD1 HTRF IC50 uM |
|---------|-----------|----------------------|----------------------|
| 10 | 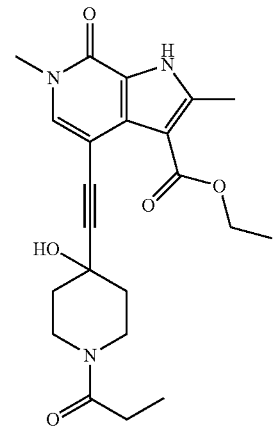 [SMILES: CCOC(=O)c1c(C)[nH]c2c(=O)n(C)cc(C#CC3(O)CCN(C(=O)CC)CC3)c12] | 0.0589 | 2.23 |
| 11 | 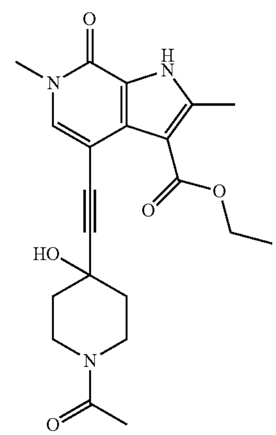 [SMILES: CCOC(=O)c1c(C)[nH]c2c(=O)n(C)cc(C#CC3(O)CCN(C(C)=O)CC3)c12] | 0.08 | 1.49 |
| 12 | 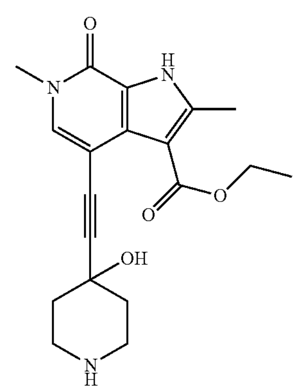 [SMILES: CCOC(=O)c1c(C)[nH]c2c(=O)n(C)cc(C#CC3(O)CCNCC3)c12] | 0.429 | 0.757 |

-continued

| Example | Structure | TAF1-BD2 HTRF IC50 uM | TAF1-BD1 HTRF IC50 uM |
|---|---|---|---|
| 13 | 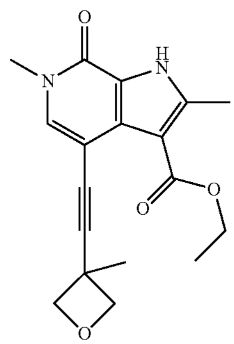 | 0.379 | 0.434 |
| 14 | 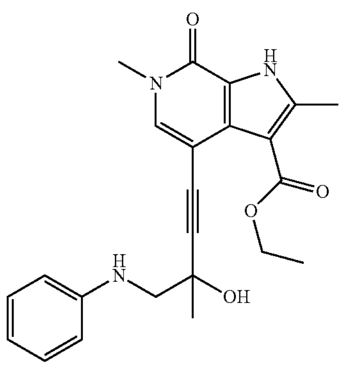 [SMILES: CCOC(=O)c1c(C)[nH]c2c(=O)n(C)cc(C#CC(C)(O)CNc3ccccc3)c12] | 14.8 | >20 |
| 15 | 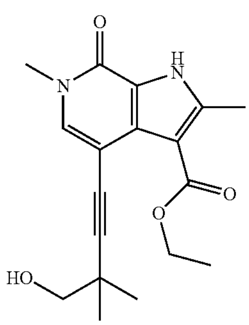 | 0.189 | 0.343 |
| 16 | 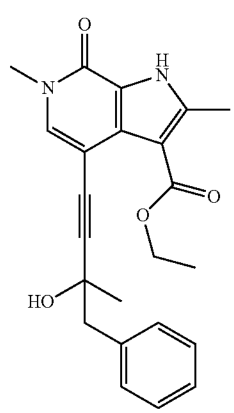 | 0.0388 | 0.212 |

-continued

| Example | Structure | TAF1-BD2 HTRF IC50 uM | TAF1-BD1 HTRF IC50 uM |
|---------|-----------|----------------------|----------------------|
| 17 | 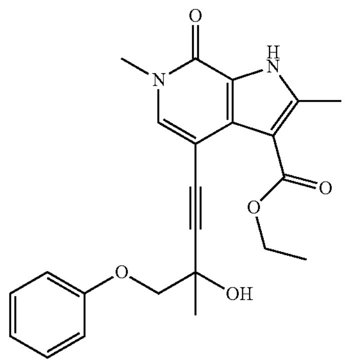 [SMILES: CCOC(=O)c1c(C)[nH]c2c(=O)n(C)cc(C#CC(C)(O)COc3ccccc3)c12] | 0.0673 | 0.404 |
| 18 | 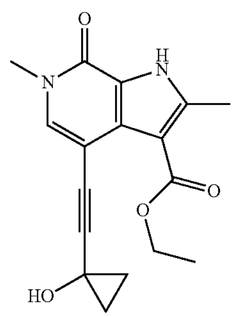 | 0.0854 | 0.632 |
| 19 | 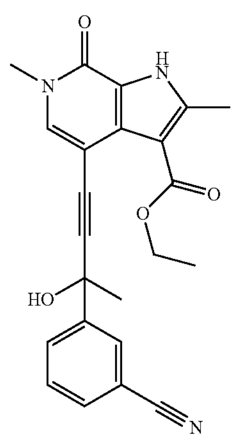 | 0.0303 | 0.146 |
| 20 | 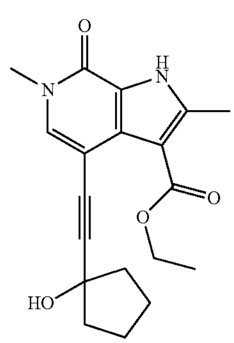 | 0.0219 | 0.282 |

-continued

| Example | Structure | TAF1-BD2 HTRF IC50 uM | TAF1-BD1 HTRF IC50 uM |
|---------|-----------|------------------------|------------------------|
| 21 | 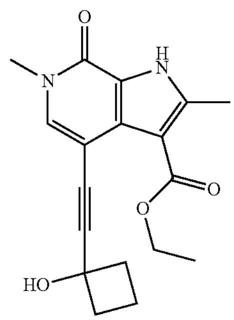 | 0.0611 | 0.407 |
| 22 | 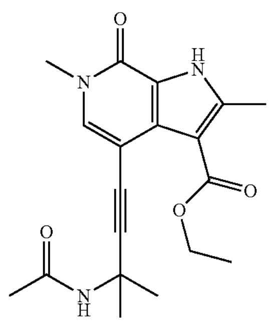 [SMILES: CCOC(=O)c1c(C)[nH]c2c(=O)n(C)cc(C#CC(C)(C)NC(C)=O)c12] | 0.523 | 0.804 |
| 23 | 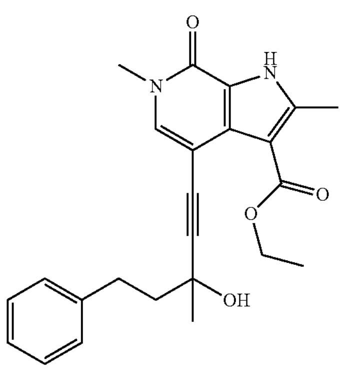 [SMILES: CCOC(=O)c1c(C)[nH]c2c(=O)n(C)cc(C#CC(C)(O)CCc3ccccc3)c12] | 0.0586 | 0.182 |
| 24 | 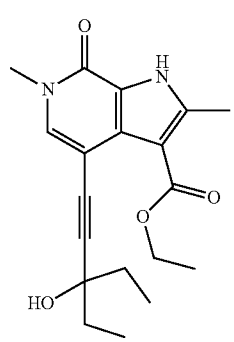 | 0.138 | 0.536 |

-continued

| Example | Structure | TAF1-BD2 HTRF IC50 uM | TAF1-BD1 HTRF IC50 uM |
|---|---|---|---|
| 25 | 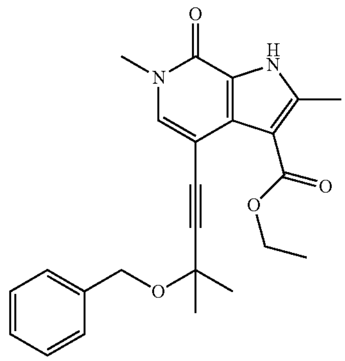 [SMILES: CCOC(=O)c1c(C)[nH]c2c(=O)n(C)cc(C#CC(C)(C)OCc3ccccc3)c12] | 0.373 | 0.848 |
| 26 | 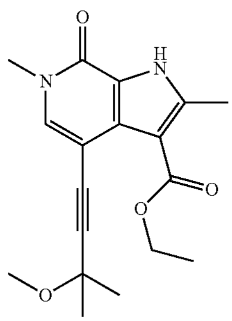 | 0.284 | 0.503 |
| 27 | 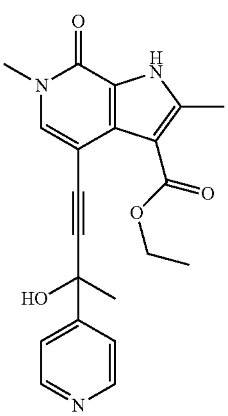 | 0.0899 | 0.338 |
| 28 | 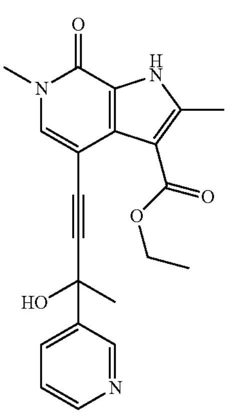 | 0.0525 | 0.234 |

-continued

| Example | Structure | TAF1-BD2 HTRF IC50 uM | TAF1-BD1 HTRF IC50 uM |
|---|---|---|---|
| 29 | 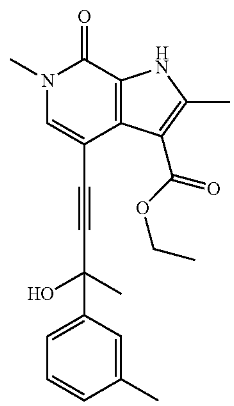 | 0.0509 | 0.303 |
| 30 | 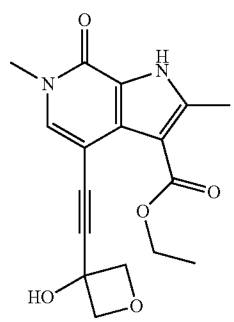 | 0.0873 | 0.634 |
| 31 | 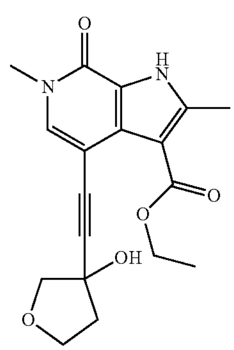 | 0.0408 | 0.511 |
| 32 | 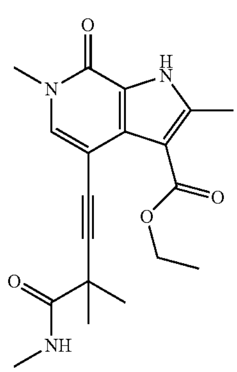 | 1.32 | 0.802 |

-continued

| Example | Structure | TAF1-BD2 HTRF IC50 uM | TAF1-BD1 HTRF IC50 uM |
|---|---|---|---|
| 33 | 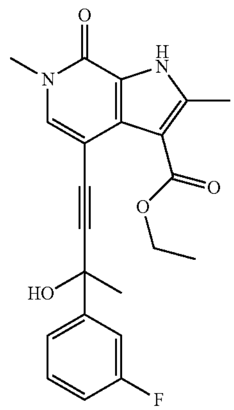 | 0.06 | 0.218 |
| 34 | 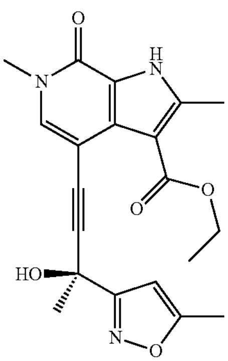 | 0.286 | 0.595 |
| 35 | 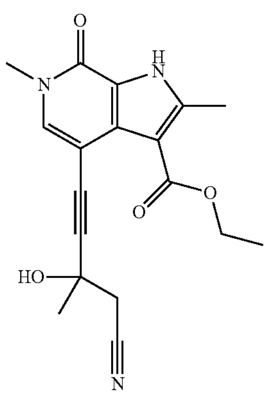 [SMILES: CCOC(=O)c1c(C)[nH]c2c(=O)n(C)cc(C#CC(C)(O)CC#N)c12] | 0.1 | 0.139 |
| 36 | 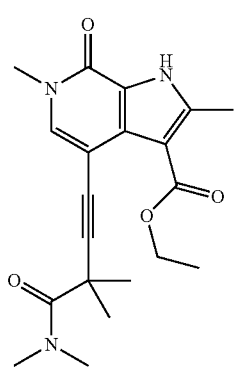 | 0.375 | 1.31 |

-continued

| Example | Structure | TAF1-BD2 HTRF IC50 uM | TAF1-BD1 HTRF IC50 uM |
|---|---|---|---|
| 37 | 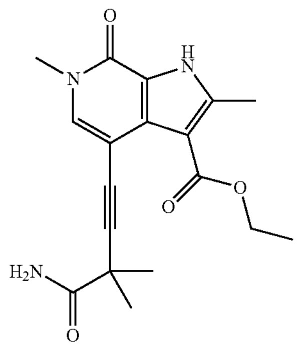 [SMILES: CCOC(=O)c1c(C)[nH]c2c(=O)n(C)cc(C#CC(C)(C)C(N)=O)c12] | 0.221 | 0.382 |
| 38 | 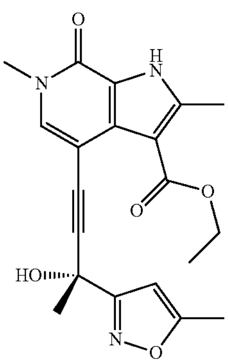 | 0.0454 | 0.136 |
| 39 | 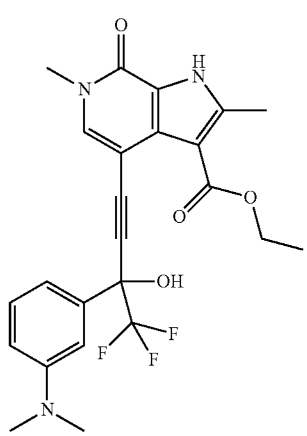 [SMILES: CCOC(=O)c1c(C)[nH]c2c(=O)n(C)cc(C#CC(O)(c3cccc(N(C)C)c3)C(F)(F)F)c12] | 0.0769 | 0.525 |

| Example | Structure | TAF1-BD2 HTRF IC50 uM | TAF1-BD1 HTRF IC50 uM |
|---|---|---|---|
| 40 | 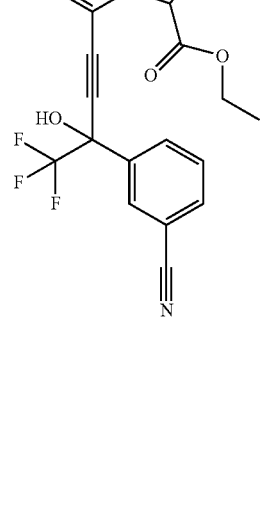 | 0.0692 | 0.355 |
| 41 | 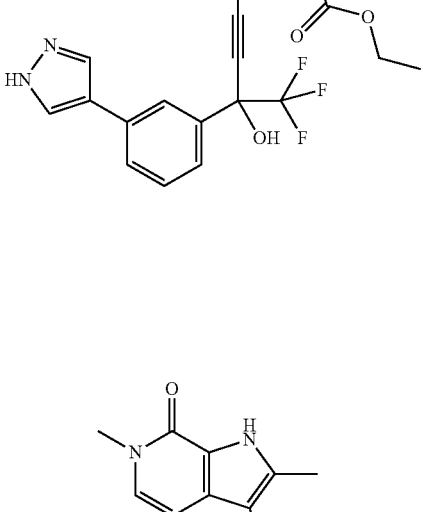 | 0.0215 | 0.171 |
| 42 | 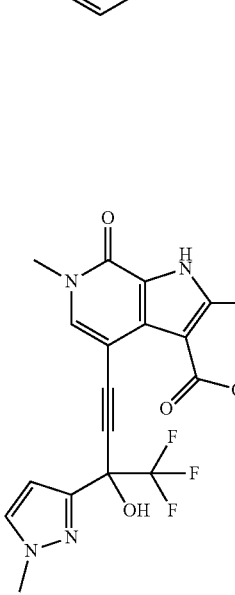 | 0.0969 | 0.657 |

-continued

| Example | Structure | TAF1-BD2 HTRF IC50 uM | TAF1-BD1 HTRF IC50 uM |
|---|---|---|---|
| 43 | 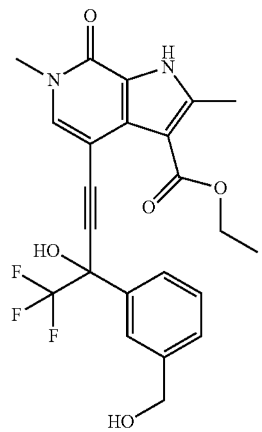 [SMILES: CCOC(=O)c1c(C)[nH]c2c(=O)n(C)cc(C#CC(O)(c3cccc(CO)c3)C(F)(F)F)c12] | 0.0355 | 0.257 |
| 44 | 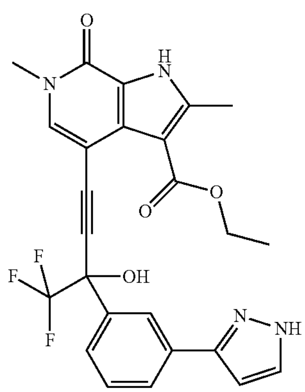 [SMILES: CCOC(=O)c1c(C)[nH]c2c(=O)n(C)cc(C#CC(O)(c3cccc(-c4cc[nH]n4)c3)C(F)(F)F)c12] | 0.017 | 0.226 |
| 45 | 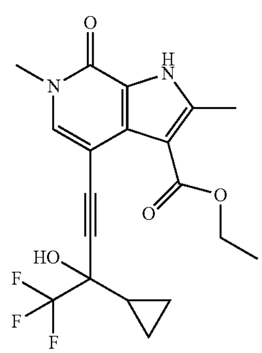 [SMILES: CCOC(=O)c1c(C)[nH]c2c(=O)n(C)cc(C#CC(O)(C3CC3)C(F)(F)F)c12] | 0.0747 | 0.271 |
| 46 | 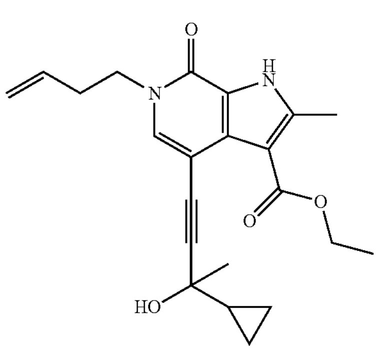 [SMILES: C=CCCn1cc(C#CC(C)(O)C2CC2)c2c(C(=O)OCC)c(C)[nH]c2c1=O] | 0.133 | 2.23 |

-continued
| Example | Structure | TAF1-BD2 HTRF IC50 uM | TAF1-BD1 HTRF IC50 uM |
|---|---|---|---|
| 47 | 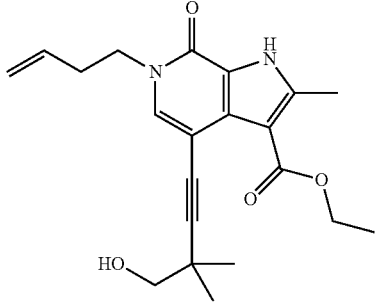 [SMILES: C=CCCn1cc(C#CC(C)(C)CO)c2c(C(=O)OCC)c(C)[nH]c2c1=O] | 0.368 | 4.9 |
| 48 | 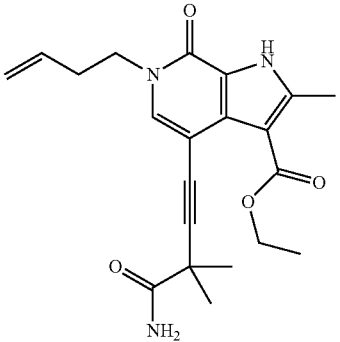 [SMILES: C=CCCn1cc(C#CC(C)(C)C(N)=O)c2c(C(=O)OCC)c(C)[nH]c2c1=O] | 0.312 | 1.28 |
| 49 | 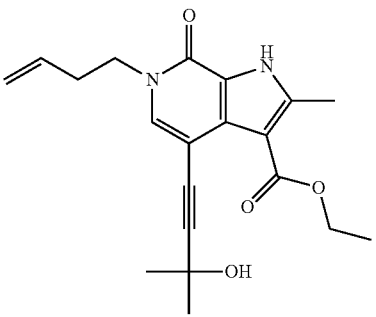 [SMILES: C=CCCn1cc(C#CC(C)(C)O)c2c(C(=O)OCC)c(C)[nH]c2c1=O] | 0.116 | 2.85 |
| 50 | 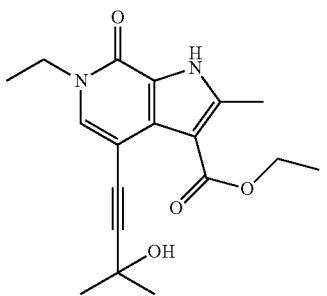 [SMILES: CCOC(=O)c1c(C)[nH]c2c(=O)n(CC)cc(C#CC(C)(C)O)c12] | 0.45 | 9.87 |

-continued

| Example | Structure | TAF1-BD2 HTRF IC50 uM | TAF1-BD1 HTRF IC50 uM |
|---------|-----------|----------------------|----------------------|
| 51 | 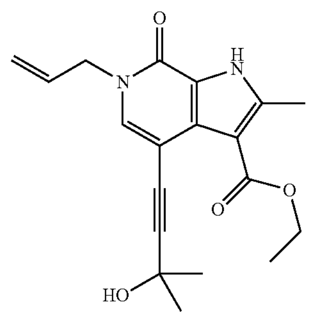 [SMILES: C=CCn1cc(C#CC(C)(C)O)c2c(C(=O)OCC)c(C)[nH]c2c1=O] | 0.227 | 7.2 |
| 52 | 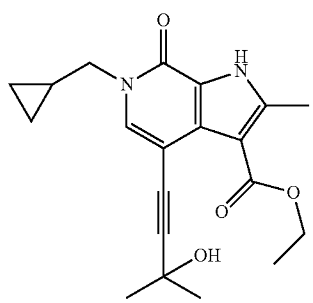 [SMILES: CCOC(=O)c1c(C)[nH]c2c(=O)n(CC3CC3)cc(C#CC(C)(C)O)c12] | 0.155 | 8.66 |
| 53 | 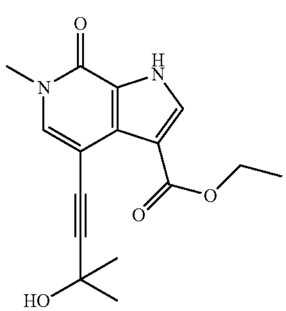 [SMILES: CCOC(=O)c1c[nH]c2c(=O)n(C)cc(C#CC(C)(C)O)c12] | 0.0952 | 0.859 |
| 54 | 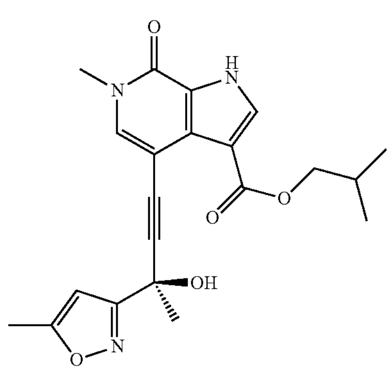 [SMILES: Cc1cc([C@](C)(O)C#Cc2cn(C)c(=O)c3[nH]cc(C(=O)OCC(C)C)c23)no1] | 0.122 | 0.179 |

-continued

| Example | Structure | TAF1-BD2 HTRF IC50 uM | TAF1-BD1 HTRF IC50 uM |
|---------|-----------|----------------------|----------------------|
| 55 | 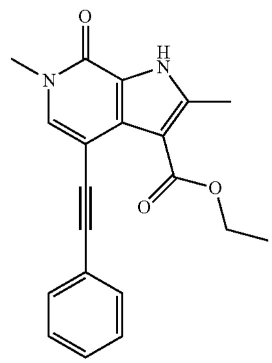 [SMILES: CCOC(=O)c1c(C)[nH]c2c(=O)n(C)cc(C#Cc3ccccc3)c12] | 0.074 | 0.457 |
| 56 | 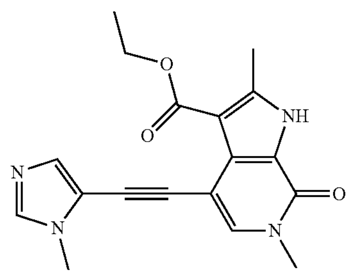 [SMILES: CCOC(=O)c1c(C)[nH]c2c(=O)n(C)cc(C#Cc3cncn3C)c12] | 0.129 | 0.337 |
| 57 | 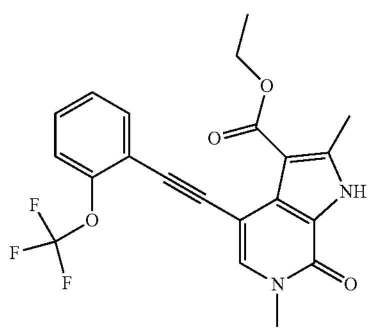 [SMILES: CCOC(=O)c1c(C)[nH]c2c(=O)n(C)cc(C#Cc3ccccc3OC(F)(F)F)c12] | 0.0596 | >20 |
| 58 | 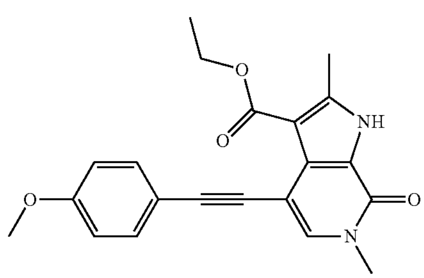 [SMILES: CCOC(=O)c1c(C)[nH]c2c(=O)n(C)cc(C#Cc3ccc(OC)cc3)c12] | 0.0384 | 0.315 |
| 59 | 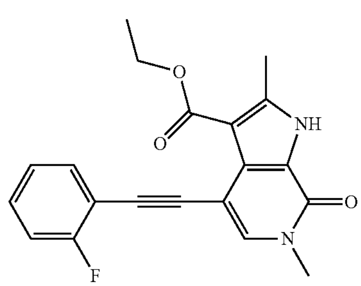 [SMILES: CCOC(=O)c1c(C)[nH]c2c(=O)n(C)cc(C#Cc3ccccc3F)c12] | 0.0562 | >2.22 |

-continued

| Example | Structure | TAF1-BD2 HTRF IC50 uM | TAF1-BD1 HTRF IC50 uM |
|---------|-----------|----------------------|----------------------|
| 60 | 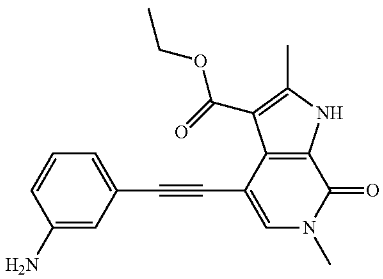 [SMILES: CCOC(=O)c1c(C)[nH]c2c(=O)n(C)cc(C#Cc3cccc(N)c3)c12] | 0.0381 | 0.12 |
| 61 | 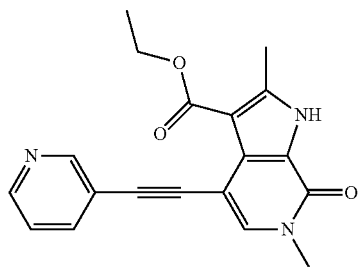 [SMILES: CCOC(=O)c1c(C)[nH]c2c(=O)n(C)cc(C#Cc3cccnc3)c12] | 0.0477 | 0.292 |
| 62 | 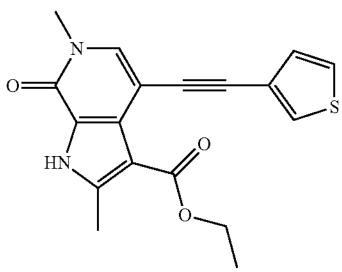 [SMILES: CCOC(=O)c1c(C)[nH]c2c(=O)n(C)cc(C#Cc3ccsc3)c12] | 0.0579 | 0.402 |
| 63 | 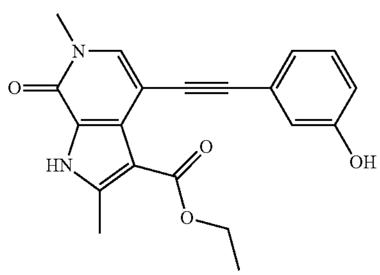 [SMILES: CCOC(=O)c1c(C)[nH]c2c(=O)n(C)cc(C#Cc3cccc(O)c3)c12] | 0.0385 | 0.195 |
| 64 | 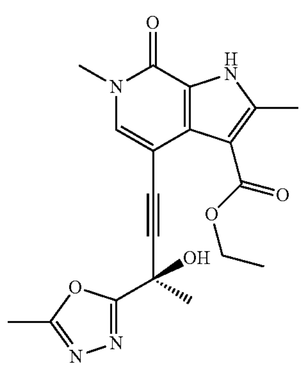 | 0.16 | 0.502 |

-continued
| Example | Structure | TAF1-BD2 HTRF IC50 uM | TAF1-BD1 HTRF IC50 uM |
|---|---|---|---|
| 65 | 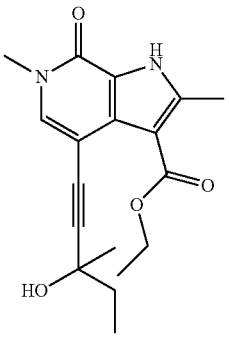 | 0.135 | 0.826 |
| 66 | 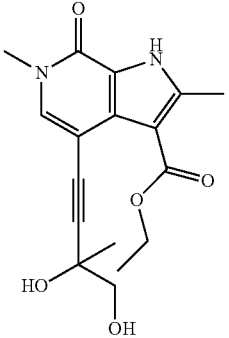 | 0.1 | 0.798 |
| 67 | 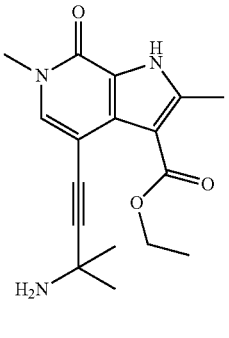 | 4.11 | 5.21 |
| 68 | 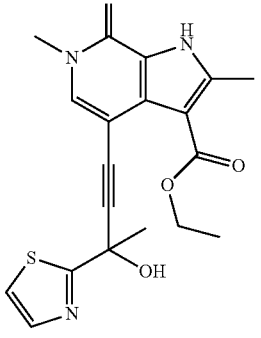 | 0.122 | 0.521 |

-continued

| Example | Structure | TAF1-BD2 HTRF IC50 uM | TAF1-BD1 HTRF IC50 uM |
|---------|-----------|----------------------|----------------------|
| 69 | 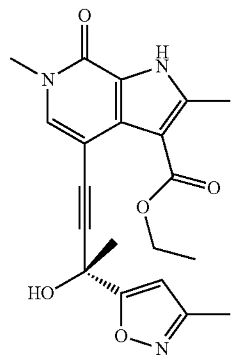 | 0.061 | 0.21 |
| 70 | 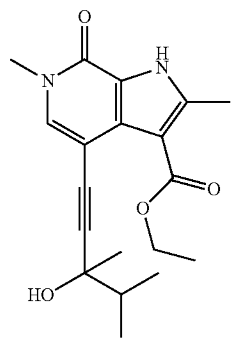 | 0.0823 | 0.515 |
| 71 | 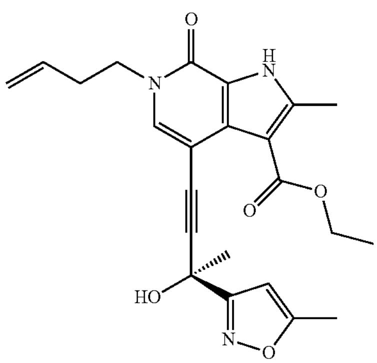 [SMILES: C=CCCn1cc(C#C[C@](C)(O)c2cc(C)on2)c2c(C(=O)OCC)c(C)[nH]c2c1=O] | 0.19 | 2.51 |
| 72 | 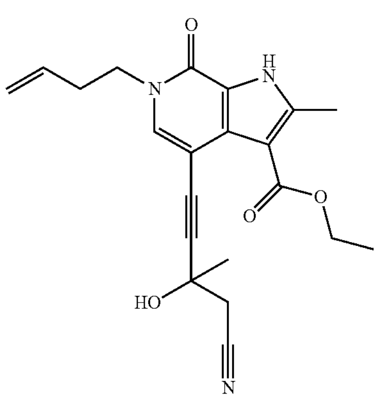 [SMILES: C=CCCn1cc(C#CC(C)(O)CC#N)c2c(C(=O)OCC)c(C)[nH]c2c1=O] | 0.181 | >20 |

-continued
| Example | Structure | TAF1-BD2 HTRF IC50 uM | TAF1-BD1 HTRF IC50 uM |
|---|---|---|---|
| 73 | 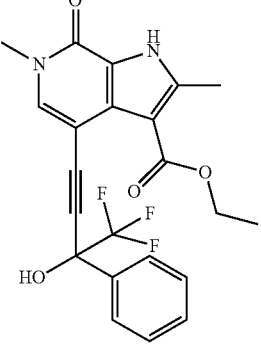 | 0.0695 | 0.287 |
| 74 | 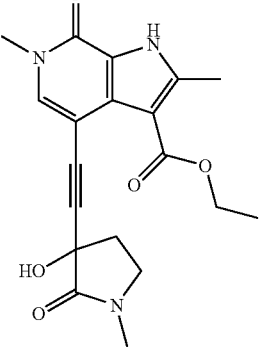 | 0.209 | 2.04 |
| 75 | 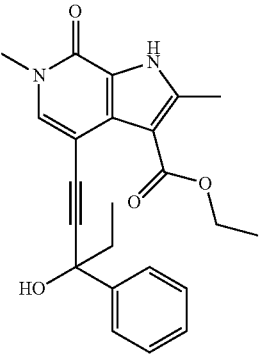 [SMILES: CCOC(=O)c1c(C)[nH]c2c(=O)n(C)cc(C#CC(O)(CC)c3ccccc3)c12] | 0.0765 | 0.427 |
| 76 | 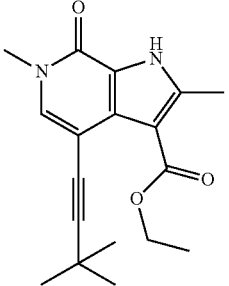 | 0.777 | 0.561 |

-continued

| Example | Structure | TAF1-BD2 HTRF IC50 uM | TAF1-BD1 HTRF IC50 uM |
|---------|-----------|----------------------|----------------------|
| 77 | 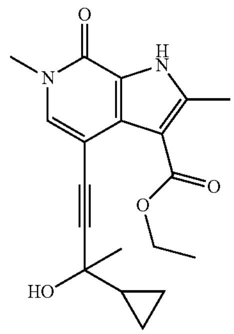 | 0.049 | 0.243 |
| 78 | 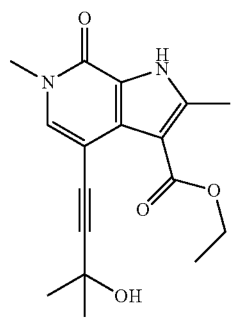 | 0.0385 | 0.616 |
| 79 | 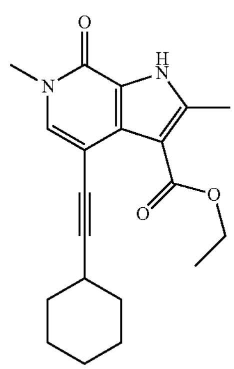 | 0.584 | 1.33 |
| 80 | 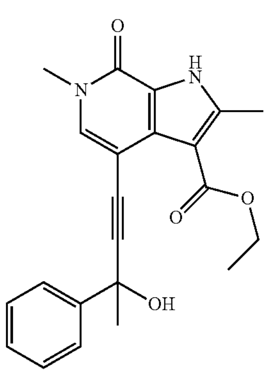 [SMILES: CCOC(=O)c1c(C)[nH]c2c(=O)n(C)cc(C#CC(C)(O)c3ccccc3)c12] | 0.0226 | 0.243 |

-continued

| Example | Structure | TAF1-BD2 HTRF IC50 uM | TAF1-BD1 HTRF IC50 uM |
|---------|-----------|----------------------|----------------------|
| 81 | 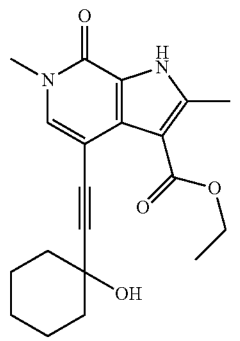 | 0.0632 | 0.257 |
| 82 | 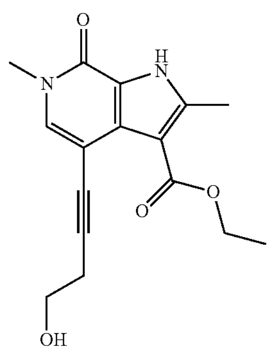 [SMILES: CCOC(=O)c1c(C)[nH]c2c(=O)n(C)cc(C#CCCO)c12] | 0.337 | 1.75 |
| 83 | 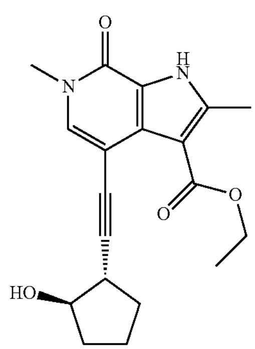 [SMILES: CCOC(=O)c1c(C)[nH]c2c(=O)n(C)cc(C#C[C@@H]3CCC[C@H]3O)c12] | 0.302 | 2.59 |
| 84 | 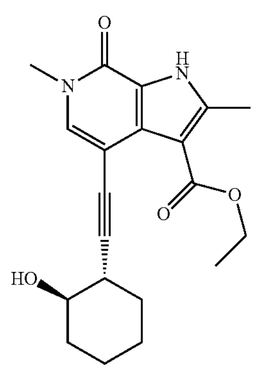 | 0.187 | 2 |

-continued

| Example | Structure | TAF1-BD2 HTRF IC50 uM | TAF1-BD1 HTRF IC50 uM |
|---|---|---|---|
| 85 | 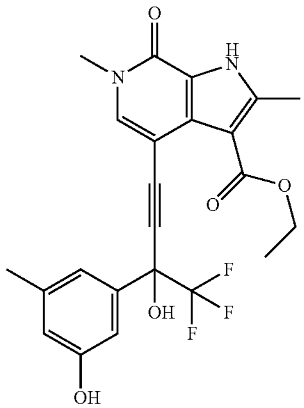 | 0.0637 | 0.395 |
| 86 | 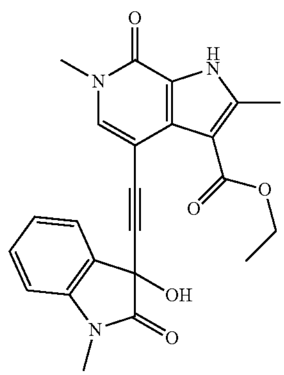 [SMILES: CCOC(=O)c1c(C)[nH]c2c(=O)n(C)cc(C#CC3(O)C(=O)N(C)c4ccccc43)c12] | 0.0981 | 0.581 |
| 87 | 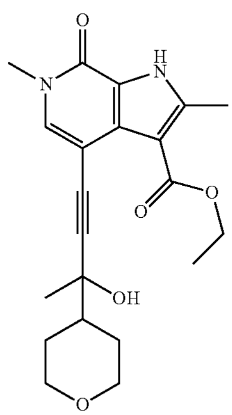 | 0.181 | 0.77 |
| 88 | 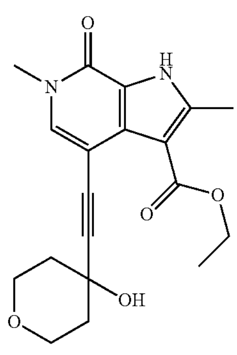 | 0.0986 | 1.11 |

-continued

| Example | Structure | TAF1-BD2 HTRF IC50 uM | TAF1-BD1 HTRF IC50 uM |
|---------|-----------|----------------------|----------------------|
| 89 | 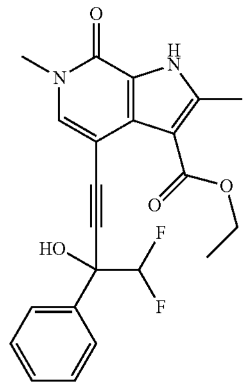 [SMILES: CCOC(=O)c1c(C)[nH]c2c(=O)n(C)cc(C#CC(O)(c3ccccc3)C(F)F)c12] | 0.0329 | 0.278 |
| 90 | 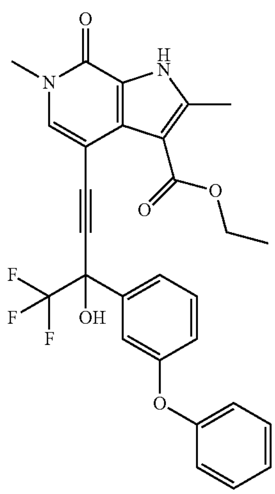 [SMILES: CCOC(=O)c1c(C)[nH]c2c(=O)n(C)cc(C#CC(O)(c3cccc(Oc4ccccc4)c3)C(F)(F)F)c12] | 0.699 | 2.28 |
| 91a | 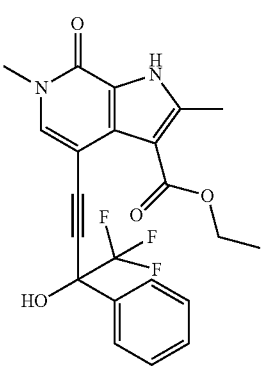 [SMILES: CCOC(=O)c1c(C)[nH]c2c(=O)n(C)cc(C#CC(O)(c3ccccc3)C(F)(F)F)c12] | 0.206 | 0.749 |

-continued

| Example | Structure | TAF1-BD2 HTRF IC50 uM | TAF1-BD1 HTRF IC50 uM |
|---------|-----------|----------------------|----------------------|
| 91b | 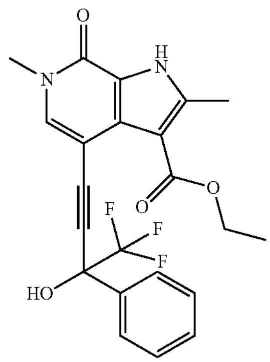 [SMILES: CCOC(=O)c1c(C)[nH]c2c(=O)n(C)cc(C#CC(O)(c3ccccc3)C(F)(F)F)c12] | 0.0422 | 0.184 |
| 92a | 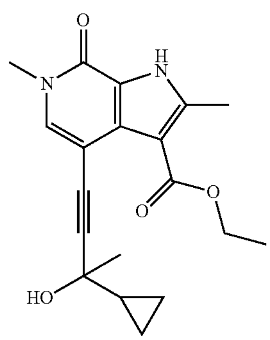 [SMILES: CCOC(=O)c1c(C)[nH]c2c(=O)n(C)cc(C#CC(C)(O)C3CC3)c12] | 0.0332 | 0.154 |
| 92b | 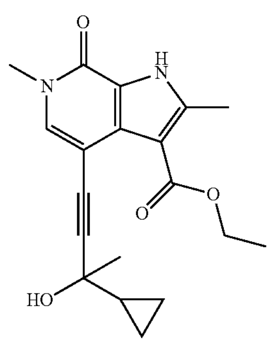 [SMILES: CCOC(=O)c1c(C)[nH]c2c(=O)n(C)cc(C#CC(C)(O)C3CC3)c12] | 0.23 | 1.09 |
| 93a | 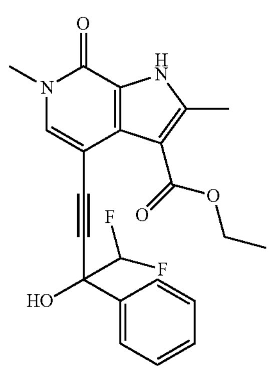 [SMILES: CCOC(=O)c1c(C)[nH]c2c(=O)n(C)cc(C#CC(O)(c3ccccc3)C(F)F)c12] | 0.0655 | 0.599 |

-continued
| Example | Structure | TAF1-BD2 HTRF IC50 uM | TAF1-BD1 HTRF IC50 uM |
|---|---|---|---|
| 93b | 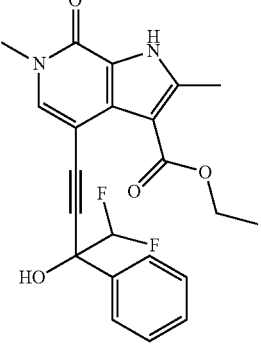 | 0.0214 | 0.176 |
| 94a | 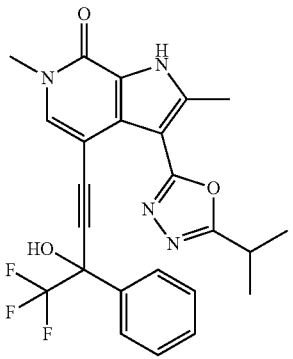 [SMILES: Cc1[nH]c2c(=O)n(C)cc(C#CC(O)(c3ccccc3)C(F)(F)F)c2c1-c1nnc(C(C)C)o1] | 0.0276 | 0.192 |
| 94b | 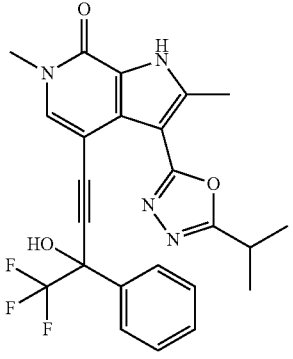 [SMILES: Cc1[nH]c2c(=O)n(C)cc(C#CC(O)(c3ccccc3)C(F)(F)F)c2c1-c1nnc(C(C)C)o1] | 0.126 | 0.949 |
| 95a | 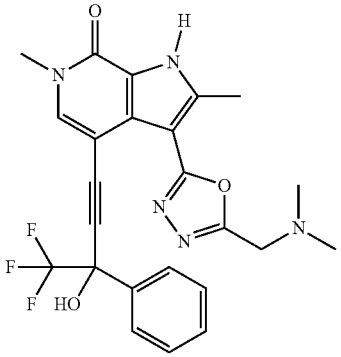 [SMILES: Cc1[nH]c2c(=O)n(C)cc(C#CC(O)(c3ccccc3)C(F)(F)F)c2c1-c1nnc(CN(C)C)o1] | 0.143 | 0.92 |

-continued

| Example | Structure | TAF1-BD2 HTRF IC50 uM | TAF1-BD1 HTRF IC50 uM |
|---------|-----------|----------------------|----------------------|
| 95b | 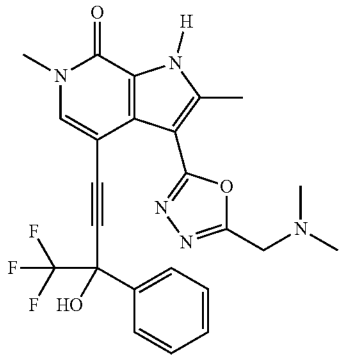 [SMILES: Cc1[nH]c2c(=O)n(C)cc(C#CC(O)(c3ccccc3)C(F)(F)F)c2c1-c1nnc(CN(C)C)o1] | 0.0398 | 0.211 |
| 96a | 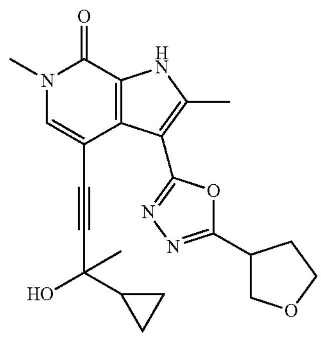 [SMILES: Cc1[nH]c2c(=O)n(C)cc(C#CC(C)(O)C3CC3)c2c1-c1nnc(C2CCOC2)o1] | 0.0407 | 0.182 |
| 96b | 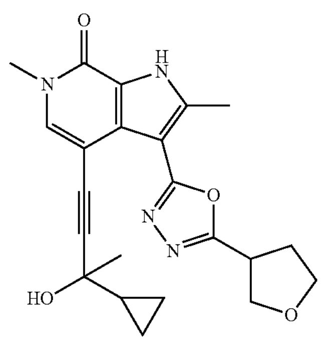 [SMILES: Cc1[nH]c2c(=O)n(C)cc(C#CC(C)(O)C3CC3)c2c1-c1nnc(C2CCOC2)o1] | 0.26 | 1.14 |
| 97a | 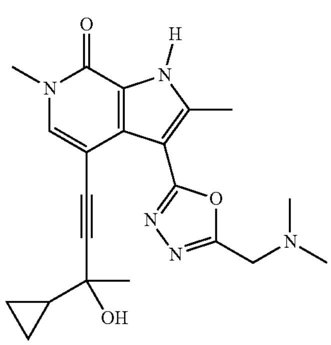 | 0.385 | 1.24 |

-continued

| Example | Structure | TAF1-BD2 HTRF IC50 uM | TAF1-BD1 HTRF IC50 uM |
|---|---|---|---|
| 97b | 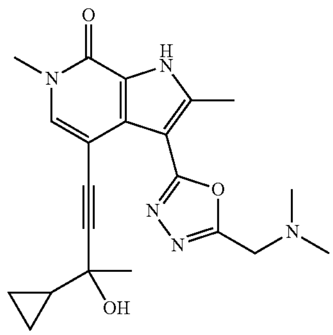 [SMILES: Cc1[nH]c2c(=O)n(C)cc(C#CC(C)(O)C3CC3)c2c1-c1nnc(CN(C)C)o1] | 0.0308 | 0.205 |
| 98a | 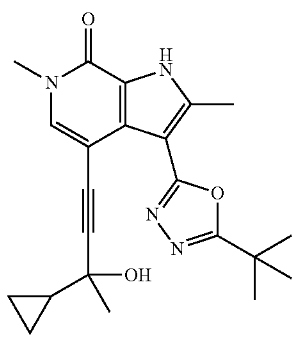 [SMILES: Cc1[nH]c2c(=O)n(C)cc(C#CC(C)(O)C3CC3)c2c1-c1nnc(C(C)(C)C)o1] | 0.227 | 0.728 |
| 98b | 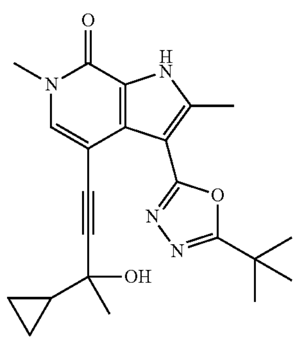 [SMILES: Cc1[nH]c2c(=O)n(C)cc(C#CC(C)(O)C3CC3)c2c1-c1nnc(C(C)(C)C)o1] | 0.0339 | 0.108 |
| 99a | 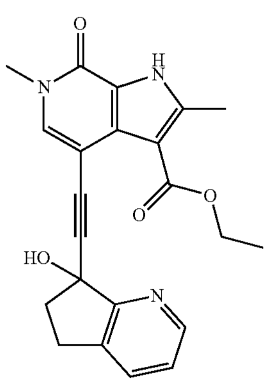 [SMILES: CCOC(=O)c1c(C)[nH]c2c(=O)n(C)cc(C#CC3(O)CCc4cccnc43)c12] | 1.18 | 2.93 |

-continued

| Example | Structure | TAF1-BD2 HTRF IC50 uM | TAF1-BD1 HTRF IC50 uM |
|---|---|---|---|
| 99b | 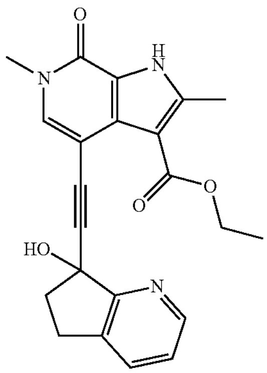 [SMILES: CCOC(=O)c1c(C)[nH]c2c(=O)n(C)cc(C#CC3(O)CCc4cccnc43)c12] | 0.0844 | 0.881 |
| 100 | 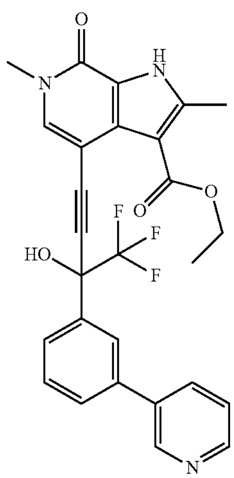 [SMILES: CCOC(=O)c1c(C)[nH]c2c(=O)n(C)cc(C#CC(O)(c3cccc(-c4cccnc4)c3)C(F)(F)F)c12] | 0.0273 | 0.189 |
| 101 | 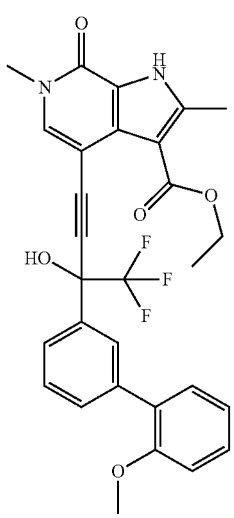 [SMILES: CCOC(=O)c1c(C)[nH]c2c(=O)n(C)cc(C#CC(O)(c3cccc(-c4ccccc4OC)c3)C(F)(F)F)c12] | 0.608 | 4.33 |

-continued
| Example | Structure | TAF1-BD2 HTRF IC50 uM | TAF1-BD1 HTRF IC50 uM |
|---|---|---|---|
| 102 | 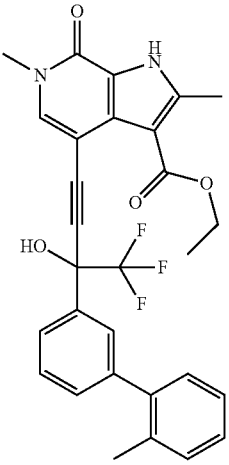 [SMILES: CCOC(=O)c1c(C)[nH]c2c(=O)n(C)cc(C#CC(O)(c3cccc(-c4ccccc4C)c3)C(F)(F)F)c12] | 0.912 | 7.51 |
| 103 | 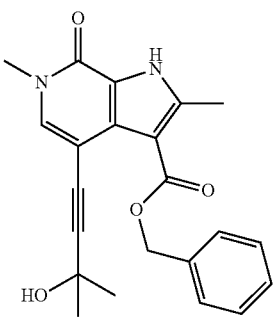 [SMILES: Cc1[nH]c2c(=O)n(C)cc(C#CC(C)(C)O)c2c1C(=O)OCc1ccccc1] | 0.0345 | 0.151 |
| 104 | 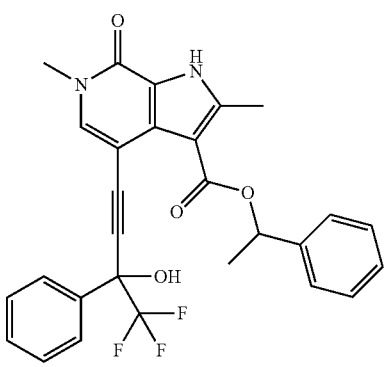 [SMILES: Cc1[nH]c2c(=O)n(C)cc(C#CC(O)(c3ccccc3)C(F)(F)F)c2c1C(=O)OC(C)c1ccccc1] | 1.2 | 3.21 |
| 105 | 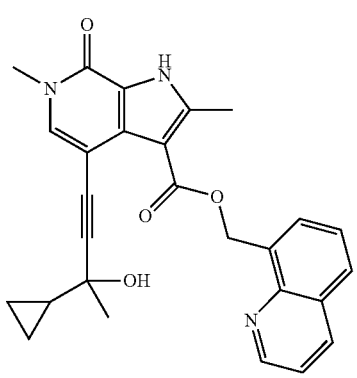 [SMILES: Cc1[nH]c2c(=O)n(C)cc(C#CC(C)(O)C3CC3)c2c1C(=O)OCc1cccc2cccnc12] | 0.0346 | 0.0939 |

-continued

| Example | Structure | TAF1-BD2 HTRF IC50 uM | TAF1-BD1 HTRF IC50 uM |
|---|---|---|---|
| 106 | 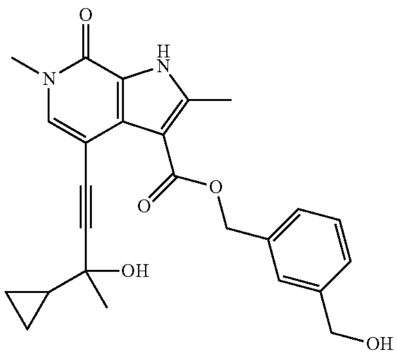 [SMILES: Cc1[nH]c2c(=O)n(C)cc(C#CC(C)(O)C3CC3)c2c1C(=O)OCc1cccc(CO)c1] | 0.0372 | 0.166 |
| 107 | 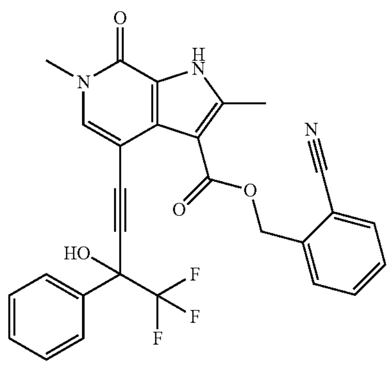 [SMILES: Cc1[nH]c2c(=O)n(C)cc(C#CC(O)(c3ccccc3)C(F)(F)F)c2c1C(=O)OCc1ccccc1C#N] | 0.344 | 1.63 |
| 108 | 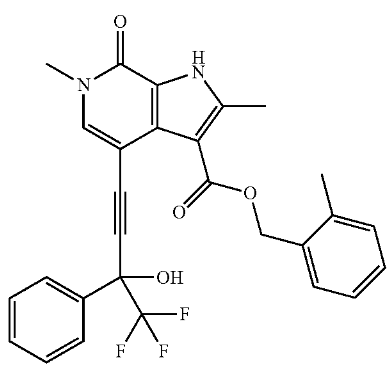 [SMILES: Cc1ccccc1COC(=O)c1c(C)[nH]c2c(=O)n(C)cc(C#CC(O)(c3ccccc3)C(F)(F)F)c12] | 1.26 | 3.35 |
| 109 | 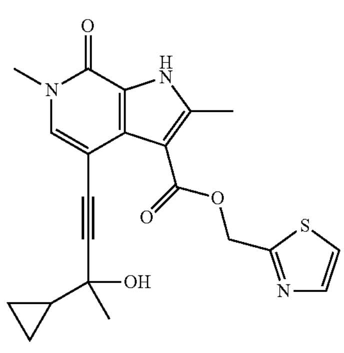 [SMILES: Cc1[nH]c2c(=O)n(C)cc(C#CC(C)(O)C3CC3)c2c1C(=O)OCc1nccs1] | 0.0679 | 0.222 |

-continued

| Example | Structure | TAF1-BD2 HTRF IC50 uM | TAF1-BD1 HTRF IC50 uM |
|---|---|---|---|
| 110 | 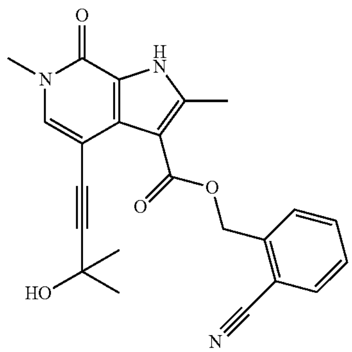 [SMILES: Cc1[nH]c2c(=O)n(C)cc(C#CC(C)(C)O)c2c1C(=O)OCc1ccccc1C#N] | 0.0294 | 0.116 |
| 111 | 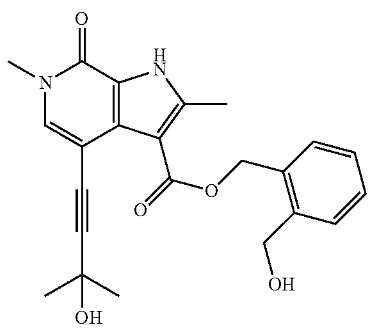 [SMILES: Cc1[nH]c2c(=O)n(C)cc(C#CC(C)(C)O)c2c1C(=O)OCc1ccccc1CO] | 0.0379 | 0.259 |
| 112 | 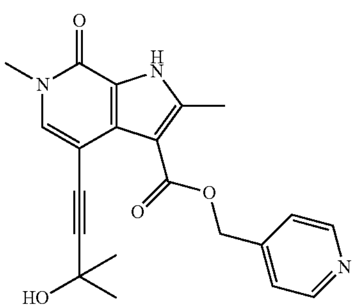 [SMILES: Cc1[nH]c2c(=O)n(C)cc(C#CC(C)(C)O)c2c1C(=O)OCc1ccncc1] | 0.61 | 4.62 |
| 113 | 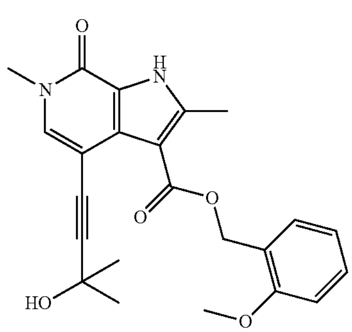 [SMILES: COc1ccccc1COC(=O)c1c(C)[nH]c2c(=O)n(C)cc(C#CC(C)(C)O)c12] | 0.024 | 0.123 |

-continued

| Example | Structure | TAF1-BD2 HTRF IC50 uM | TAF1-BD1 HTRF IC50 uM |
|---|---|---|---|
| 114 | 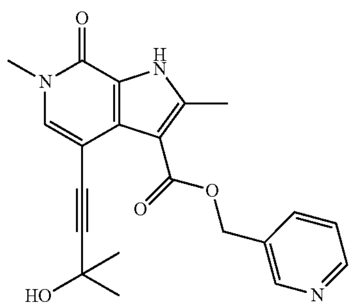 [SMILES: Cc1[nH]c2c(=O)n(C)cc(C#CC(C)(C)O)c2c1C(=O)OCc1cccnc1] | 0.0483 | 0.304 |
| 115 | 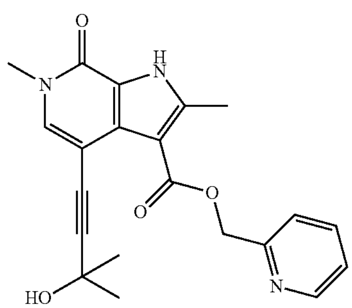 [SMILES: Cc1[nH]c2c(=O)n(C)cc(C#CC(C)(C)O)c2c1C(=O)OCc1ccccn1] | 0.0341 | 0.282 |
| 116 | 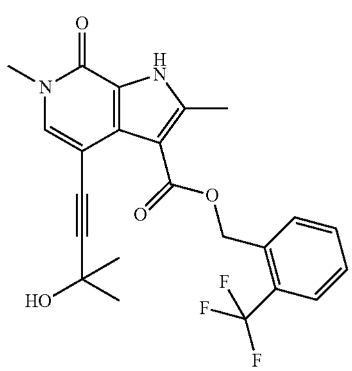 [SMILES: Cc1[nH]c2c(=O)n(C)cc(C#CC(C)(C)O)c2c1C(=O)OCc1ccccc1C(F)(F)F] | 0.0277 | 0.105 |
| 117 | 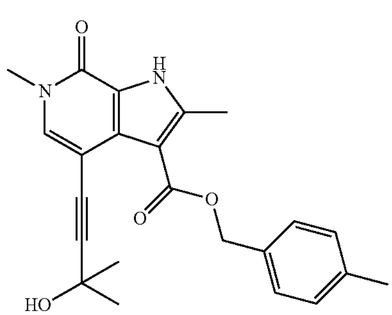 | 0.0397 | 0.128 |

-continued

| Example | Structure | TAF1-BD2 HTRF IC50 uM | TAF1-BD1 HTRF IC50 uM |
|---------|-----------|----------------------|----------------------|
| 118 | 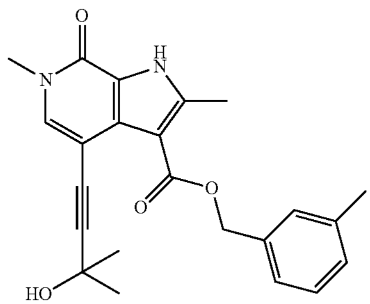 | 0.0389 | 0.167 |
| 119 | 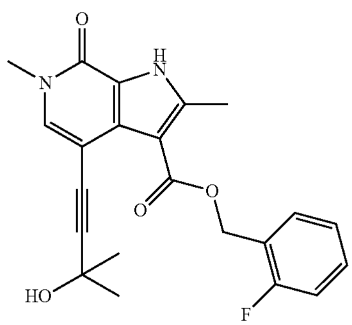 [SMILES: Cc1[nH]c2c(=O)n(C)cc(C#CC(C)(C)O)c2c1C(=O)OCc1ccccc1F] | 0.0267 | 0.145 |
| 120 | 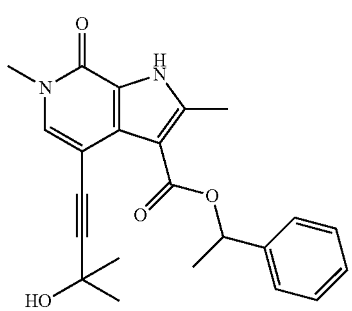 [SMILES: Cc1[nH]c2c(=O)n(C)cc(C#CC(C)(C)O)c2c1C(=O)OC(C)c1ccccc1] | 0.0832 | 0.26 |
| 121 | 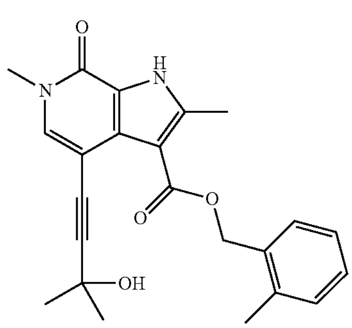 [SMILES: Cc1ccccc1COC(=O)c1c(C)[nH]c2c(=O)n(C)cc(C#CC(C)(C)O)c12] | 0.0215 | 0.085 |

-continued

| Example | Structure | TAF1-BD2 HTRF IC50 uM | TAF1-BD1 HTRF IC50 uM |
|---|---|---|---|
| 122 | 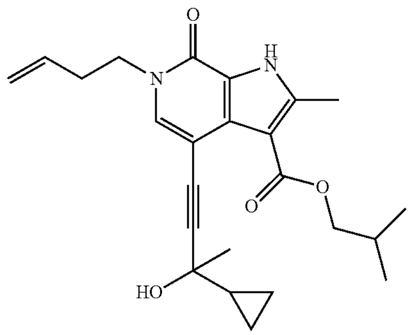 [SMILES: C=CCCn1cc(C#CC(C)(O)C2CC2)c2c(C(=O)OCC(C)C)c(C)[nH]c2c1=O] | 0.116 | 1.71 |
| 123 | 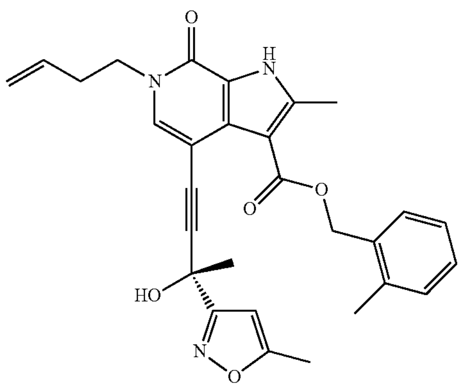 [SMILES: C=CCCn1cc(C#C[C@@](C)(O)c2cc(C)on2)c2c(C(=O)OCc3ccccc3C)c(C)[nH]c2c1=O] | 0.243 | >20 |
| 124 | 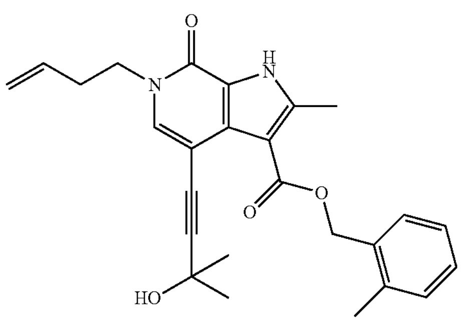 [SMILES: C=CCCn1cc(C#CC(C)(C)O)c2c(C(=O)OCc3ccccc3C)c(C)[nH]c2c1=O] | 0.0597 | >20 |
| 125 | 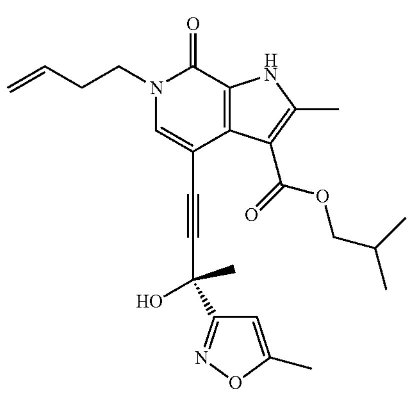 [SMILES: C=CCCn1cc(C#C[C@@](C)(O)c2cc(C)on2)c2c(C(=O)OCC(C)C)c(C)[nH]c2c1=O] | 0.169 | 3.05 |

-continued

| Example | Structure | TAF1-BD2 HTRF IC50 uM | TAF1-BD1 HTRF IC50 uM |
|---|---|---|---|
| 126 | 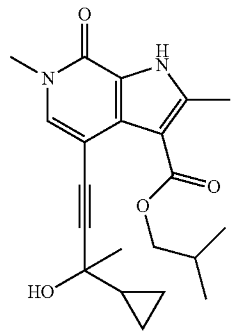 | 0.0401 | 0.123 |
| 127 | 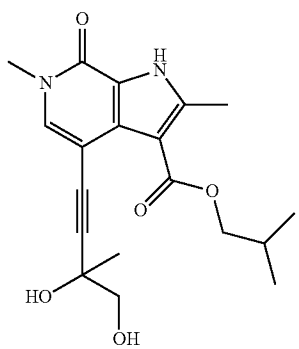 [SMILES: Cc1[nH]c2c(=O)n(C)cc(C#CC(C)(O)CO)c2c1C(=O)OCC(C)C] | 0.0684 | 0.727 |
| 128 | 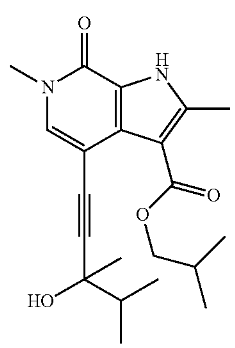 | 0.062 | 0.253 |
| 129 | 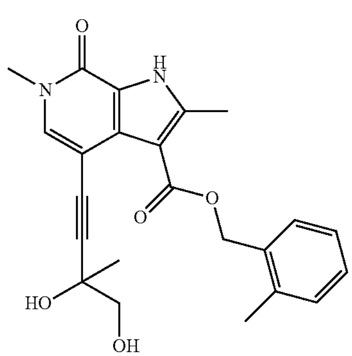 [SMILES: Cc1ccccc1COC(=O)c1c(C)[nH]c2c(=O)n(C)cc(C#CC(C)(O)CO)c12] | 0.0413 | 0.274 |

-continued
| Example | Structure | TAF1-BD2 HTRF IC50 uM | TAF1-BD1 HTRF IC50 uM |
|---|---|---|---|
| 130 | 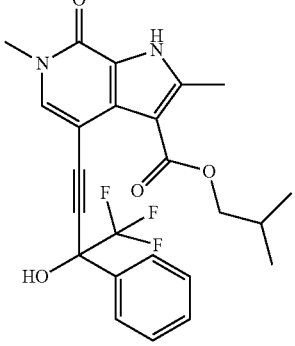 | 0.28 | 1.54 |
| 131 | 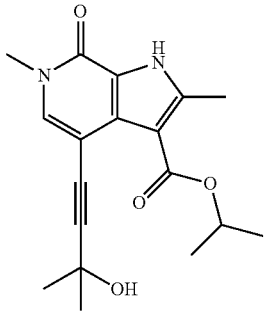 | 0.0483 | 0.36 |
| 132 | 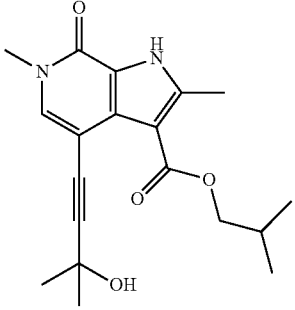 [SMILES: Cc1[nH]c2c(=O)n(C)cc(C#CC(C)(C)O)c2c1C(=O)OCC(C)C] | 0.0299 | 0.173 |
| 133 | 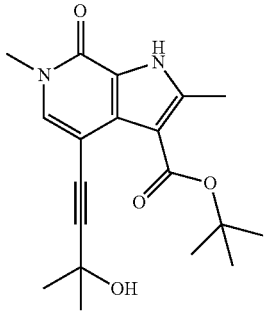 [SMILES: Cc1[nH]c2c(=O)n(C)cc(C#CC(C)(C)O)c2c1C(=O)OC(C)(C)C] | 0.0311 | 0.308 |

-continued

| Example | Structure | TAF1-BD2 HTRF IC50 uM | TAF1-BD1 HTRF IC50 uM |
|---|---|---|---|
| 134 | 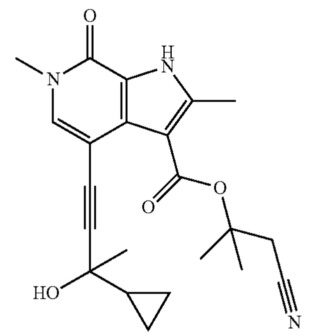 [SMILES: Cc1[nH]c2c(=O)n(C)cc(C#CC(C)(O)C3CC3)c2c1C(=O)OC(C)(C)CC#N] | 0.0268 | 0.222 |
| 135 | 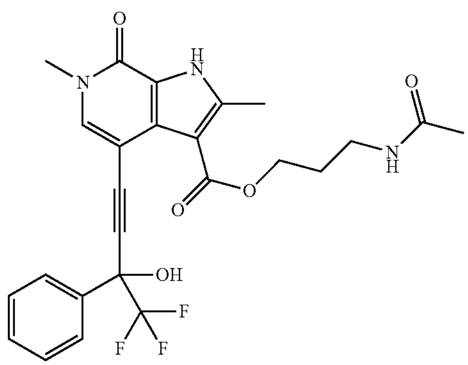 [SMILES: CC(=O)NCCCOC(=O)c1c(C)[nH]c2c(=O)n(C)cc(C#CC(O)(c3ccccc3)C(F)(F)F)c12] | 0.0408 | 0.295 |
| 136 | 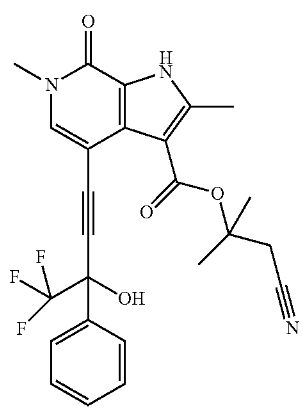 [SMILES: Cc1[nH]c2c(=O)n(C)cc(C#CC(O)(c3ccccc3)C(F)(F)F)c2c1C(=O)OC(C)(C)CC#N] | 0.0365 | 0.267 |
| 137 | 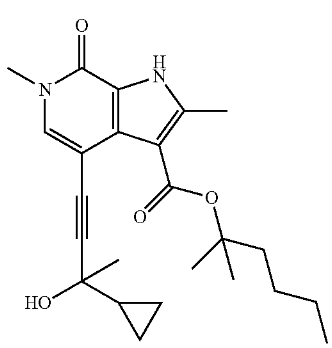 [SMILES: CCCCC(C)(C)OC(=O)c1c(C)[nH]c2c(=O)n(C)cc(C#CC(C)(O)C3CC3)c12] | 0.079 | 0.481 |

-continued

| Example | Structure | TAF1-BD2 HTRF IC50 uM | TAF1-BD1 HTRF IC50 uM |
|---|---|---|---|
| 138 | 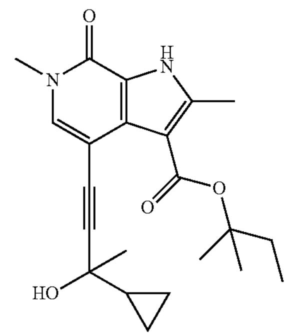 [SMILES: CCC(C)(C)OC(=O)c1c(C)[nH]c2c(=O)n(C)cc(C#CC(C)(O)C3CC3)c12] | 0.0479 | 0.251 |
| 139 | 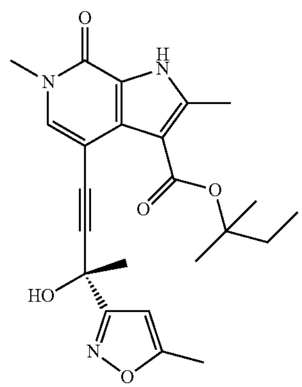 [SMILES: CCC(C)(C)OC(=O)c1c(C)[nH]c2c(=O)n(C)cc(C#C[C@@](C)(O)c3cc(C)on3)c12] | 0.0477 | 0.232 |
| 140 | 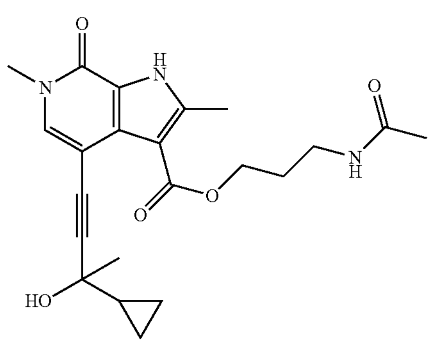 [SMILES: CC(=O)NCCCOC(=O)c1c(C)[nH]c2c(=O)n(C)cc(C#CC(C)(O)C3CC3)c12] | 0.0375 | 0.35 |
| 141 | 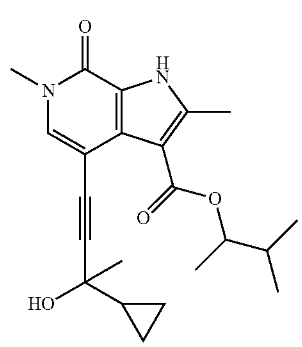 [SMILES: Cc1[nH]c2c(=O)n(C)cc(C#CC(C)(O)C3CC3)c2c1C(=O)OC(C)C(C)C] | 0.0756 | 0.244 |

-continued

| Example | Structure | TAF1-BD2 HTRF IC50 uM | TAF1-BD1 HTRF IC50 uM |
|---------|-----------|------------------------|------------------------|
| 142 | 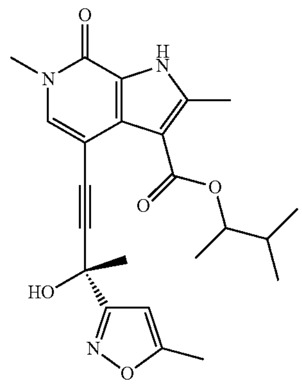 [SMILES: Cc1cc([C@](C)(O)C#Cc2cn(C)c(=O)c3[nH]c(C)c(C(=O)OC(C)C(C)C)c23)no1] | 0.0528 | 0.16 |
| 143 | 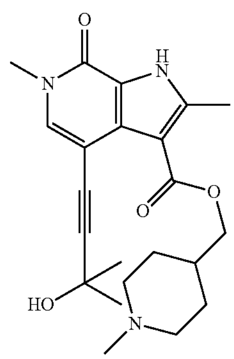 | 0.0748 | 1.87 |
| 144 | 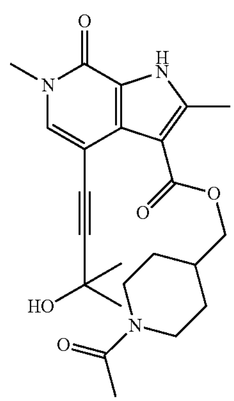 | 0.0201 | 0.267 |
| 145 | 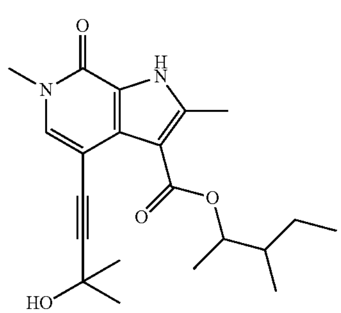 [SMILES: CCC(C)C(C)OC(=O)c1c(C)[nH]c2c(=O)n(C)cc(C#CC(C)(C)O)c12] | 0.0533 | 0.272 |

| Example | Structure | TAF1-BD2 HTRF IC50 uM | TAF1-BD1 HTRF IC50 uM |
|---|---|---|---|
| 146 | 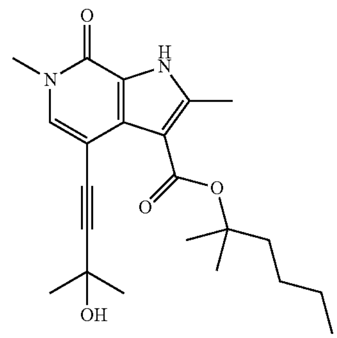 [SMILES: CCCCC(C)(C)OC(=O)c1c(C)[nH]c2c(=O)n(C)cc(C#CC(C)(C)O)c12] | 0.0432 | 0.288 |
| 147 | 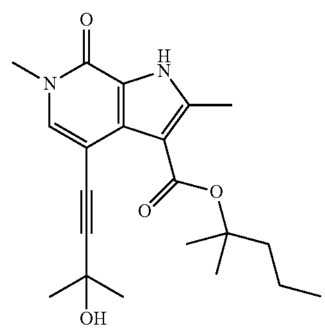 [SMILES: CCCC(C)(C)OC(=O)c1c(C)[nH]c2c(=O)n(C)cc(C#CC(C)(C)O)c12] | 0.0388 | 0.331 |
| 148 | 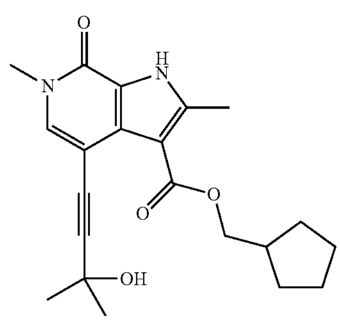 [SMILES: Cc1[nH]c2c(=O)n(C)cc(C#CC(C)(C)O)c2c1C(=O)OCC1CCCC1] | 0.0237 | 0.0968 |
| 149 | 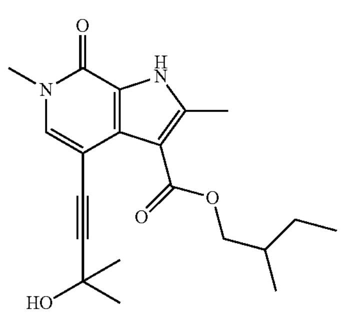 [SMILES: CCC(C)COC(=O)c1c(C)[nH]c2c(=O)n(C)cc(C#CC(C)(C)O)c12] | 0.0194 | 0.101 |

-continued

| Example | Structure | TAF1-BD2 HTRF IC50 uM | TAF1-BD1 HTRF IC50 uM |
|---------|-----------|----------------------|----------------------|
| 150 | 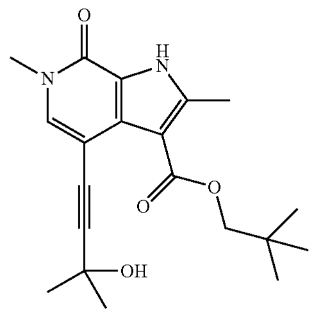 [SMILES: Cc1[nH]c2c(=O)n(C)cc(C#CC(C)(C)O)c2c1C(=O)OCC(C)(C)C] | 0.0304 | 0.0936 |
| 151 | 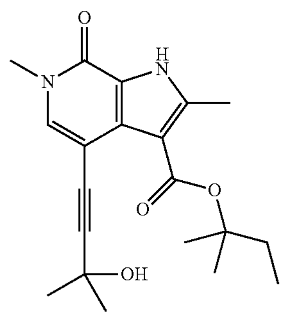 [SMILES: CCC(C)(C)OC(=O)c1c(C)[nH]c2c(=O)n(C)cc(C#CC(C)(C)O)c12] | 0.0351 | 0.221 |
| 152 | 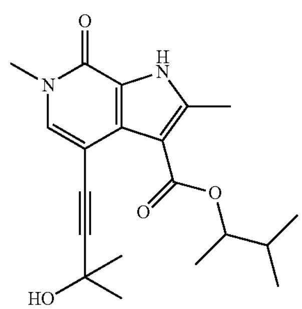 [SMILES: Cc1[nH]c2c(=O)n(C)cc(C#CC(C)(C)O)c2c1C(=O)OC(C)C(C)C] | 0.0536 | 0.235 |
| 153 | 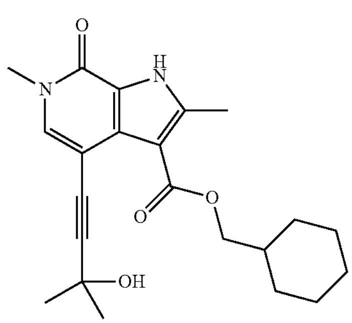 [SMILES: Cc1[nH]c2c(=O)n(C)cc(C#CC(C)(C)O)c2c1C(=O)OCC1CCCCC1] | 0.0226 | 0.0853 |

-continued
| Example | Structure | TAF1-BD2 HTRF IC50 uM | TAF1-BD1 HTRF IC50 uM |
|---|---|---|---|
| 154 | 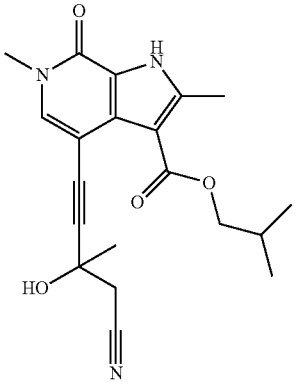 [SMILES: Cc1[nH]c2c(=O)n(C)cc(C#CC(C)(O)CC#N)c2c1C(=O)OCC(C)C] | 0.0998 | 0.15 |
| 155 | 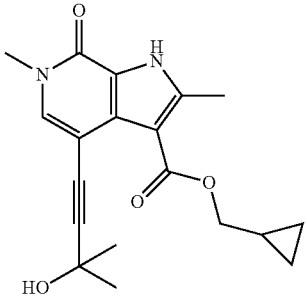 [SMILES: Cc1[nH]c2c(=O)n(C)cc(C#CC(C)(C)O)c2c1C(=O)OCC1CC1] | 0.0528 | 0.274 |
| 156 | 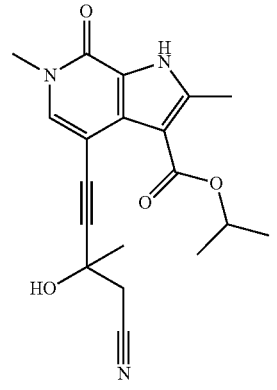 [SMILES: Cc1[nH]c2c(=O)n(C)cc(C#CC(C)(O)CC#N)c2c1C(=O)OC(C)C] | 0.106 | 0.276 |
| 157 | 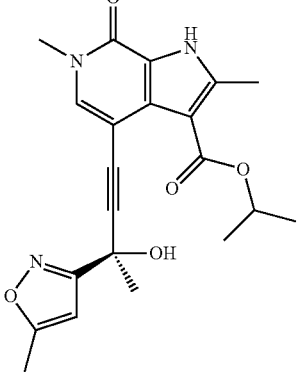 | 0.0712 | 0.233 |

-continued

| Example | Structure | TAF1-BD2 HTRF IC50 uM | TAF1-BD1 HTRF IC50 uM |
|---------|-----------|----------------------|----------------------|
| 158 | 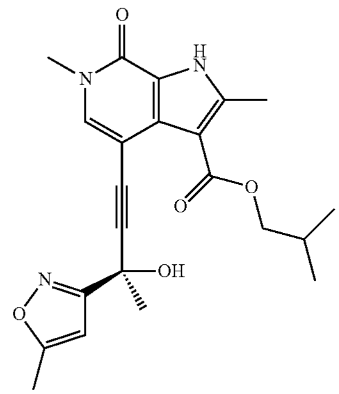 [SMILES: Cc1cc([C@](C)(O)C#Cc2cn(C)c(=O)c3[nH]c(C)c(C(=O)OCC(C)C)c23)no1] | 0.0502 | 0.112 |
| 159 | 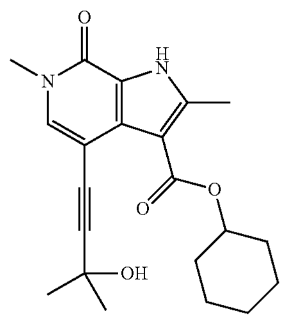 [SMILES: Cc1[nH]c2c(=O)n(C)cc(C#CC(C)(C)O)c2c1C(=O)OC1CCCCC1] | 0.0369 | 0.295 |
| 160 | 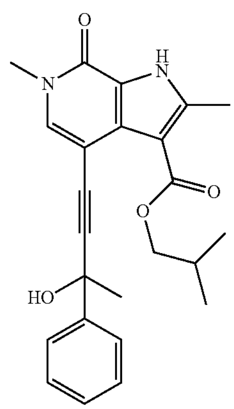 | 0.0324 | 0.13 |
| 161 | 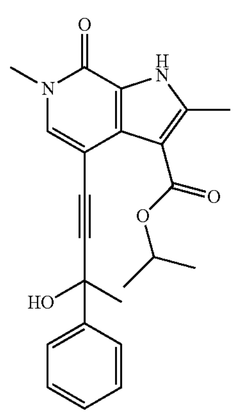 | 0.0511 | 0.274 |

-continued

| Example | Structure | TAF1-BD2 HTRF IC50 uM | TAF1-BD1 HTRF IC50 uM |
|---|---|---|---|
| 162 | 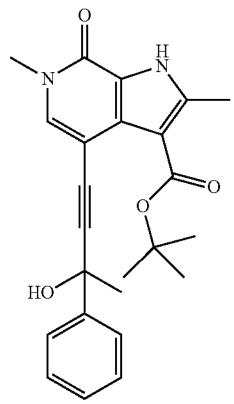 | 0.0544 | 0.318 |
| 163 | 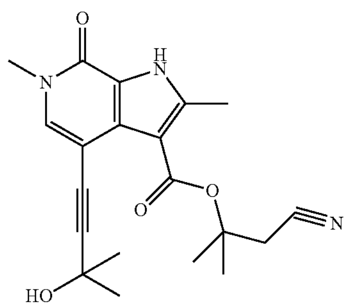 [SMILES: Cc1[nH]c2c(=O)n(C)cc(C#CC(C)(C)O)c2c1C(=O)OC(C)(C)CC#N] | 0.0273 | 0.283 |
| 164 | 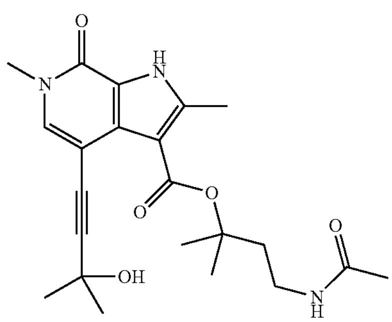 [SMILES: CC(=O)NCCC(C)(C)OC(=O)c1c(C)[nH]c2c(=O)n(C)cc(C#CC(C)(C)O)c12] | 0.0485 | 0.514 |
| 165 | 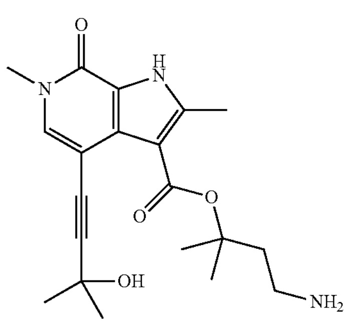 [SMILES: Cc1[nH]c2c(=O)n(C)cc(C#CC(C)(C)O)c2c1C(=O)OC(C)(C)CCN] | 0.0217 | 0.551 |

-continued

| Example | Structure | TAF1-BD2 HTRF IC50 uM | TAF1-BD1 HTRF IC50 uM |
|---|---|---|---|
| 166 | 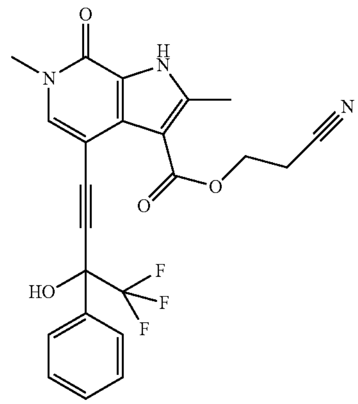 [SMILES: Cc1[nH]c2c(=O)n(C)cc(C#CC(O)(c3ccccc3)C(F)(F)F)c2c1C(=O)OCCC#N] | 0.0312 | 0.214 |
| 167 | 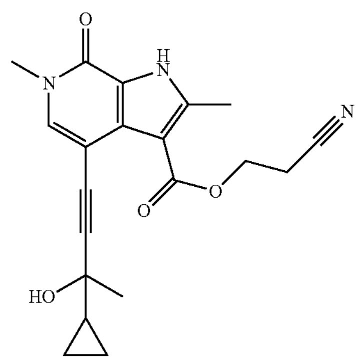 [SMILES: Cc1[nH]c2c(=O)n(C)cc(C#CC(C)(O)C3CC3)c2c1C(=O)OCCC#N] | 0.0468 | 0.282 |
| 168 | 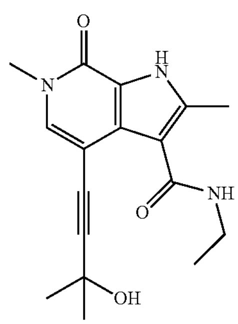 | 1.63 | 5.79 |
| 169 | 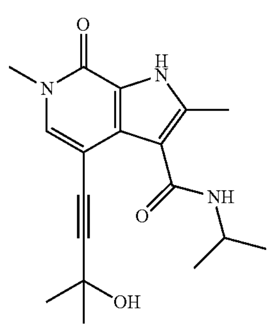 | 2.67 | 5.31 |

-continued

| Example | Structure | TAF1-BD2 HTRF IC50 uM | TAF1-BD1 HTRF IC50 uM |
|---------|-----------|----------------------|----------------------|
| 170 | 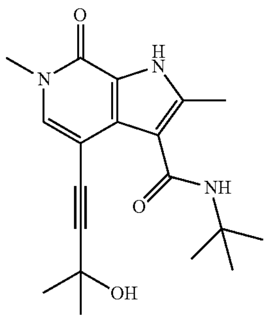 | 0.347 | 3.62 |
| 171 | 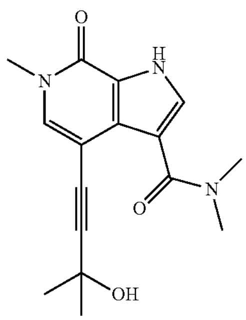 | 1.73 | 4.42 |
| 172 | 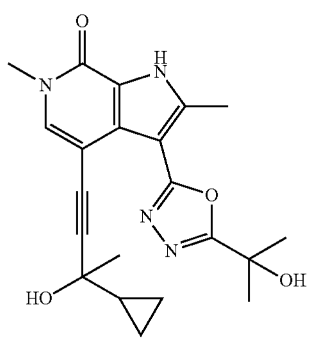 [SMILES: Cc1[nH]c2c(=O)n(C)cc(C#CC(C)(O)C3CC3)c2c1-c1nnc(C(C)(C)O)o1] | 0.11 | 0.451 |
| 173 | 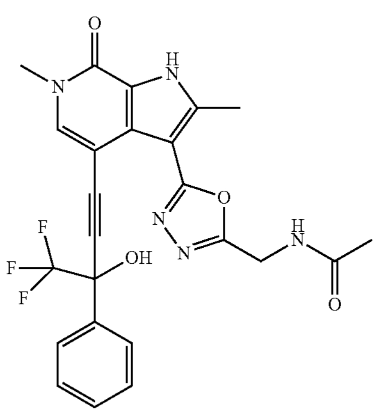 [SMILES: CC(=O)NCc1nnc(-c2c(C)[nH]c3c(=O)n(C)cc(C#CC(O)(c4ccccc4)C(F)(F)F)c23)o1] | 0.117 | 0.49 |

-continued

| Example | Structure | TAF1-BD2 HTRF IC50 uM | TAF1-BD1 HTRF IC50 uM |
|---------|-----------|----------------------|----------------------|
| 174 | 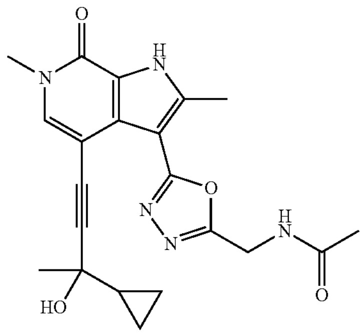 [SMILES: CC(=O)NCc1nnc(-c2c(C)[nH]c3c(=O)n(C)cc(C#CC(C)(O)C4CC4)c23)o1] | 0.0864 | 0.521 |
| 175 | 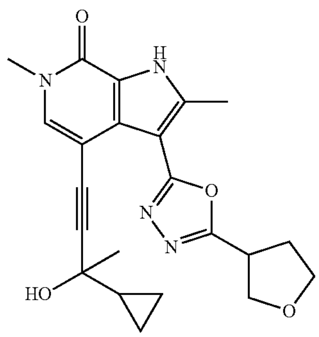 [SMILES: Cc1[nH]c2c(=O)n(C)cc(C#CC(C)(O)C3CC3)c2c1-c1nnc(C2CCOC2)o1] | 0.0467 | 0.248 |
| 176 | 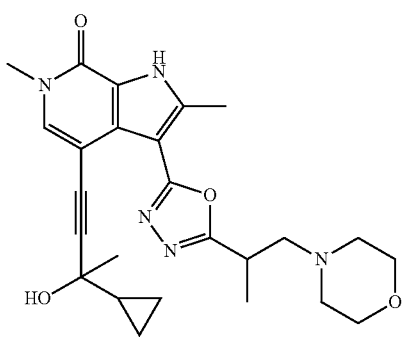 [SMILES: Cc1[nH]c2c(=O)n(C)cc(C#CC(C)(O)C3CC3)c2c1-c1nnc(C(C)CN2CCOCC2)o1] | 0.0383 | 0.241 |
| 177 | 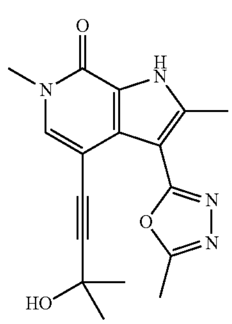 | 0.0507 | 0.543 |

-continued
| Example | Structure | TAF1-BD2 HTRF IC50 uM | TAF1-BD1 HTRF IC50 uM |
|---|---|---|---|
| 178 | 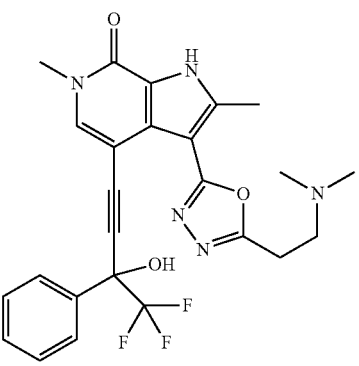 [SMILES: Cc1[nH]c2c(=O)n(C)cc(C#CC(O)(c3ccccc3)C(F)(F)F)c2c1-c1nnc(CCN(C)C)o1] | 0.0881 | 0.725 |
| 179 | 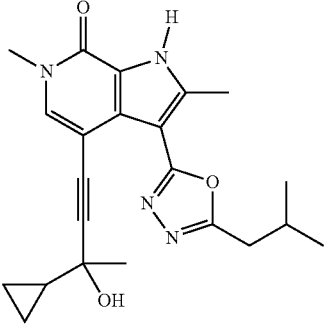 | 0.0292 | 0.137 |
| 180 | 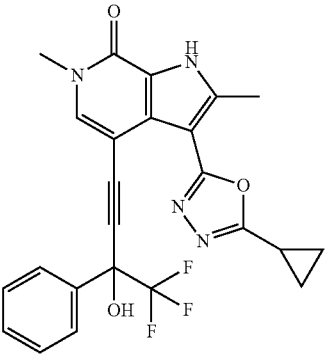 [SMILES: Cc1[nH]c2c(=O)n(C)cc(C#CC(O)(c3ccccc3)C(F)(F)F)c2c1-c1nnc(C2CC2)o1] | 0.0471 | 0.249 |
| 181 | 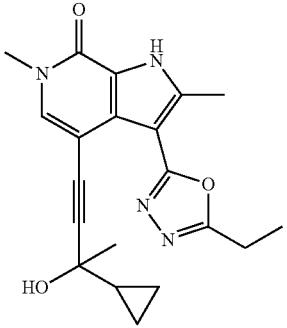 [SMILES: CCc1nnc(-c2c(C)[nH]c3c(=O)n(C)cc(C#CC(C)(O)C4CC4)c23)o1] | 0.0448 | 0.199 |

-continued

| Example | Structure | TAF1-BD2 HTRF IC50 uM | TAF1-BD1 HTRF IC50 uM |
|---|---|---|---|
| 182 | 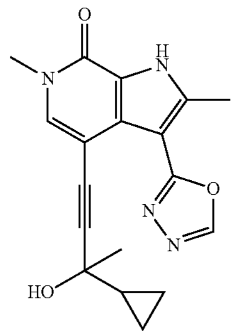 | 0.0535 | 0.285 |
| 183 | 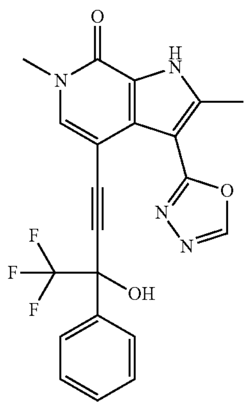 [SMILES: Cc1[nH]c2c(=O)n(C)cc(C#CC(O)(c3ccccc3)C(F)(F)F)c2c1-c1nnco1] | 0.0502 | 0.598 |
| 184 | 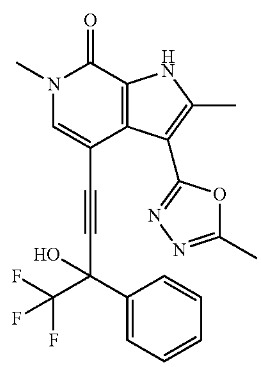 | 0.0627 | 0.327 |
| 185 | 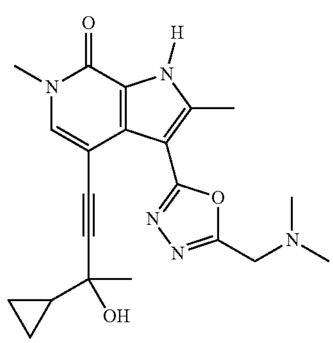 [SMILES: Cc1[nH]c2c(=O)n(C)cc(C#CC(C)(O)C3CC3)c2c1-c1nnc(CN(C)C)o1] | 0.0561 | 0.324 |

-continued

| Example | Structure | TAF1-BD2 HTRF IC50 uM | TAF1-BD1 HTRF IC50 uM |
|---|---|---|---|
| 186 | 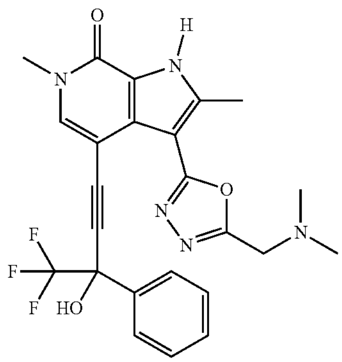 [SMILES: Cc1[nH]c2c(=O)n(C)cc(C#CC(O)(c3ccccc3)C(F)(F)F)c2c1-c1nnc(CN(C)C)o1] | 0.0687 | 0.484 |
| 187 | 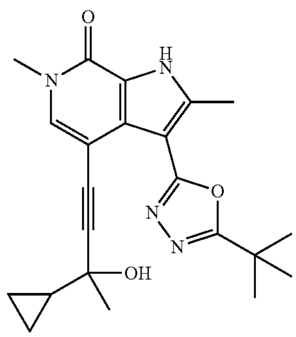 [SMILES: Cc1[nH]c2c(=O)n(C)cc(C#CC(C)(O)C3CC3)c2c1-c1nnc(C(C)(C)C)o1] | 0.058 | 0.216 |
| 188 | 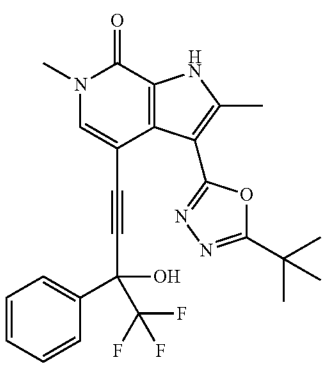 [SMILES: Cc1[nH]c2c(=O)n(C)cc(C#CC(O)(c3ccccc3)C(F)(F)F)c2c1-c1nnc(C(C)(C)C)o1] | 0.0862 | 0.385 |
| 189 | 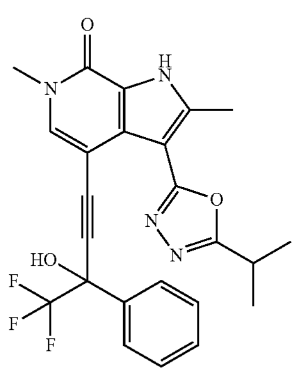 [SMILES: Cc1[nH]c2c(=O)n(C)cc(C#CC(O)(c3ccccc3)C(F)(F)F)c2c1-c1nnc(C(C)C)o1] | 0.0495 | 0.492 |

-continued

| Example | Structure | TAF1-BD2 HTRF IC50 uM | TAF1-BD1 HTRF IC50 uM |
|---------|-----------|----------------------|----------------------|
| 190 | 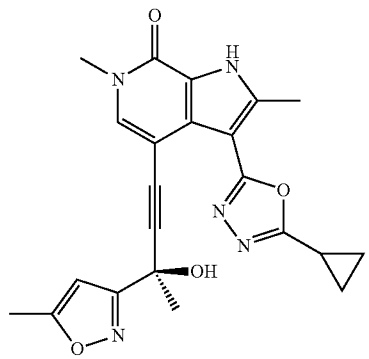 [SMILES: Cc1cc([C@](C)(O)C#Cc2cn(C)c(=O)c3[nH]c(C)c(-c4nnc(C5CC5)o4)c23)no1] | 0.0499 | 0.239 |
| 191 | 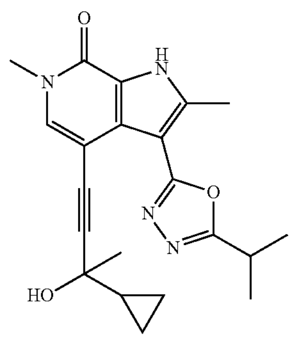 [SMILES: Cc1[nH]c2c(=O)n(C)cc(C#CC(C)(O)C3CC3)c2c1-c1nnc(C(C)C)o1] | 0.0364 | 0.27 |
| 192 | 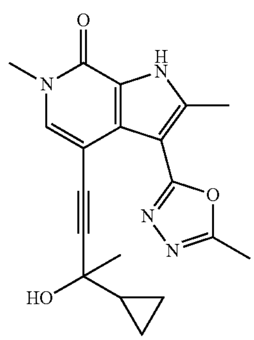 | 0.0616 | 0.335 |
| 193 | 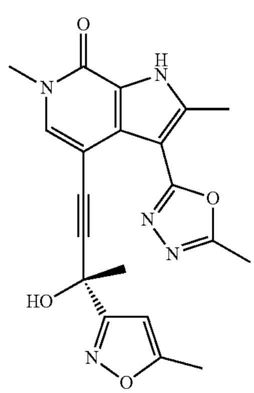 | 0.153 | 0.517 |

-continued

| Example | Structure | TAF1-BD2 HTRF IC50 uM | TAF1-BD1 HTRF IC50 uM |
|---|---|---|---|
| 194 | 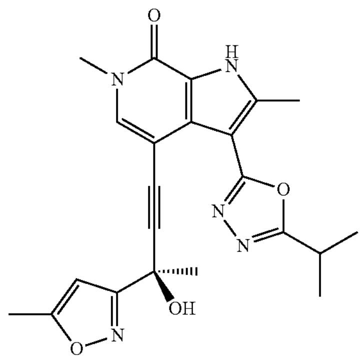 [SMILES: Cc1cc([C@](C)(O)C#Cc2cn(C)c(=O)c3[nH]c(C)c(-c4nnc(C(C)C)o4)c23)no1] | 0.0691 | 0.244 |
| 195 | 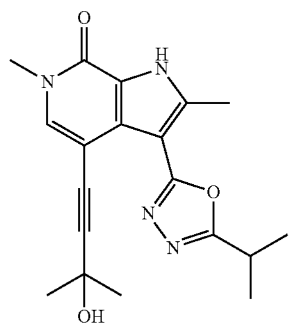 [SMILES: Cc1[nH]c2c(=O)n(C)cc(C#CC(C)(C)O)c2c1-c1nnc(C(C)C)o1] | 0.0294 | 0.36 |
| 196 | 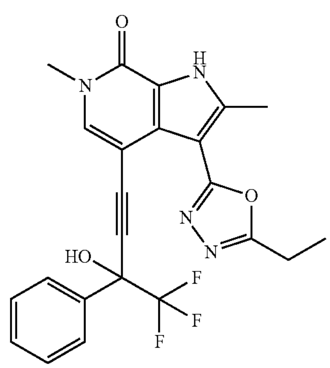 [SMILES: CCc1nnc(-c2c(C)[nH]c3c(=O)n(C)cc(C#CC(O)(c4ccccc4)C(F)(F)F)c23)o1] | | |
| 197 | 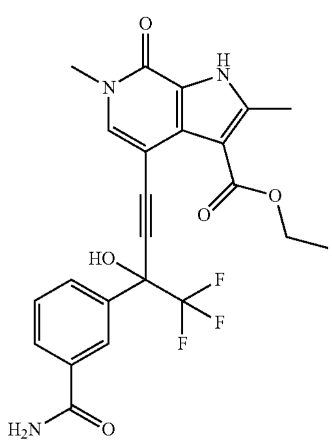 [SMILES: CCOC(=O)c1c(C)[nH]c2c(=O)n(C)cc(C#CC(O)(c3cccc(C(N)=O)c3)C(F)(F)F)c12] | 0.0341 | 0.185 |

-continued

| Example | Structure | TAF1-BD2 HTRF IC50 uM | TAF1-BD1 HTRF IC50 uM |
|---------|-----------|----------------------|----------------------|
| 198 | 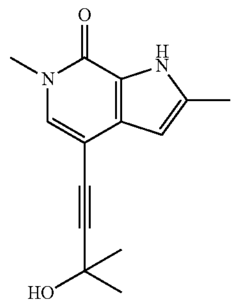 | 0.536 | 1.74 |
| 199a | 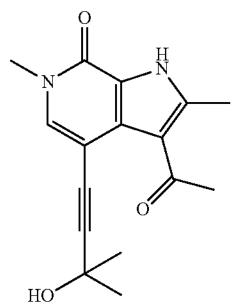 | 0.13 | 1.3 |
| 199b | 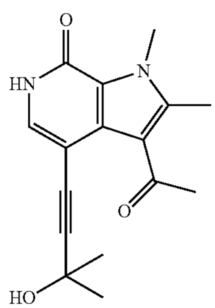 [SMILES: CC(=O)c1c(C)n(C)c2c(=O)[nH]cc(C#CC(C)(C)O)c12] | 20 | 20 |
| 200 | 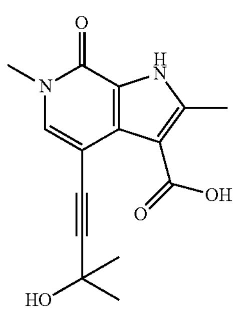 | 13.7 | 20 |
| 201 | 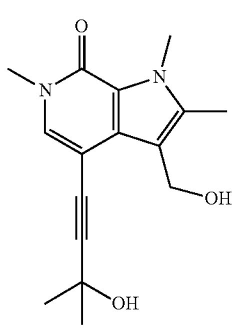 | 2.25 | 6.05 |

-continued

| Example | Structure | TAF1-BD2 HTRF IC50 uM | TAF1-BD1 HTRF IC50 uM |
|---------|-----------|-----------------------|-----------------------|
| 202 | 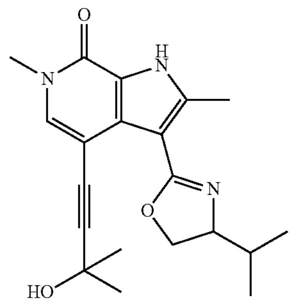 [SMILES: Cc1[nH]c2c(=O)n(C)cc(C#CC(C)(C)O)c2c1C1=NC(C(C)C)CO1] | 0.176 | 1.23 |
| 203 | 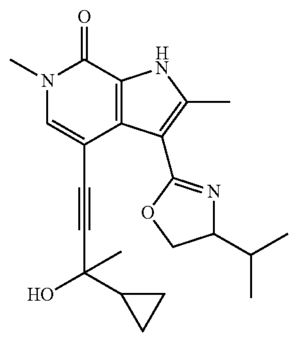 [SMILES: Cc1[nH]c2c(=O)n(C)cc(C#CC(C)(O)C3CC3)c2c1C1=NC(C(C)C)CO1] | 0.307 | 1.12 |
| 204 | 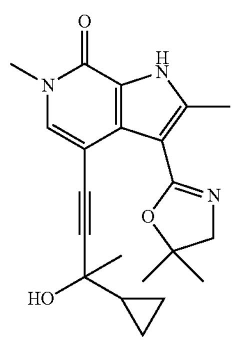 | 0.147 | 1.03 |
| 205 | 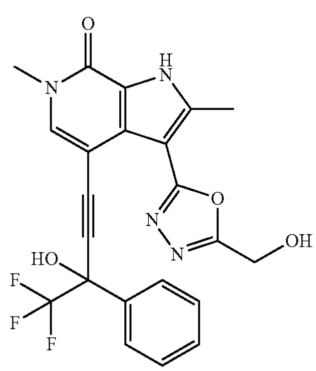 [SMILES: Cc1[nH]c2c(=O)n(C)cc(C#CC(O)(c3ccccc3)C(F)(F)F)c2c1-c1nnc(CO)o1] | 0.0888 | 0.334 |

-continued

| Example | Structure | TAF1-BD2 HTRF IC50 uM | TAF1-BD1 HTRF IC50 uM |
|---|---|---|---|
| 206 | 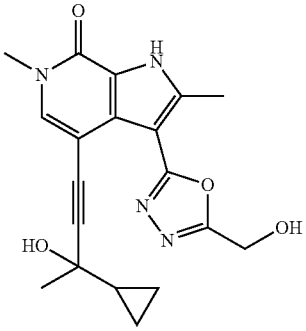 [SMILES: Cc1[nH]c2c(=O)n(C)cc(C#CC(C)(O)C3CC3)c2c1-c1nnc(CO)o1] | 0.0735 | 0.425 |
| 207 | 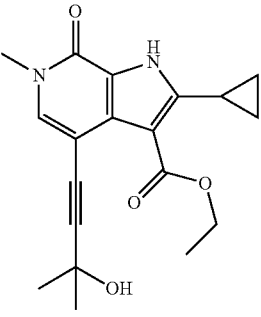 [SMILES: CCOC(=O)c1c(C2CC2)[nH]c2c(=O)n(C)cc(C#CC(C)(C)O)c12] | 0.353 | 0.957 |
| 208 | 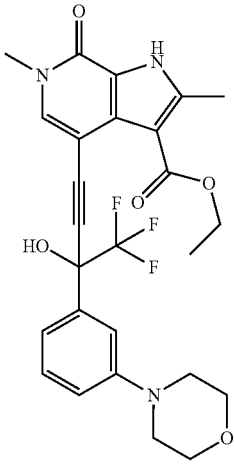 [SMILES: CCOC(=O)c1c(C)[nH]c2c(=O)n(C)cc(C#CC(O)(c3cccc(N4CCOCC4)c3)C(F)(F)F)c12] | 0.0795 | 0.438 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:
1. A compound of formula (I):

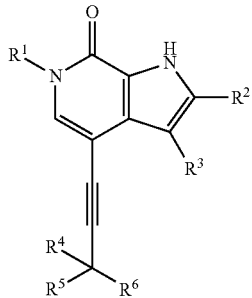

or a salt thereof wherein:
R$^1$ is C$_{1-6}$alkyl or C$_{2-6}$alkenyl, which C$_{1-6}$alkyl or C$_{2-6}$alkenyl is optionally substituted with one or more groups independently selected from the group consisting of halo, cyano, C$_{1-3}$ alkoxy, and C$_{3-8}$ carbocyclyl that is optionally substituted with one or more groups independently selected from halo;
R$^2$ is C$_{1-6}$alkyl or carbocyclyl;
R$^3$ is H, C$_{1-6}$alkyl, —N(R$^b$)$_2$, —C(=O)R$^a$, —C(=O)OR$^a$, or a 5-6 membered heteroaryl ring, which C$_{1-6}$ alkyl and 5-6 membered heteroaryl ring are optionally substituted with one or more groups independently selected from the group consisting of C$_{1-6}$alkyl, C$_{2-6}$ alkenyl, C$_{2-6}$alkynyl, carbocyclyl, heterocyclyl, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$, wherein any C$_{1-6}$alkyl, C$_{2-6}$alkenyl, C$_{2-6}$alkynyl, carbocyclyl, and heterocyclyl is optionally substituted with one or more groups independently selected from the group consisting of R$^f$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$;
R$^a$ is selected from the group consisting of hydrogen, C$_{1-10}$alkyl, C$_{2-10}$alkenyl, C$_{2-10}$alkynyl, carbocyclyl, and heterocyclyl, wherein any C$_{1-10}$alkyl, C$_{2-10}$alkenyl, C$_{2-10}$alkynyl, carbocyclyl, and heterocyclyl is optionally substituted with one or more groups independently selected from the group consisting of R$^d$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$;
each R$^b$ is independently selected from the group consisting of hydrogen, C$_{1-6}$alkyl, C$_{2-6}$alkenyl, C$_{2-6}$ alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from the group consisting of R$^c$, oxo, halo, —NO$_2$, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—OR$^c$, —S(O)—R$^c$, —S(O)$_2$—R$^c$, —N(R$^c$)—C(O)—R$^c$, —N(R$^c$)—S(O)—R$^c$, —N(R$^c$)—C(O)—N(R$^c$)$_2$, and —N(R$^c$)—S(O)$_2$—R$^c$; or two R$^c$ are taken together with the nitrogen to which they are attached to form a heterocyclyl that is optionally substituted with one or more groups independently selected from the group consisting of oxo, halo and C$_{1-3}$alkyl that is optionally substituted with one or more groups independently selected from the group consisting of oxo and halo; and
each R$^c$ is independently selected from the group consisting of hydrogen, C$_{1-6}$alkyl, C$_{2-6}$alkenyl, C$_{2-6}$ alkynyl, carbocyclyl, and heterocyclyl, wherein each C$_{1-6}$alkyl, C$_{2-6}$ alkenyl, C$_{2-6}$ alkynyl, carbocyclyl, and heterocyclyl is optionally substituted with one or more groups independently selected from the group consisting of oxo, halo, amino, hydroxy, C$_{1-6}$alkoxy, carbocyclyl, heterocyclyl, and C$_1$-C$_6$ alkyl that is optionally substituted with one or more groups independently selected from the group consisting of oxo and halo; or two R$^c$ are taken together with the nitrogen to which they are attached to form a heterocyclyl that is optionally substituted with one or more groups independently selected from the group consisting of oxo, halo and C$_{1-3}$alkyl that is optionally substituted with one or more groups independently selected from the group consisting of oxo and halo;
each R$^d$ is independently selected from the group consisting of C$_{1-6}$alkyl, C$_{2-6}$ alkenyl, C$_{2-6}$alkynyl, C$_{1-6}$alkoxy, carbocyclyl, and heterocyclyl, wherein each C$_{1-6}$alkyl, C$_{2-6}$ alkenyl, C$_{2-6}$alkynyl, C$_{1-6}$alkoxy, carbocyclyl, and heterocyclyl is optionally substituted with one or more groups independently selected from the group consisting of R$^e$, oxo, halo, —NO$_2$, —N(R$^e$)$_2$, —CN, —C(O)—N(R$^e$)$_2$, —S(O)—N(R$^e$)$_2$, —S(O)$_2$—N(R$^e$)$_2$, —O—R$^e$—, —S—R$^e$, —O—C(O)—R$^e$, —C(O)—R$^e$, —C(O)—OR$^c$, —S(O)—R$^c$, —S(O)$_2$—R$^c$, —N(R$^c$)—C(O)—R$^c$, —N(R$^c$)—S(O)—R$^c$, —N(R$^c$)—C(O)—N(R$^c$)$_2$, and —N(R$^e$)—S(O)$_2$—R$^e$,
each R$^e$ is independently selected from the group consisting of hydrogen, C$_{1-6}$alkyl, C$_{2-6}$alkenyl, C$_{2-6}$ alkynyl, C$_{1-6}$alkoxy, carbocyclyl, and heterocyclyl, wherein each C$_{1-6}$alkyl, C$_{2-6}$alkenyl, C$_{2-6}$alkynyl, C$_{1-6}$alkoxy, carbocyclyl, and heterocyclyl is optionally substituted with one or more groups independently selected from the group consisting of oxo, halo, amino, hydroxy, C$_{1-6}$alkoxy, carbocyclyl, heterocyclyl, and C$_1$-C$_6$ alkyl that is optionally substituted with one or more groups independently selected from the group consisting of oxo and halo; or two R$^e$ are taken together with the nitrogen to which they are attached to form a heterocyclyl that is optionally substituted with one or more groups independently selected from the group consisting of oxo, halo and C$_{1-3}$alkyl that is optionally substituted with one or more groups independently selected from the group consisting of oxo and halo;
each R$^f$ is independently selected from the group consisting of C$_{1-6}$alkyl, C$_{2-6}$ alkenyl, C$_{2-6}$alkynyl, C$_{1-6}$alkoxy, carbocyclyl, and heterocyclyl, wherein each C$_{1-6}$alkyl, C$_{2-6}$ alkenyl, C$_{2-6}$ alkynyl, C$_{1-6}$alkoxy, carbocyclyl, and heterocyclyl is optionally substituted with one or more groups independently selected from the group consisting of oxo, halo, amino, hydroxy, C$_{1-6}$alkoxy, carbocyclyl, heterocyclyl, and C$_1$-C$_6$ alkyl that is optionally substituted with one or more groups independently selected from the group consisting of oxo and halo;

R⁴ is absent, H, hydroxy, or C₁₋₆alkyl that is optionally substituted with one or more groups independently selected from the group consisting of halo;

R⁵ is H or C₁₋₆alkyl that is optionally substituted with one or more groups independently selected from the group consisting of halo; and R⁶ is C₁₋₆ alkyl, carbocyclyl, or heterocyclyl, which C₁₋₆alkyl, carbocyclyl, and heterocyclyl is optionally substituted with one or more R$^g$; or R⁵ and R⁶ taken together with the carbon to which they are attached form a carbocyclyl, or heterocyclyl, which carbocyclyl and heterocyclyl is optionally substituted with one or more R$^g$;

each R$^g$ is independently selected from the group consisting of C₁₋₆alkyl, C₂₋₆ alkenyl, C₂₋₆alkynyl, carbocyclyl, and heterocyclyl, R$^k$, halo, oxo (=O), —NO₂, —N(R$^h$)₂, —CN, —C(O)—N(R$^h$)₂, —S(O)—N(R$^h$)₂, —S(O)₂—N(R$^h$)₂, —O—R$^h$, —S—R$^h$, —O—C(O)—R$^h$, —C(O)—R$^h$, —C(O)—OR$^h$, —S(O)—R$^h$, —S(O)₂—R$^h$, —N(R$^h$)—C(O)—R$^h$, —N(R$^h$)—S(O)—R$^h$, —N(R$^h$)—C(O)—N(R$^h$)₂, and —N(R$^h$)—S(O)₂—R$^h$;

each R$^h$ is independently selected from the group consisting of hydrogen, C₁₋₆alkyl, C₂₋₆alkenyl, C₂₋₆ alkynyl, C₁₋₆alkoxy, carbocyclyl, and heterocyclyl, wherein each C₁₋₆alkyl, C₂₋₆alkenyl, C₂₋₆alkynyl, C₁₋₆alkoxy, carbocyclyl, and heterocyclyl is optionally substituted with one or more groups independently selected from the group consisting of oxo, halo, amino, hydroxy, C₁₋₆alkoxy, carbocyclyl, heterocyclyl, and C₁-C₆ alkyl that is optionally substituted with one or more groups independently selected from the group consisting of oxo and halo; or two R$^h$ are taken together with the nitrogen to which they are attached to form a heterocyclyl that is optionally substituted with one or more groups independently selected from the group consisting of oxo, halo and C₁₋₃alkyl that is optionally substituted with one or more groups independently selected from the group consisting of oxo and halo; and each R$^k$ is independently selected from the group consisting of C₁₋₆alkyl, C₂₋₆ alkenyl, C₂₋₆alkynyl, carbocyclyl, and heterocyclyl, which C₁₋₆alkyl, C₂₋₆alkenyl, C₂₋₆alkynyl, carbocyclyl, and heterocyclyl, is substituted with one or more groups independently selected from the group consisting halo, —NO₂, —N(R$^h$)₂, —CN, —C(O)—N(R$^h$)₂, —S(O)—N(R$^h$)₂, —S(O)₂—N(R$^h$)₂, —O—R$^h$, —S—R$^h$, —O—C(O)—R$^h$, —C(O)—R$^h$, —C(O)—OR$^h$, —S(O)—R$^h$, —S(O)₂—R$^h$, —N(R$^h$)—C(O)—R$^h$, —N(R$^h$)—S(O)—R$^h$, —N(R$^h$)—C(O)—N(R$^h$)₂, and —N(R$^h$)—S(O)₂—R$^h$.

2. The compound of claim 1 wherein R³ is —N(R$^b$)₂.

3. The compound of claim 1 wherein R³ is —C(=O)R$^a$.

4. The compound of claim 1 wherein R³ is —C(=O)OR$^a$.

5. The compound of claim 1 wherein R³ is a 5-6 membered heteroaryl ring that is optionally substituted with one or more groups independently selected from the group consisting of C₁₋₆alkyl, C₂₋₆ alkenyl, C₂₋₆alkynyl, carbocyclyl, heterocyclyl, oxo, halo, —NO₂, —N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, and —N(R$^b$)—S(O)₂—R$^b$, wherein any C₁₋₆alkyl, C₂₋₆ alkenyl, C₂₋₆alkynyl, carbocyclyl, and heterocyclyl is optionally substituted with one or more groups independently selected from the group consisting of R$^f$, oxo, halo, —NO₂, —N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—O—R$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, and —N(R$^b$)—S(O)₂—R$^b$.

6. The compound of claim 1 wherein R³ is selected from the group consisting of:

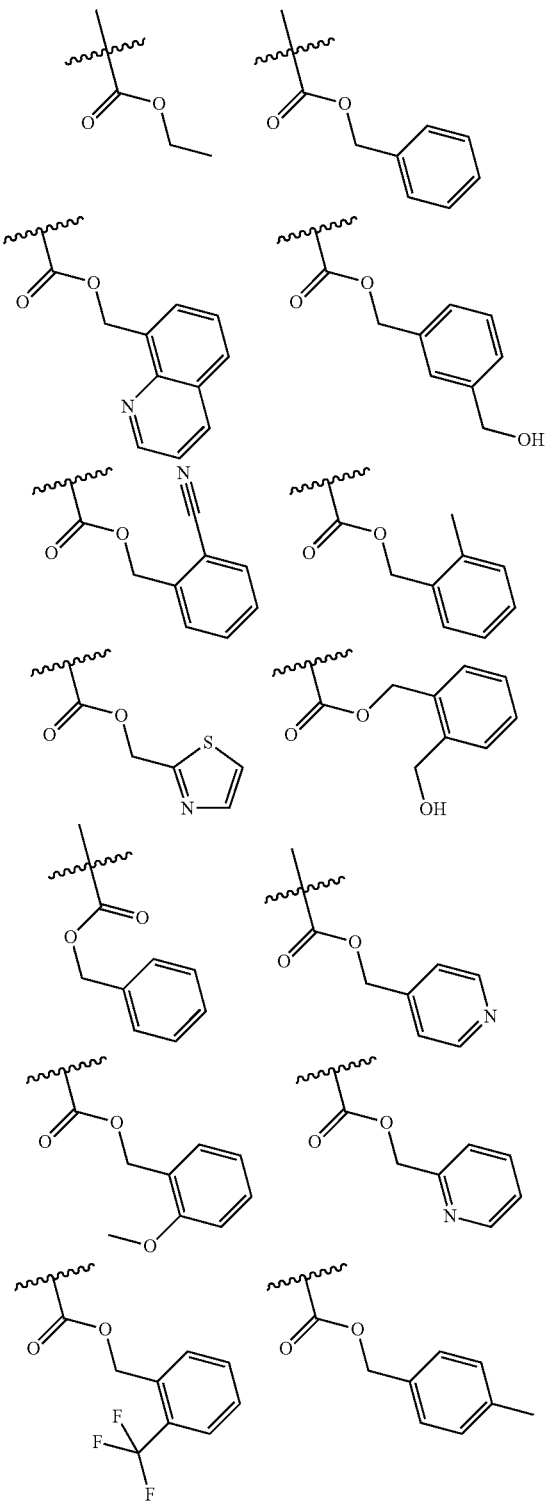

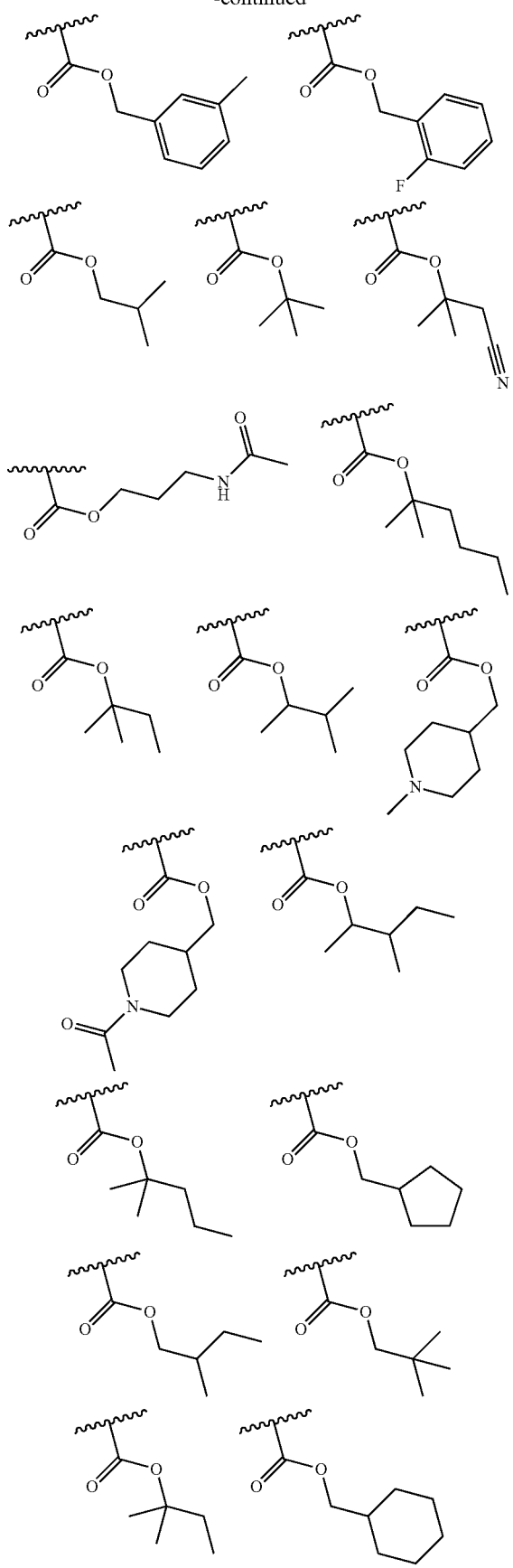
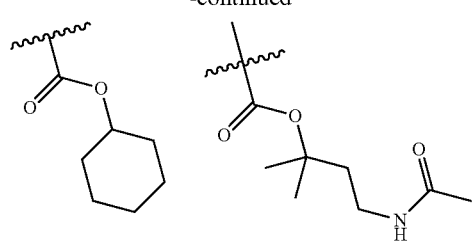
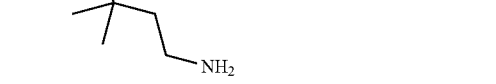
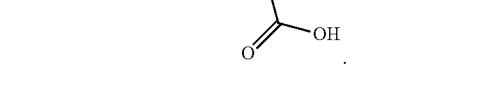
and
7. The compound of claim 1 wherein $R^3$ is selected from the group consisting of:
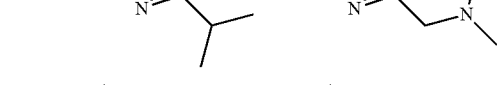
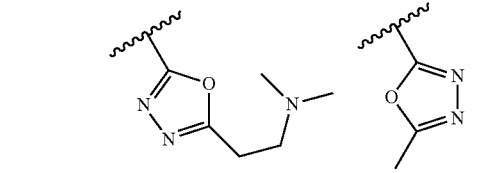
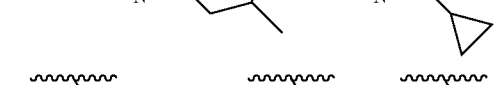
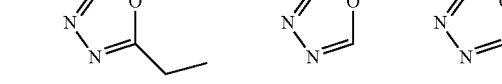

-continued
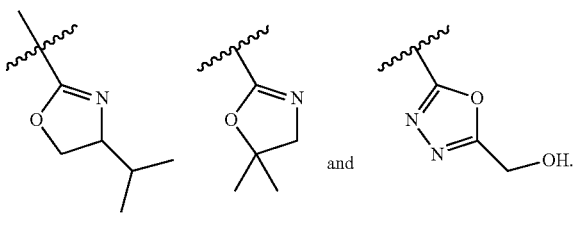
and
8. The compound of claim 1 wherein R³ is selected from the group consisting of:
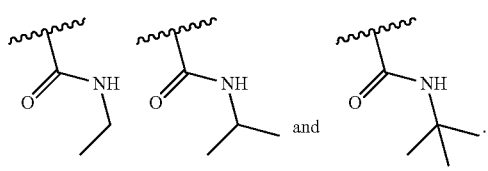
and
9. The compound of claim 1 wherein R³ is selected from the group consisting of:
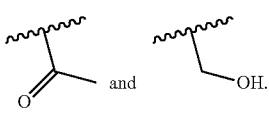
and
10. The compound claim 1 which is a compound of formula (Ia):
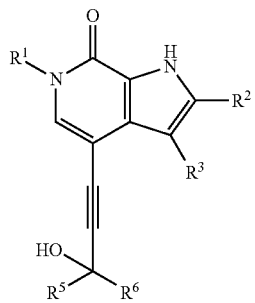
(Ia)
or a salt thereof.
11. The compound of claim 1 wherein the group:
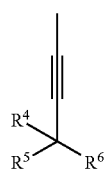
is selected from the group consisting of:
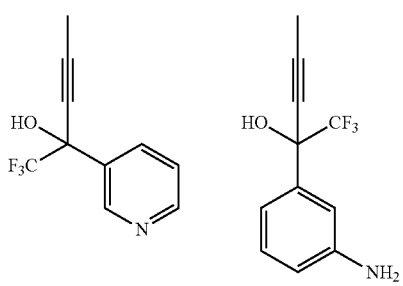
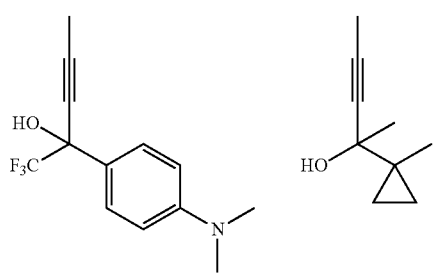
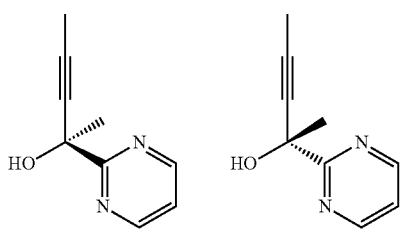
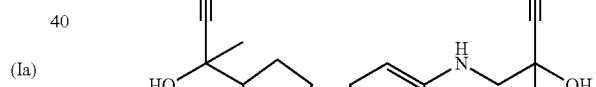
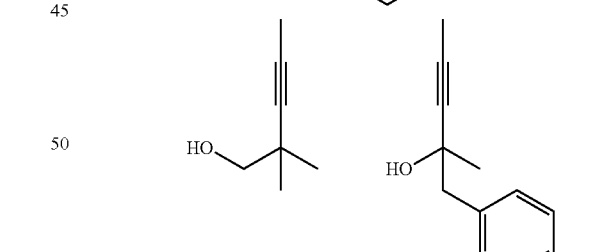
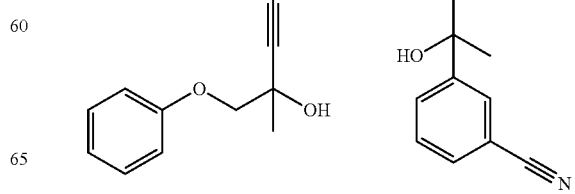

337
-continued
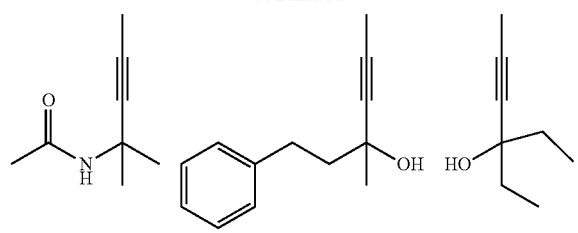
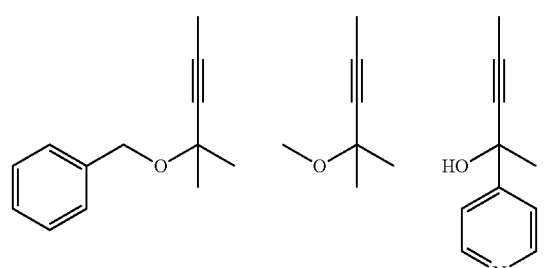
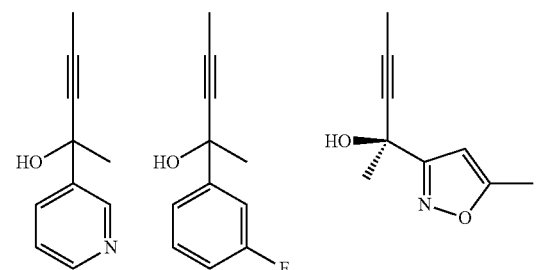
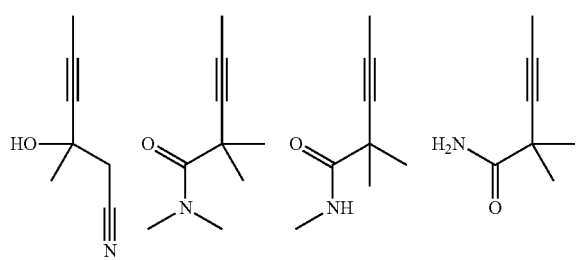
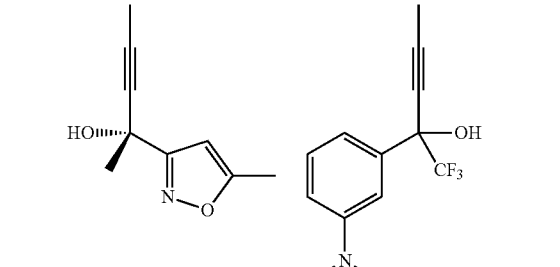
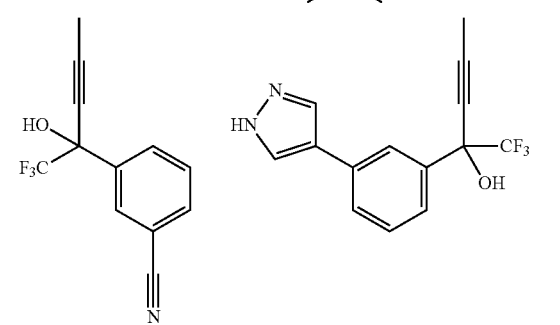
338
-continued
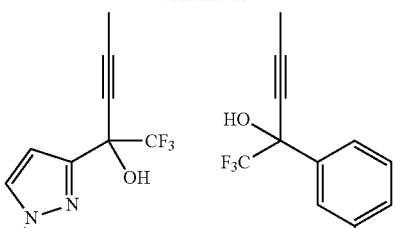
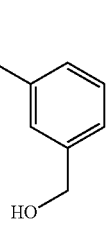
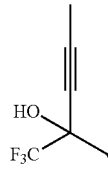
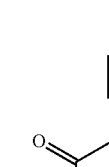
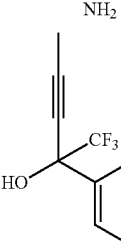
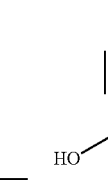
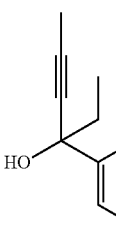

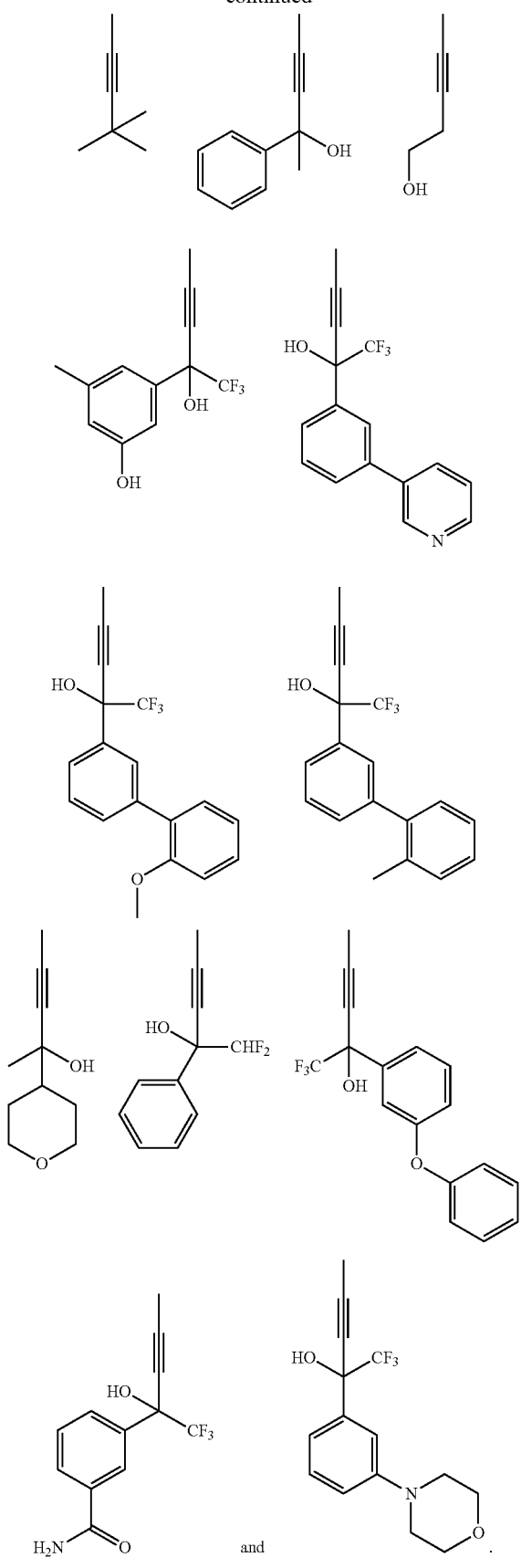
12. The compound of claim 1 wherein the group:
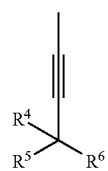
is selected from the group consisting of:
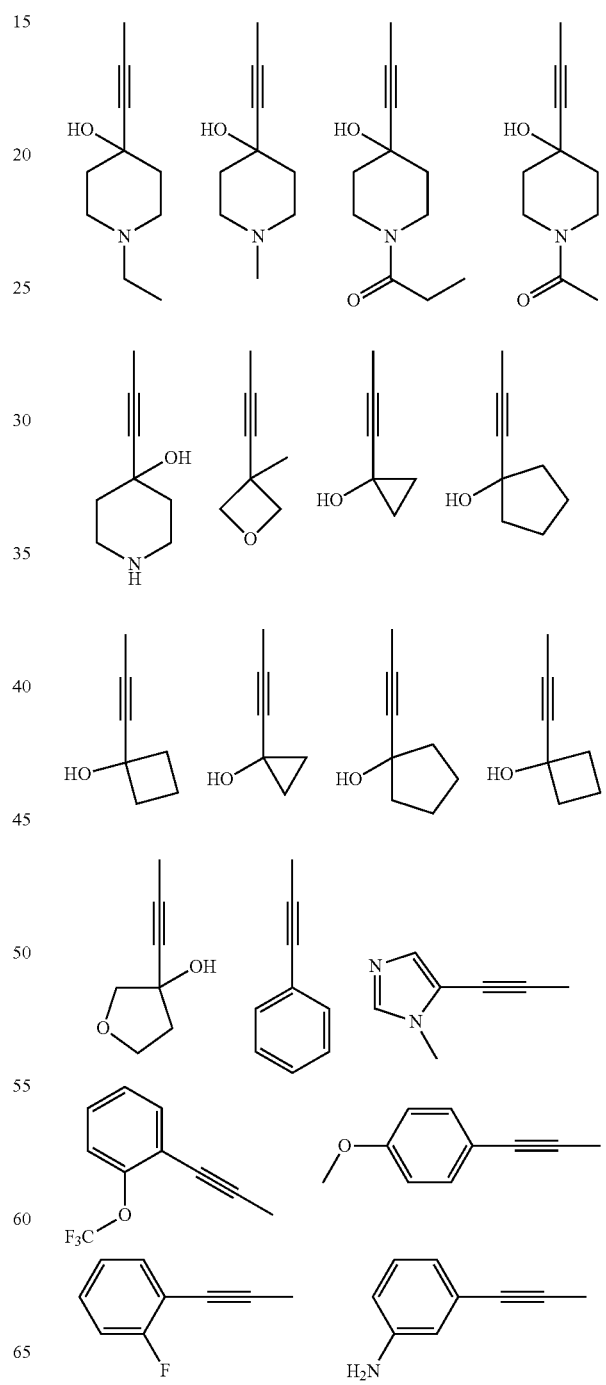

-continued

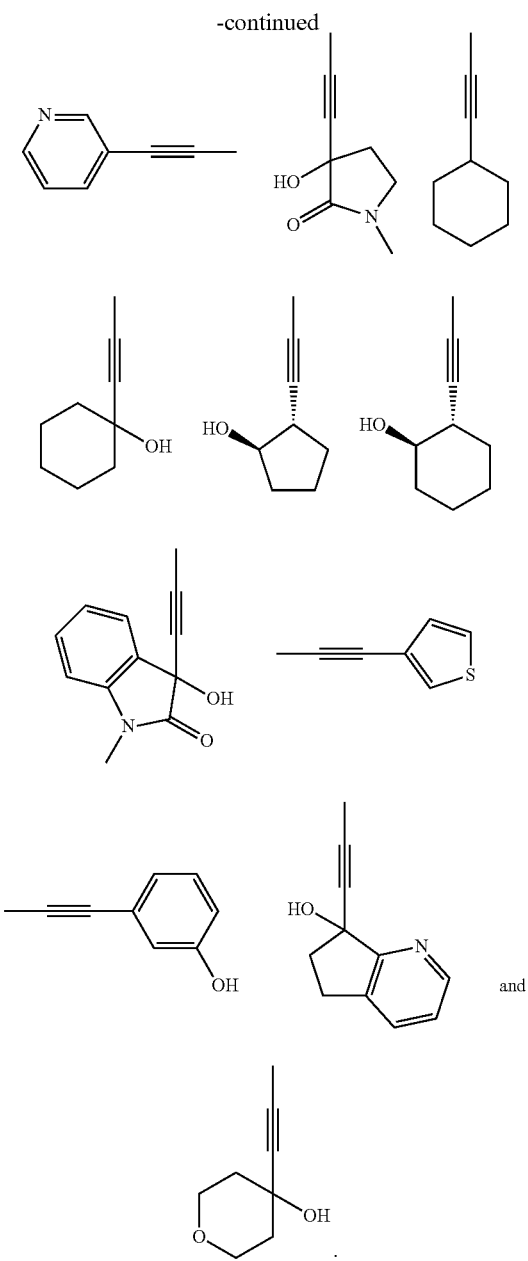

13. The compound of claim 1 or a salt thereof wherein:
$R^1$ is $C_{1-6}$ alkyl that is optionally substituted with one or more groups independently selected from the group consisting of halo, cyano, $C_{1-3}$ alkoxy, and $C_{3-8}$ carbocyclyl that is optionally substituted with one or more groups independently selected from halo;
$R^2$ is $C_{1-6}$ alkyl; and
$R^3$ is —N(R$^b$)$_2$.

14. The compound of claim 1 or a salt thereof wherein:
$R^1$ is $C_{1-6}$ alkyl that is optionally substituted with one or more groups independently selected from the group consisting of halo, cyano, $C_{1-3}$ alkoxy, and $C_{3-8}$ carbocyclyl that is optionally substituted with one or more groups independently selected from halo;
$R^2$ is $C_{1-6}$ alkyl; and
$R^3$ is —C(=O)OR$^a$.

15. The compound of claim 1 or a salt thereof wherein:
$R^1$ is $C_{1-6}$ alkyl that is optionally substituted with one or more groups independently selected from the group consisting of halo, cyano, $C_{1-3}$ alkoxy, and $C_{3-8}$ carbocyclyl that is optionally substituted with one or more groups independently selected from halo;
$R^2$ is $C_{1-6}$ alkyl, $C_{3-8}$ carbocyclyl; and
$R^3$ is a 5-6 membered heteroaryl ring that is optionally substituted with one or more groups independently selected from the group consisting of $C_{1-6}$alkyl, $C_{2-6}$alkenyl, $C_{2-6}$alkynyl, carbocyclyl, heterocyclyl, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$, wherein any $C_{1-6}$alkyl, $C_{2-6}$alkenyl, $C_{2-6}$ alkynyl, carbocyclyl, and heterocyclyl is optionally substituted with one or more groups independently selected from the group consisting of R$^f$, oxo, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—O—R$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$.

16. The compound of claim 1, wherein $R^1$ is $C_{1-6}$alkyl or $C_{2-6}$ alkenyl, which $C_{1-6}$alkyl or $C_{2-6}$alkenyl is optionally substituted with one or more groups independently selected from the group consisting of $C_{3-8}$ carbocyclyl.

17. The compound of claim 1 selected from the group consisting of:

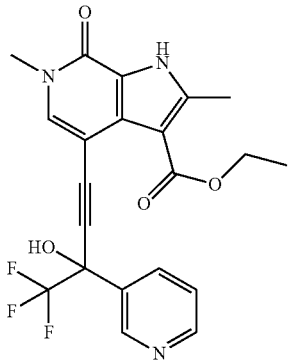

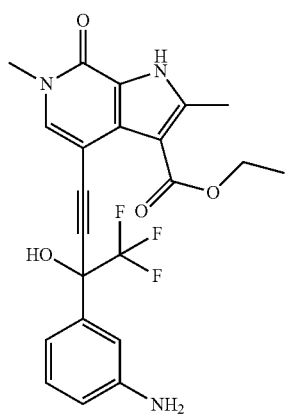

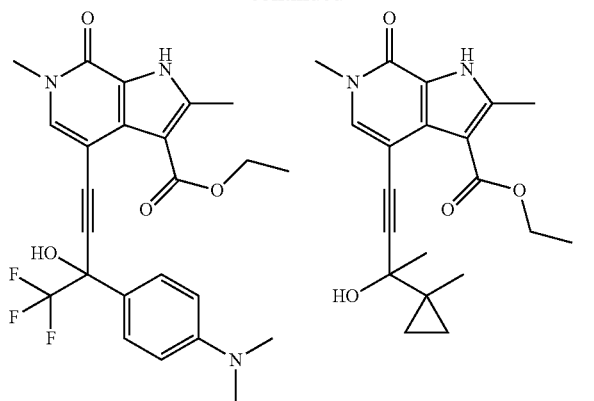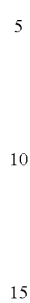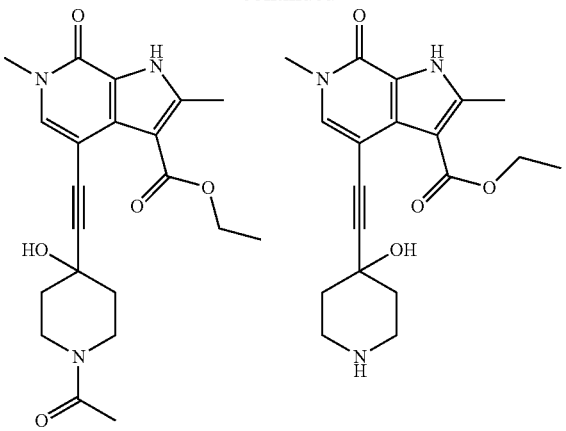
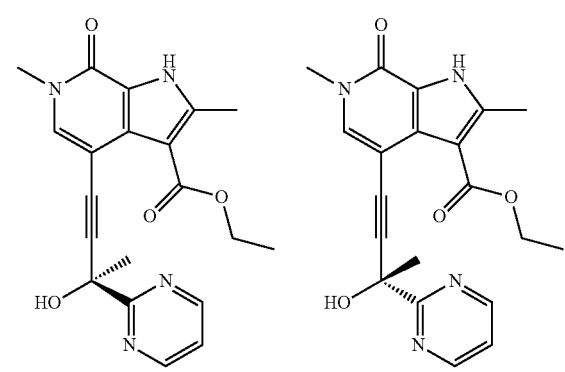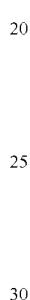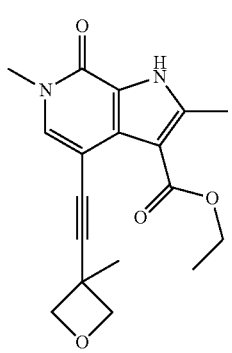
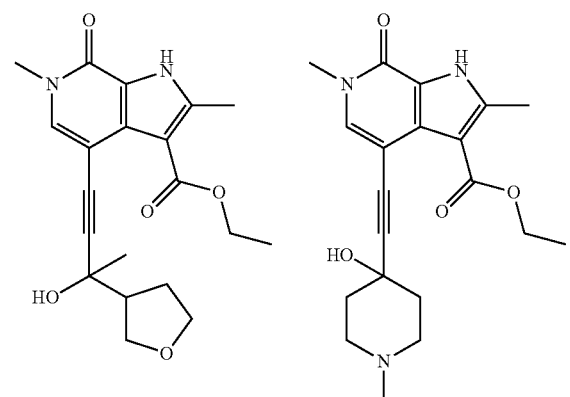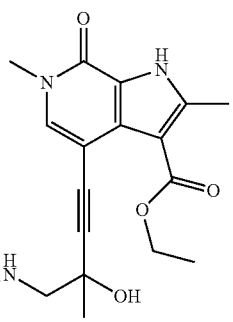
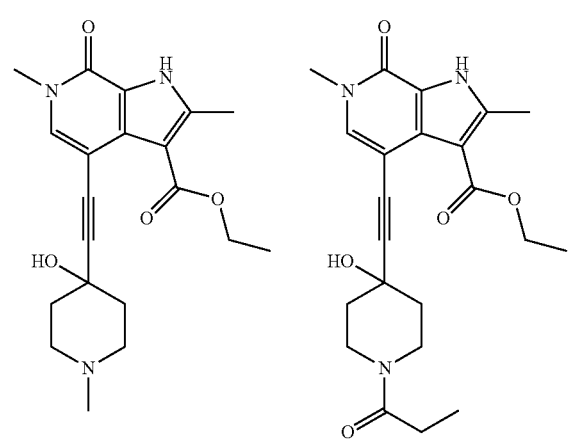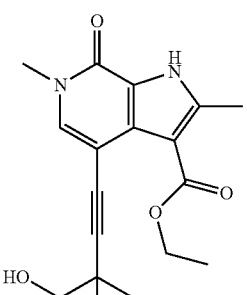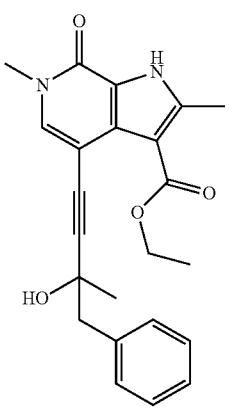

345
-continued
346
-continued
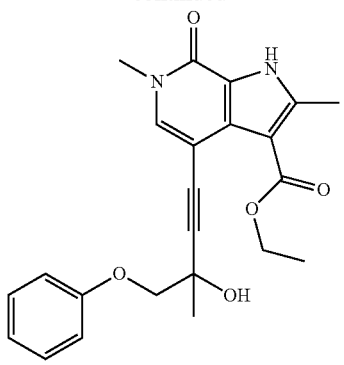
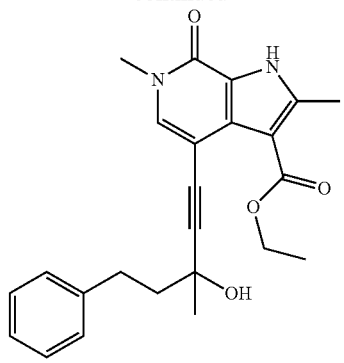
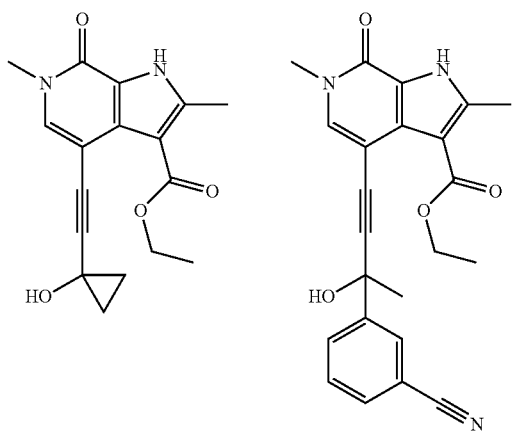
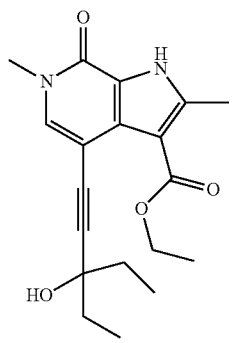
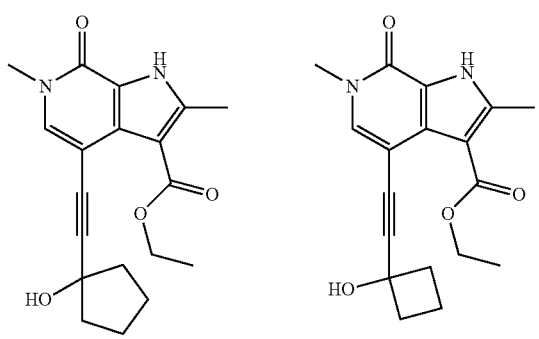
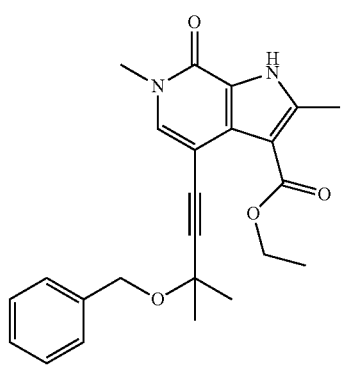
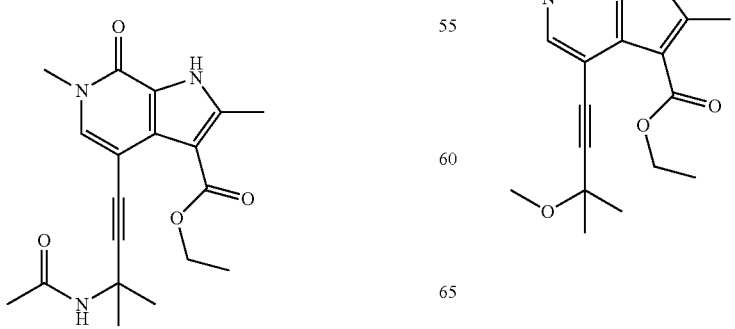
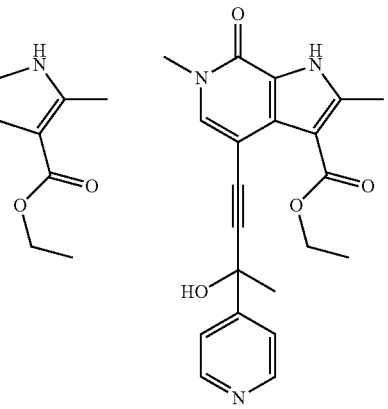

-continued
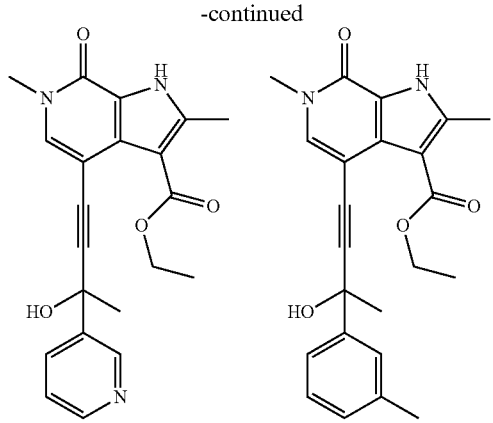
-continued
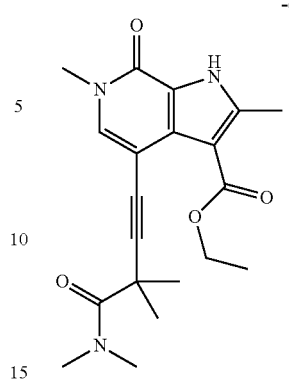
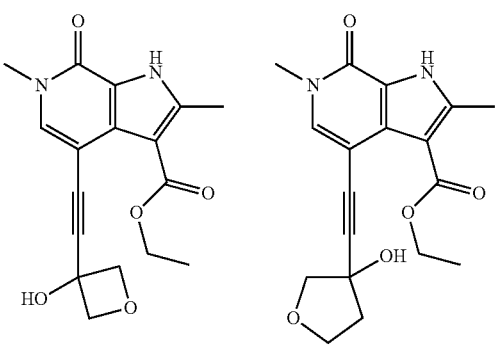
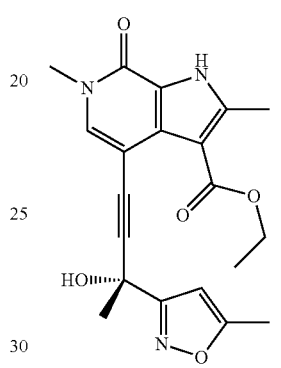
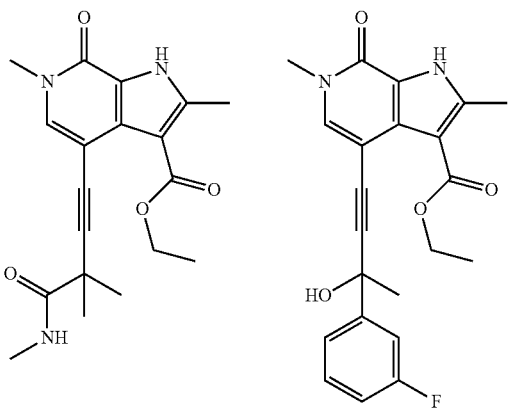
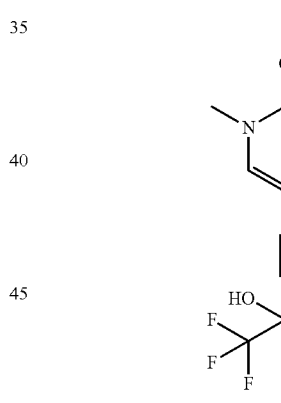
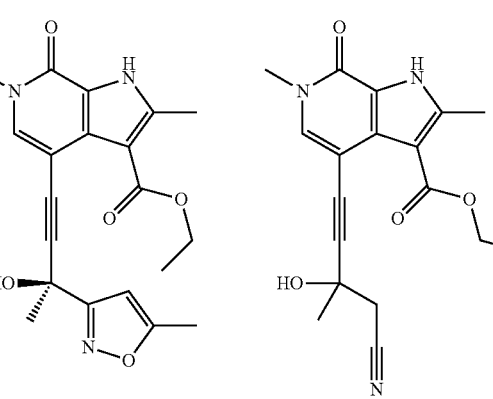
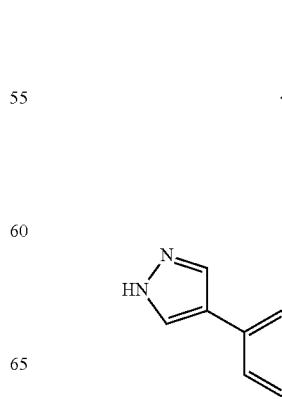
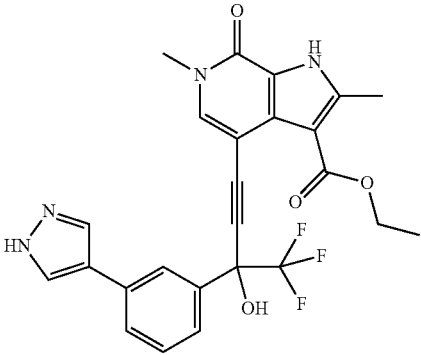

349
-continued
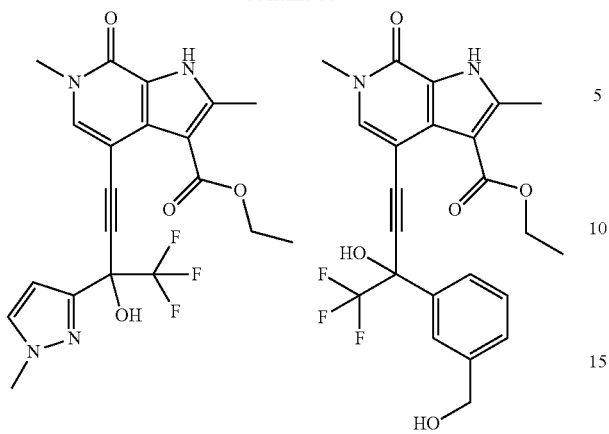
350
-continued
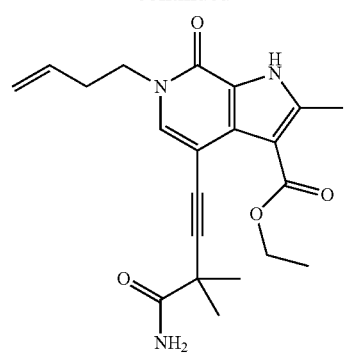
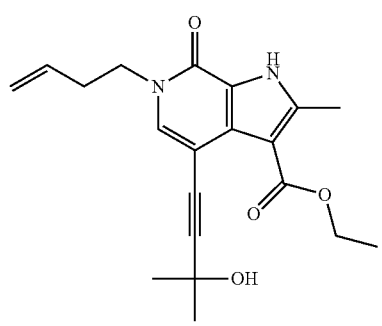
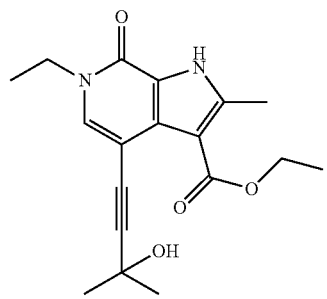
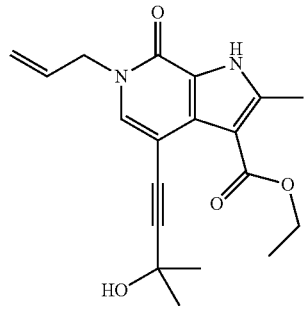
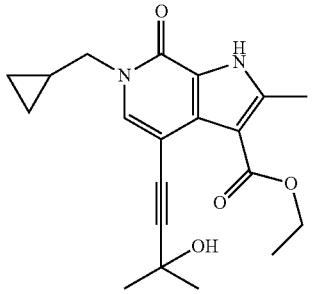

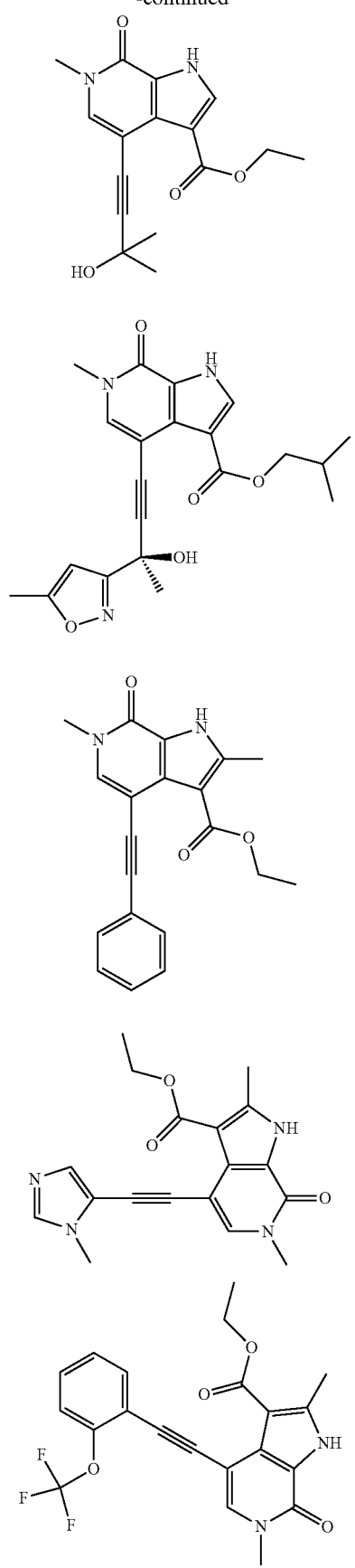
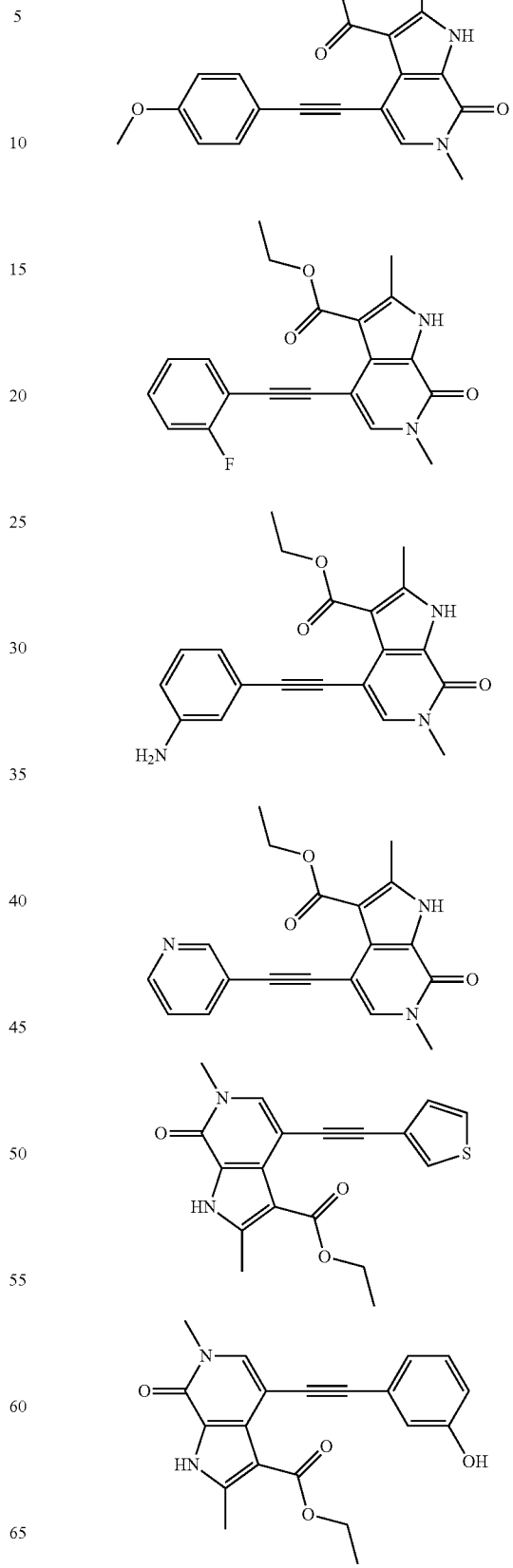

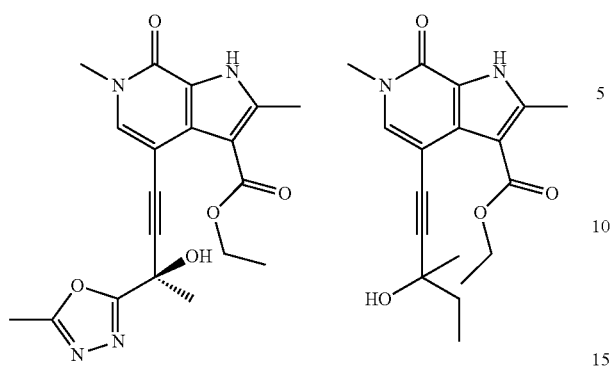
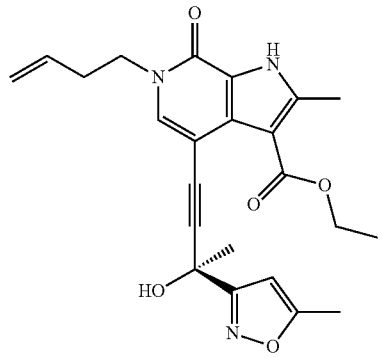
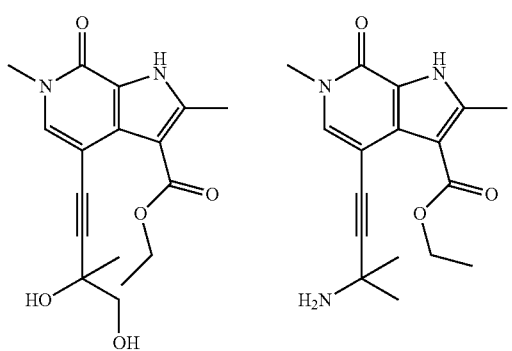
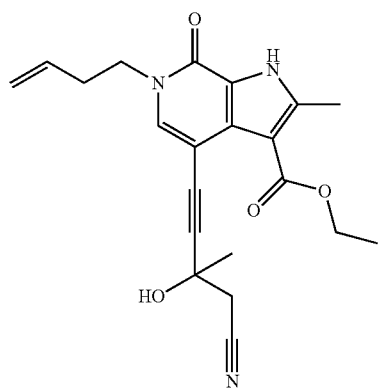
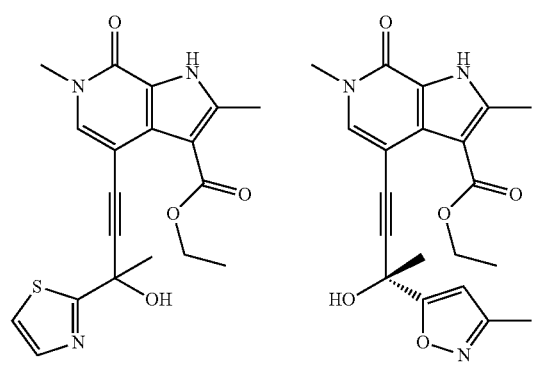
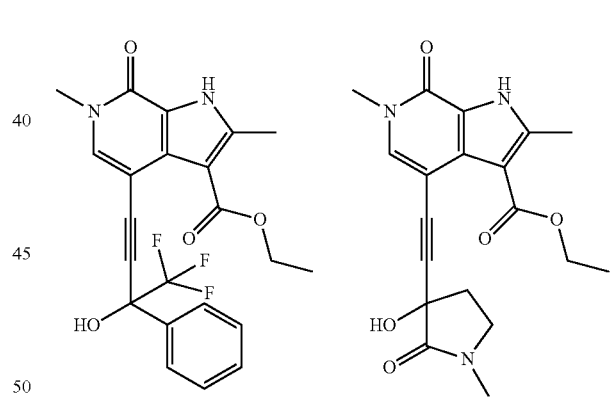
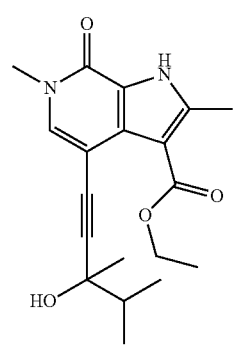
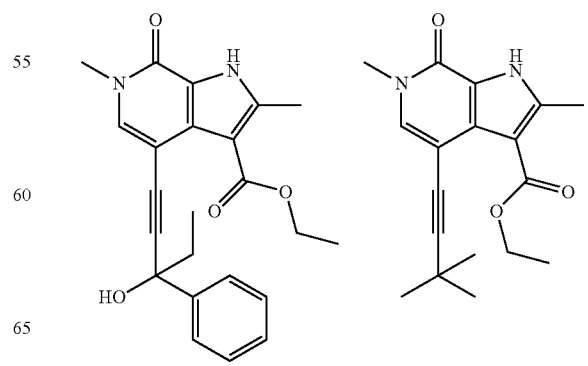

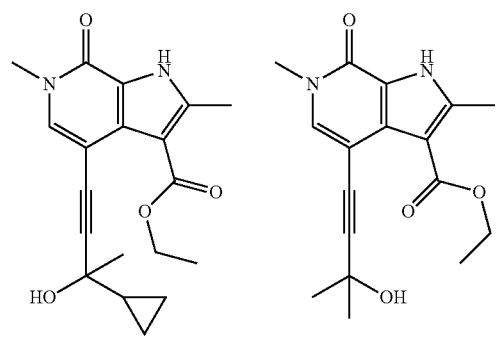
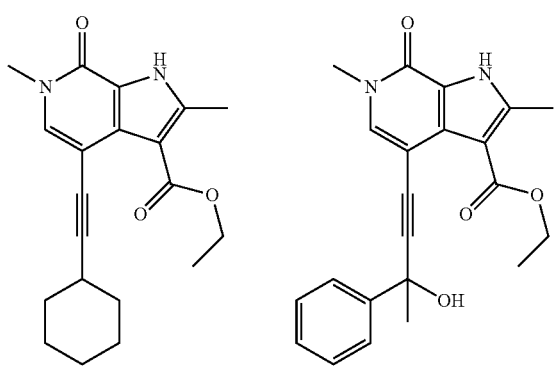
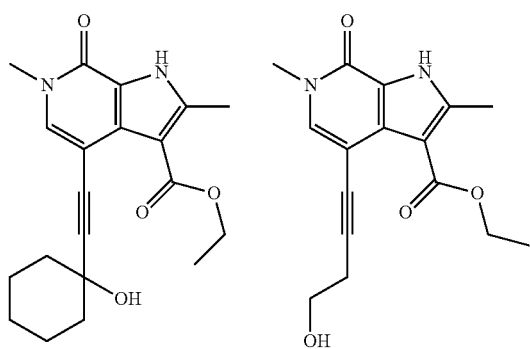
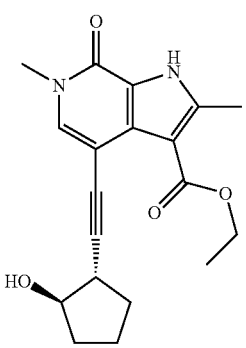
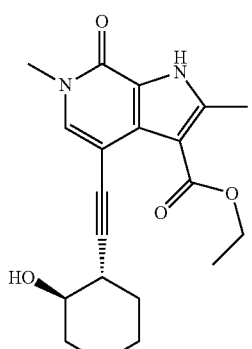
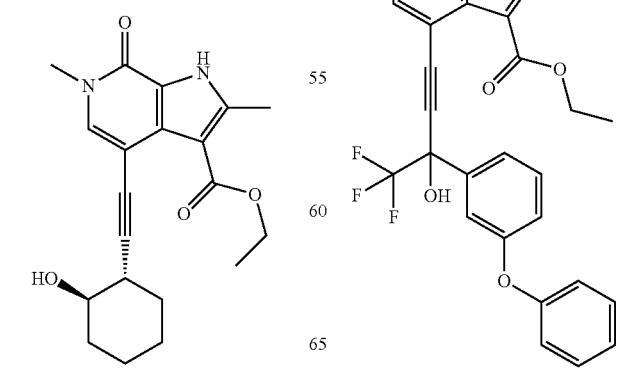

-continued
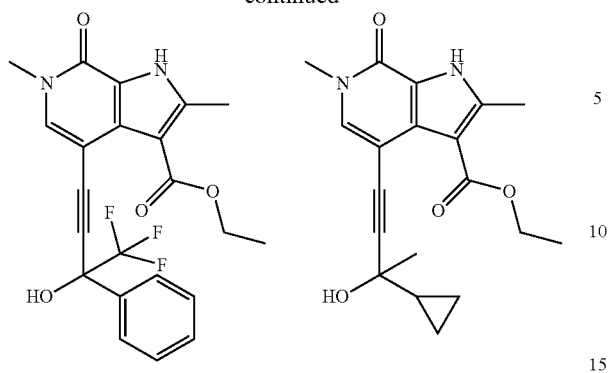
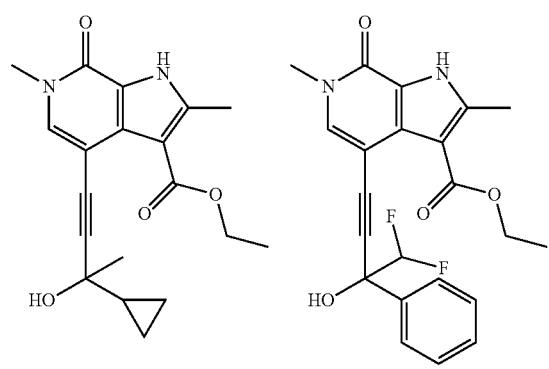
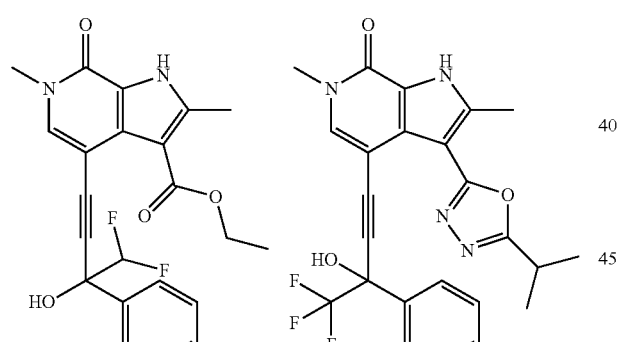
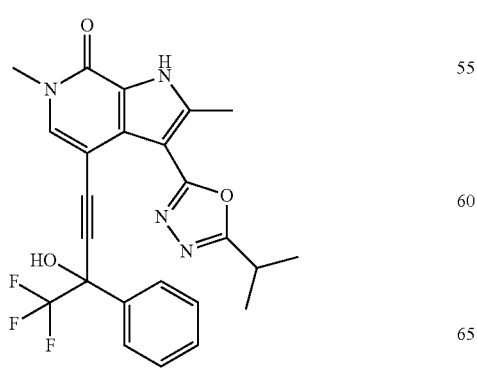
-continued
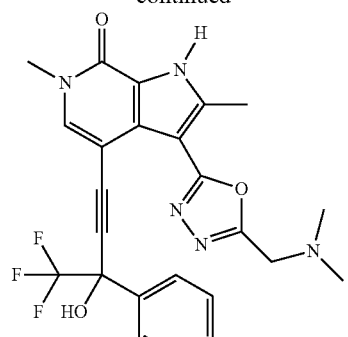
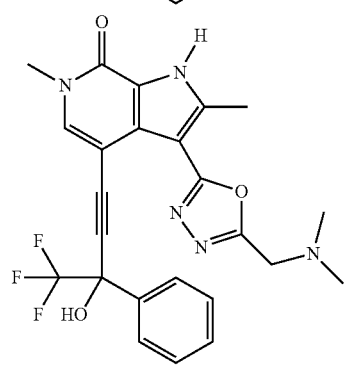
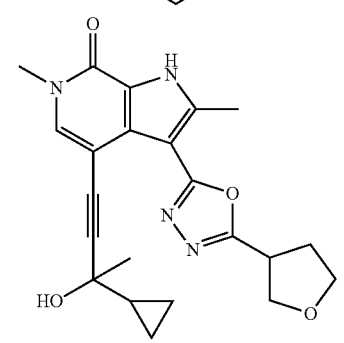
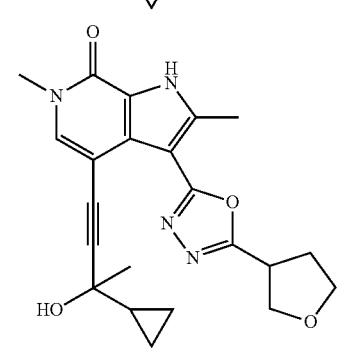
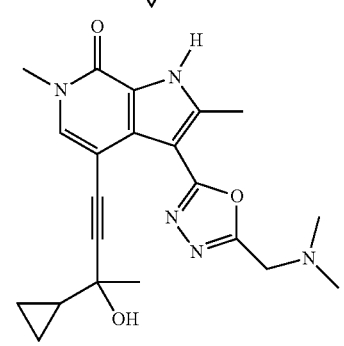

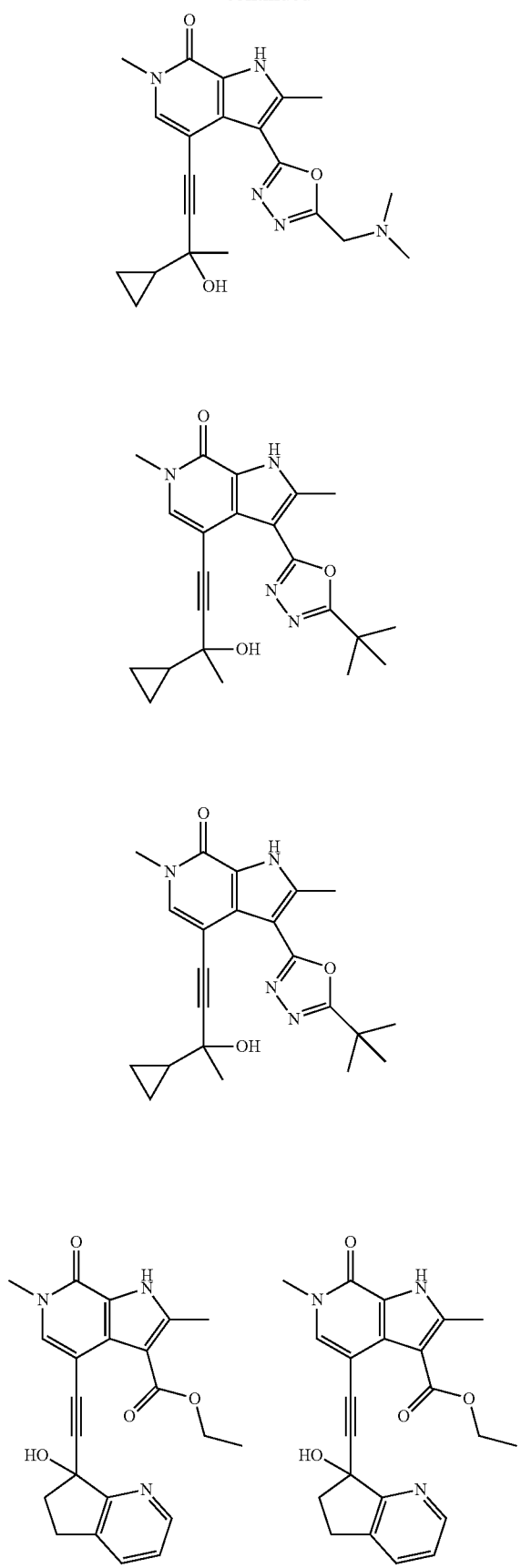
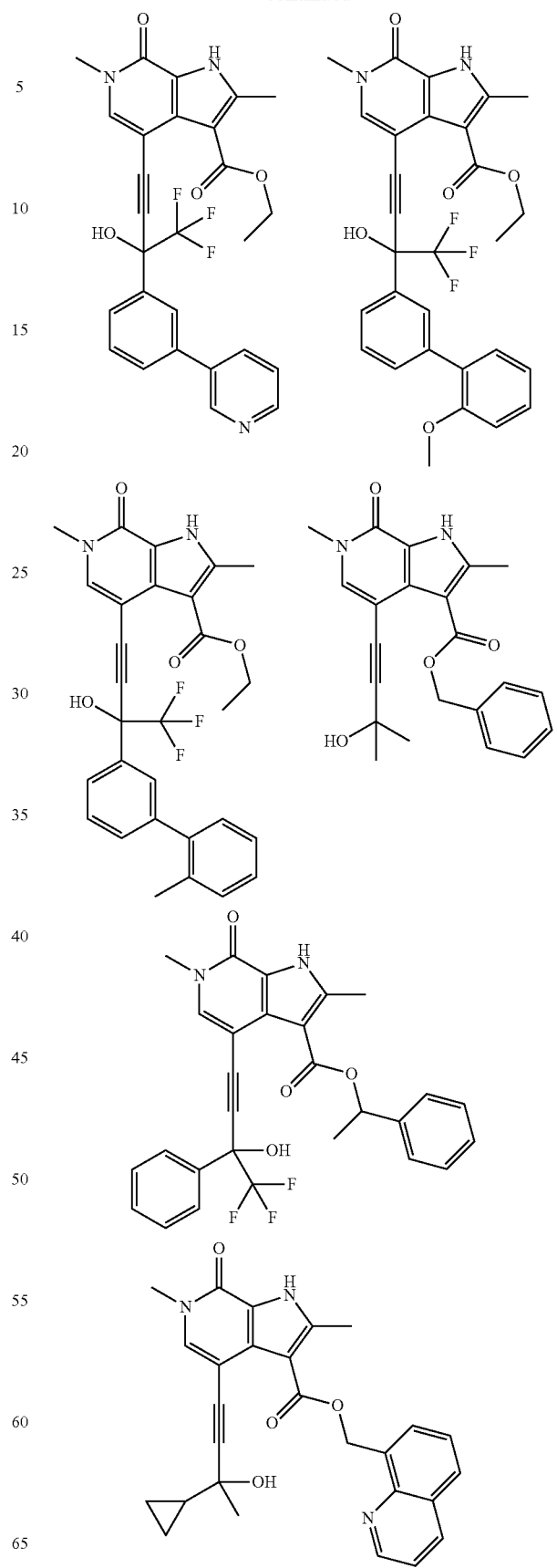

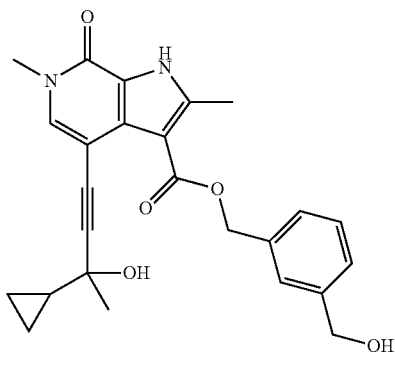
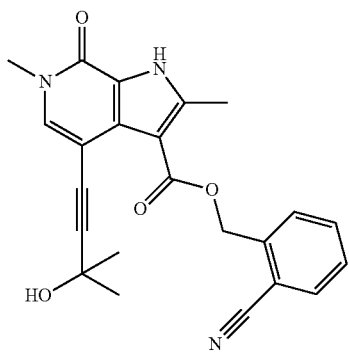
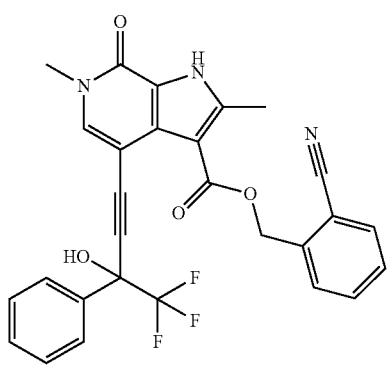
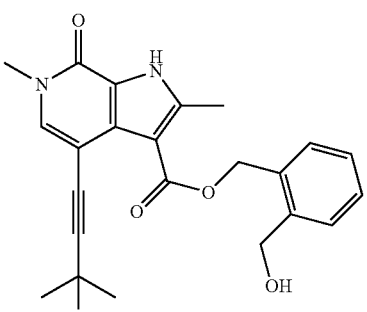
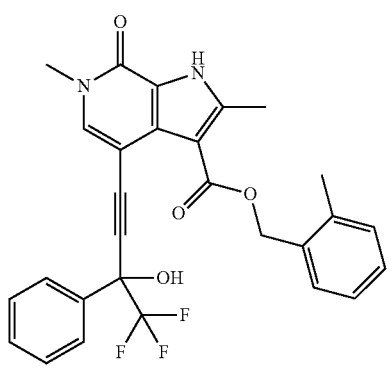
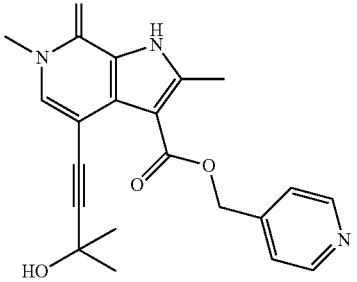
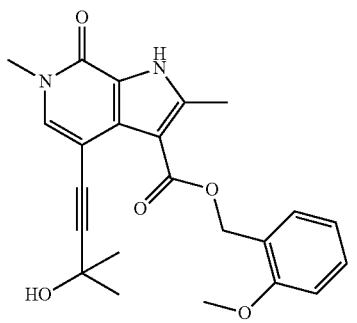
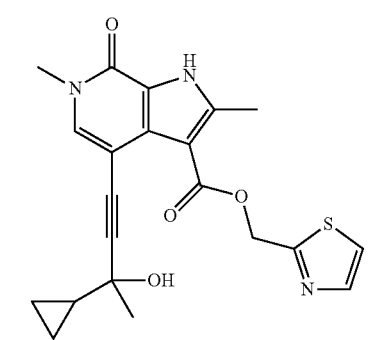
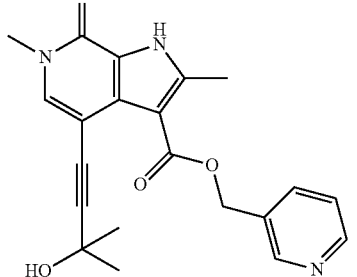

363
-continued
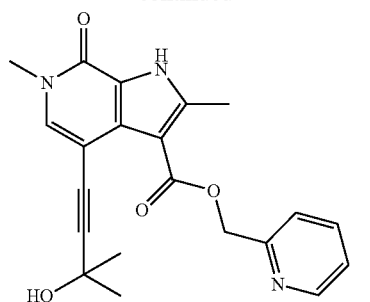
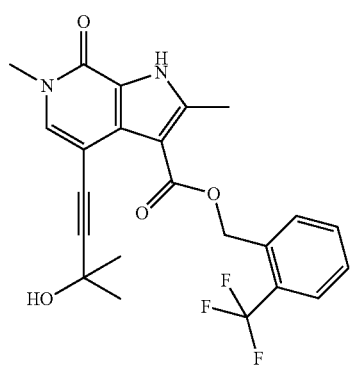
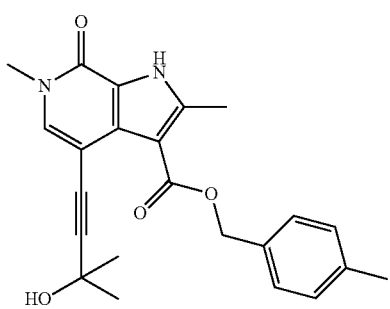
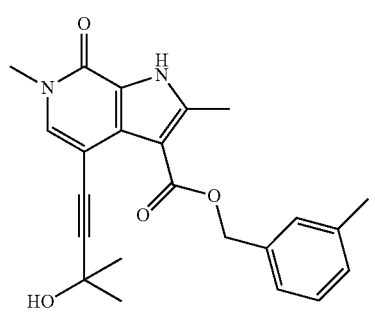
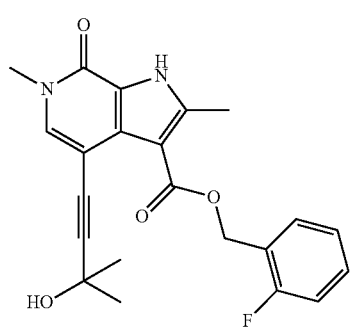
364
-continued
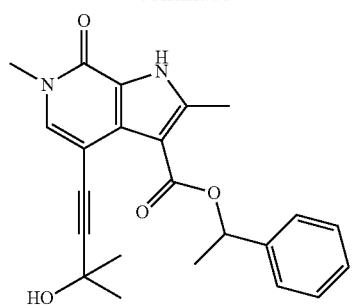
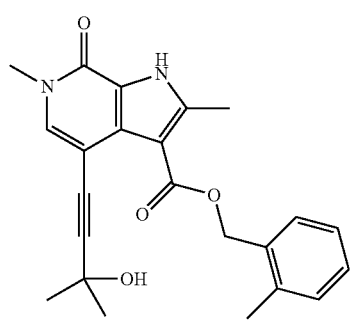
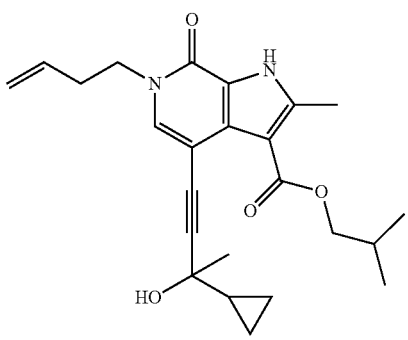
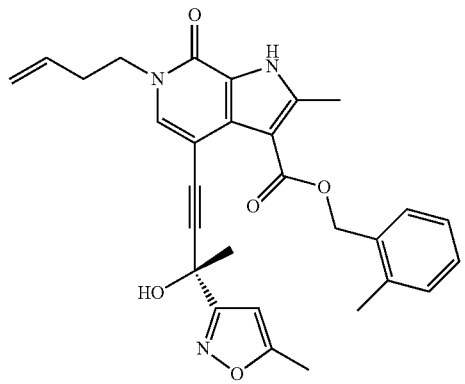
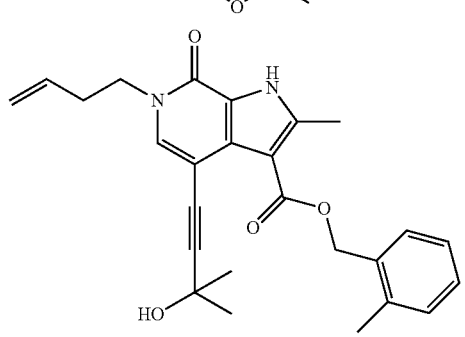

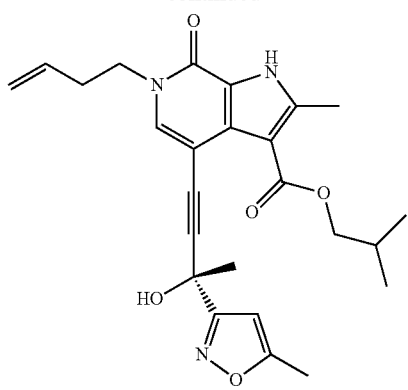
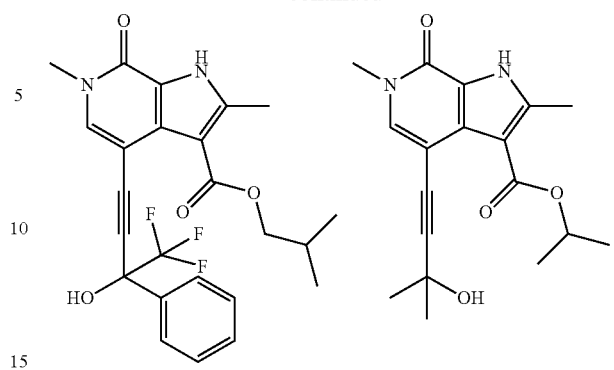
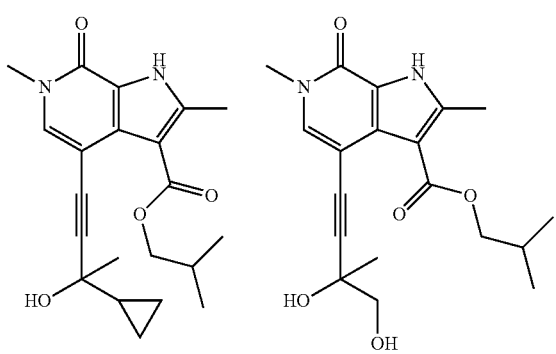
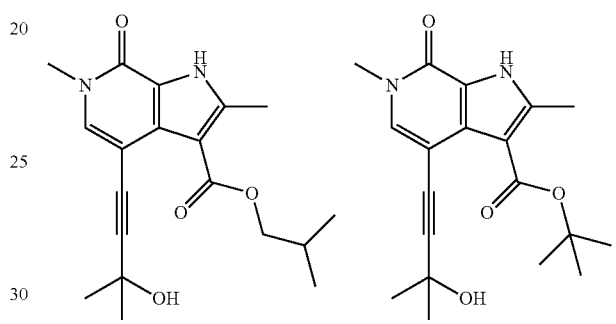
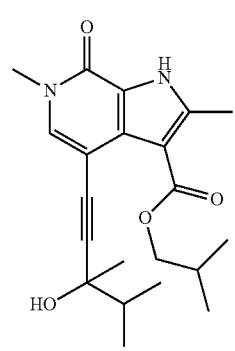
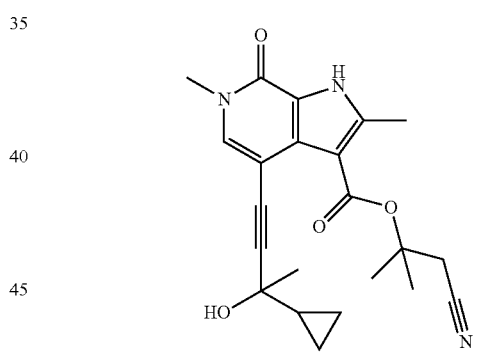
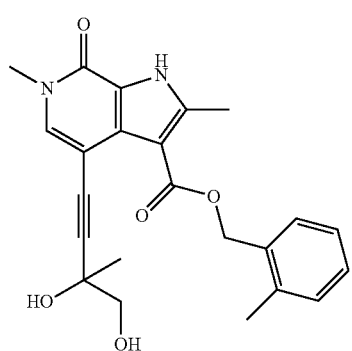
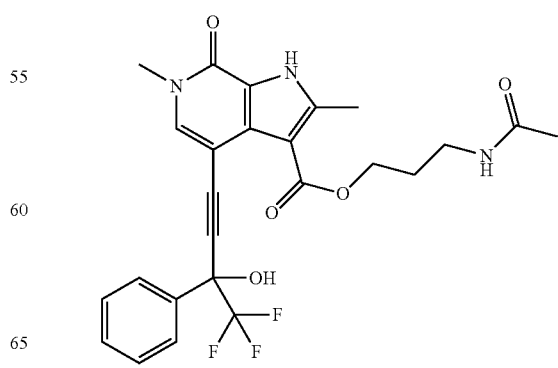

367
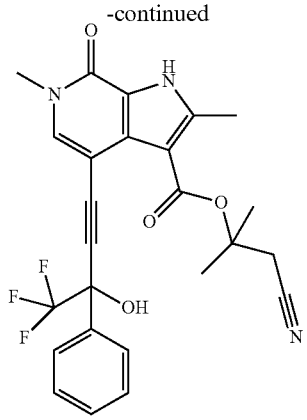
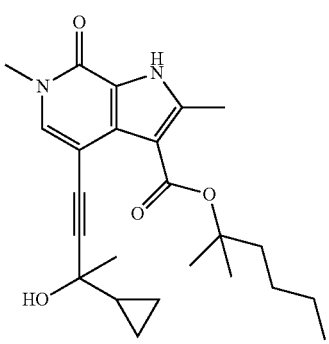
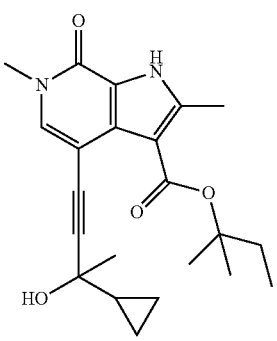
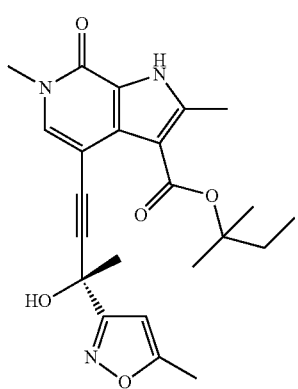
368
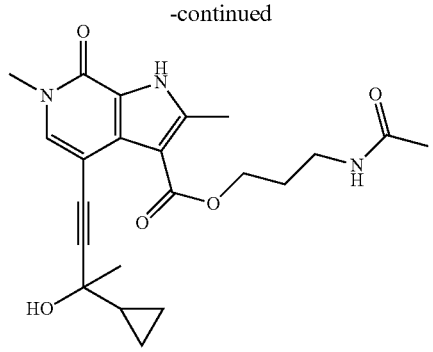
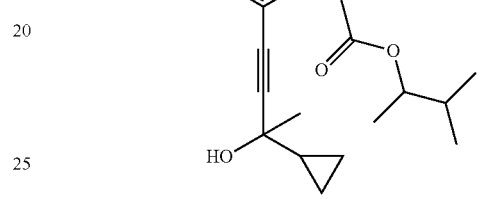
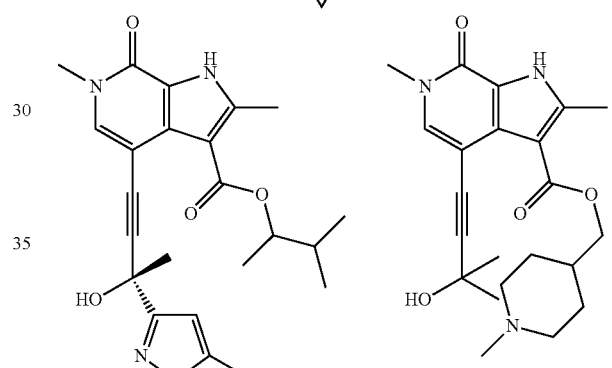
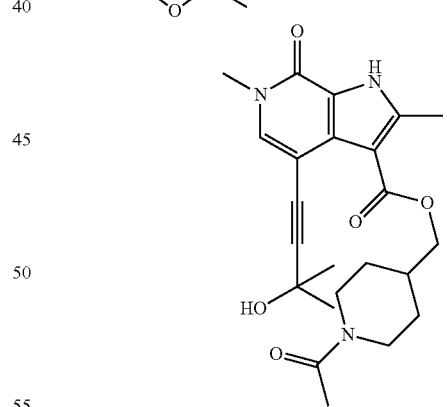
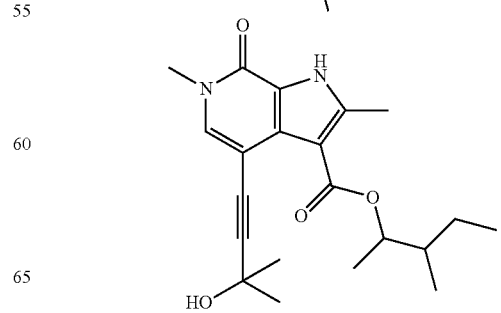

369
-continued
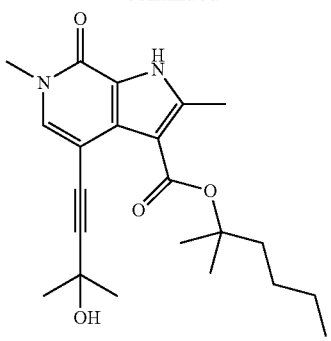
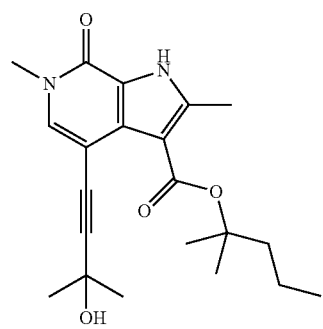
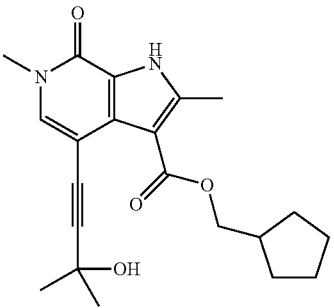
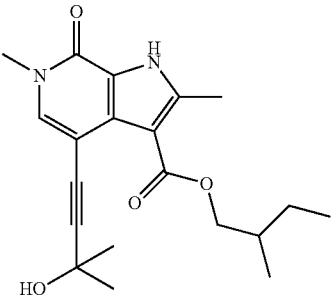
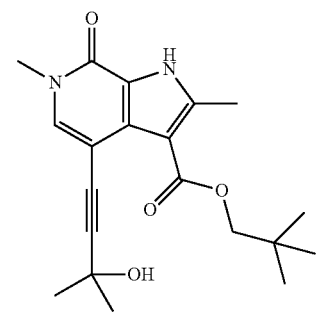
370
-continued
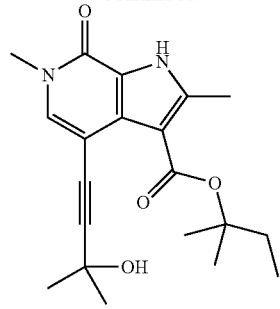
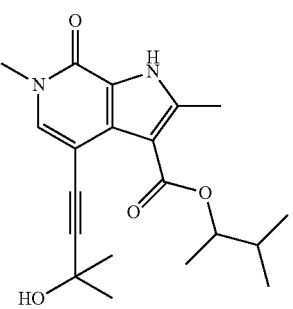
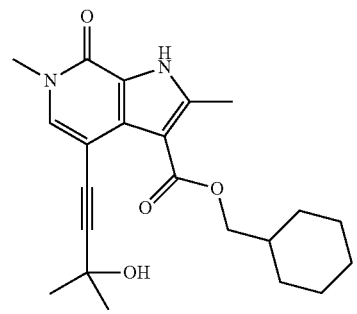
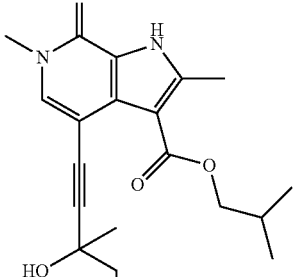
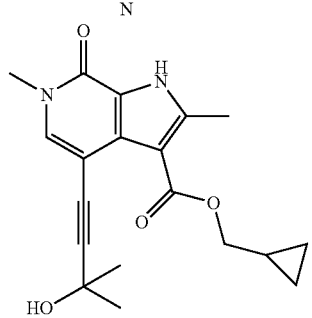

371
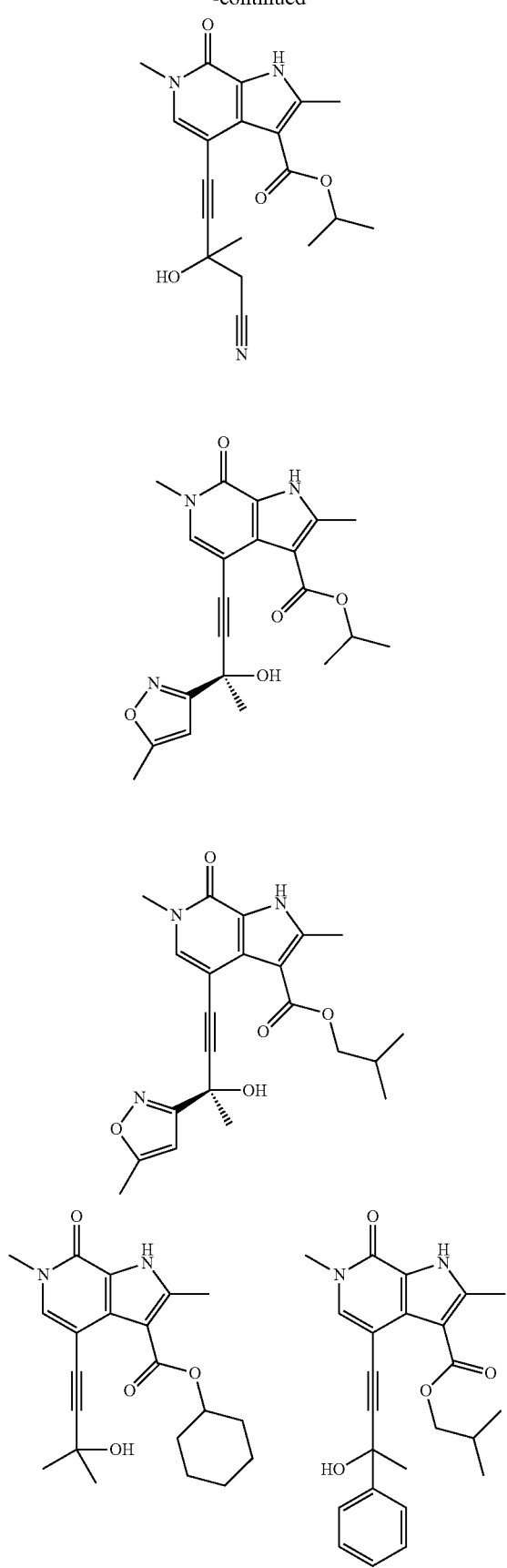
372
-continued
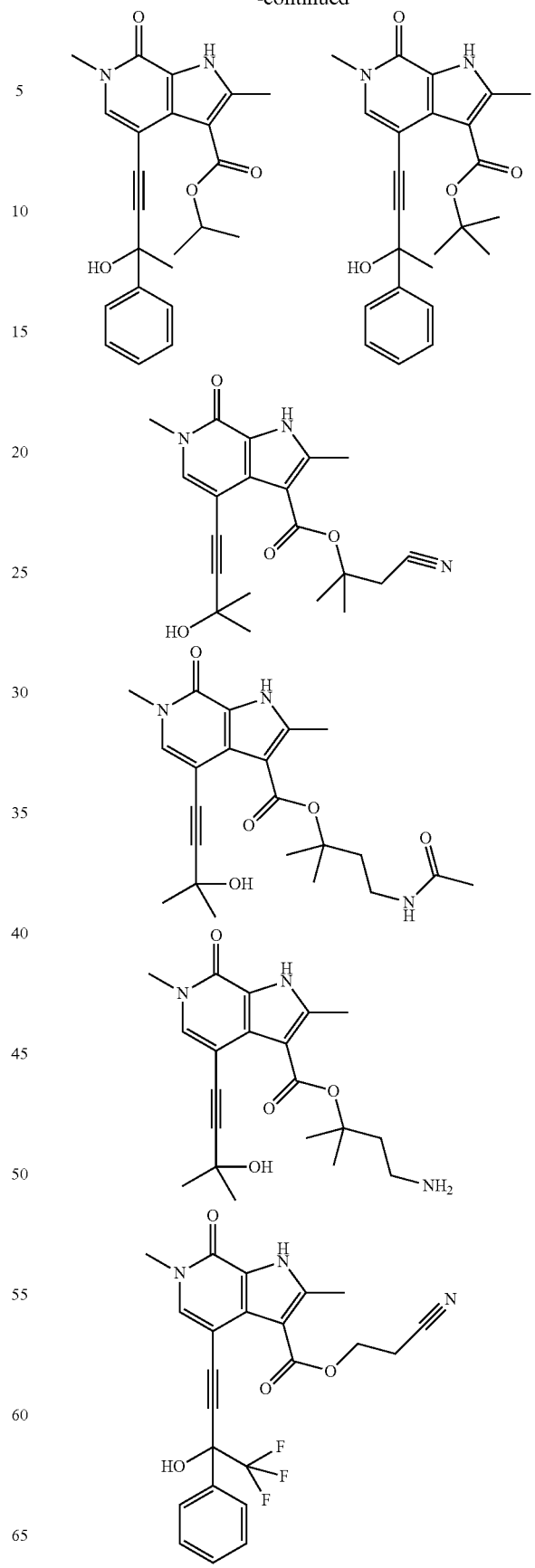

373
-continued
374
-continued
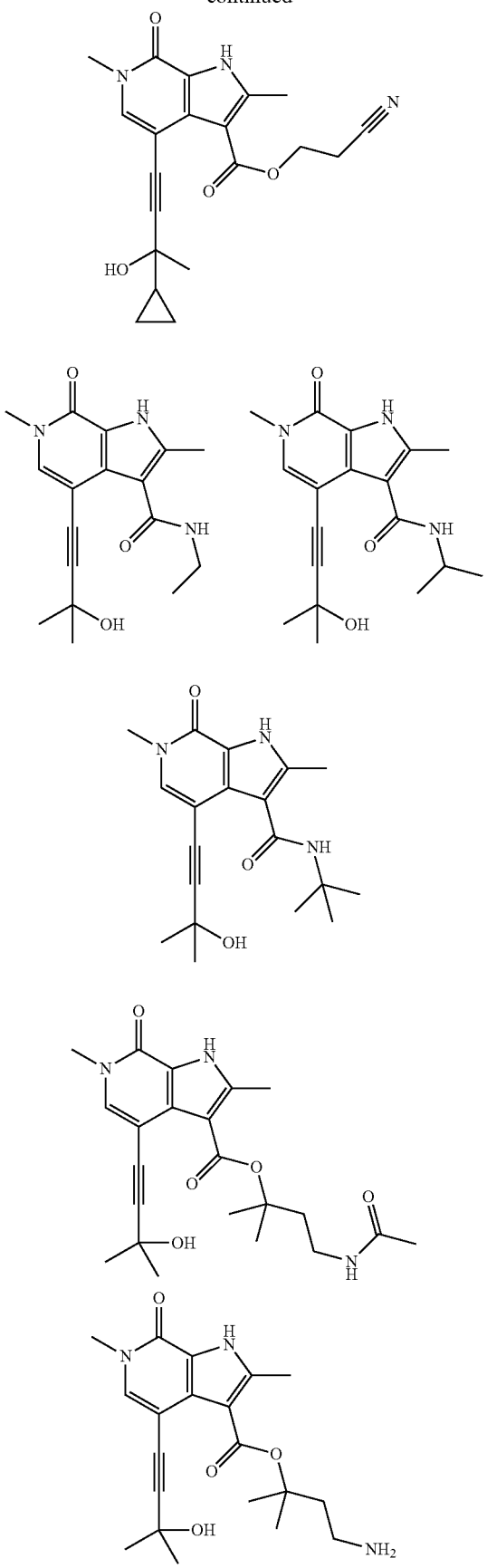
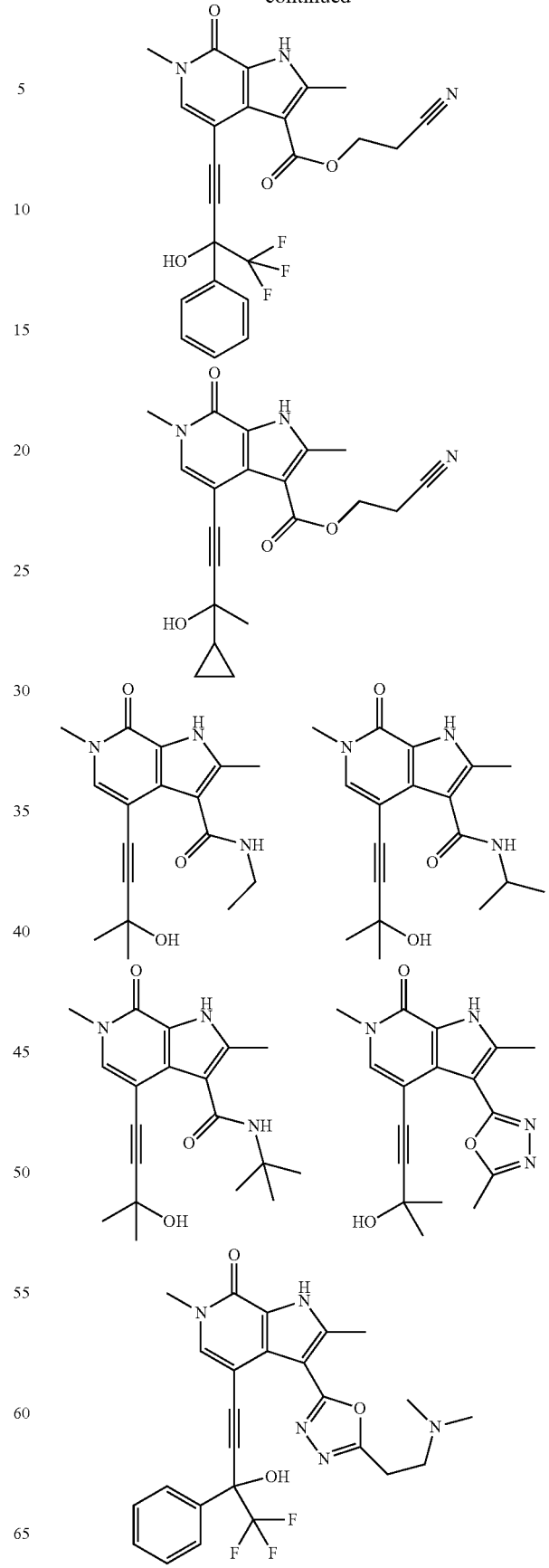

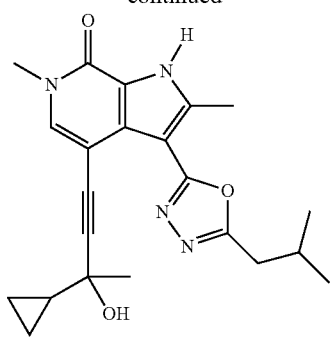
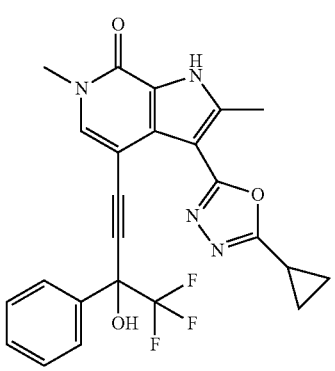
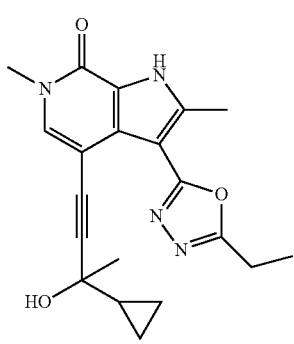
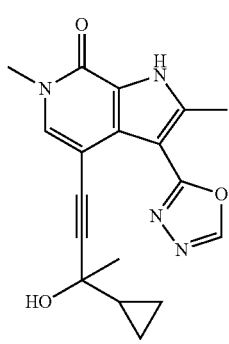
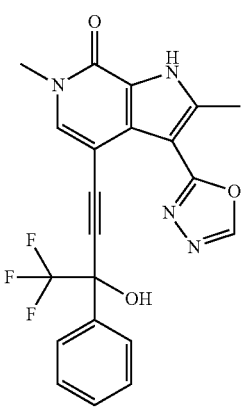
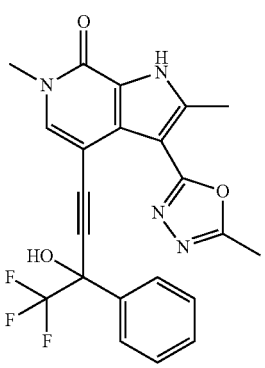
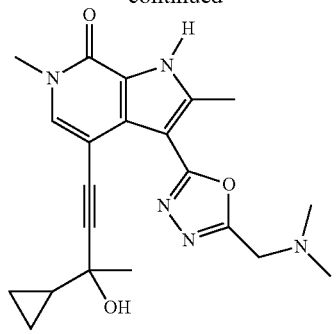
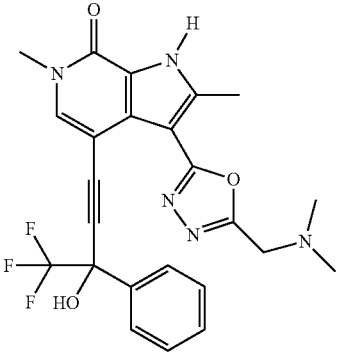
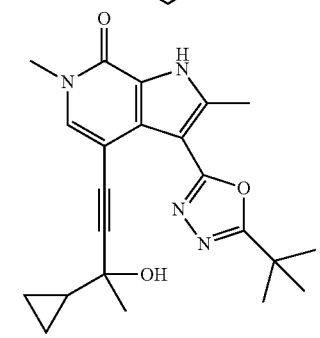
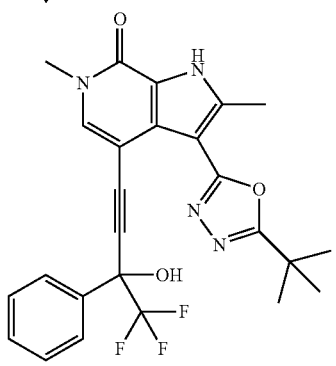
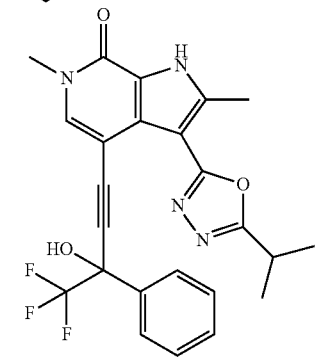

377
-continued
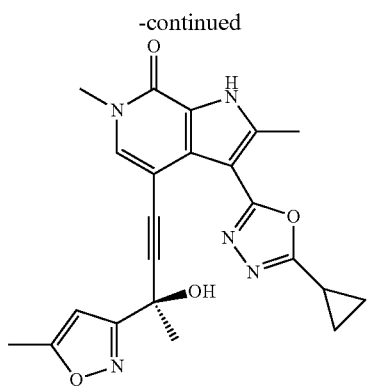
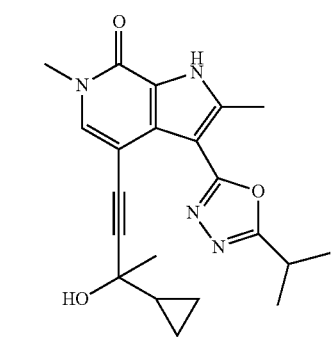
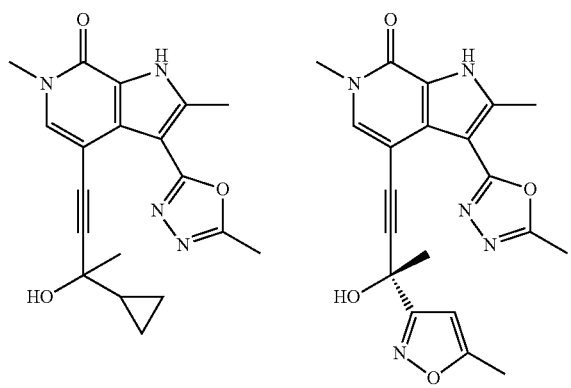
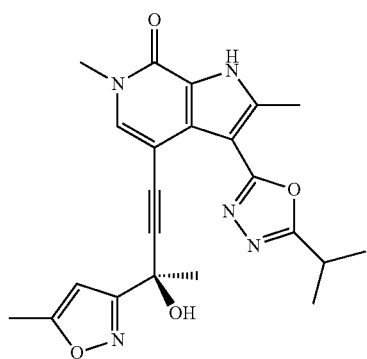
378
-continued
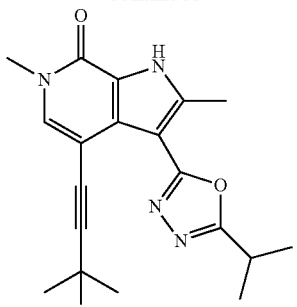
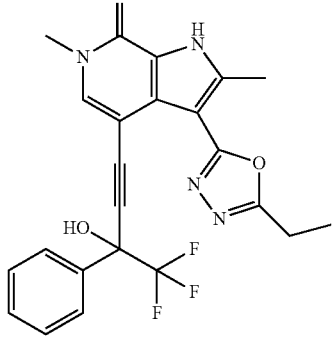
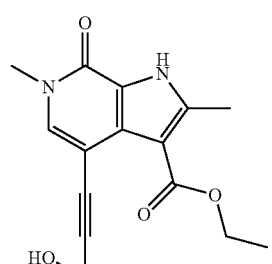
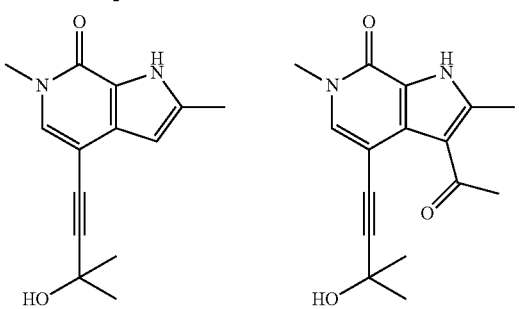
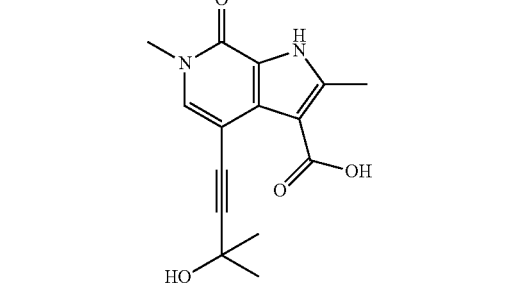

-continued
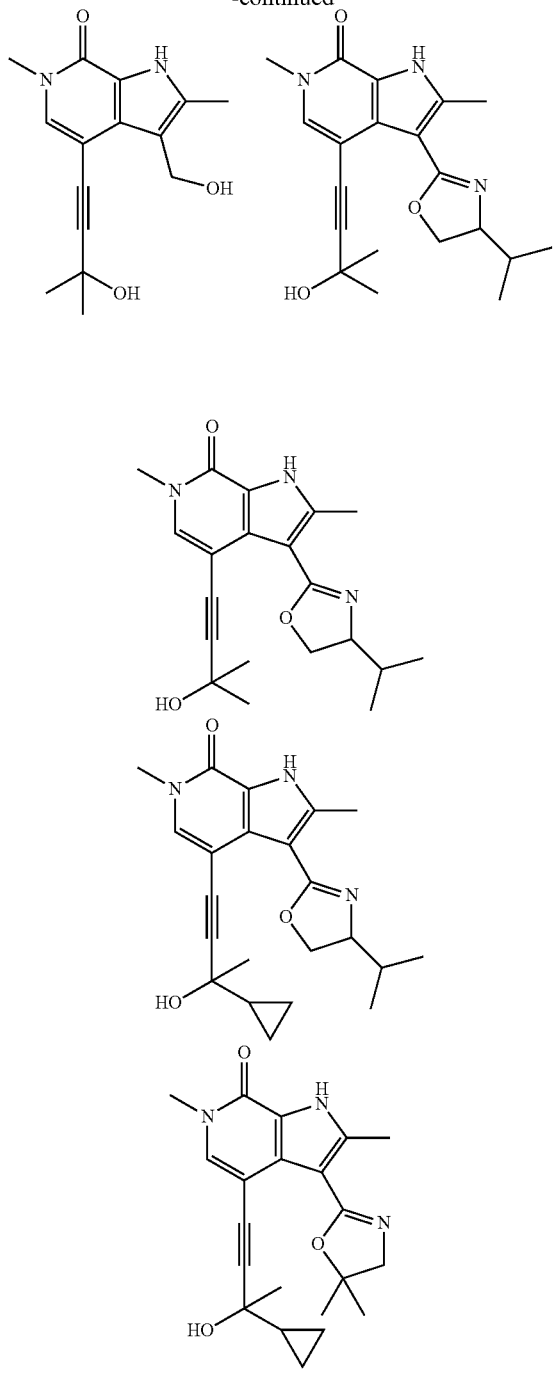
-continued
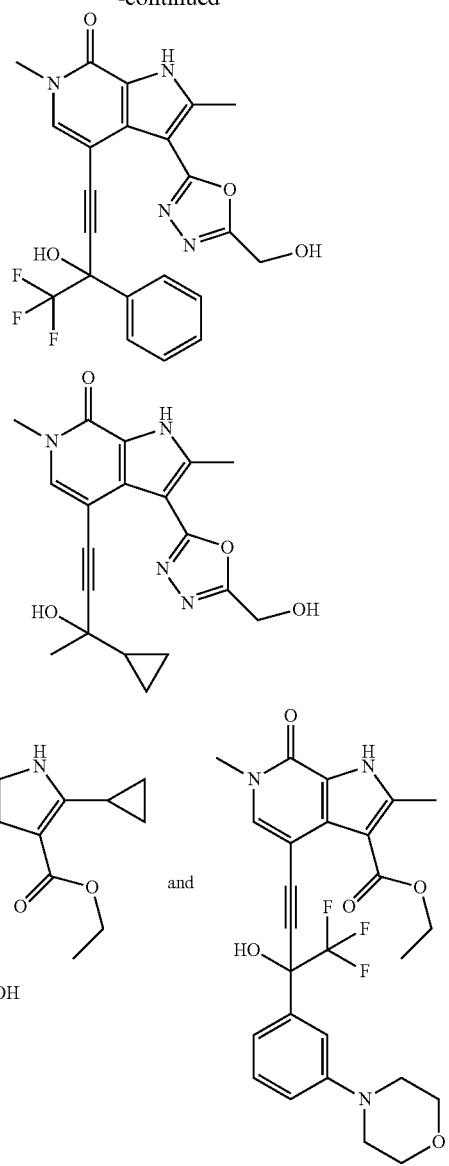
or a salt thereof.
18. A composition comprising a compound of formula (I) as described in claim 1, or a pharmaceutically acceptable salt thereof, and a pharmaceutically acceptable adjuvant, carrier, or vehicle.
* * * * *

UNITED STATES PATENT AND TRADEMARK OFFICE
CERTIFICATE OF CORRECTION

PATENT NO. : 10,202,378 B2
APPLICATION NO. : 15/658213
DATED : February 12, 2019
INVENTOR(S) : Marc Adler et al.

It is certified that error appears in the above-identified patent and that said Letters Patent is hereby corrected as shown below:

In the Claims

Column 330, Line 14, Claim 1, please delete "$C_{2-6}$ alkynyl" and insert -- $C_{2-6}$alkynyl --;

Column 330, Line 16, Claim 1, please delete "$C_{2-6}$ alkenyl, $C_{2-6}$ alkynyl," and insert -- $C_{2-6}$alkenyl, $C_{2-6}$alkynyl, --;

Column 330, Line 20, Claim 1, please delete "$C_{1-6}$ alkyl" and insert -- $C_{1-6}$alkyl --;

Column 330, Line 63, Claim 1, please delete "$C_{2-6}$ alkenyl, $C_{2-6}$ alkynyl," and insert -- $C_{2-6}$alkenyl, $C_{2-6}$alkynyl, --;

Column 331, Line 8, Claim 1, please delete "$C_{1-6}$ alkyl" and insert -- $C_{1-6}$alkyl --;

Column 331, Line 16, Claim 1, please delete "$C_{2-6}$ alkenyl" and insert -- $C_{2-6}$alkenyl --;

Column 331, Line 25, Claim 1, please delete "$C_{2-6}$ alkynyl" and insert -- $C_{2-6}$alkynyl --;

Column 331, Line 58, Claim 5, please delete "$C_{2-6}$ alkenyl" and insert -- $C_{2-6}$alkenyl --;

Column 331, Lines 64-65, Claim 5, please delete "$C_{2-6}$ alkenyl" and insert -- $C_{2-6}$alkenyl --;

Column 341, Line 51, Claim 13, please delete "$C_{1-6}$ alkyl" and insert -- $C_{1-6}$alkyl --;

Column 341, Line 53, Claim 13, please delete "$C_{1-3}$ alkoxy" and insert -- $C_{1-3}$alkoxy --;

Column 341, Line 58, Claim 14, please delete "$C_{1-6}$ alkyl" and insert -- $C_{1-6}$alkyl --;

Column 341, Line 60, Claim 14, please delete "$C_{1-3}$ alkoxy" and insert -- $C_{1-3}$alkoxy --;

Signed and Sealed this
Seventeenth Day of September, 2019

Andrei Iancu
*Director of the United States Patent and Trademark Office*

CERTIFICATE OF CORRECTION (continued)
U.S. Pat. No. 10,202,378 B2

Column 341, Line 63, Claim 14, please delete "$R^2$ is $C_{1-6}$ alkyl" and insert -- $R^2$ is $C_{1-6}$alkyl --;

Column 341, Line 66, Claim 15, please delete "$C_{1-6}$ alkyl" and insert -- $C_{1-6}$alkyl --;

Column 342, Line 1, Claim 15, please delete "$C_{1-3}$ alkoxy" and insert -- $C_{1-3}$alkoxy --;

Column 342, Line 4, Claim 15, please delete "$R^2$ is $C_{1-6}$ alkyl" and insert -- $R^2$ is $C_{1-6}$alkyl --;

Column 342, Line 16, Claim 15, please delete "$C_{2-6}$ alkynyl" and insert -- $C_{2-6}$alkynyl --;

Column 342, Line 27, Claim 16, please delete "$C_{2-6}$ alkenyl" and insert -- $C_{2-6}$alkenyl -- therefor.